United States Patent
Qian et al.

(12) 
(10) Patent No.: US 11,434,232 B2
(45) Date of Patent: Sep. 6, 2022

(54) ATR INHIBITOR AND APPLICATION THEREOF

(71) Applicant: WUXI BIOCITY BIOPHARMACEUTICS CO., LTD., Jiangsu (CN)

(72) Inventors: Wenyuan Qian, Shanghai (CN); Jian Wang, Shanghai (CN); Jie Li, Shanghai (CN); Jian Li, Shanghai (CN); Shuhui Chen, Shanghai (CN)

(73) Assignee: Wuxi Biocity Biopharmaceutics Co., Ltd., Jiangsu (CN)

( * ) Notice: Subject to any disclaimer, the term of this patent is extended or adjusted under 35 U.S.C. 154(b) by 0 days.

(21) Appl. No.: 16/968,429

(22) PCT Filed: Feb. 2, 2019

(86) PCT No.: PCT/CN2019/074578
§ 371 (c)(1),
(2) Date: Aug. 7, 2020

(87) PCT Pub. No.: WO2019/154365
PCT Pub. Date: Aug. 15, 2019

(65) Prior Publication Data
US 2020/0399260 A1    Dec. 24, 2020

(30) Foreign Application Priority Data

Feb. 7, 2018 (CN) .......................... 201810124494.2
Nov. 15, 2018 (CN) .......................... 201811361512.5

(51) Int. Cl.
| | | |
|---|---|---|
| C07D 413/14 | (2006.01) | |
| C07D 471/04 | (2006.01) | |
| A61P 35/00 | (2006.01) | |

(52) U.S. Cl.
CPC ............ C07D 413/14 (2013.01); A61P 35/00 (2018.01); C07D 471/04 (2013.01)

(58) Field of Classification Search
CPC ...... C07D 413/14; C07D 471/04; A61P 35/00
See application file for complete search history.

(56) References Cited

FOREIGN PATENT DOCUMENTS

| | | |
|---|---|---|
| CN | 103068391 A | 4/2013 |
| RU | 2537945 C2 | 1/2015 |
| WO | 2009093981 A1 | 7/2009 |
| WO | 2010073034 A1 | 7/2010 |
| WO | 2011154737 A1 | 12/2011 |
| WO | 2012101654 A2 | 8/2012 |
| WO | 2014140644 A1 | 9/2014 |
| WO | 2019050889 A1 | 3/2019 |
| WO | 2010052569 A2 | 5/2020 |

OTHER PUBLICATIONS

Golub et al. Science, vol. 286, Oct. 15, 1999, pp. 531-537.*
Extended European Search Report dated Jun. 7, 2021 in corresponding European Patent Application No. 19750376.6.
International Search Report dated May 9, 2019 in corresponding International Application No. PCT/CN2019/074578.
Written Opinion dated May 9, 2019 in corresponding International Application No. PCT/CN2019/074578.
Russian Office Action dated Dec. 21, 2021 in corresponding RU Application No. 2020128324.

* cited by examiner

*Primary Examiner* — Samira J Jean-Louis
(74) *Attorney, Agent, or Firm* — Ice Miller LLP

(57) ABSTRACT

Disclosed are a compound as an ATR inhibitor and an application in preparing a drug as an ATR inhibitor. In particular, disclosed is a compound represented by formula (I) or an isomer or pharmaceutically acceptable salt thereof.

19 Claims, 1 Drawing Sheet

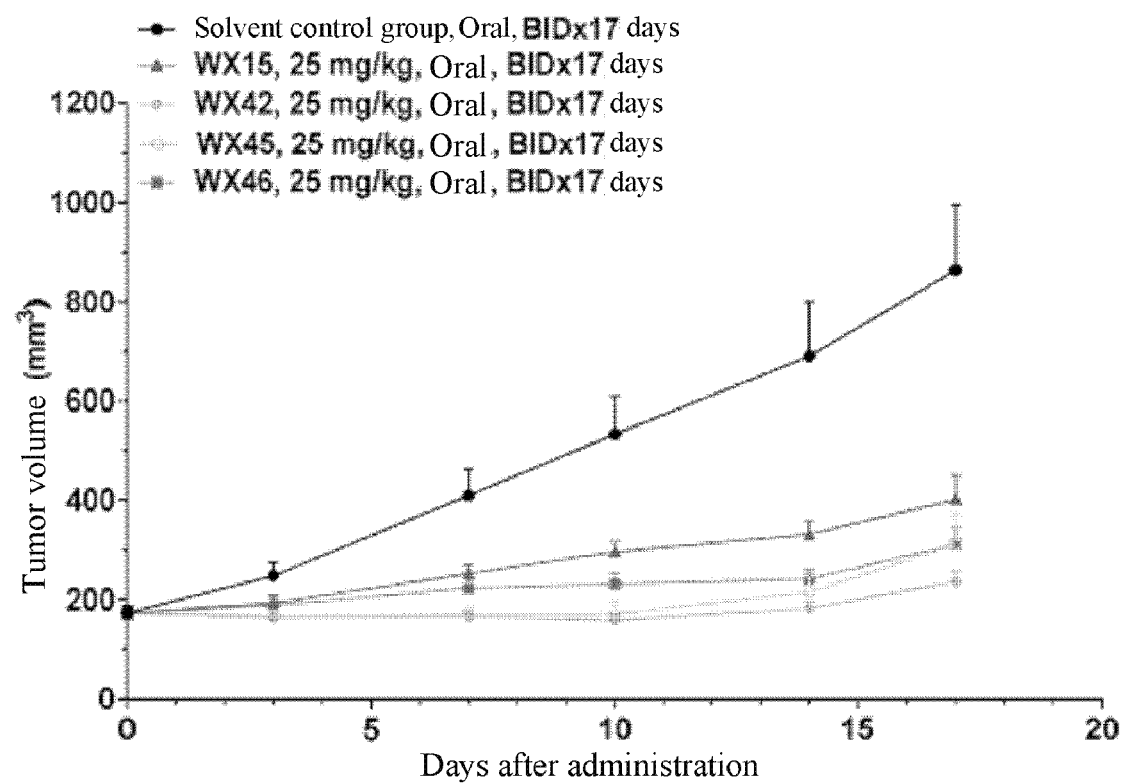

ATR INHIBITOR AND APPLICATION THEREOF

CROSS-REFERENCE TO RELATED APPLICATION

This application is a Section 371 of International Application No. PCT/CN2019/074578, filed Feb. 2, 2019, which was published in the Chinese language Aug. 15, 2019, under International Publication No. WO 2019/154365 A1, which claims priority under 35 U.S.C. § 119(b) to Chinese Patent Application No. 201810124494.2, filed Feb. 7, 2018, and Chinese Patent Application No. 201811361512.5 filed Nov. 15, 2018, the disclosures of which are incorporated herein by reference in their entireties.

TECHNICAL FIELD

Provided are compounds as ATR inhibitor and use thereof for the manufacture of ATR inhibitor and particularly, a compound of formula (I), an isomer or a pharmaceutically acceptable salt thereof.

BACKGROUND

ATR (Ataxia Telangiectasia-mutated and Rad3-Related protein kinase) belongs to the PIKKs (phosphatidylinositol-3-kinase-related kinase) family and participates in DNA damage repair to maintain gene stability. ATR protein kinase has a synergistic response on DNA damage, replication stress and cell cycle disturbances. ATR and ATM belong to the PIKK family of serine/threonine protein kinases, and they are common component of the cell cycle and DNA damage repairing, and other members include Chkl, BRCA1, p53. ATR is mainly responsible for DNA replication stress (duplication fork arrest) and repair of single strand break.

When the double-stranded DNA breaks and the replication fork arrests, ATR is activated by the single-stranded DNA structure. DNA polymerase stays in the process of DNA replication, and the replication helicase continues to unwind at the leading end of the DNA replication fork, resulting in the production of long single-stranded DNA (ssDNA), which is then bound by the single-stranded DNA and RPA (replication protein A). ATR/ATR acting protein complex is recruited by RPA upon replication stress or DNA damage to the damage site, RPA-single-stranded DNA complex activates the RAD17/rfc2-5 complex to bind to the damage site, DNA-ssDNA junction activates Rad9-HUS-RAD1 (9-1-1) heterotrimer, 9-1-1 in turn recruits TopBP1 to activate ATR. Once ATR is activated, ATR promotes DNA repair through downstream targets, stabilizing and restarting arrested replication forks and transient cell cycle arrest. These functions are achieved by ATR via mediating the downstream target Chk1. ATR acts as checkpoint for DNA damage in the cell cycle during S phase. It can mediate the degradation of CDC25A through Chk1, thereby delaying the DNA replication process and providing time to repair the replication fork. ATR is also the main regulator of G2/M cell cycle checkpoint, preventing cells from entering mitosis prematurely before DNA replication is completed or DNA damage. This ATR-dependent G2/M cell cycle arrest is mainly mediated by two mechanisms: 1. Degradation of CDC25A; 2. Phosphorylation of Cdc25C by Chk1 to bind to 14-3-protein. The binding of Cdc25C to 14-3-3 protein promotes its export from the nucleus and cytoplasmic isolation, thereby inhibiting its ability to dephosphorylate and activate nuclear Cdc2, which in turn prevents entry into mitosis.

ATR gene mutations are very rare, and only few patients with Seckel syndrome have ATR gene mutations, which are characterized by stunting and microcephaly. Disruption of ATR-related pathways can lead to genome instability, and ATR protein is activated by most cancer chemotherapy. In addition, the duplication of the ATR gene has been described as a risk factor for rhabdomyosarcoma.

ATR is essential for cell self-replication and is activated in the S phase to regulate the origin of replication and repair damaged replication forks. Damage to the replication forks can increase the sensitivity of cancer cells to platinum and hydroxyurea anticancer agents and reduce the resistance of cancer cells. Therefore, inhibiting ATR may be an effective method in cancer treatment in the future.

WO2011154737 discloses Compound AZD6738 as ATR inhibitor having the following structure:

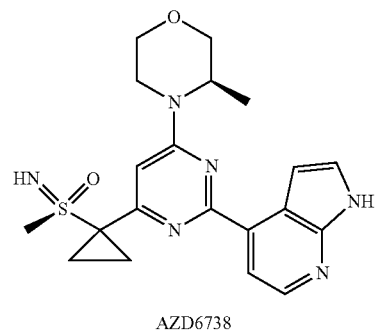 [SMILES: C[C@@H]1COCCN1c1cc(C2([S@](C)(=N)=O)CC2)nc(-c2ccnc3[nH]ccc23)n1]

AZD6738

SUMMARY

In an aspect, provided is a compound of formula (I), or an isomer or a pharmaceutically acceptable salt thereof,

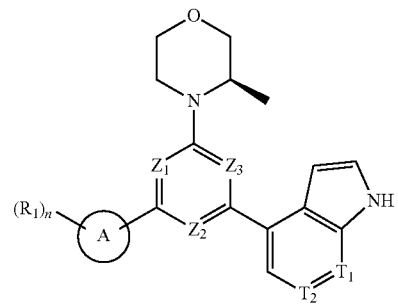

wherein, n is 1, 2, 3 or 4;

$Z_1$, $Z_2$, and $Z_3$ are each independently selected from the group consisting of CH and N, and at least one of $Z_1$, $Z_2$ and $Z_3$ is N;

$T_1$, and $T_2$ are each independently selected from the group consisting of $C(R_2)$ and N;

ring A is selected from the group consisting of 5-6 membered heteroaryl;

$R_1$ is each independently selected from the group consisting of H, F, Cl, Br, I, OH, $NH_2$, $C_{1-6}$ alkyl, $C_{1-6}$ alkoxy and $C_{3-6}$ cycloalkyl, wherein the $C_{1-6}$ alkyl, $C_{1-6}$ alkoxy and $C_{3-6}$ cycloalkyl are optionally substituted by 1, 2 or 3 R;

$R_2$ is each independently selected from the group consisting of H, F, Cl, Br, I, OH, $NH_2$, COOH and $C_{1-3}$ alkyl, wherein the $C_{1-3}$ alkyl is optionally substituted by 1, 2 or 3 R;

R is each independently selected from the group consisting of F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted by 1, 2 or 3 R';

R' is each independently selected from the group consisting of F, Cl, Br, I, OH and $NH_2$;

the 5-6 membered heteroaryl comprises 1, 2, 3 or 4 heteroatoms or heteroradicals independently selected from the group consisting of —NH—, —O—, —S— and N.

In some embodiments according to the present disclosure, R is each independently selected from the group consisting of H, F, Cl, Br, I, OH, $NH_2$, $CH_3$, Et and —O—$CH_3$, and other variables are defined as herein.

In some embodiments according to the present disclosure, $R_1$ is each independently selected from the group consisting of H, F, Cl, Br, I, OH, $NH_2$, $C_{1-3}$ alkyl, $C_{1-3}$ alkoxy and cyclopropyl, wherein the $C_{1-3}$ alkyl, $C_{1-3}$ alkoxy and cyclopropyl are optionally substituted by 1, 2 or 3 R, and other variables are defined as herein.

In some embodiments according to the present disclosure, $R_1$ is each independently selected from the group consisting of H, F, Cl, Br, I, OH, $NH_2$, $CH_3$, $H_2$, $CHF_2$, $CF_3$, Et, —$CH_2OH$, —O—$CH_3$,

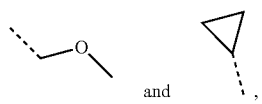

and and other variables are defined as herein.

In some embodiments according to the present disclosure, $R_2$ is each independently selected from the group consisting of H, F, Cl, Br, I, OH, $NH_2$, COOH, $CH_3$, Et and —$CH_2$—OH, and other variables are defined as herein.

In some embodiments according to the present disclosure, ring A is selected from the group consisting of pyrazolyl, isoxazolyl, oxazolyl, imidazolyl, 1,2,3-triazolyl, 1,2,4-triazolyl and pyridyl, and other variables are defined as herein.

In some embodiments according to the present disclosure, ring A is selected from the group consisting of

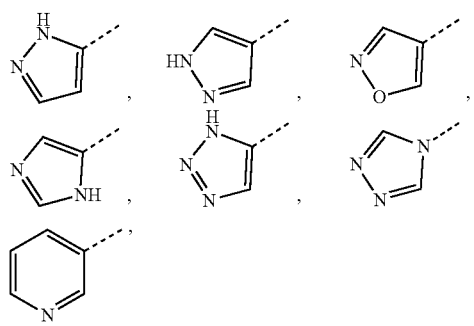

and other variables are defined as herein.

In some embodiments according to the present disclosure, the structural unit

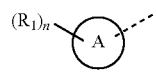

is selected from the group consisting of

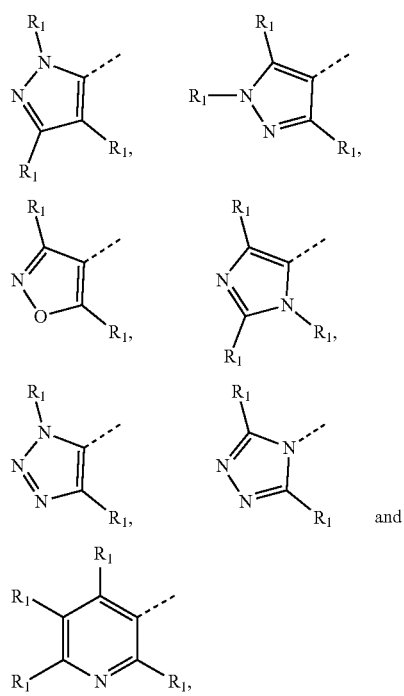

and and other variables are defined as herein.

In some embodiments according to the present disclosure, the structural unit

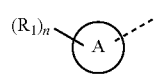

is selected from the group consisting of

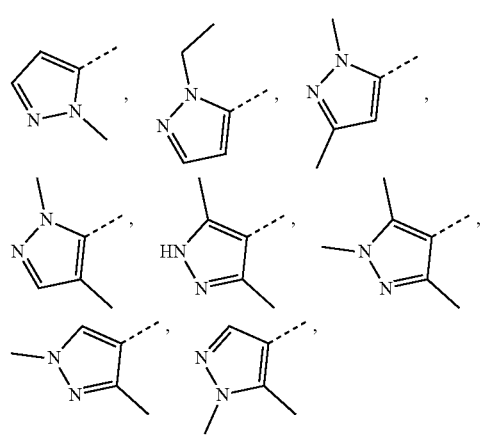

-continued

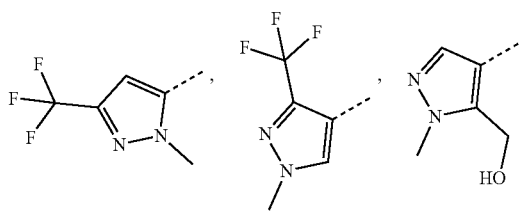
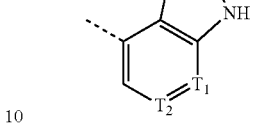

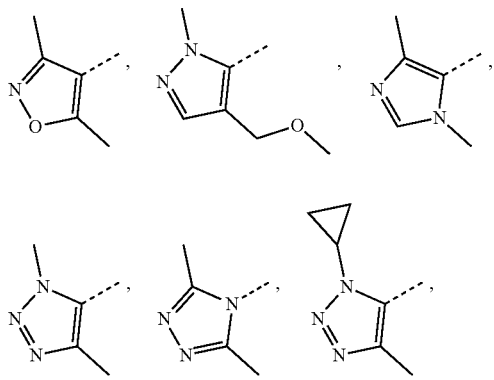
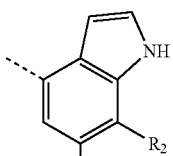
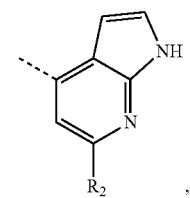

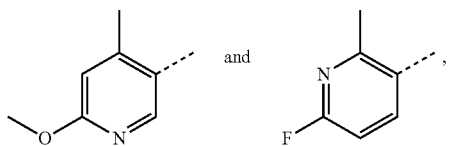 and 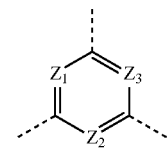, and other variables are defined as herein.

In some embodiments according to the present disclosure, the structural unit

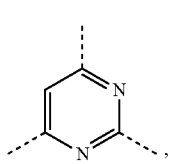

is selected from the group consisting of

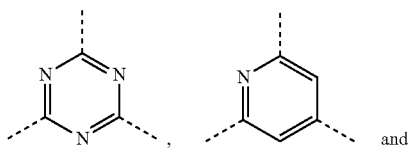

and other variables are defined as herein.

In some embodiments according to the present disclosure, the structural unit is selected from the group consisting of

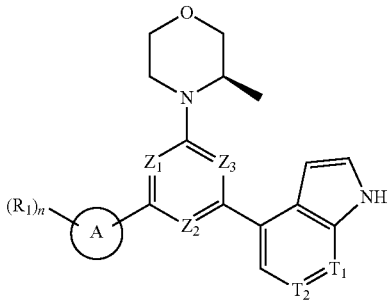

and other variables are defined as herein.

Provided is also a compound of formula (I) or an isomer or a pharmaceutically acceptable salt thereof, wherein, n is 1, 2, 3 or 4;

$Z_1$, $Z_2$, and $Z_3$ are each independently selected from the group consisting of CH and N, and at least one of $Z_1$, $Z_2$ and $Z_3$ is N;

$T_1$, and $T_2$ are each independently selected from the group consisting of $C(R_2)$ and N;

ring A is selected from the group consisting of 5-6 membered heteroaryl;

$R_1$ is each independently selected from the group consisting of H, F, Cl, Br, I, OH, $NH_2$, $C_{1-6}$ alkyl, $C_{1-6}$ alkoxy and $C_{3-6}$ cycloalkyl, wherein the $C_{1-6}$ alkyl, $C_{1-6}$ alkoxy and $C_{3-6}$ cycloalkyl are optionally substituted by 1, 2 or 3 R;

$R_2$ is each independently selected from the group consisting of H, F, Cl, Br, I, OH, $NH_2$ and $C_{1-3}$ alkyl, wherein the $C_{1-3}$ alkyl is optionally substituted by 1, 2 or 3 R;

R is each independently selected from the group consisting of F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted by 1, 2 or 3 R';

R' is each independently selected from the group consisting of F, Cl, Br, I, OH and $NH_2$; the 5-6 membered heteroaryl comprises 1, 2, 3 or 4 heteroatoms or heteroradicals independently selected from the group consisting of —NH—, —O—, —S— and N.

In some embodiments according to the present disclosure, R is each independently selected from the group consisting of H, F, Cl, Br, I, OH, NH$_2$, CH$_3$, Et and —O—CH$_3$, and other variables are defined as herein.

In some embodiments according to the present disclosure, R$_1$ is each independently selected from the group consisting of H, F, Cl, Br, I, OH, NH$_2$, C$_{1-3}$ alkyl, C$_{1-3}$ alkoxy and cyclopropyl, wherein the C$_{1-3}$ alkyl, C$_{1-3}$ alkoxy and cyclopropyl are optionally substituted by 1, 2 or 3 R, and other variables are defined as herein.

In some embodiments according to the present disclosure, R$_1$ is each independently selected from the group consisting of H, F, Cl, Br, I, OH, NH$_2$, CH$_3$, CH$_2$F, CHF$_2$, CF$_3$, Et, —CH$_2$OH, —O—CH$_3$,

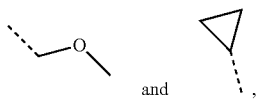

and and other variables are defined as herein.

In some embodiments according to the present disclosure, R$_2$ is each independently selected from the group consisting of H, F, Cl, Br, I, OH, NH$_2$, CH$_3$, Et and —CH$_2$—OH, and other variables are defined as herein.

In some embodiments according to the present disclosure, ring A is selected from the group consisting of pyrazolyl, isoxazolyl, oxazolyl, imidazolyl, 1,2,3-triazolyl, 1,2,4-triazolyl and pyridyl, and other variables are defined as herein.

In some embodiments according to the present disclosure, ring A is selected from the group consisting of

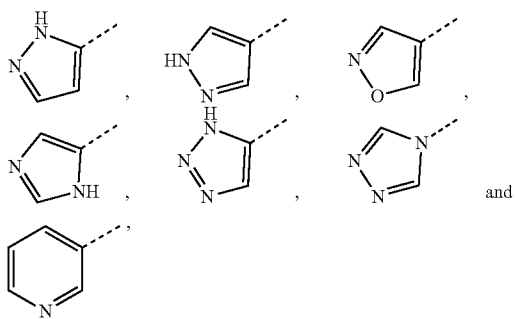

and and other variables are defined as herein.

In some embodiments according to the present disclosure, the structural unit

is selected from the group consisting of

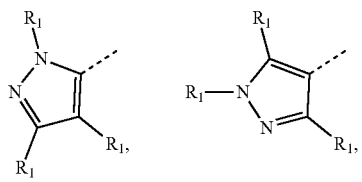

and other variables are defined as herein.

In some embodiments according to the present disclosure, the structural unit

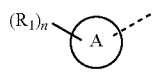

is selected from the group consisting of

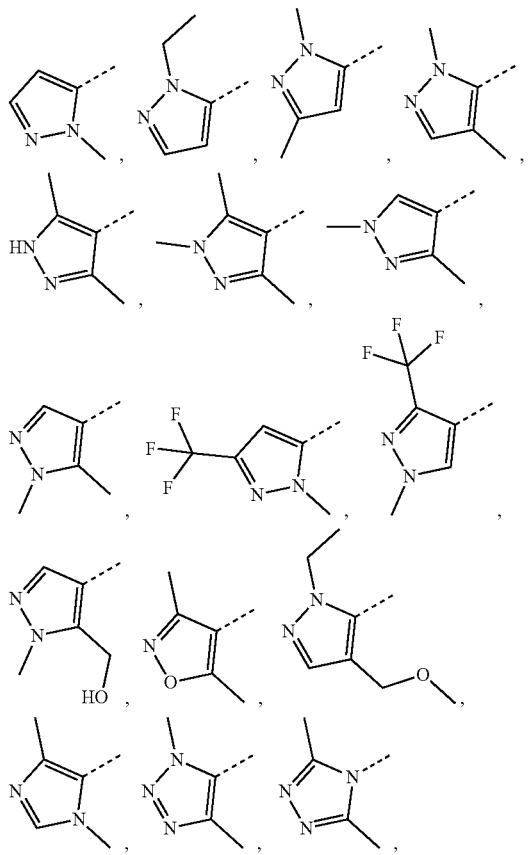

and other variables are defined as herein.

In some embodiments according to the present disclosure, the structural unit is selected from the group consisting of and other variables are defined as herein.

In some embodiments according to the present disclosure, the structural unit is selected from the group consisting of and other variables are defined as herein.

Provided is further a compound of formula (I) or an isomer or a pharmaceutically acceptable salt thereof, (I)

wherein, n is 1, 2, 3 or 4;

$Z_1$, $Z_2$, and $Z_3$ are each independently selected from the group consisting of CH and N, and at least one of $Z_1$, $Z_2$ and $Z_3$ is N;

$T_1$, and $T_2$ are each independently selected from the group consisting of $C(R_2)$ and N;

ring A is selected from the group consisting of 5-6 membered heteroaryl;

$R_1$ is each independently selected from the group consisting of H, F, Cl, Br, I, OH, $NH_2$ and $C_{1-3}$ alkyl, wherein the $C_{1-3}$ alkyl is optionally substituted by 1, 2 or 3 R;

$R_2$ is each independently selected from the group consisting of H, F, Cl, Br, I, OH, $NH_2$ and $C_{1-3}$ alkyl, wherein the $C_{1-3}$ alkyl is optionally substituted by 1, 2 or 3 R;

R is each independently selected from the group consisting of F, Cl, Br, I, OH, $NH_2$ and $C_{1-3}$ alkyl, wherein the $C_{1-3}$ alkyl is optionally substituted by 1, 2 or 3 R';

R' is each independently selected from the group consisting of F, Cl, Br, I, OH and $NH_2$;

the 5-6 membered heteroaryl comprises 1, 2, 3 or 4 heteroatoms or heteroradicals independently selected from the group consisting of —NH—, —O—, —S— and N.

In some embodiments according to the present disclosure, R is each independently selected from the group consisting of H, F, Cl, Br, I, OH, $NH_2$, $CH_3$ and Et, and other variables are defined as herein.

In some embodiments according to the present disclosure, $R_1$ is each independently selected from the group consisting of H, F, Cl, Br, I, OH, $NH_2$, $CH_3$, $CH_2F$, $CHF_2$, $CF_3$, Et and —$CH_2OH$, and other variables are defined as herein.

In some embodiments according to the present disclosure, $R_2$ is each independently selected from the group consisting of H, F, Cl, Br, I, OH, $NH_2$, $CH_3$ and Et, and other variables are defined as herein.

In some embodiments according to the present disclosure, ring A is selected from the group consisting of pyrazolyl, isoxazolyl, oxazolyl and imidazolyl, and other variables are defined as herein.

In some embodiments according to the present disclosure, ring A is selected from the group consisting of and other variables are defined as herein.

In some embodiments according to the present disclosure, the structural unit

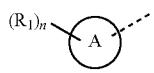

is selected from the group consisting of

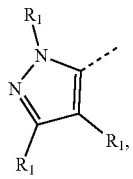 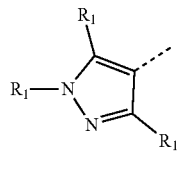 and

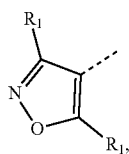

and other variables are defined as herein.

In some embodiments according to the present disclosure, the structural unit

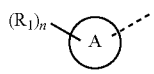

is selected from the group consisting of

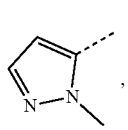, 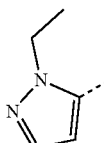, 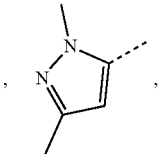,

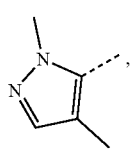, 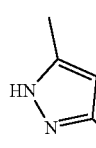, 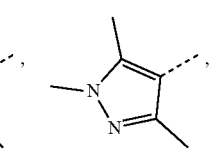,

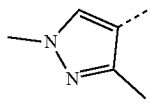, 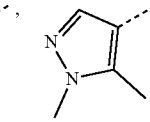,

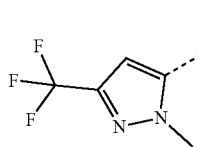, 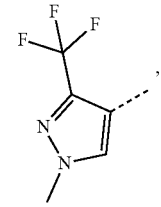,

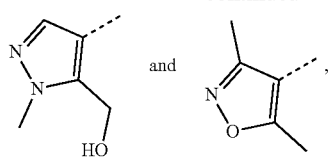 and

-continued

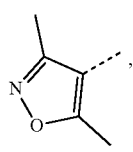, and other variables are defined as herein.

In some embodiments according to the present disclosure, the structural unit

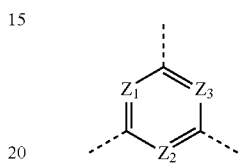

is selected from the group consisting of

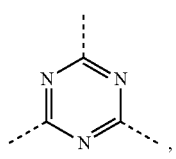, 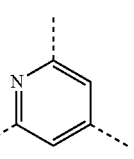 and

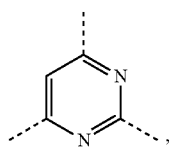, and other variables are defined as herein.

In some embodiments according to the present disclosure, the structural unit

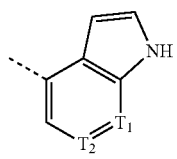

is selected from the group consisting of

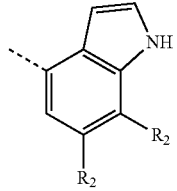 and 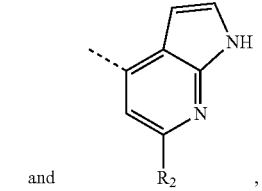, and other variables are defined as herein.

Some embodiments of the present disclosure are derived from the combination of the above variables In some embodiments according to the present disclosure, provided is the above compound or the isomer thereof or the pharmaceutically acceptable salt, selected from

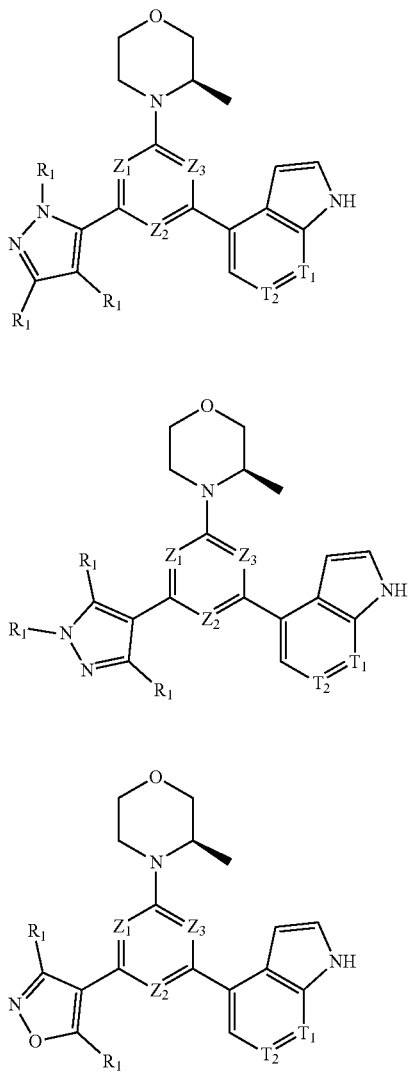

(II-1)

(II-2)

(II-3)

(II-4)

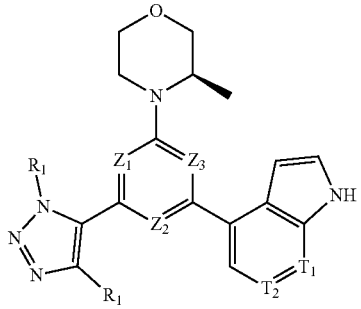

(II-5)

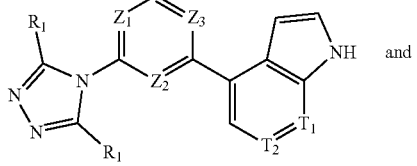

(II-6) and

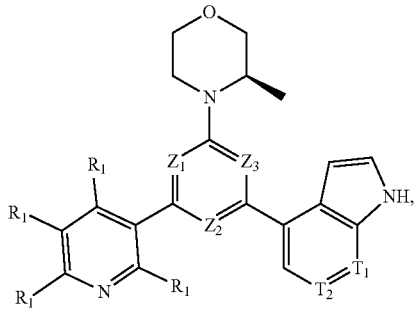

(II-7)

wherein, $T_1$, and $T_2$ are each independently selected from the group consisting of $C(R_2)$ and N;

$R_1$, $R_2$, $Z_1$, $Z_2$ and $Z_3$ are defined as herein.

In some embodiments according to the present disclosure, provided is the above compound or the isomer thereof or the pharmaceutically acceptable salt, selected from

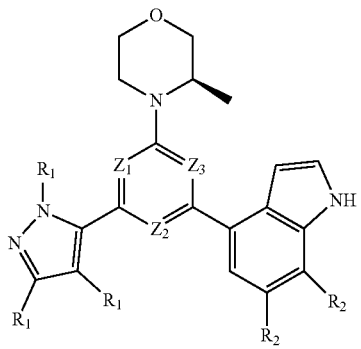

(I-1)

(I-2)
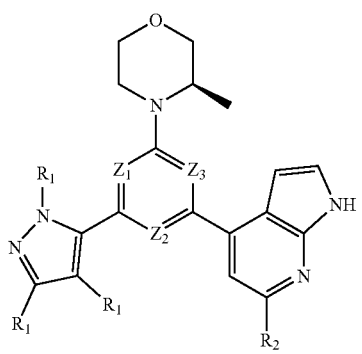
(I-3)
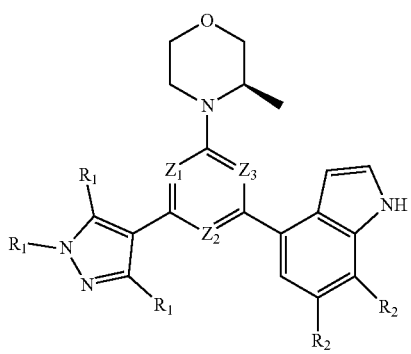
(I-4)
(I-5)
(I-6)
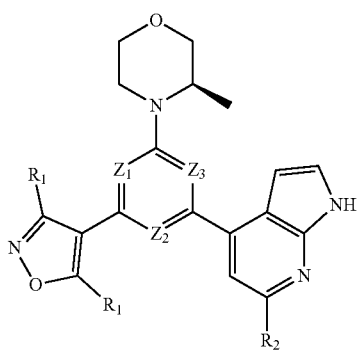
(II-4A)
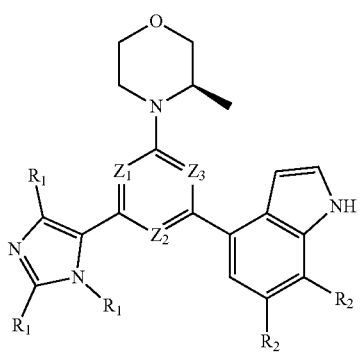
(II-4B)
(II-5A)
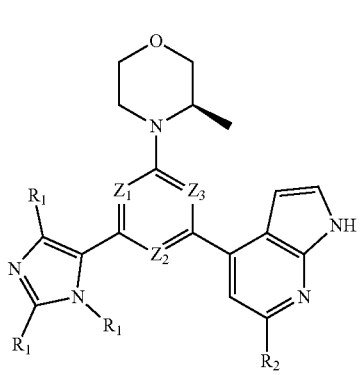
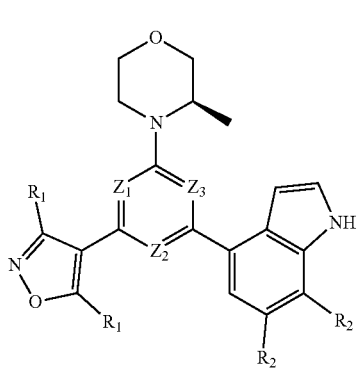
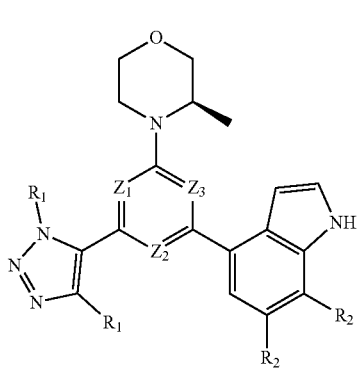

(II-5B)
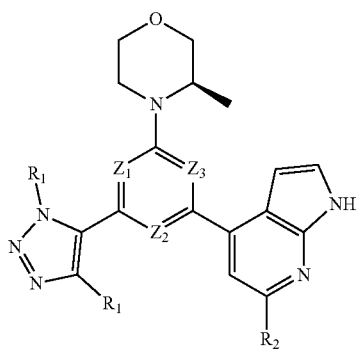
(II-6A)
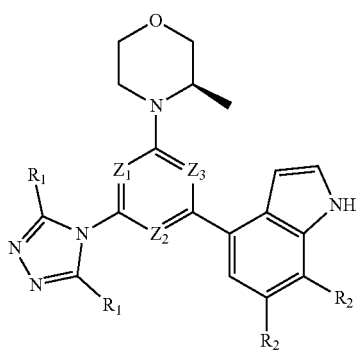
(II-6B)
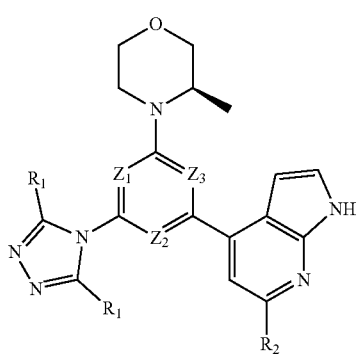
(II-7A)
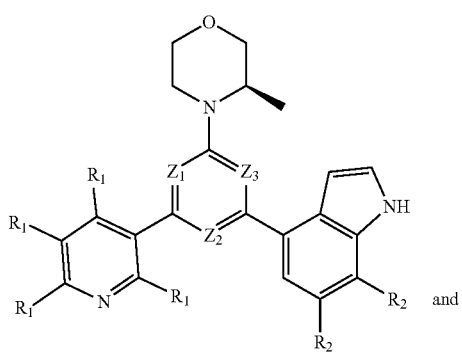 and
(II-7B)
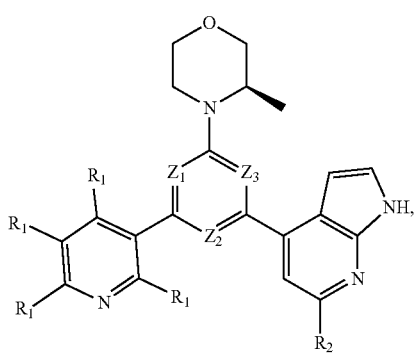
wherein,
$R_1$, $R_2$, $Z_1$, $Z_2$ and $Z_3$ are defined as herein.
Provided is also the following compound or an isomer or a pharmaceutically acceptable salt thereof
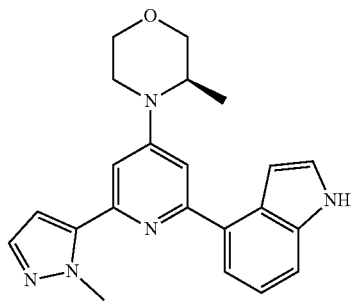
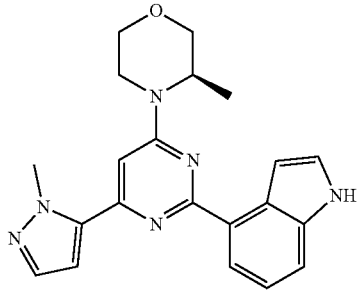
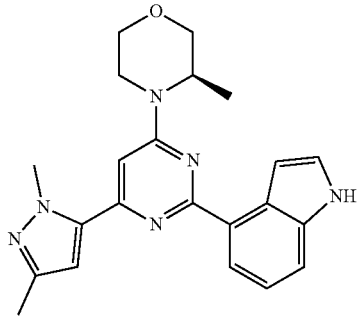

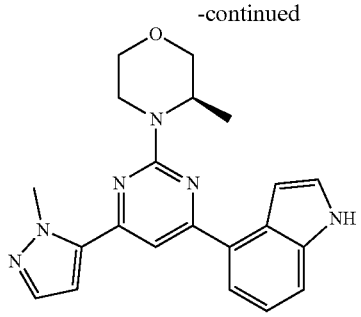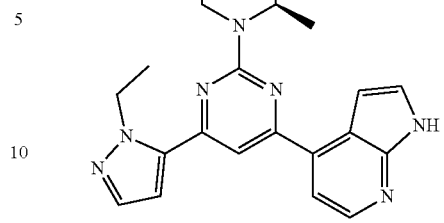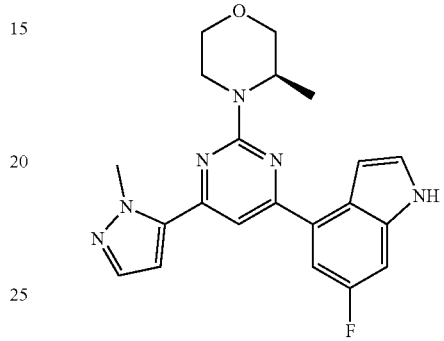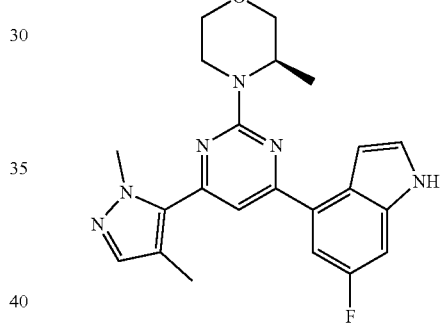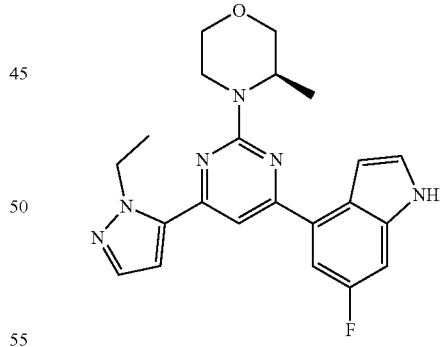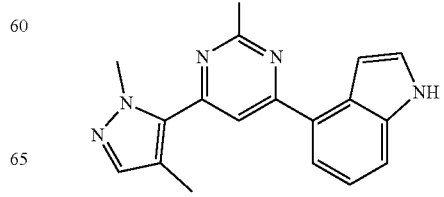

-continued
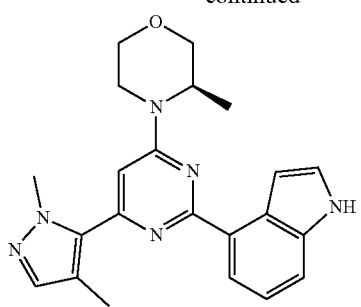
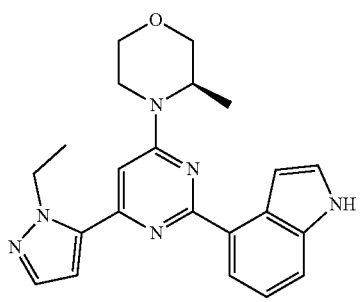
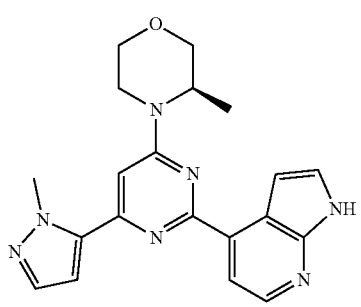
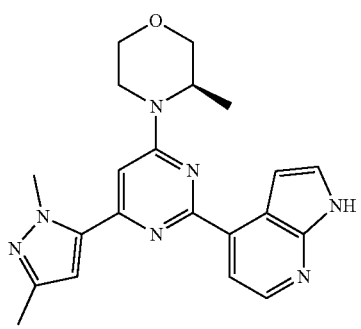
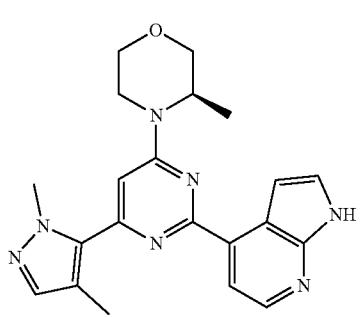
-continued
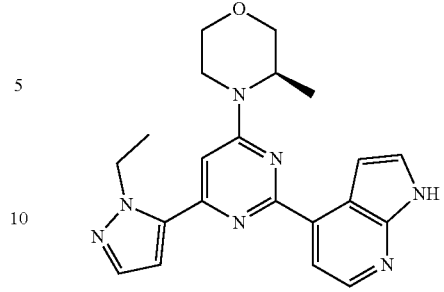
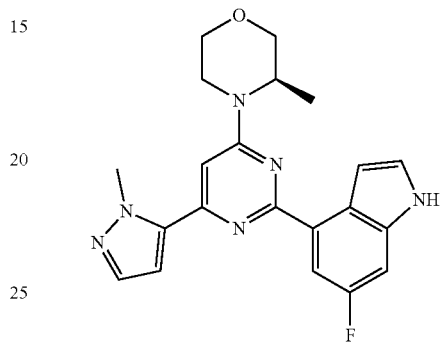
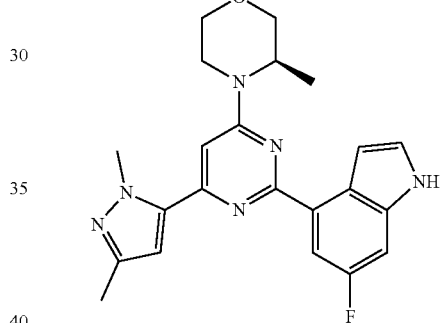
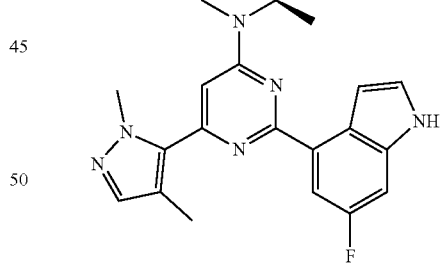
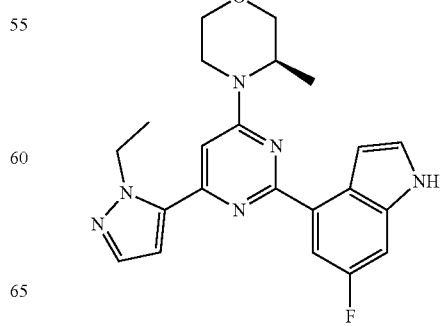

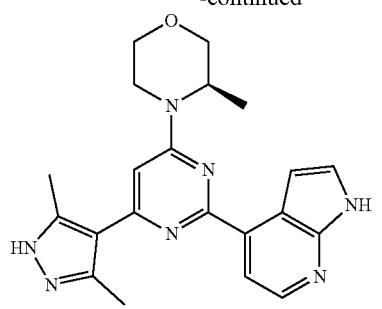
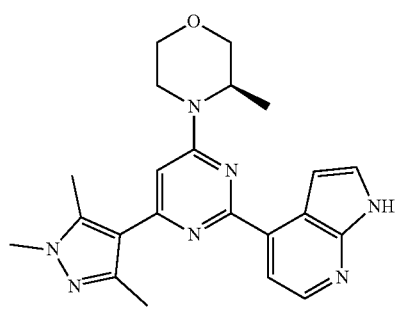
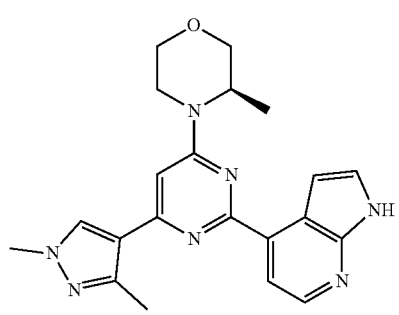
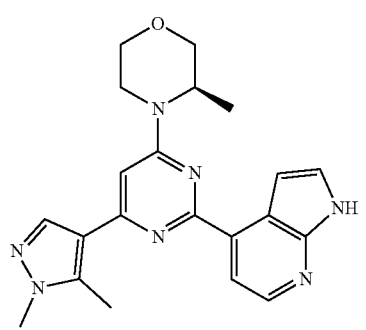
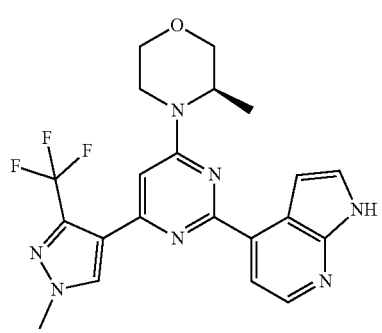
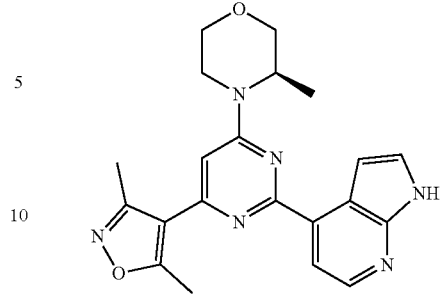
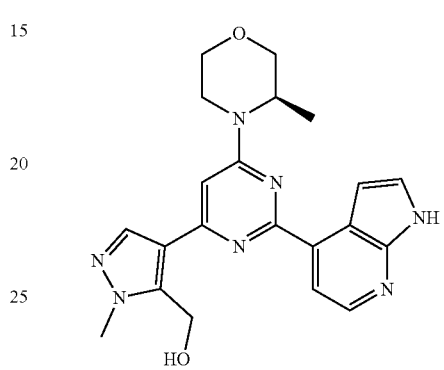
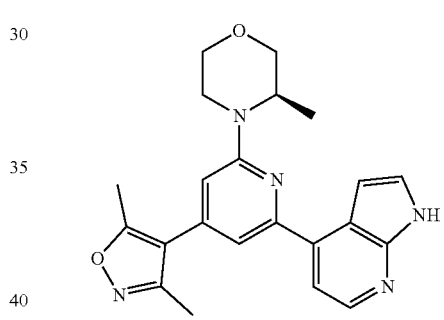
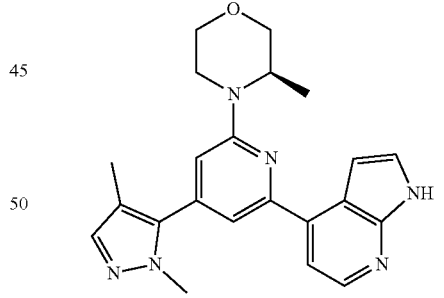
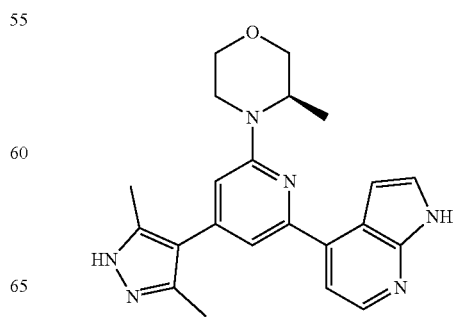

-continued
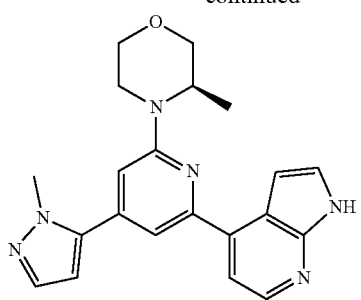
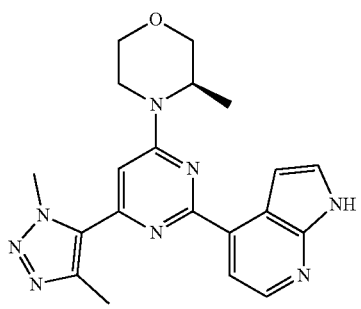
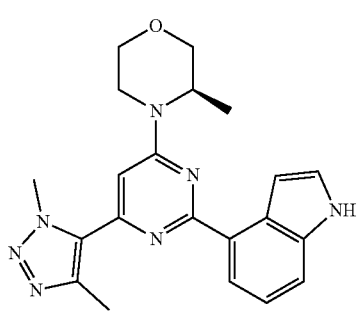
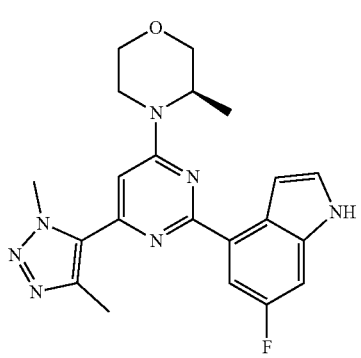
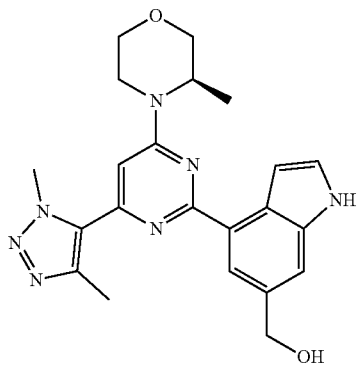
-continued
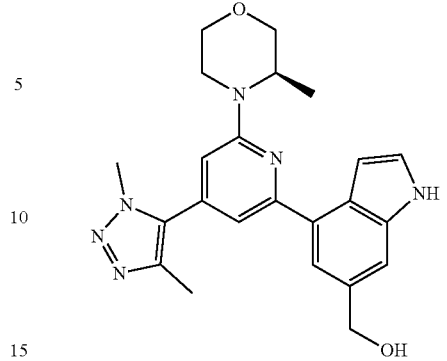
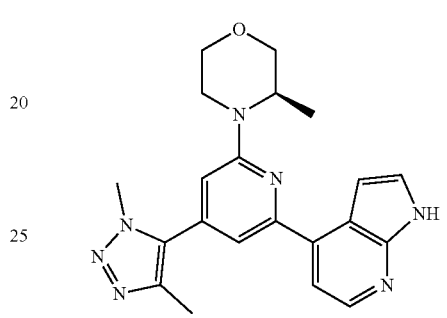
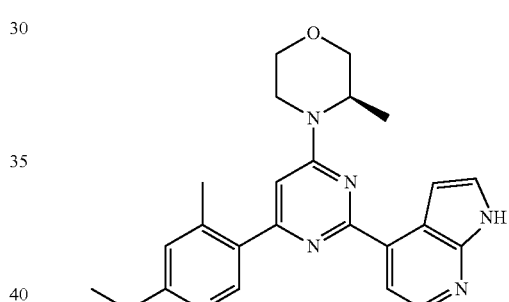
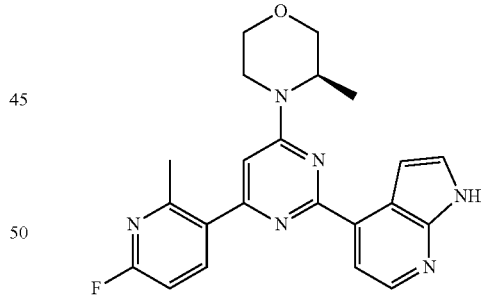
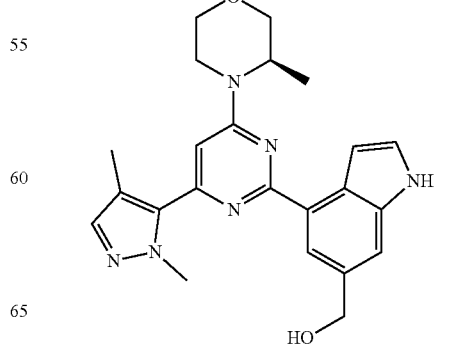

-continued
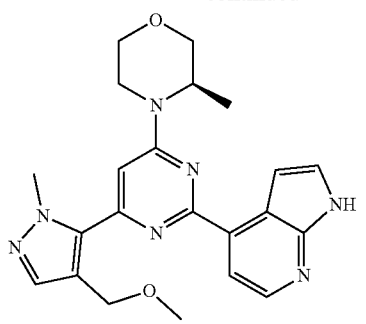
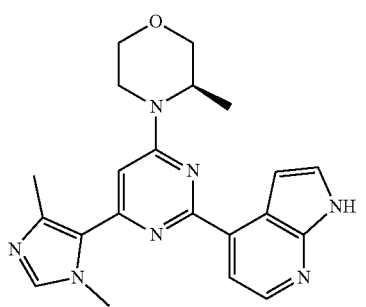
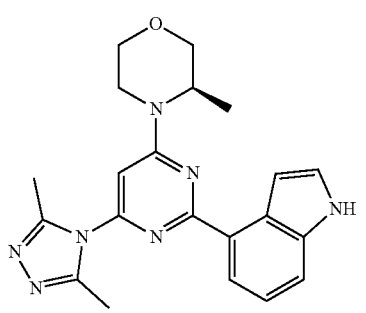
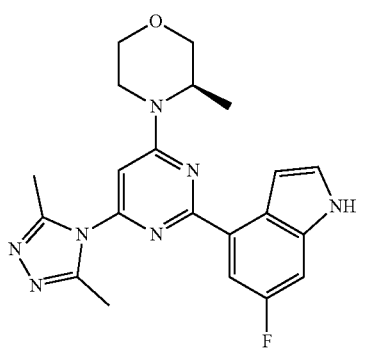
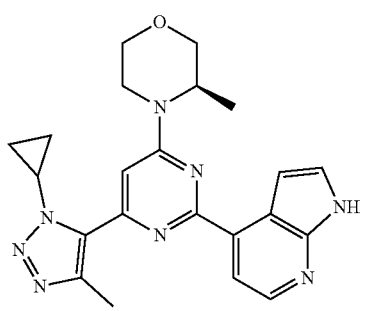
-continued
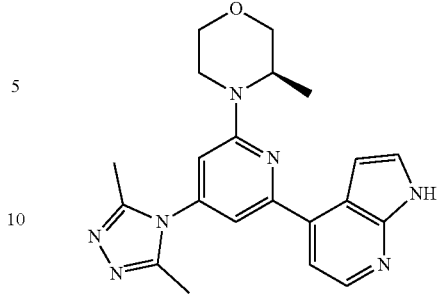
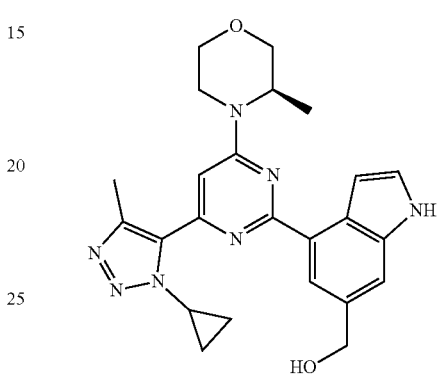
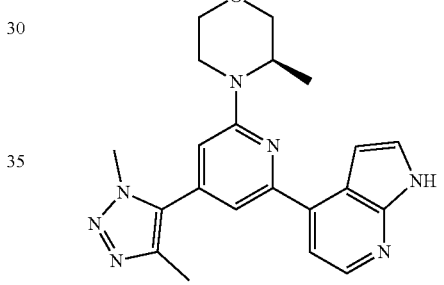
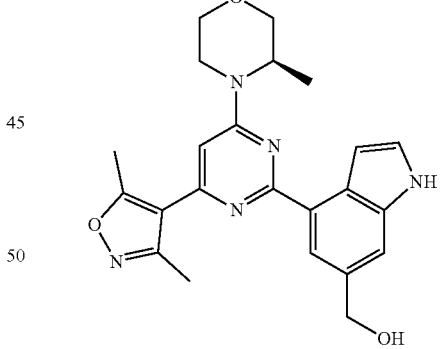
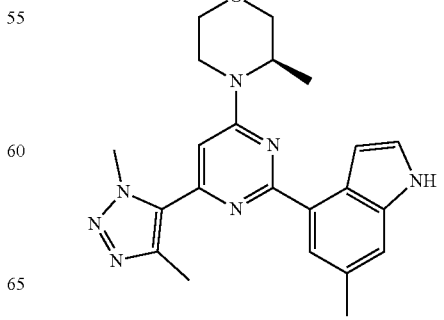

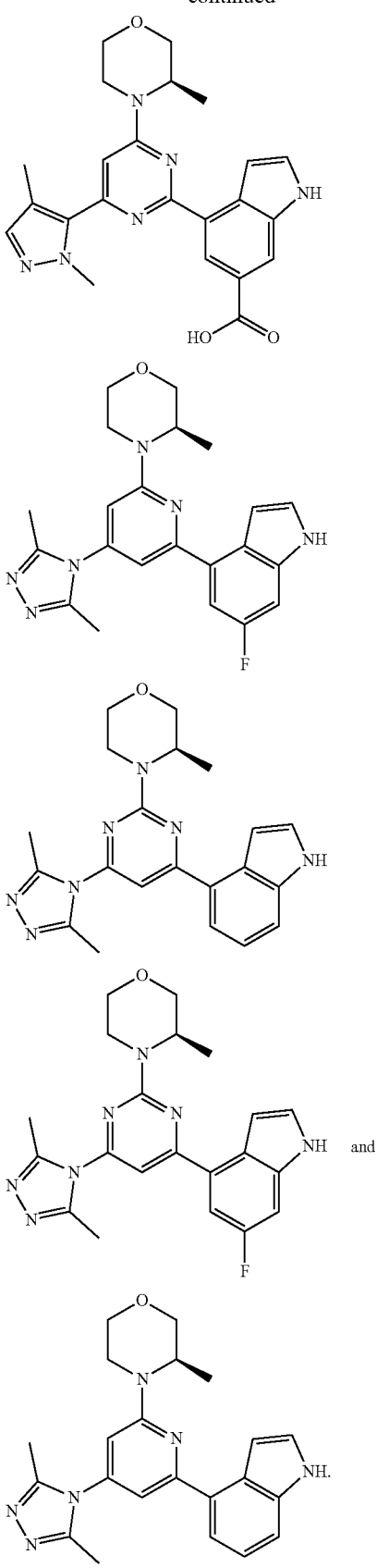

In another aspect, provided is use of the above compound or a pharmaceutically acceptable salt thereof for the manufacture of a medicament for treating an ATR associated disease.

In some embodiments according to the present disclosure, the medicament is used in treating solid tumor or hematologic tumor.

Technical Effect

As a novel ATR inhibitor, the present compounds have good inhibitory activity against ATR kinase. Moreover, they show good tumor suppressing effects in animal models and have the potential as novel anti-tumor agents.

Definition and Description

Unless stated otherwise, the following terms and phrases have the following definitions. A specific term or phrase should not be considered as indefinite or unclear without specific definition and should be understood according to the normal meanings. A tradename used herein shall refer to the corresponding article or the active ingredient. The term "pharmaceutically acceptable" means that, for the compounds, materials, compositions and/or dosage form, with reliable medical judgement, they are suitable for use in contact with tissues of humans and animals without excessive toxicity, irritation, allergic reaction or other problems or complications and commensurate with a reasonable benefit/risk ratio.

The term "pharmaceutically acceptable salt" refers to a salt of the compound of the present disclosure, which is prepared using a compound found in the present disclosure which has a specific substituent with a relatively non-toxic acid or base. When the compound of the present disclosure contains a relatively acidic functional group, the base addition salt can be obtained by contacting the neutral form of such compound with a sufficient amount of base in a pure solution or a suitable inert solvent. Pharmaceutically acceptable base addition salts include sodium, potassium, calcium, ammonium, organic amine or magnesium salt or the like. When the compound of the present disclosure contains a relatively basic functional group, the acid addition salt can be obtained by contacting the neutral form of such compound with a sufficient amount of acid in a pure solution or a suitable inert solvent. Examples of pharmaceutically acceptable acid addition salts include inorganic acid salts including, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, etc.; and organic acid salts including, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid, etc.; and also includes salts of amino acids (such as arginine, etc.), and salts of organic acids such as glucuronic acid. Some specific compounds of the present disclosure contain basic and acidic functional groups, which can be converted to any base or acid addition salt.

The pharmaceutically acceptable salts of the present disclosure can be synthesized from the parent compound containing acid radicals or basic groups by conventional chemical processes. In general, the preparation process of such salts is: in water or an organic solvent or a mixture thereof, by reacting these compounds in free acid or base form with a stoichiometric amount of appropriate base or acid.

The compounds of the present disclosure may exist in specific geometric or stereoisomer forms. The present disclosure encompasses all such compounds, including cis and trans isomers, (−)- and (+)-enantiomers, (R)- and (S)-enantiomers, diastereomers, (D)-isomer, (L)-isomer, and their racemic mixtures and other mixtures, such as enantiomer or diastereomer-enriched mixtures. All of these mixtures are included within the scope of the present disclosure. There may be additional asymmetric carbon atoms in alkyl and other substituents. All these isomers and mixtures thereof are included in the scope of the present disclosure.

Unless stated otherwise, the term "enantiomer" or "optical isomer" refers to stereoisomers that are mirror images to each other.

Unless stated otherwise, the term "cis-trans isomer" or "geometric isomer" is caused by a double bond or a single bond of the ring-forming carbon atom which cannot rotate freely.

Unless stated otherwise, the term "diastereomer" refers to a stereoisomer in which the molecule has two or more chiral centers and there is a non-mirror relationship between the molecules.

Unless stated otherwise, "(D)" or "(+)" means right-handed, "(L)" or "(−)" means left-handed, and "(DL)" or "(±)" means racemic.

Unless stated otherwise, the wedge-shaped solid line bond ( ⌿ ) and the wedge-shaped dotted line bond ( ⌿ ) indicate the absolute configuration of a stereocenter; the straight solid line bond ( ⌿ ) and the straight dotted line bond ( ⌿ ) indicate the relative configuration of a stereocenter; and the wavy line ( ⌿ ) indicates a wedge-shaped solid line bond ( ⌿ ) or a wedge-shaped dotted line bond ( ⌿ ), or a wavy line ( ⌿ ) indicates a straight solid line bond ( ⌿ ) and a straight dotted line bond ( ⌿ ).

The present compounds may be present in particular tautomeric forms. Unless stated otherwise, the term "tautomer" or "tautomeric form" means that at room temperature, different functional groups of an isomer are in dynamic equilibrium and can be transformed to each other quickly. If a tautomer is possible (e.g., in solution), the chemical equilibrium of tautomers can be achieved. For example, proton tautomer (also known as prototropic tautomer) includes interconversion through protolysis, such as ketone-enol isomerization and imine-enamine isomerization. The valence tautomer includes some recombination of bonding electrons for interconversion. A specific example of keto-enol tautomerization is the interconversion between two tautomers pentane-2,4-dione and 4-hydroxypent-3-en-2-one.

Unless stated otherwise, the term "enriched with an isomer", "isomer enriched", "enriched with an enantiomer" or "enantiomerically enriched" means that the content of an isomer or enantiomer is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless stated otherwise, the term "isomer excess" or "enantiomeric excess" refers to the difference between the relative percentages of two isomers or two enantiomers. For example, if the content of one isomer or enantiomer is 90% and the content of the other isomer or enantiomer is 10%, the excess of isomer or enantiomer (ee value) is 80%.

The optically active (R)- and (S)-isomers and D and L isomers can be prepared by chiral synthesis or chiral reagents or other conventional techniques. If an enantiomer of a compound of the present disclosure is desired, it can be prepared by asymmetric synthesis or derivatization with a chiral auxiliary, wherein the resulting mixture of diastereomers is separated and the auxiliary group is cleaved to provide pure and required enantiomer. Alternatively, when the molecule contains a basic functional group (such as amino) or an acidic functional group (such as, carboxyl group), a diastereomer salt is formed with an appropriate optically active acid or base, and the diastereomer resolution is performed by conventional processes known in the art, and then the pure enantiomer is recovered. In addition, the separation of enantiomers and diastereomers is usually accomplished by using chromatography, which employs a chiral stationary phase optionally with chemical derivatization processes (e.g., carbamate formation from amine). The present compounds may contain unnatural proportions of atomic isotopes at one or more of the atoms constituting the compound. For example, compounds can be labeled with radioactive isotopes, such as tritium ($^3$H), iodine-125 ($^{125}$I) or C-14 ($^{14}$C). As another example, hydrogen can be replaced by heavy hydrogen to form a deuterated drug. The bond formed by deuterium and carbon is stronger than that formed by ordinary hydrogen and carbon. Compared with non-deuterated drugs, the deuterated drugs have advantages such as less side effects, increased stability, improved efficacy, prolonged biological half-life and the like. Alternation of all the radioisotopes of the compound, either radioactive or not, is encompassed within the scope of the invention.

"Optional" or "optionally" means that the subsequently described event or condition may but does not necessarily occur, and the description includes the situation in which the event or condition occurs and the situation in which the event or condition does not occur.

The term "substituted" means any one or more hydrogen atoms on a specific atom are replaced by a substituent, which may include heavy hydrogen and hydrogen variants, provided that the valence state of the specific atom is normal and the compound after substitution is stable. A substituent as oxygen (i.e. =O) means two hydrogen atoms are substituted. Oxygen substitution will not occur on an aromatic group. The term "optional substitution" or "optionally substituted" encompasses the cases that being unsubstituted or substituted. Unless stated otherwise, the type and number of substituents may be arbitrary given that they can be achieved chemically.

When any variable (e.g., R) appears more than once in the composition or structure of a compound, it is defined independently in each case. Thus, for example, if a group is substituted with 0-2 R, the group can be optionally substituted with at most two R, and R in each case has independent options. In addition, combinations of substituents and/or their variants are allowed provided that such combinations will produce stable compounds.

When the number of a linking group is 0, —(CRR)$_0$—, it means that the linking group is a single bond.

When one of the variables is selected from the group consists of single bonds, it means that the two groups connected thereby are directly connected. For example, when L represents a single bond in A-L-Z, the actual structure is A-Z.

When a substituent is absent, it means that the substituent does not exist. For example, when X is absent in A-X, it means that the actual structure is A. When the listed substituents do not indicate to which atom they are connected, such substituents can be bonded through any of the atoms. For example, pyridyl as a substituent can be attached to the substituted group through any carbon on the pyridine ring.

When the listed linking group does not indicate the connection direction, the connection direction is arbitrary. For example, the linking group L in

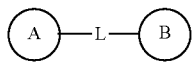

is -MW—, in which -MW— can connect ring A and ring B in the same direction as the reading order from left to right to form

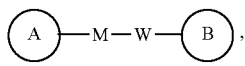

or can connect ring A and ring B in the opposite direction as the reading order from left to right to form

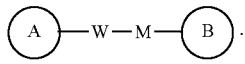

The combination of the linking group, substituents and/or variants thereof is allowed provided that such a combination will produce a stable compound.

Unless stated otherwise, the term "hetero" refers to heteroatom or heteroradical (i.e. a radical containing heteroatom), including atoms other than carbon (C) and hydrogen (H) and radicals containing such heteroatoms, including for example Oxygen (O), Nitrogen (N), Sulfur (S), Silicon (Si), Germanium (Ge), Aluminum (Al), Boron (B), —O—, —S—, —C(=O)O—, —C(=O)—, —C(=S)—, —S(=O), —S(=O)$_2$—, and —C(=O)N(H)—, —N(H)—, —C(=NH)—, —S(=O)$_2$N(H)— or —S(=O)N(H)—, which is optionally substituted.

Unless stated otherwise, "cyclo" refers to substituted or unsubstituted cycloalkyl, heterocycloalkyl, cycloalkenyl, heterocycloalkenyl, cycloalkynyl, heterocycloalkynyl, aryl or heteroaryl. The ring includes single ring, and also includes bicyclic or polycyclic ring systems, such as spiro ring, fused ring, bridge ring or the like. The number of atoms in the ring is usually defined as the member number of the ring. For example, "5-7 membered ring" refers to 5-7 atoms which are arranged around. Unless stated otherwise, the ring optionally contains 1-3 heteroatoms. Accordingly, "5-7 membered ring" includes for example phenyl, pyridyl and piperidinyl. In another aspect, the term "5-7 membered heterocycloalkyl" includes pyridyl and piperidinyl but does not include phenyl. The term "ring" also includes a ring system containing at least one ring, wherein each "ring" independently complies with the above definition.

Unless stated otherwise, the term "alkyl" refers to a linear or branched saturated hydrocarbon group. In some embodiments, the alkyl is $C_{1-12}$ alkyl; in other embodiments, the alkyl is $C_{1-6}$ alkyl; in other embodiments, the alkyl is $C_{1-3}$ alkyl. The alkyl may be monosubstituted (such as, —CH$_2$F) or polysubstituted (such as, —CF$_3$), may be monovalent (such as, methyl), divalent (such as, methylene) or polyvalent (such as, methine). Examples of alkyl include but are not limited to methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl or the like.

Unless stated otherwise, the term "$C_{1-6}$ alkyl" refers to a linear or branched saturated hydrocarbon group composed of 1-6 carbon atoms. The $C_{1-6}$ alkyl comprises $C_{1-5}$, $C_{1-4}$, $C_{1-3}$, $C_{1-2}$, $C_{2-6}$, $C_{2-4}$, $C_6$ and $C_5$ alkyl or the like. The alkyl may be monovalent (such as, methyl), divalent (such as, methylene) or polyvalent (such as, methine). Examples of $C_{1-6}$ alkyl include but are not limited to methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl or the like.

Unless stated otherwise, the term "$C_{1-3}$ alkyl" refers to a linear or branched saturated hydrocarbon group composed of 1-3 carbon atoms. The $C_{1-3}$ alkyl includes $C_{1-2}$ and $C_{2-3}$ alkyl or the like. The alkyl may be monovalent (such as, methyl), divalent (such as, methylene) or polyvalent (such as, methine). Examples of $C_{1-3}$ alkyl include but are not limited to methyl (Me), ethyl (Et), propyl (including n-propyl and isopropyl), or the like.

Unless stated otherwise, "alkenyl" refers to a linear or branched hydrocarbon group containing one or more carbon-carbon double bonds. The carbon-carbon double bond can be located at any position of the group. In some embodiments, the alkenyl is $C_{2-8}$ alkenyl; in other embodiments, the alkenyl is $C_{2-6}$ alkenyl; in other embodiments, the alkenyl is $C_{2-4}$ alkenyl. The alkenyl may be monosubstituted or polysubstituted, and may be monovalent, divalent or polyvalent. Examples of alkenyl include but are not limited to ethenyl, propenyl, butenyl, pentenyl, hexenyl, butadienyl, pentadienyl, hexadienyl, or the like.

Unless stated otherwise, "alkynyl" refers to a linear or branched hydrocarbon group containing one or more carbon-carbon triple bonds. The carbon-carbon triple bond can be located at any position of the group. In some embodiments, the alkynyl is $C_{2-8}$ alkynyl; in other embodiments, the alkynyl is $C_{2-6}$ alkynyl; in other embodiments, the alkynyl is $C_{2-4}$ alkynyl. The alkynyl may be monosubstituted or polysubstituted, and may be monovalent, divalent or polyvalent. Examples of alkynyl include but are not limited to ethynyl, propynyl, butynyl, pentynyl or the like.

Unless stated otherwise, the term "heteroalkyl", alone or in combination with another term, refers to a stable linear or branched alkyl radical or composition thereof, which is composed of a certain number of carbon atoms and at least one heteroatom or heteroradical. In some embodiments, the heteroatom is selected from the group consisting of B, O, N and S, wherein the N and S atoms are optionally oxidized, the N heteroatom is optionally quaternarized. In some other embodiments, the heteroradical is selected from the group consisting of —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is $C_{1-6}$ heteroalkyl; in some other embodiments, the heteroalkyl is $C_{1-3}$ heteroalkyl. The heteroatom or heteroradical can be located at any internal position of the heteroalkyl, including the connecting position of the alkyl to the rest of the molecule, but the terms "alkoxy", "alkylamino" and "alkylthio" (or thioalkoxy) are conventional expressions and refer to the alkyl groups which are connected to the rest of the molecule via an oxygen atom, an amino group or a sulfur atom, respectively. Examples of heteroalkyl include, but are not limited to —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH₃)(CH₂CH₃), —CH₂—CH₂—NH—CH₃, —CH₂—CH₂—N(CH₃)—CH₃, —SCH₃, —SCH₂CH₃, —SCH₂CH₂CH₃, —SCH₂(CH₃)₂, —CH₂—S—CH₂—CH₃, —CH₂—CH₂, —S(═O)—CH₃, —CH₂—CH₂—S(═O)₂—CH₃, —CH═CH—O—CH₃, —CH₂—CH═N—OCH₃ and —CH═CH—N(CH₃)—CH₃. At most two heteroatoms can be continuous, for example —CH₂—NH—OCH₃.

Unless stated otherwise, the term "heteroalkenyl" alone or in combination with another term, refers to a stable linear or branched alkenyl radical or composition thereof, which is composed of a certain number of carbon atoms and at least one heteroatom or heteroradical. In some embodiments, the heteroatom is selected from the group consisting of B, O, N and S, wherein the N and S atoms are optionally oxidized, the N heteroatom is optionally quaternarized. In some other embodiments, the heteroradical is selected from the group consisting of —C(═O)O—, —C(═O)—, —C(═S)—, —S(═O)—, —S(═O)₂—, —C(═O)N(H)—, —N(H)—, —C(═NH)—, —S(═O)₂N(H)— and —S(═O)N(H)—. In some embodiments, the heteroalkenyl is C₂₋₆ heteroalkenyl; in some other embodiments, the heteroalkyl is C₂₋₄ heteroalkenyl. The heteroatom or heteroradical can be located at any internal position of the heteroalkenyl, including the connecting position of the alkenyl to the rest of the molecule, but the terms "alkenyloxy", "alkenylamino" and "alkenylthio" are conventional expressions and refer to the alkenyl groups which are connected to the rest of the molecule via an oxygen atom, an amino group or a sulfur atom, respectively. Examples of heteroalkenyl include, but are not limited to —O—CH═CH₂, —O—CH═CHCH₃, —O—CH═C(CH₃)₂, —CH═CH—O—CH₃, —O—CH═CHCH₂CH₃, —CH₂—CH═CH—OCH₃, —NH—CH═CH₂, —N(CH═CH₂)—CH₃, —CH═CH—NH—CH₃, —CH═CH—N(CH₃)₂, —S—CH═CH₂, —S—CH═CHCH₃, —S—CH═C(CH₃)₂, —CH₂—S—CH═CH₂, —S(═O)—CH═CH₂ and —CH═CH—S(═O)₂—CH₃. At most two heteroatoms can be continuous, for example —CH═CH—NH—OCH₃.

Unless stated otherwise, the term "heteroalkynyl", alone or in combination with another term, refers to a stable linear or branched alkynyl radical or composition thereof, which is composed of a certain number of carbon atoms and at least one heteroatom or heteroradical. In some embodiments, the heteroatom is selected from the group consisting of B, O, N and S, wherein the N and S atoms are optionally oxidized, the N heteroatom is optionally quaternarized. In some other embodiments, the heteroradical is selected from the group consisting of —C(═O)O—, —C(═O)—, —C(═S)—, —S(═O)—, —S(═O)₂—, —C(═O)N(H)—, —N(H)—, —C(═NH)—, —S(═O)₂N(H)— and —S(═O)N(H)—. In some embodiments, the heteroalkynyl is C₂₋₆ heteroalkynyl; in some other embodiments, the heteroalkyl is C₂₋₄ heteroalkynyl. The heteroatom or heteroradical can be located at any internal position of the heteroalkynyl, including the connecting position of the alkynyl to the rest of the molecule, but the terms "alkynyloxy", "alkynylamino" and "alkynylthio" are conventional expressions and refer to the alkynyl groups which are connected to the rest of the molecule via an oxygen atom, an amino group or a sulfur atom, respectively. Examples of heteroalkynyl include, but are not limited to

-continued

At most two heteroatoms can be continuous, for example

Unless stated otherwise, "cycloalkyl" comprises any stable cyclic alkyl, including monocyclic, bicyclic or tricyclic systems, in which bicyclic and tricyclic systems include spiro ring, fused ring and bridge ring. In some embodiments, the cycloalkyl is C₃₋₈ cycloalkyl. In some other embodiments, the cycloalkyl is C₃₋₆cycloalkyl. In some other embodiments, the cycloalkyl is C₅₋₆cycloalkyl. The cycloalkyl may be monosubstituted or polysubstituted, and may be monovalent, divalent or polyvalent. Examples of cycloalkyl include but are not limited to cyclopropyl, cyclobutyl, cyclopentyl, cyclohexyl, cycloheptyl, norbornyl alkyl, [2.2.2]bicyclooctane, [4.4.0]bicyclodecane, or the like.

Unless stated otherwise, "C₃₋₆cycloalkyl" represents a saturated cyclic hydrocarbon group composed of 3-6 carbon atoms, which is a monocyclic and bicyclic system. The C₃₋₆cycloalkyl includes C₃₋₅, C₄₋₅ and C₅₋₆ cycloalkyl or the like. The cycloalkyl may be monovalent, divalent or polyvalent. Examples of C₃ cycloalkyl include but are not limited to cyclopropyl, cyclobutyl, cyclopentyl, cyclohexyl, or the like.

Unless stated otherwise, "cycloalkenyl" comprises any stable cyclic alkenyl containing one or more unsaturated carbon-carbon double bonds at any position, which includes monocyclic, bicyclic or tricyclic systems, wherein the bicyclic and tricyclic systems include spiro ring, fused ring and bridge ring, but all the rings in this system are non-aromatic. In some embodiments, the cycloalkenyl is C₃₋₈ cycloalkenyl. In some other embodiments, the cycloalkenyl is C₃₋₆ cycloalkenyl. In some other embodiments, the cycloalkenyl is C₅₋₆ cycloalkenyl. The cycloalkenyl may be monovalent, divalent or polyvalent. Examples of cycloalkenyl include but are not limited to cyclopentenyl, cyclohexenyl, or the like.

Unless stated otherwise, "cycloalkynyl" comprises any stable cyclic alkynyl containing one or more carbon-carbon triple bonds at any position, which includes monocyclic, bicyclic or tricyclic system, wherein the bicyclic and tricyclic systems include spirocyclic, fused ring and bridge ring.

The cycloalkynyl may be monosubstituted or polysubstituted, and may be monovalent, divalent or polyvalent.

Unless stated otherwise, the term "heterocycloalkyl", alone or in combination with another term, refers to cyclic "heteroalkyl", including monocyclic, bicyclic and tricyclic systems, wherein the bicyclic and tricyclic systems include spiro ring, fused ring and bridge ring. In addition, with respect to the "heterocycloalkyl", the heteroatom can occupy the connecting position of the heterocycloalkyl to the rest of the molecule. In some embodiments, the heterocycloalkyl is 4-6 membered heterocycloalkyl. In some other embodiments, the heterocycloalkyl is 5-6 membered heterocycloalkyl. Examples of heterocycloalkyl include, but are not limited to azetidinyl, oxetanyl, thietanyl, pyrrolidinyl, pyrazolidinyl, imidazolidinyl, tetrahydrothienyl (including tetrahydrothien-2-yl and tetrahydrothien-3-yl or the like), tetrahydrofuranyl (including tetrahydrofuran-2-yl or the like), tetrahydropyranyl, piperidinyl (including 1-piperidinyl, 2-piperidinyl and 3-piperidinyl or the like), piperazinyl (including 1-piperazinyl and 2-piperazinyl or the like), morpholinyl (including 3-morpholinyl and 4-morpholinyl or the like), dioxanyl, dithianyl, isoxazolealkyl, isothiazolidinyl, 1,2-oxazinyl, 1,2-thiazinyl, hexahydropyridazinyl, homopiperazinyl, homopiperidinyl or oxepanyl.

Unless stated otherwise, the term "heterocycloalkenyl", alone or in combination with another term, refers to cyclic "heteroalkenyl", including monocyclic, bicyclic and tricyclic systems, wherein the bicyclic and tricyclic systems include spiro ring, fused ring and bridge ring, but all the rings in this system are non-aromatic. In addition, with respect to the "heterocycloalkenyl", the heteroatom can occupy the connecting position of the heterocycloalkenyl to the rest of the molecule. In some embodiments, the heterocycloalkenyl is 4-6 membered heterocycloalkenyl. In some other embodiments, the heterocycloalkenyl is 5-6 membered heterocycloalkenyl. Examples of heterocycloalkenyl include but are not limited to

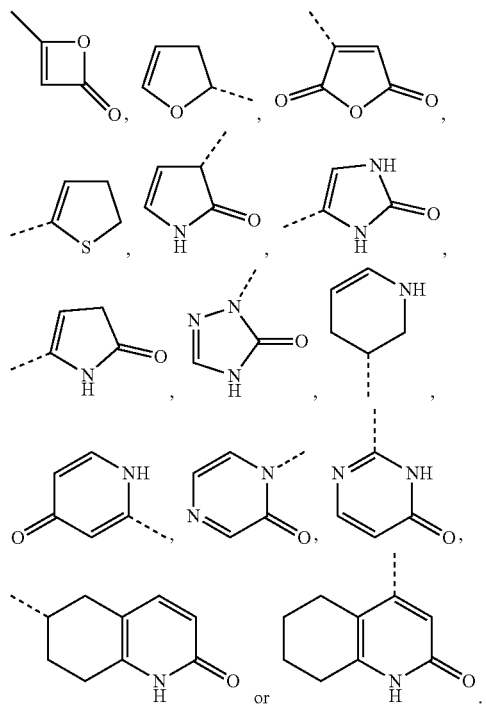

Unless stated otherwise, the term "heterocycloalkynyl", alone or in combination with another term, refers to cyclic "heteroalkynyl", including monocyclic, bicyclic and tricyclic systems, wherein the bicyclic and tricyclic systems include spiro ring, fused ring and bridge ring. In addition, with respect to the "heterocycloalkynyl", the heteroatom can occupy the connecting position of the heterocycloalkynyl to the rest of the molecule. In some embodiments, the heterocycloalkynyl is 4-6 membered heterocycloalkynyl. In some other embodiments, the heterocycloalkynyl is 5-6 membered heterocycloalkynyl.

Unless stated otherwise, the term "halogen" or "halo", alone or as part of another substituent, refers to F, Cl, Br or I atom. In addition, the term "haloalkyl" is intended to include monohaloalkyl and polyhaloalkyl. For example, the term "halo($C_1$-$C_4$)alkyl" is intended to include but is not limited to trifluoromethyl, 2,2,2-trifluoroethyl, 4-chlorobutyl, and 3-bromopropyl, or the like. Unless stated otherwise, examples of haloalkyl include, but are not limited to trifluoromethyl, trichloromethyl, pentafluoroethyl and pentachloroethyl.

"Alkoxy" refers to the above alkyl having a specific number of carbon atoms connected via an oxygen bridge. Unless stated otherwise, $C_{1-6}$ alkoxy comprises $C_1$, $C_2$, $C_3$, $C_4$, $C_5$ and $C_6$ alkoxy. In some embodiments, the alkoxy is $C_{1-3}$ alkoxy. Examples of alkoxy include but are not limited to methoxyl, ethoxy, n-propoxy, isopropoxy, n-butoxy, sec-butoxy, tert-butoxy, n-pentoxy and S-pentoxy.

Unless stated otherwise, the term "$C_{1-6}$ alkoxy" refers to an alkyl group containing 1-6 carbon atoms connected to the rest of the molecule via an oxygen atom. The $C_{1-6}$ alkoxy comprises $C_{1-4}$, $C_{1-3}$, $C_{1-2}$, $C_{2-6}$, $C_{2-4}$, $C_6$, $C_5$, $C_4$ and $C_3$ alkoxy or the like. Examples of $C_{1-6}$ alkoxy include but are not limited to methoxyl, ethoxy, propoxy (including n-propoxy and isopropoxy), butoxy (including n-butoxy, isobutoxy, s-butoxy and t-butoxy), pentoxy (including n-pentoxy, isopentoxy and neopentoxy), hexyloxy, or the like.

Unless stated otherwise, the term "$C_{1-3}$ alkoxy" refers to an alkyl group containing 1-3 carbon atoms connected to the rest of the molecule via an oxygen atom. The $C_{1-3}$ alkoxy comprises $C_{1-2}$, $C_{2-3}$, $C_3$ f $C_2$ alkoxy or the like. Examples of $C_{1-3}$ alkoxy include but are not limited to methoxyl, ethoxy, propoxy (including n-propoxy and isopropoxy), or the like.

Unless stated otherwise, the terms "aromatic ring" and "aryl" can be used interchangeably herein. The term "aromatic ring" or "aryl" refers to a polyunsaturated carbocyclic system, which can be monocyclic, bicyclic or polycyclic system, wherein at least one ring is aromatic. Each ring in the bicyclic and polycyclic system are fused together. It may be mono- or poly-substituted, and may be monovalent, divalent or polyvalent. In some embodiments, the aryl is $C_{6-12}$ aryl. In some other embodiments, the aryl is $C_{6-10}$ aryl. Examples of aryl include but are not limited to phenyl, naphthyl (including 1-naphthyl and 2-naphthyl, or the like). The substituent of any one of the above aryl ring systems may be selected from the group consisting of acceptable substituents described herein.

Unless stated otherwise, the terms "heteroaromatic ring" and "heteroaryl" can be used interchangeably herein. The term "heteroaryl" refers to an aryl (or aromatic ring) containing 1, 2, 3 or 4 heteroatoms independently selected from the group consisting of B, N, O and S, which may be monocyclic, bicyclic or tricyclic system, wherein the nitrogen atom can be substituted or unsubstituted (i.e., N or NR, where R is H or other substituents defined herein), and is optionally quaternarized; and nitrogen and sulfur heteroatoms can be optionally oxidized (i.e., NO and S(O)$_p$, p is 1 or 2). Heteroaryl can be connected to the rest of the molecule via heteroatom. In some embodiments, the heteroaryl is 5-10 membered heteroaryl. In some other embodiments, the heteroaryl is 5-6 membered heteroaryl. Examples of the heteroaryl include but are not limited to pyrrolyl (including N-pyrrolyl, 2-pyrrolyl and 3-pyrrolyl or the like), pyrazolyl (including 2-pyrazolyl and 3-pyrazolyl or the like), imidazolyl (including N-imidazolyl, 2-imidazolyl, 4-imidazolyl and 5-imidazolyl or the like), oxazolyl (including 2-oxazolyl, 4-oxazolyl and 5-oxazolyl or the like), triazolyl (1H-1,2,3-triazolyl, 2H-1,2,3-triazolyl, 1H-1,2,4-triazolyl and 4H-1,2,4-triazolyl or the like), tetrazolyl, isoxazolyl (3-isoxazolyl, 4-isoxazolyl and 5-isoxazolyl or the like), thiazolyl (including 2-thiazolyl, 4-thiazolyl and 5-thiazolyl or the like), furyl (including 2-furyl and 3-furyl or the like), thienyl (including 2-thienyl and 3-thienyl or the like), pyridyl (including 2-pyridyl, 3-pyridyl and 4-pyridyl or the like), pyrazinyl, pyrimidinyl (including 2-pyrimidinyl and 4-pyrimidinyl or the like), benzothiazolyl (including 5-benzothiazolyl or the like), purinyl, benzimidazolyl (including 2-benzimidazolyl or the like), indolyl (including 5-indolyl or the like), isoquinolinyl (including 1-isoquinolinyl and 5-isoquinolinyl or the like), quinoxalinyl (including 2-quinoxalinyl and 5-quinoxalinyl or the like), quinolinyl (including 3-quinolinyl and 6-quinolinyl or the like), pyrazinyl, purinyl, benzoxazolyl. The substituent of any one of the above heteroaryl ring systems may be selected from the group consisting of acceptable substituents described herein.

Unless stated otherwise, the terms "5-6 membered heteroaromatic ring" and "5-6 membered heteroaryl" can be used interchangeably herein. The term "5-6 membered heteroaryl" refers to a monocyclic group composed of 5-6 ring atoms with a conjugated 1 electron system, wherein 1, 2, 3 or 4 ring atoms are heteroatoms independently selected from the group consisting of O, S and N, and the rest are carbon atoms, and wherein the nitrogen atom is optionally quaternarized, and the nitrogen and sulfur heteroatoms can be optionally oxidized (i.e., NO and S(O)$_p$, p is 1 or 2). The 5-6 membered heteroaryl can be connected to the rest of the molecule through heteroatom or carbon atom. The 5-6 membered heteroaryl comprises 5 membered and 6 membered heteroaryl. Examples of the 5-6 membered heteroaryl include but are not limited to pyrrolyl (including N-pyrrolyl, 2-pyrrolyl and 3-pyrrolyl or the like), pyrazolyl (including 2-pyrazolyl and 3-pyrazolyl or the like), imidazolyl (including N-imidazolyl, 2-imidazolyl, 4-imidazolyl and 5-imidazolyl or the like), oxazolyl (including 2-oxazolyl, 4-oxazolyl and 5-oxazolyl or the like), triazolyl (1H-1,2,3-triazolyl, 2H-1,2,3-triazolyl, 1H-1,2,4-triazolyl and 4H-1,2,4-triazolyl or the like), tetrazolyl, isoxazolyl (3-isoxazolyl, 4-isoxazolyl and 5-isoxazolyl or the like), thiazolyl (including 2-thiazolyl, 4-thiazolyl and 5-thiazolyl or the like), furyl (including 2-furyl and 3-furyl or the like), thienyl (including 2-thienyl and 3-thienyl or the like), pyridyl (including 2-pyridyl, 3-pyridyl and 4-pyridyl or the like), pyrazinyl or pyrimidinyl (including 2-pyrimidinyl and 4-pyrimidinyl or the like).

Unless stated otherwise, the term "aralkyl" is intended to include those groups in which aryl is attached to the alkyl. In some embodiments, the aralkyl is $C_{6-10}$ aryl-$C_{1-4}$ alkyl. In some other embodiments, the aralkyl is $C_{6-10}$ aryl-$C_{1-2}$ alkyl. Examples of the aralkyl include but are not limited to benzyl, phenethyl, naphthylmethyl or the like. "Aryloxy" and "arylthio" refer to those groups in which a carbon atom (such as methyl) in aralkyl has been replaced by O or S atom. In some embodiments, the aryloxy is $C_{6-10}$ aryl-O—$C_{1-2}$ alkyl. In some other embodiments, the aryloxy is $C_{6-10}$ aryl-$C_{1-2}$ alkyl-O—. In some embodiments, the arylthio is $C_{6-10}$ aryl-S—$C_{1-2}$ alkyl. In some other embodiments, the arylthio is $C_{6-10}$ aryl-$C_{1-2}$ alkyl-S—. Examples of the aryloxy and arylthio include but are not limited to phenoxymethyl, 3-(1-naphthyloxy)propyl, phenylthiomethyl, or the like.

Unless stated otherwise, the term "heteroaralkyl" is intended to include those groups in which the heteroaryl is attached to the alkyl group. In some embodiments, the heteroaralkyl is 5-8 membered heteroaryl-$C_{1-4}$ alkyl. In some other embodiments, the heteroaralkyl is 5-6 membered heteroaryl-$C_{1-2}$ alkyl.

Examples of the heteroaralkyl include but are not limited to pyrrolylmethyl, pyrazolylmethyl, pyridylmethyl, pyrimidinylmethyl or the like. "Heteroaryloxy" and "heteroarylthio" refer to those groups in which a carbon atom (such as methyl) in the heteroaralkyl group has been replaced by O or S atom. In some embodiments, the heteroaryloxy is 5-8 membered heteroaryl-O—$C_{1-2}$ alkyl. In some other embodiments, the heteroaryloxy is 5-6 membered heteroaryl-$C_{1-2}$ alkyl-O—. In some other embodiments, the heteroarylthio is 5-8 membered heteroaryl-S—$C_{1-2}$ alkyl. In some other embodiments, the heteroarylthio is 5-6 membered heteroaryl-$C_{1-2}$ alkyl-S—. Examples of heteroaryloxy and heteroarylthio include but are not limited to pyrrolyloxymethyl, pyrazolyloxymethyl, 2-pyridyloxymethyl, pyrrolylthiomethyl, pyrazolylthiomethyl, 2-pyridylthiomethyl or the like.

Unless stated otherwise, $C_{n-n+m}$ or $C_n$—$C_{n+m}$ includes any specific case of n to n+m carbon. For example, $C_{1-12}$ comprises $C_1$, $C_2$, $C_3$, $C_4$, $C_5$, $C_6$, $C_7$, $C_8$, $C_9$, $C_{10}$, $C_{11}$, and $C_{12}$ and also comprises any range within n to n+m, for example, $C_{1-12}$ comprises $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ or the like. Likewise, n membered to n+m membered means that the atom number in the ring is n to n+m, for example, 3-12 membered ring comprises 3 membered ring, 4 membered ring, 5 membered ring, 6 membered ring, 7 membered ring, 8 membered ring, 9 membered ring, 10 membered ring, 11 membered ring, and 12 membered ring, and also comprises any range within n to n+m, for example, 3-12 membered ring comprises 3-6 membered ring, 3-9 membered ring, 5-6 membered ring, 5-7 membered ring, 6-7 membered ring, 6-8 membered ring, and 6-10 membered ring or the like.

The term "leaving group" refers to a functional group or atom which can be replaced by another functional group or atom through substitution reaction (e.g., affinity substitution reaction). For example, representative leaving groups include triflate; Cl, Br, I; sulfonate, such as mesylate, tosylate, p-bromobesylate, p-toluenesulfonate or the like; acyloxy, such as acetoxy, trifluoroacetoxy, or the like.

The term "protecting group" includes but are not limited to "amino protecting group", "hydroxyl protecting group" or "mercapto protecting group". The term "amino protecting group" refers to a protecting group suitable for preventing side reactions on the nitrogen position of an amino group. Representative amino protecting groups include but are not limited to formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorene methoxycarbonyl (Fmoc); arylmethyl, such as benzyl (Bn), triphenylmethyl (Tr), 1,1-bis-(4'-methoxyphenyl)methyl; silyl, such as trimethylsilyl (TMS) and tert-butyldimethylsilyl (TBS), or the like. The term "hydroxyl protecting group" refers to a protecting group suitable for preventing hydroxyl side reactions. Representative hydroxyl protecting groups include but are not limited to alkyl, such as methyl, ethyl and tert-butyl; acyl, such as alkanoyl (such as acetyl); arylmethyl, such as benzyl (Bn), p-methoxylbenzyl (PMB), 9-fluorenylmethyl (Fm) and diphenylmethyl (benzhydryl, DPM); methylsilyl, such as trimethylsilyl (TMS) and tert-butyldimethylsilyl (TBS), or the like.

The present compounds can be prepared by various synthetic processes well-known to a person skilled in the art, including the specific embodiments listed below. The embodiments formed by the combination with other chemical synthesis processes and equivalence well-known to a person skilled in the art and preferable embodiments include but are not limited to Example herein.

The present compounds may have multiple applications or indications, including but not limited to those specifically listed herein.

The solvents used herein are commercially available. The following abbreviations are used herein: aq: water; HATU: 0-(7-azabenzotriazol-1-yl)-N,N,N'N'-tetramethylurea hexafluorophosphate; EDC: N-(3-dimethylaminopropyl)-N'-ethyl carbodiimide hydrochloride; m-CPBA: 3-chloroperoxybenzoic acid; eq: equivalent, equivalence; CDI: carbonyldiimidazole; DCM: dichloromethane; PE: petroleum ether; DIAD: diisopropyl azodicarboxylate; DMF: N,N-dimethylformamide; DMSO: dimethyl sulfoxide; EtOAc: ethyl acetate; EtOH: ethanol; MeOH: methanol; CBz: benzyloxycarbonyl, an amine protecting group; BOC: tert-butoxycarbonyl, an amine protecting group; HOAc: acetic acid; NaCNBH$_3$: cyano sodium borohydride; r.t.: room temperature; O/N: overnight; THF: tetrahydrofuran; Boc$_2$O: di-tert-butyl dicarbonate; TFA: trifluoroacetate; DIPEA: diisopropylethylamine; SOCl$_2$: thionyl chloride; CS$_2$: carbon disulfide; TsOH: p-toluenesulfonic acid; NFSI: N-fluoro-N-(benzenesulfonyl) benzenesulfonamide; NCS: N-chlorosuccinimide; n-Bu$_4$NF: tetrabutylammonium fluoride; iPrOH: 2-propanol; mp: melting point; LDA: lithium diisopropylamide.

The compounds are named manually or by ChemDraw® software. The compound names on catalog by the providers are used.

BRIEF DESCRIPTION OF THE DRAWINGS

FIG. 1: Tumor growth curve of human colorectal cancer LoVo cell subcutaneous xenograft model tumor-bearing mice after administration of the compound according the present disclosure.

EXAMPLES

The present disclosure will be described in detail by the following Examples, which do not mean any limitation thereto. The present disclosure has been described in detail herein, which also discloses its specific embodiments. It will be apparent for a person skilled in the art that various changes and modifications can be made to specific embodiments of the present disclosure without departing from its spirit and scope.

Intermediate 1

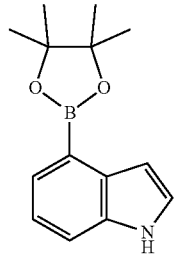

A1

Synthesis Scheme

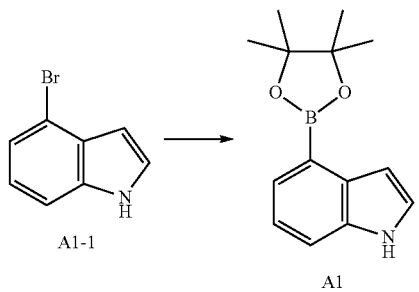

Step 1: Synthesis of Compound A1

To a solution of Compound A1-1 (65 g, 331.56 mmol) in dimethyl sulfoxide (1 L) were added bispinacol borate (126.29 g, 497.34 mmol), 1,1-bis(diphenylphosphino)ferrocene palladium chloride (12.13 g, 16.58 mmol) and potassium acetate (113.89 g, 1.16 mol). The reaction solution was stirred under the protection of nitrogen at 90° C. for 16 h. After the reaction solution was filtered through celite, the filtrate was extracted with 1 L of ethyl acetate (500 mL×2), and the organic phase was washed with 3 L of water (1 L×3) and dried over anhydrous sodium sulfate. After the desiccant was filtered off, the solvent was removed under reduced pressure to give the crude product, which was purified with silica gel column (petroleum ether/ethyl acetate=1:0, 4:1) to give Compound A1.

MS-ESI m/z: 243.9 [M+H]+. $^1$H NMR (400 MHz, CHLOROFORM-d) δ ppm 1.42 (s, 13H) 7.09 (t, J=2.13 Hz, 1H) 7.21-7.25 (m, 1H) 7.52 (d, J=8.03 Hz, 1H) 7.67 (d, J=7.03 Hz, 1H) 8.23 (br s, 1H).

Intermediate 2

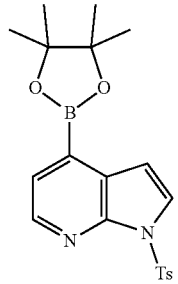

B1

Synthesis Scheme

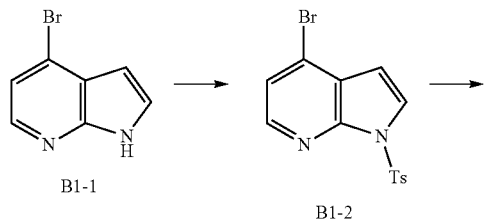
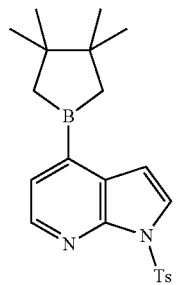

Step 1: Synthesis of Compound B1-2

To a solution of Compound B1-1 (90 g, 456.78 mmol) in dichloromethane (1 L) were added sodium hydroxide solution (2 M, 685.17 mL) and tetrabutylammonium hydrogen sulfate (7.75 g, 22.84 mmol) and then added p-toluenesulfonyl chloride (174.17 g, 913.56 mmol) slowly. The reaction solution was stirred at 25° C. for 15 h and extracted with 500 mL of dichloromethane (250 mL×2), and the organic phase was washed with 3 L of water (1 L×3) and dried over anhydrous sodium sulfate. After the desiccant was filtered off, the solvent was removed under reduced pressure to give the crude product, which was purified with silica gel column (petroleum ether/ethyl acetate=1:0,1:0) to give Compound B1-2.

MS-ESI m/z: 352.9 [M+H]+.

Step 2: Synthesis of Compound B1

To a solution of Compound B-2 (25 g, 71.18 mmol) in N,N-dimethylformamide (500 mL) were added bispinacol borate (36.15 g, 142.36 mmol), 1,1-bis(diphenylphosphino)ferrocene palladium chloride (5.21 g, 7.12 mmol) and potassium acetate (20.96 g, 213.54 mmol). The reaction solution was stirred under the protection of nitrogen at 90° C. for 16 h. After the reaction solution was filtered through celite, the filtrate was extracted with 1 L of ethyl acetate (500 mL×2), and the organic phase was washed with 3 L of water (1 L×3) and dried over anhydrous sodium sulfate. After the desiccant was filtered off, the solvent was removed under reduced pressure to give the crude product, which was purified with silica gel column (petroleum ether/ethyl acetate=1:0,4:1) to give Compound B1.

MS-ESI m/z: 399.1 [M+H]+. $^1$H NMR (400 MHz, CHLOROFORM-d) δ ppm 1.27 (d, J=2.76 Hz, 3H) 1.32-1.39 (m, 1H) 1.33-1.38 (m, 1H) 1.36 (s, 10H) 6.95-7.05 (m, 1H) 7.02 (d, J=4.02 Hz, 1H) 7.20-7.26 (m, 1H) 7.24 (d, J=8.03 Hz, 1H) 7.52 (d, J=4.77 Hz, 1H) 7.72-7.78 (m, 1H) 7.75 (d, J=3.76 Hz, 1H) 8.02-8.04 (m, 2H) 8.43 (d, J=4.77 Hz, 1H).

Intermediate 3

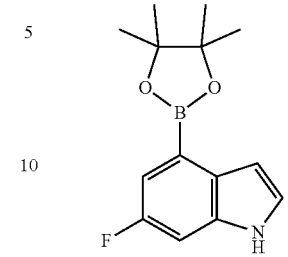

Synthesis Scheme

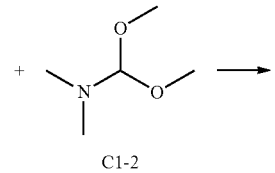

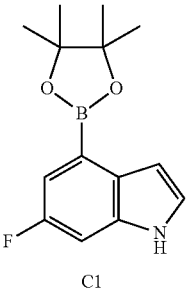

Step 1: Synthesis of Compound C1-3

At room temperature, to a solution of Compound C-1 (3.00 g, 12.82 mmol) in N,N-dimethylformamide (30.00 mL) was added C1-2 (7.65 g, 64.23 mmol, 8.50 mL), which was stirred under nitrogen atmosphere at 160° C. for 8 h. The reaction system was cooled, diluted with dichloromethane (50 mL), washed with water (20 ml×5) and dried over anhydrous sodium sulfate. After the desiccant was filtered off, the solvent was removed under reduced pressure to give the crude product. The crude product was dissolved with acetic acid (5 ml) and was added dropwise to a boiling solution of iron powder (7.16 g, 128.19 mmol) in acetic acid (5 mL). The reaction solution was refluxed for 40 min. The reaction solution was cooled to room temperature, adjusted to basic pH with saturated sodium carbonate solution and extracted with dichloromethane (30 ml×3). The organic phases were combined, dried over anhydrous sodium sulfate. After the desiccant was filtered off, the solvent was removed under reduced pressure to give the crude product, which was purified with column chromatography (petroleum ether/dichloromethane=3/1) to give Compound C1-3.

$^1$H NMR (400 MHz, CHLOROFORM-d) δ ppm 6.50 (t, J=2.26 Hz, 1H) 6.96-7.00 (m, 1H) 7.05 (dd, J=9.04, 2.01 Hz, 1H) 7.16 (t, J=2.76 Hz, 1H) 7.47 (dd, J=8.52, 5.52 Hz, 1H) 8.20 (br s, 1H).

Step 2: Synthesis of Compound C1

At room temperature, to a solution of Compound C1-3 (1.00 g, 4.67 mmol) in 1,4-dioxane (15.00 mL) were added bispinacol borate (1.78 g, 7.00 mmol), 1,1-bis(diphenylphosphino)ferrocene palladium chloride (341.71 mg, 467.00 μmol), potassium acetate (1.37 g, 14.01 mmol), which was stirred under nitrogen atmosphere for 12 h. After cooling, the reaction system was diluted with ethyl acetate (40 mL) and filtered. The organic phase was washed with water (20 mL×2) and dried over anhydrous sodium sulfate. After the desiccant was filtered off, the solvent was removed under reduced pressure to give the crude product, which was purified with column chromatography (petroleum ether/dichloromethane=3/1) to give Compound C1.

$^1$H NMR (400 MHz, DMSO-$d_6$) δ ppm 1.34 (s, 12H) 6.74 (br s, 1H) 7.12 (dd, J=10.04, 2.51 Hz, 1H) 7.30 (dd, J=10.04, 2.01 Hz, 1H) 7.38 (t, J=2.76 Hz, 1H) 11.18 (br s, 1H).

Intermediate 4

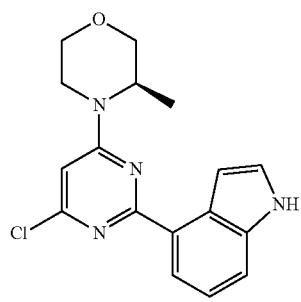

Synthesis Scheme

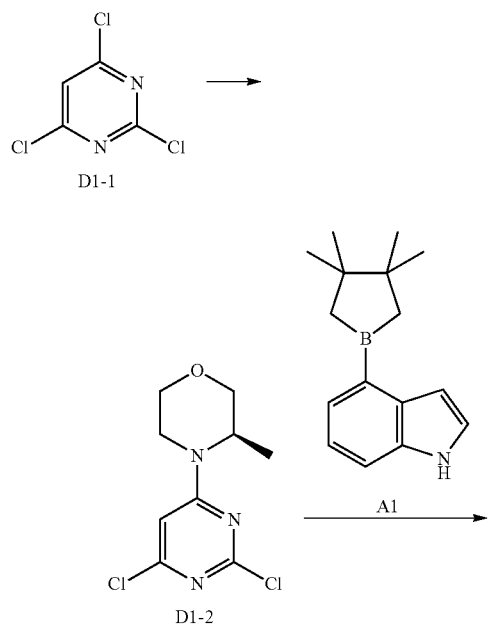

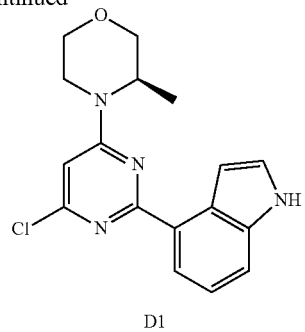

D1

Step 1: Synthesis of Compound D1-2

To a solution of Compound D1-1 (2.00 g, 10.90 mmol, 1.25 mL) in dichloromethane (20 mL) was added triethylamine (3.15 g, 31.14 mmol, 4.32 mL), and added dropwise (R)-3-methylmorpholine slowly at −5° C. The reaction solution was warmed slowly to 15° C. and stirred for 15 h. The compound was concentrated to dryness and the crude product was purified with silica gel column (petroleum ether/ethyl acetate=10:1,5:1) to give Compound D1-2.

MS-ESI m/z: 247.9 [M+H]+.

Step 2: Synthesis of Compound D1

To a solution of Compound D1-2 (1.5 g, 6.05 mmol) in 1,4-dioxane (40 mL) were added A1 (1.62 g, 6.65 mmol), bistriphenylphosphine palladium dichloride (424.35 mg, 604.57 μmol) and sodium carbonate (2 M, 9.07 mL). The reaction mixture was stirred under the protection of nitrogen at 110° C. for 15 h. After the reaction solution was filtered through celite, the filtrate was extracted with 50 mL of ethyl acetate (25 mL×2). The organic phase was washed with 60 mL of water (20 mL×3) and dried over anhydrous sodium sulfate. After the desiccant was filtered off, the solvent was removed under reduced pressure to give the crude product, which was purified with silica gel column (petroleum ether/ethyl acetate=1:0,1:1) to give Compound D1.

MS-ESI m/z: 328.9 [M+H]+.

Intermediate 5

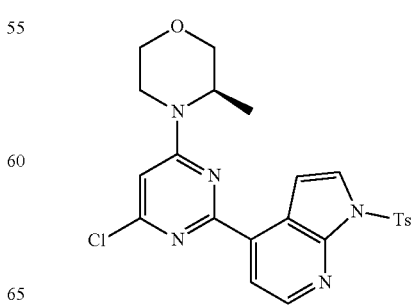

E1

Synthesis Scheme

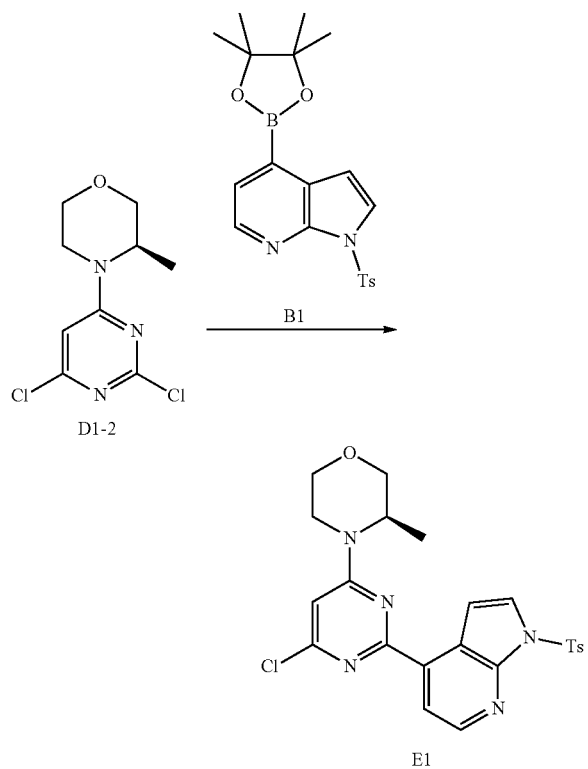

Step 1: Synthesis of Compound E1

To a solution of Compound D1-2 (9.03 g, 36.41 mmol) in 1,4-dioxane (100 mL) were added B1 (14.5 g, 36.41 mmol), bistriphenylphosphine palladium dichloride (2.555 g, 3.641 mmol) and sodium carbonate (2 M, 54.61 mL). The reaction solution was stirred under the protection of nitrogen at 110° C. for 15 h. After the reaction solution was filtered through celite, the filtrate was extracted with 600 mL of ethyl acetate (200 mL×3). The organic phase was washed with 600 mL of water (200 mL×3) and dried over anhydrous sodium sulfate. After the desiccant was filtered off, the solvent was removed under reduced pressure to give the crude product, which was purified with silica gel column (petroleum ether/ethyl acetate=4:1,4:3) to give Compound E1.

MS-ESI m/z: 484.2 [M+H]+.

Intermediate 6

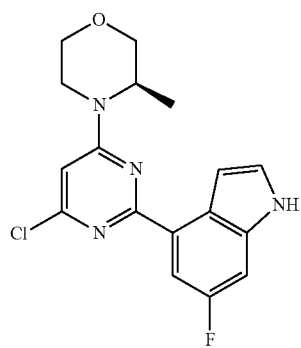

Synthesis Scheme

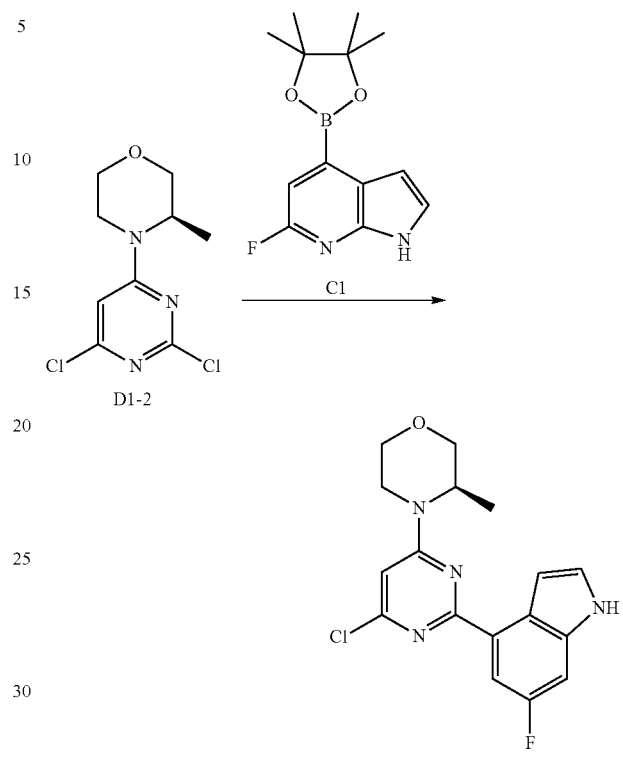

Step 1: Synthesis of Compound F1

To a solution of Compound D1-2 (0.5 g, 2.02 mmol) in 1,4-dioxane (10 mL) were added C1 (578.80 mg, 2.22 mmol), bistriphenylphosphine palladium dichloride (70.73 mg, 100.76 μmol) and sodium carbonate (2 M, 3.02 mL). The reaction mixture was stirred under the protection of nitrogen at 110° C. for 15 h. After the reaction solution was filtered through celite, the filtrate was extracted with 60 mL of ethyl acetate (20 mL×3). The organic phase was washed with 60 mL of water (20 mL×3) and dried over anhydrous sodium sulfate. After the desiccant was filtered off, the solvent was removed under reduced pressure to give the crude product, which was purified with silica gel column (petroleum ether/ethyl acetate=4:1,1:1) to give Compound F1.

MS-ESI m/z: 347.1[M+H]+.

Intermediate 7

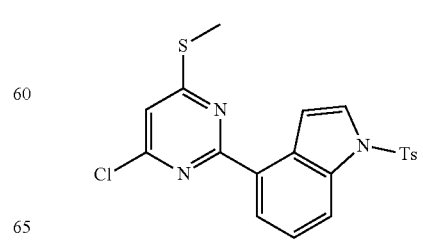

Synthesis Scheme

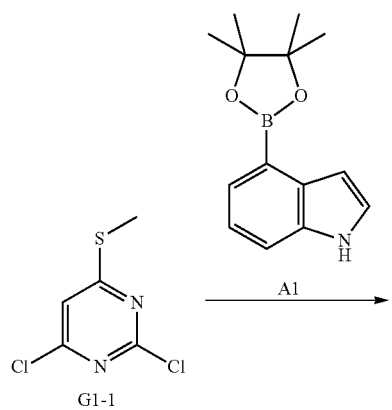

Step 1: Synthesis of Compound G1-2

To a solution of Compound G1-1 (1 g, 5.13 mmol) in 1,4-dioxane (25 mL) were added A1 (1.37 g, 5.64 mmol), bistriphenylphosphine palladium dichloride (359.82 mg, 512.64 μmol) and sodium carbonate (2 M, 7.69 mL). The reaction mixture was stirred under the protection of nitrogen at 90° C. for 15 h. After the reaction solution was filtered through celite, the filtrate was extracted with 90 mL of ethyl acetate (30 mL×3). The organic phase was washed with 90 mL of water (30 mL×3) and dried over anhydrous sodium sulfate. After the desiccant was filtered off, the solvent was removed under reduced pressure to give the crude product, which was purified with silica gel column (petroleum ether/ethyl acetate=1:0,4:1) to give Compound G1-2.

MS-ESI m/z: 275.9 [M+H]+

Step 2: Synthesis of Compound G1

To a solution of Compound G1-2 (1.09 g, 3.95 mmol) in dichloromethane (20 mL) were added sodium hydroxide solution (2 M, 5.93 mL) and tetrabutylammonium hydrogen sulfate (671.36 mg, 1.98 mmol) and then added p-toluenesulfonyl chloride (1.13 g, 5.93 mmol) slowly. The reaction solution was stirred at 25° C. for 15 h. The reaction solution was extracted with 90 mL of dichloromethane (30 mL×3). The organic phase was washed with 90 mL of water (30 mL×3) and dried over anhydrous sodium sulfate. After the desiccant was filtered off, the solvent was removed under reduced pressure to give the crude product, which was purified with silica gel column (petroleum ether/ethyl acetate=1:0,4:1) to give Compound G1.

MS-ESI m/z: 429.8[M+H]+.

Intermediate 8

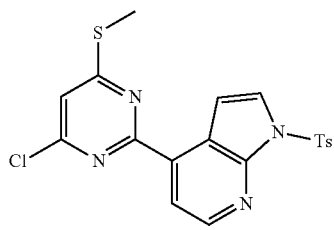

H1

Synthesis Scheme

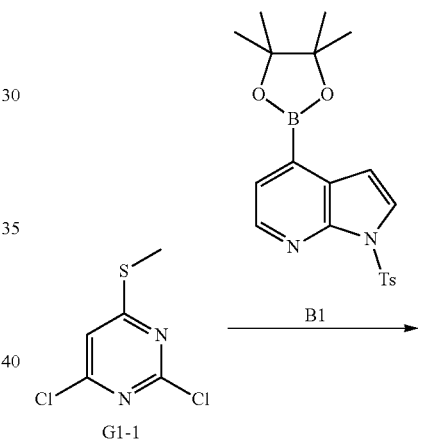

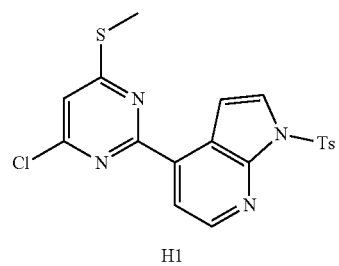

Step 1: Synthesis of Compound H1

To a solution of Compound G1-1 (487.08 mg, 2.50 mmol) in 1,4-dioxane (20 mL) were added B1 (1 g, 2.50 mmol), bistriphenylphosphine palladium dichloride (87.63 mg, 124.85 μmol) and sodium carbonate (2 M, 3.75 mL). The reaction mixture was stirred under the protection of nitrogen at 90° C. for 15 h. After the reaction solution was filtered through celite, the filtrate was extracted with 90 mL of ethyl acetate (30 mL×3). The organic phase was washed with 90 mL of water (30 mL×3) and dried over anhydrous sodium sulfate. After the desiccant was filtered off, the solvent was removed under reduced pressure to give the crude product, which was purified with silica gel column (petroleum ether/ethyl acetate=1:0,5:1) to give Compound H1.

MS-ESI m/z: 431.0 [M+H]+.

Intermediate 9

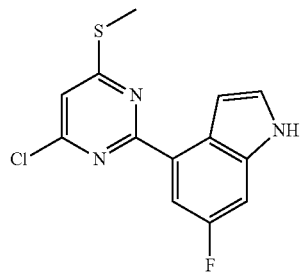

Synthesis Scheme

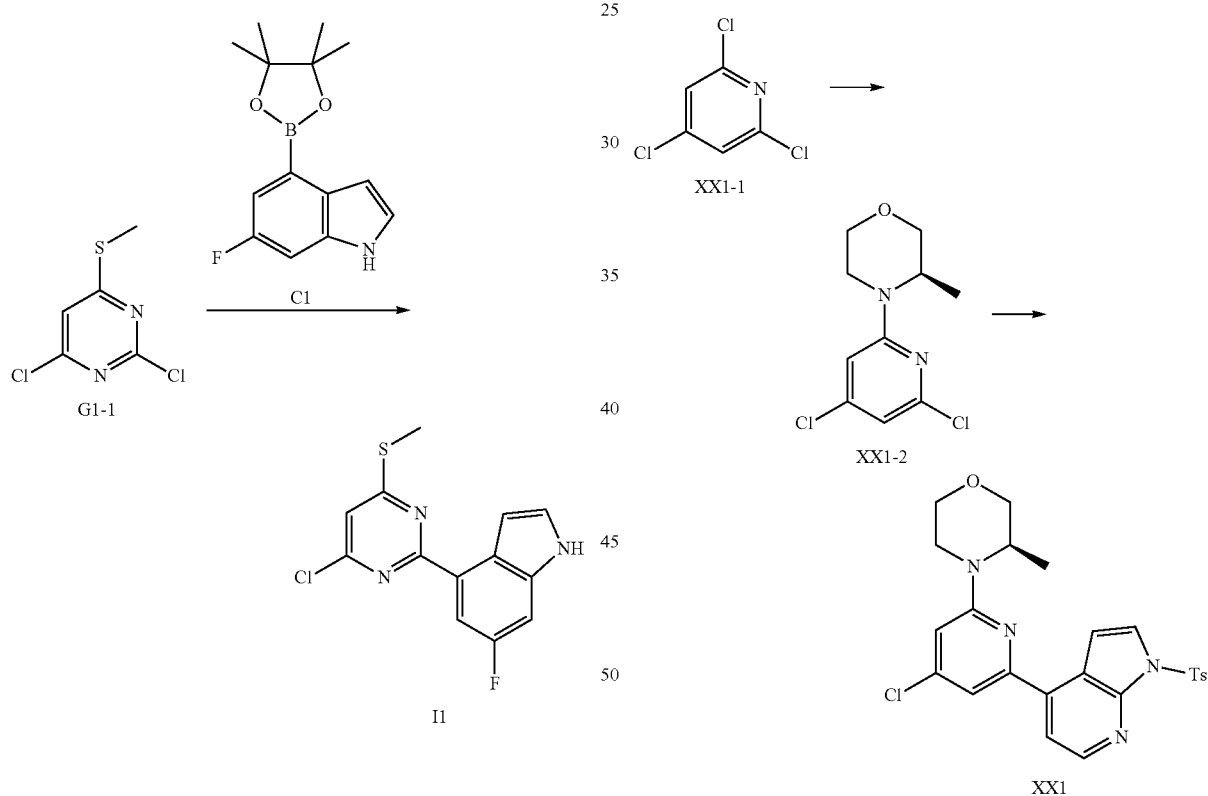

Step 1: Synthesis of Compound I1

To a solution of Compound G1-1 (493.09 mg, 2.53 mmol) in 1,4-dioxane (20 mL) were added C1 (0.66 g, 2.53 mmol), bistriphenylphosphine palladium dichloride (88.71 mg, 126.39 μmol) and sodium carbonate (2 M, 3.79 mL). The reaction mixture was stirred under the protection of nitrogen at 90° C. for 15 h. After the reaction solution was filtered through celite, the filtrate was extracted with 90 mL of ethyl acetate (30 mL×3). The organic phase was washed with 90 mL of water (30 mL×3) and dried over anhydrous sodium sulfate. After the desiccant was filtered off, the solvent was removed under reduced pressure to give the crude product, which was purified with silica gel column (petroleum ether/ethyl acetate=1:0,5:1) to give Compound I1.

MS-ESI m/z: 293.9 [M+H]+.

Intermediate 10

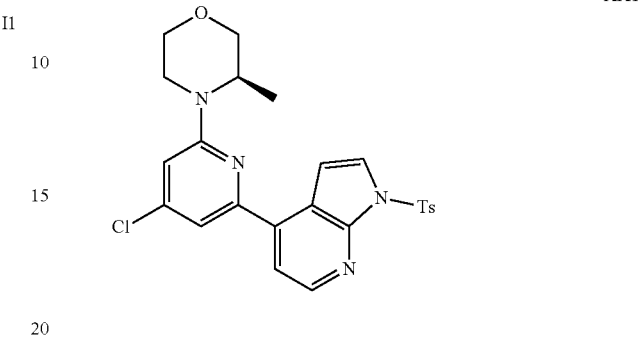

Synthesis Scheme

Step 1: Synthesis of Compound XX1-2

At room temperature, to a solution of Compound XX1-1 (500.00 mg, 2.74 mmol) in N,N-dimethylformamide (10.00 mL) were added (R)-3-methylmorpholine (304.87 mg, 3.01 mmol), potassium carbonate (946.74 mg, 6.85 mmol), which was stirred under nitrogen atmosphere at 100° C. for 12 h. The reaction system was diluted with ethyl acetate (30 mL). The organic phase was washed with water (20 mL×3) and saturated brine (20 mL) and dried over anhydrous sodium sulfate. After the desiccant was filtered off, the solvent was removed under reduced pressure to give the crude product, which was purified with column chromatography (petroleum ether/ethyl acetate=10/1,5/1) to give Compound XX1-2. ¹H NMR (400 MHz, DMSO-d$_6$) δ ppm 1.14 (d, J=6.53 Hz, 3H) 3.09 (td, J=12.80, 3.51 Hz, 1H) 3.44 (td, J=11.80, 3.01 Hz, 1H) 3.56-3.62 (m, 1H) 3.67-3.73 (m, 1H) 3.82-3.96 (m, 2H) 4.28 (br dd, J=6.52, 2.51 Hz, 1H) 6.83 (d, J=1.00 Hz, 1H) 6.87 (d, J=1.50 Hz, 1H).

Step 2: Synthesis of Compound XX1

At room temperature, to a solution of Compound XX1-2 (1.05 g, 4.25 mmol) in 1,4-dioxane (10.00 mL) were added Compound B1 (1.69 g, 4.25 mmol), dichlorobis(triphenylphosphine) palladium (298.23 mg, 424.89 μmol), sodium carbonate solution (2 M, 6.37 mL), which was stirred under nitrogen atmosphere at 100° C. for 9 h. The reaction system was diluted with 20 mL of water and extracted with ethyl acetate (30 mL). The organic phase was washed with water (20 mL) and saturated brine (20 mL) and dried over anhydrous sodium sulfate. After the desiccant was filtered off, the solvent was removed under reduced pressure to give the crude product, which was purified with column chromatography (petroleum ether/ethyl acetate=3/1, 1/1) to give Compound XX1.

MS m/z: 483.1 [M+H]⁺

¹H NMR (400 MHz, DMSO-d$_6$) δ ppm 1.19 (d, J=6.78 Hz, 3H) 2.34 (s, 3H) 3.17 (td, J=12.74, 3.89 Hz, 1H) 3.45-3.54 (m, 1H) 3.62-3.67 (m, 1H) 3.71-3.78 (m, 1H) 3.92-3.99 (m, 2H) 4.42 (br d, J=6.27 Hz, 1H) 6.99 (d, J=1.00 Hz, 1H) 7.23 (d, J=4.02 Hz, 1H) 7.33 (d, J=1.25 Hz, 1H) 7.43 (d, J=8.03 Hz, 2H) 7.74 (d, J=5.27 Hz, 1H) 7.99 (d, J=4.02 Hz, 1H) 8.02 (d, J=8.53 Hz, 2H) 8.44 (d, J=5.02 Hz, 1H).

Intermediate 11

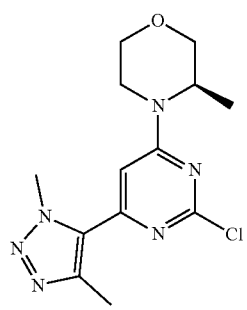

XX2

Synthesis Scheme

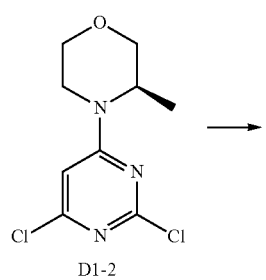

D1-2

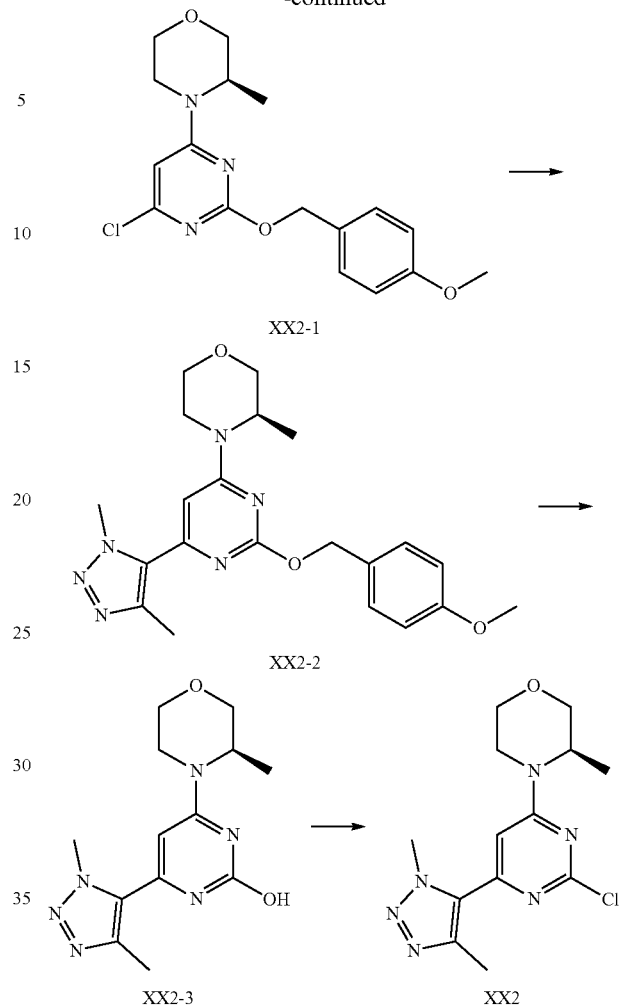

XX2-1

XX2-2

XX2-3    XX2

Step 1: Synthesis of Compound XX2-1

At 0° C., to a solution of 4-methoxylbenzyl alcohol (1.11 g, 8.06 mmol) in tetrahydrofuran (30 mL) was added sodium hydride (386.89 mg, 9.67 mmol, 60%) with stirring for 0.5 h. To the reaction solution was added D1-2 (2 g, 8.09 mmol), which was purged with nitrogen three times. The reaction mixture was stirred at 20° C. with heating for 12 h, quenched with water (30 ml) and extracted with ethyl acetate (50 ml). The organic phase was washed with saturated brine (30 ml), dried over anhydrous sodium sulfate and filtered. The solution was concentrated to give the crude product, which was separated with column chromatography to give Compound XX2-1.

MS-ESI m/z: 350.2 [M+H]+.

Step 2: Synthesis of Compound XX2-2

To a solution of Compound XX2-1 (4.5 g, 12.86 mmol) in N,N-dimethylformamide (50 mL) were added 1,4-dimethyltriazole (1.87 g, 19.30 mmol) bis(triphenylphosphine) palladium dichloride (451.46 mg, 643.2 μmol), and tetramethylammonium acetate (2.06 g, 15.44 mmol). The reaction mixture was stirred in a sealed tube at 130° C. with heating for 12 h, and then diluted with ethyl acetate (200 mL), washed with water (80 mL×2) and saturated brine (80 ml×2), dried over anhydrous sodium sulfate, and filtered. The solution was concentrated to give the crude product, which was separated with column chromatography to give Compound XX2-2.

MS-ESI m/z: 411.3 [M+H]+.

Step 3: Synthesis of Compound XX2-3

To a solution of Compound XX2-2 (0.85 g, 2.07 mmol) in ethanol (20 mL) was added wet Pd/C (0.2 g, 2.07 mmol, 10%), which was purged with hydrogen three times. The reaction mixture was stirred at 30° C. with heating for 12 h, and then filtered. The filtrate was concentrated to give crude Compound XX2-3.

MS-ESI m/z: 291.2 [M+H]+.

Step 4: Synthesis of Compound XX2

To phosphorus oxychloride (20.35 g, 132.72 mmol) was added Compound XX2-3 (0.6 g, 2.07 mmol) and the reaction mixture was stirred at 100° C. for 1 h. The reaction solution was quenched with saturated sodium bicarbonate solution at 0° C., adjusted to pH 9, extracted with dichloromethane (100 ml), washed with saturated brine (30 ml), dried over anhydrous sodium sulfate and filtered. The filtrate was concentrated to give crude Compound XX2.

MS-ESI m/z: 309.1 [M+H]+.

Inrermediate 12

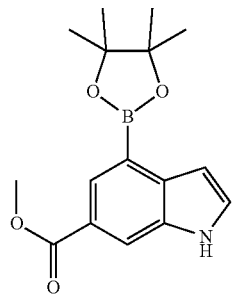

XX3

Step 1: Synthesis of Compound XX3

To a solution of Compound XX3-1 (2 g, 7.87 mmol), bispinacol borate (4.00 g, 15.74 mmol) and 1,1-bis(diphenylphosphino)ferrocene palladium chloride (0.3 g, 410.00 μmol) in 1,4-dioxane (25 mL) was added potassium acetate (2.32 g, 23.61 mmol), which was purged with nitrogen three times. The reaction mixture was stirred at 100° C. with heating for 8 h and then filtered. The solution was concentrated to give the crude product, which was separated with column chromatography to give Compound XX3.

MS-ESI m/z: 302.1 [M+H]+.

Intermediate 13

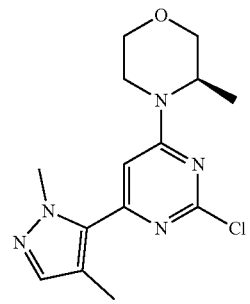

XX4

Synthesis Scheme

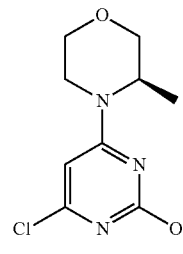 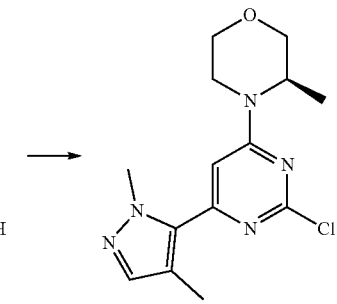

D1-2    XX4

Step 1: Synthesis of Compound 1

To a solution of Compound D1-2 (3.70 g, 14.91 mmol), 1,4-dimethylpyrazole-5-pinacol borate (3.31 g, 14.91 mmol) and bis(triphenylphosphine) palladium dichloride (523.36 mg, 745.64 μmol) in 1,4-dioxane (90 mL) was added 2M sodium carbonate (22.37 mL) aqueous solution, which was purged with nitrogen three times. The reaction mixture was stirred at 110° C. with heating for 15 h and then filtered. The solution was concentrated to give the crude product, which was separated with column chromatography to give Compound XX4.

MS-ESI m/z: 308.2 [M+H]+.

Synthesis Scheme

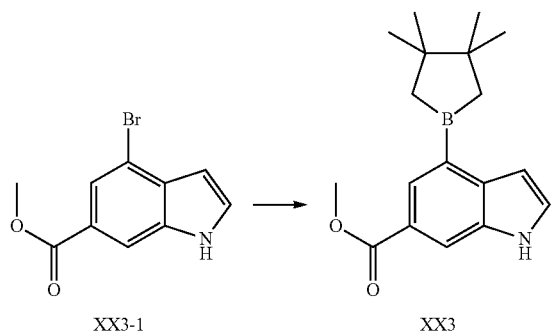

XX3-1    XX3

Intermediate 14

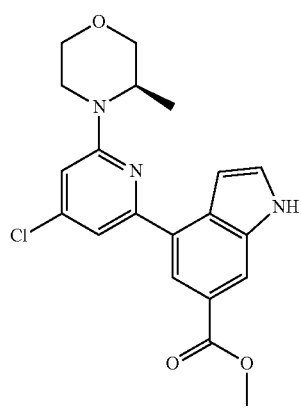

Synthesis Scheme

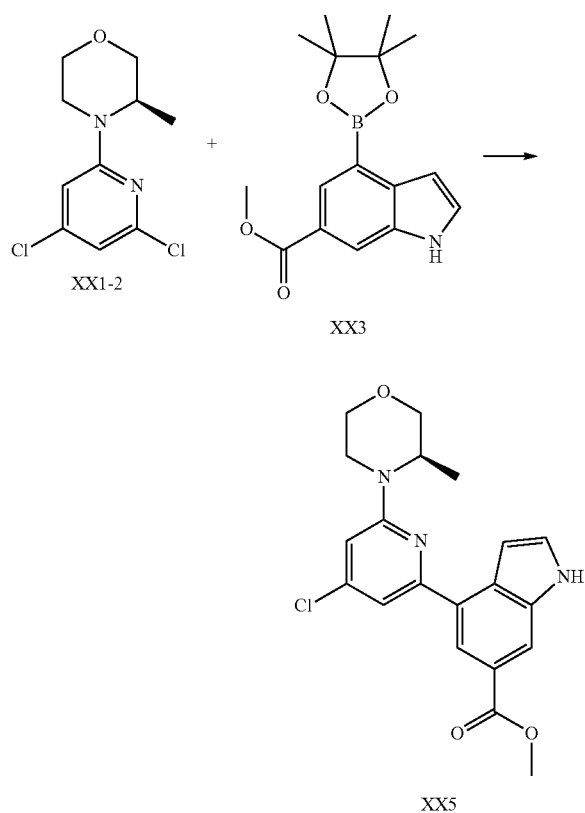

Step 1: Synthesis of Compound XX5

Except using corresponding raw materials, the procedures identical to those used for Compound D1 in synthesis Example Intermediate D1 were used to give Compound XX5.

MS-ESI m/z: 386.2 [M+H]+.

Intermediate 15

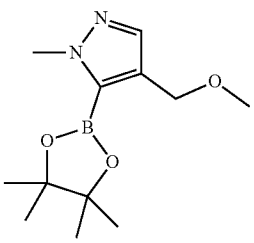

Synthesis Scheme

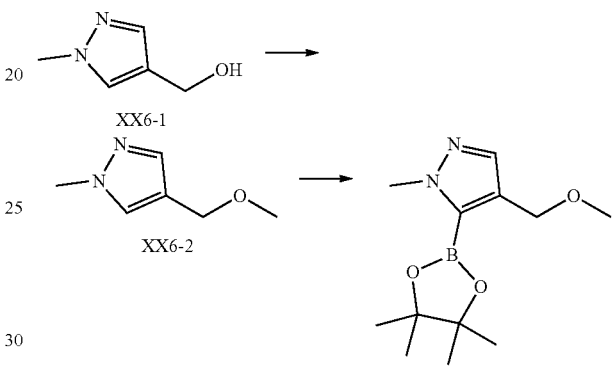

Step 1: Synthesis of Compound XX6-2

At 0° C., to a solution of Compound XX6-1 (2 g, 17.84 mmol) in tetrahydrofuran (20 mL) was added sodium hydride (856.07 mg, 21.40 mmol, purity: 60%). The reaction mixture was stirred at 25° C. for 1 h and then cooled to 0° C. and added with methyl iodide (11.4 g, 80.32 mmol, 5.00 mL). The reaction mixture was stirred at 25° C. for 10 h. The reaction was added with saturated brine (30 mL) and extracted with ethyl acetate (50 mL×3). The organic phases were combined and successively washed with (70 mL) and brine (70 mL). The organic phase was dried over anhydrous sodium sulfate, filtered and concentrated under reduced to give crude Compound XX6-2.

MS-ESI m/z: 253.1 [M+H]+.

Step 2: Synthesis of Compound XX6

At 0° C., to a solution of Compound XX6-2 (0.5 g, 3.96 mmol) in tetrahydrofuran (15 mL) was added n-butyllithium (2.5 M, 4.76 mL). The reaction mixture was stirred at 25° C. for 1 h and then cooled to −78° C., and added with isopropanol pinacol borate (818.52 mg, 4.40 mmol). The reaction mixture was stirred at −78° C. for 0.5 h and warmed to 0° C. with stirring for 1 h. The reaction was quenched with saturated brine at 0-5° C., adjusted to pH=6-7 with 1 M hydrochloric acid and extracted with ethyl acetate (40 mL×3). The organic phases were combined, dried over anhydrous sodium sulfate, and concentrated to give the crude product, which was separated with column chromatography to give Compound XX6.

MS-ESI m/z: 127.0 [M+H]+.

Intermediate 16

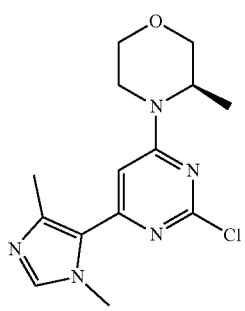

Synthesis Scheme

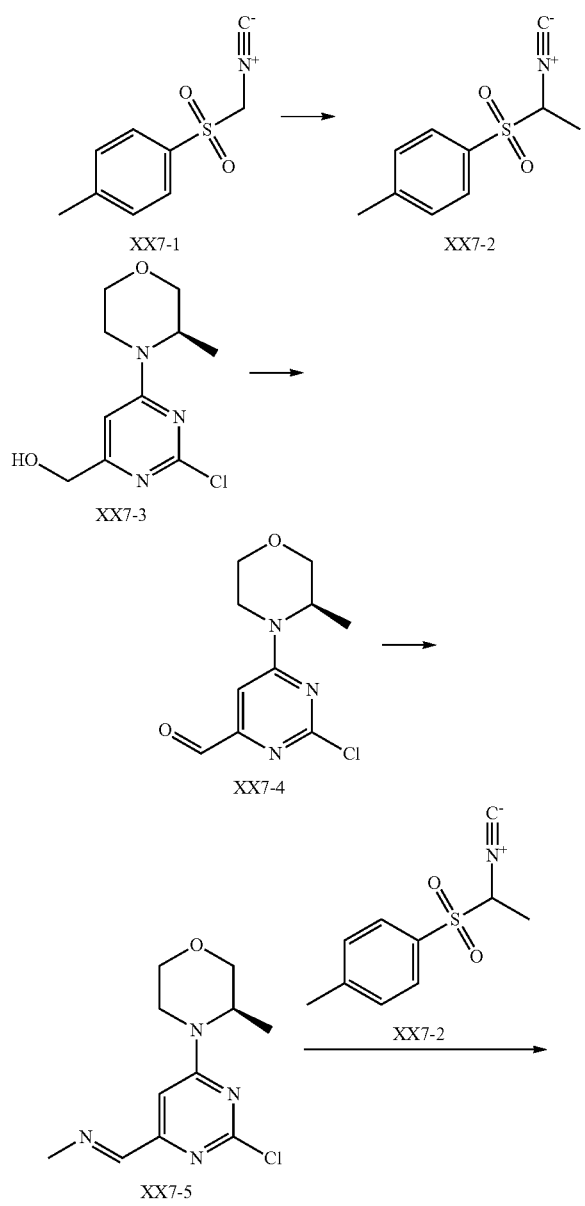

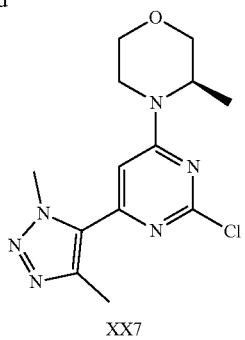

XX7

Step 1: Synthesis of Compound XX7-2

At 0° C., to a solution of Compound XX7-1 (1 g, 5.12 mmol) in dichloromethane (10 mL) were successively added benzyltriethyl ammonium chloride (233.33 mg, 1.02 mmol), methyl iodide (2.06 g, 14.51 mmol, 903.51 µL) and sodium hydroxide (10 mL) aqueous solution with the concentration of 30%. The reaction mixture was stirred at 0° C. for 3 h and at 25° C. for 2 h. The reaction was diluted with water (130 mL) and extracted with dichloromethane (75 mL×2). The organic phases were combined, dried over anhydrous sodium sulfate, filtered and concentrated to give the crude product, which was separated with column chromatography to give Compound XX7-2.

$^1$H NMR (CHLOROFORM-d, 400 MHz): δ=7.90 (d, J=8.3 Hz, 2H), 7.46 (d, J=8.3 Hz, 2H), 4.61 (q, J=6.9 Hz, 1H), 2.52 (s, 3H), 1.77 ppm (d, J=6.8 Hz, 3H)

Step 2: Synthesis of Compound XX7-4

To a solution of Compound XX7-3 (1 g, 4.10 mmol) in dichloromethane (20 mL) was added Dess-Martin periodiodine (2.61 g, 6.16 mmol). The reaction mixture was stirred at 30° C. for 8 h, diluted with water (20 mL), extracted with dichloromethane (20 mL×3). The organic phases were combined, washed with saturated brine (20 mL), filtered, and concentrated to give the crude product, which was separated with column chromatography to give Compound XX7-4.

MS-ESI m/z: 242.0 [M+H]+.

$^1$H NMR (CHLOROFORM-d, 400 MHz): δ=9.86 (s, 1H), 6.95 (s, 1H), 4.38 (br s, 1H), 4.06 (dd, J=11.8, 3.8 Hz, 1H), 4.14 (br d, J=7.5 Hz, 1H), 3.80-3.87 (m, 1H), 3.69-3.76 (m, 1H), 3.58 (td, J=12.0, 2.9 Hz, 1H), 3.37 (br t, J=11.8 Hz, 1H), 1.38 ppm (d, J=6.8 Hz, 3H).

Step 3: Synthesis of Compound XX7-5

To a solution of Compound XX7-4 (0.51 g, 2.11 mmol) and methylamine hydrochloride (712.41 mg, 10.55 mmol) in toluene (20 mL) were successively added triethylamine (2.14 g, 21.10 mmol) and anhydrous sodium sulfate (4.50 g, 31.65 mmol). The reaction mixture was stirred at 50° C. for 13 h, and the organic solvent was filtered and concentration to give crude Compound XX7-5.

$^1$H NMR (CHLOROFORM-d, 400 MHz): δ=8.13 (d, J=1.8 Hz, 1H), 6.97 (s, 1H), 4.37 (br s, 1H), 4.08 (br s, 1H), 4.00 (dd, J=11.4, 3.6 Hz, 1H), 3.75-3.81 (m, 1H), 3.64-3.71 (m, 1H), 3.49-3.57 (m, 4H), 3.25-3.35 (m, 1H), 1.33 ppm (d, J=6.8 Hz, 3H)

Step 4: Synthesis of Compound XX7

To a solution of Compound XX7-5 (0.535 g, 2.10 mmol) and XX7-2 (439.54 mg, 2.10 mmol) in ethanol (25 mL) was added potassium carbonate (725.71 mg, 5.25 mmol). The reaction mixture was stirred at 25° C. for 48 h and heated to 70° C. with stirring for 12 h. The reaction solution was filtered and concentrated to give the crude product, which was separated with column chromatography to give Compound XX7.

MS-ESI m/z: 308.1[M+H]+.

Intermediate 17

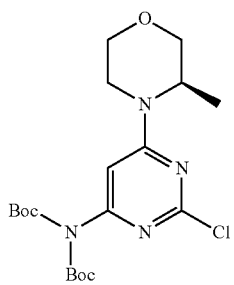

Synthesis Scheme

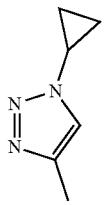

Step 1: Synthesis of Compound XX8-2

At 0° C., to a solution of Compound XX8-1 (10 g, 60.98 mmol) and 4-dimethylaminopyridine (744.96 mg, 6.10 mmol) in dichloromethane (100 mL) was slowly added di-tert-butyl decarbonate (29.28 g, 134.15 mmol). The reaction mixture was stirred at 30° C. for 36 h and added with ice water (120 mL) and extracted with dichloromethane (150 mL×2). The organic phases were combined, washed with saturated brine (100 mL), dried over anhydrous magnesium sulfate, filtered and concentrated to give the crude product, which was separated with column chromatography to give Compound XX8-2.

MS-ESI m/z: 364.1 [M+H]+.

Step 2: Synthesis of Compound XX8

To a solution of Compound XX8-2 (6 g, 16.47 mmol) and (R)-3-methylmorpholine (1.83 g, 18.12 mmol) in 1,4-dioxane (50 mL) was added N,N-diisopropylethylamine (2.13 g, 16.47 mmol). The reaction mixture was stirred at 50° C. for 10 and then concentrated under reduced pressure to give the crude product, which was separated with column chromatography to give Compound XX8.

MS-ESI m/z: 429.3 [M+H]+.

$^1$H NMR (CHLOROFORM-d, 400 MHz): δ=6.76 (s, 1H), 4.30 (br s, 1H), 3.99 (br dd, J=11.5, 3.5 Hz, 2H), 3.74-3.81 (m, 1H), 3.64-3.72 (m, 1H), 3.54 (td, J=11.9, 3.0 Hz, 1H), 3.28 (td, J=12.9, 3.9 Hz, 1H), 1.54 (s, 18H), 1.31 ppm (d, J=6.8 Hz, 3H).

Intermediate 18

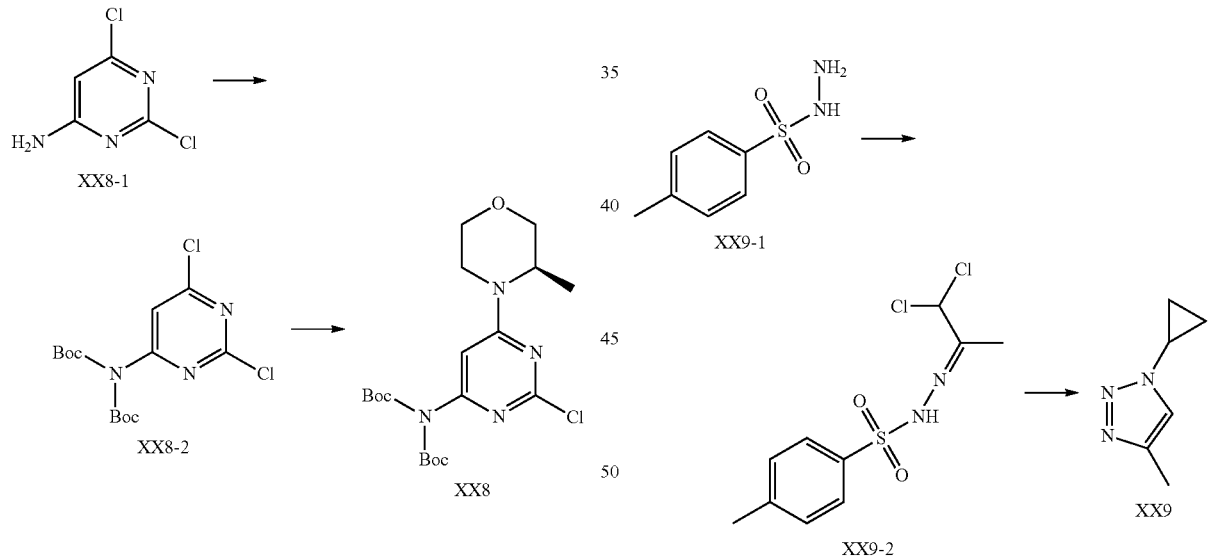

Synthesis Scheme

Step 1: Synthesis of Compound XX9-2

To as solution of Compound XX9-1 (6.2 g, 33.29 mmol) in propionic acid (10 mL) was added 1,1-dichloroacetone (4.57 g, 35.96 mmol). The reaction mixture was stirred at 30° C. for 14 h and filtered. The filter cake was washed with cyclohexane (100 mL) and the solid was rotated to remove the solvent to give crude Compound XX9-2.

$^1$H NMR (DMSO-d6, 400 MHz): δ=11.88 (br s, 1H), 9.19 (s, 1H), 7.80 (d, J=8.3 Hz, 2H), 7.43 (d, J=8.0 Hz, 2H), 2.39 (s, 3H), 1.84 ppm (s, 3H)

Step 2: Synthesis of Compound XX9

At 0° C., to a solution of compound cyclopropylamine (1.25 g, 21.89 mmol, 1.52 mL) in ethanol (50 mL) was added triethylamine (11.08 g, 109.45 mmol). The reaction mixture was stirred at 0° C. for 10 h, then added with a solution of XX9-2 (7.11 g, 24.08 mmol) in acetonitrile (50 mL) and heated to 30° C. with stirring for 16 h. The reaction solution was concentrated to give the crude product, which was separated with column chromatography to give Compound XX9.

MS-ESI m/z: 124.0 [M+H]+.

$^1$H NMR (CHLOROFORM-d, 400 MHz): δ=7.32 (s, 1H), 3.73 (m, 1H), 2.34 (s, 3H), 1.20-1.27 (m, 2H), 1.10-1.17 ppm (m, 2H).

Intermediate 19

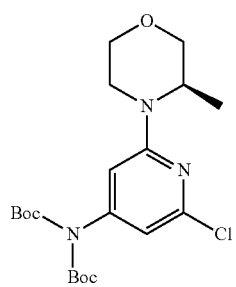

Synthesis Scheme was heated with microwave at 180° C. for 1 h and the reaction solution was concentrated to give the crude product, which was separated with column chromatography to give Compound XX10-2.

MS-ESI m/z: 228.0 M+H]+.

Step 2: Synthesis of Compound XX10

At 0-5° C., to a solution of Compound XX10-2 (1.4 g, 6.15 mmol) and 4-dimethylaminopyridine (1 g, 8.19 mmol) in dichloromethane (30 mL) was slowly added di-tert-butyl decarbonate (4.03 g, 18.45 mmol). The reaction mixture was stirred at 30° C. for 5 h, then added with water (30 mL) and extracted with dichloromethane (50 mL×3). The organic phases were combined, washed with saturated brine (70 mL), dried over anhydrous sodium sulfate, filtered and concentrated to give the crude product, which was separated with column chromatography to give Compound XX10.

MS-ESI m/z: 428.6 M+H]+.

Example 1: Compound WX01

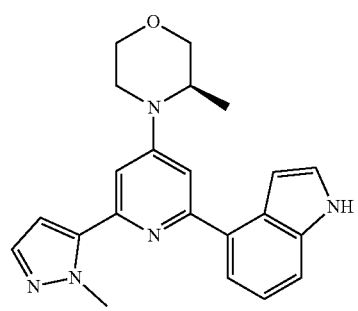

Synthesis Scheme

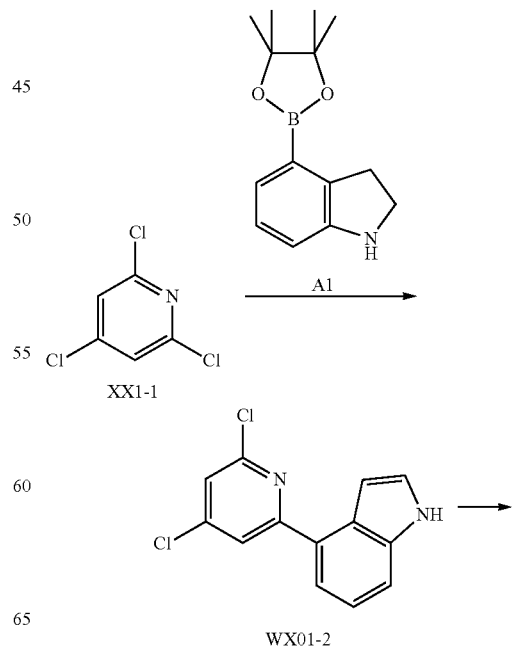

Step 1: Synthesis of Compound XX10-2

To a solution of Compound XX10-1 (2 g, 12.27 mmol) and (R)-3-methylmorpholine (1.61 g, 15.95 mmol) 的 1-methyl-2-pyrrolidone (5 mL) was added N,N-diisopropylethylamine (1.74 g, 13.50 mmol). The reaction

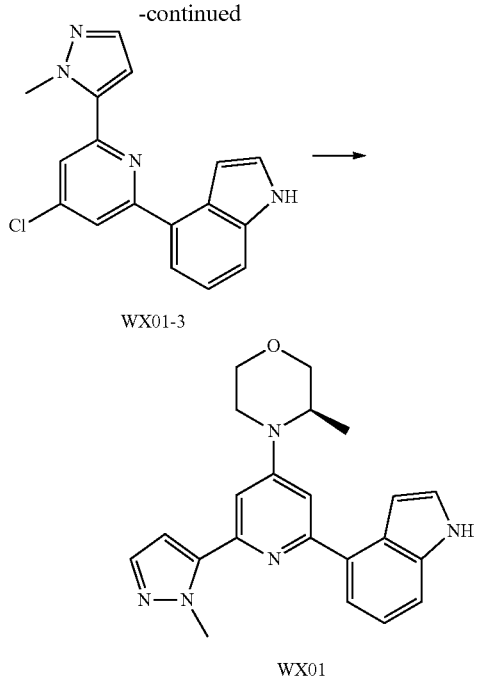

WX01-3

WX01

Step 1: Synthesis of Compound WX01-2

At room temperature, to as solution of Compound A1 (300.00 mg, 1.64 mmol) in 1,4-dioxane (10.00 mL) were added Compound XX1-1 (398.70 mg, 1.64 mmol), dichlorobis(triphenylphosphine) palladium (115.11 mg, 164.00 µmol), sodium carbonate solution (2 M, 2.46 mL), which was stirred at 90° C. for 12 h. The reaction system was diluted with 20 mL of water and extracted with ethyl acetate (40 mL). The organic phase was washed with saturated brine (20 mL×2) and dried over anhydrous sodium sulfate. After the desiccant was filtered off, the solvent was removed under reduced pressure to give the crude product, which was purified with column chromatography (petroleum ether/ethyl acetate=10/1,6/1) to give Compound WX01-2.

$^1$H NMR (400 MHz, DMSO-d$_6$) δ ppm 7.03 (br s, 1H) 7.23 (t, J=7.78 Hz, 1H) 7.51 (t, J=2.76 Hz, 1H) 7.57 (d, J=8.03 Hz, 1H) 7.63 (d, J=7.53 Hz, 1H) 7.71 (d, J=1.51 Hz, 1H) 8.07 (d, J=1.51 Hz, 1H) 11.41 (br s, 1H).

Step 2: Synthesis of Compound WX01-3

At room temperature, to a solution of Compound WX01-2 (100.00 mg, 380.05 µmol) in 1,4-dioxane (3.00 mL) were added 1-methyl-1H-pyrazole-5-boric acid (47.86 mg, 380.05 µmol), dichlorobis(triphenylphosphine) palladium (26.68 mg, 38.00 µmol) and sodium carbonate solution (2 M, 570.08 uL), which was stirred at 90° C. for 12 h. The reaction system was diluted with 20 mL of water and extracted with ethyl acetate (30 mL). The organic phase was washed with saturated brine (20 mL×2) and dried over anhydrous sodium sulfate. After the desiccant was filtered off, the solvent was removed under reduced pressure to give the crude product, which was separated and purified with silica gel plate (petroleum ether/ethyl acetate=2/1) to give Compound WX01-3.

MS m/z: 308.9[M+H]$^+$

Step 3: Synthesis of Compound WX01

At room temperature, to a solution of Compound WX01-3 (70.00 mg, 226.71 µmol) in 1,4-dioxane (3.00 mL) were added (R)-3-methylmorpholine (45.86 mg, 453.43 µmol), palladium acetate (26.68 mg, 38.00 µmol), 2-dicyclohexylphosphono-2,4,6-triisopropylbiphenyl (21.62 mg, 45.34 µmol), cesium carbonate (221.60 mg, 680.14 µmol), which was stirred at 100° C. under nitrogen atmosphere for 12 h. The reaction system was diluted with 20 mL of water and extracted with ethyl acetate (25 mL). The organic phase was washed with saturated brine (15 mL×2) and dried over anhydrous sodium sulfate. After the desiccant was filtered off, the solvent was removed under reduced pressure to give the crude product, which was separated with preparative HPLC (neutral) to give Compound WX01.

$^1$H NMR (400 MHz, CHLOROFORM-d) δ ppm 1.34 (d, J=6.52 Hz, 3H) 3.31-3.38 (m, 1H) 3.49 (br s, 1H) 3.70-3.77 (m, 1H) 3.88 (s, 2H) 4.04-4.13 (m, 2H) 4.32 (s, 3H) 6.60 (d, J=2.00 Hz, 1H) 6.93 (d, J=2.52 Hz, 1H) 7.00 (br s, 1H) 7.19 (d, J=2.00 Hz, 1H) 7.31-7.36 (m, 2H) 7.50 (d, J=8.52 Hz, 1H) 7.53 (d, J=2.00 Hz, 1H) 7.61 (d, J=7.52 Hz, 1H) 8.33 (br s, 1H). MS m/z: 374.0[M+H]$^+$.

Example 2: Compound WX02

WX02

Synthesis Scheme

D1

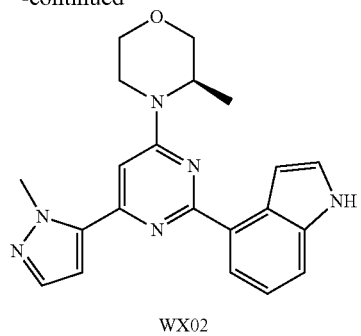

WX02

Step 1: Synthesis of Compound WX02

To a solution of Compound D1 (0.08 g, 243.31 μmol) in 1,4-dioxane (5 mL) were added 1-methylpyrazole-5-pinacol borate (75.94 mg, 364.97 μmol), bistriphenylphosphine palladium dichloride (17.08 mg, 24.33 μmol) and sodium carbonate (2 M, 364.97 uL). The reaction solution was stirred at 90° C. under the protection of nitrogen for 15 h. The reaction solution was filtered through celite and the filtrate was extracted with 30 mL of ethyl acetate (10 mL×3). The organic phase was washed with 30 mL of water (10 mL×3) and dried over anhydrous sodium sulfate. After the desiccant was filtered off, the solvent was removed under reduced pressure to give the crude product, which was separated with preparative HPLC (neutral condition) to give Compound WX02.

MS-ESI m/z: 375.0 [M+H]+.

$^1$H NMR (400 MHz, DMSO-d6) δ ppm 1.30 (d, J=6.78 Hz, 3H) 3.28-3.32 (m, 1H) 3.31 (s, 1H) 3.55 (td, J=11.80, 2.76 Hz, 1H) 3.70 (dd, J=11.29, 2.76 Hz, 1H) 3.79-3.86 (m, 1H) 4.03 (dd, J=11.17, 3.14 Hz, 1H) 4.29 (s, 4H) 4.68 (br s, 1H) 6.98-7.04 (m, 1H) 7.01 (s, 1H) 7.00 (d, J=2.01 Hz, 1H) 7.22 (t, J=7.78 Hz, 1H) 7.30 (br s, 1H) 7.47 (t, J=2.64 Hz, 1H) 7.52-7.57 (m, 2H) 8.13 (d, J=7.28 Hz, 1H) 11.22-11.34 (m, 1H) 11.29 (br s, 1H).

Example 3: Compound WX03

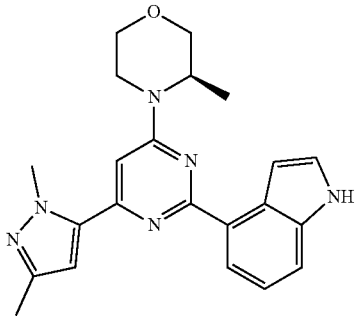

WX03

Synthesis Scheme

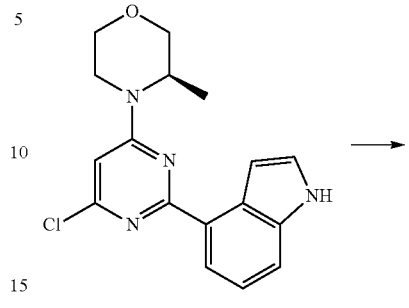

D1

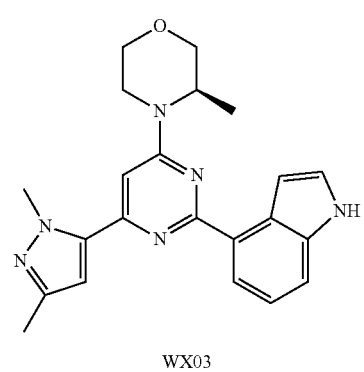

WX03

Step 1: Synthesis of Compound WX03

To a solution of Compound D1 (0.08 g, 243.31 μmol) in 1,4-dioxane (5 mL) were added 1,3-dimethylpyrazole-5-pinacol borate (54.04 mg, 243.31 μmol), bistriphenylphosphine palladium dichloride (17.08 mg, 24.33 μmol) and sodium carbonate (2 M, 364.97 uL). The reaction solution was stirred at 90° C. under the protection of nitrogen for 15 h. The reaction solution was filtered through celite and the filtrate was extracted with 30 mL of ethyl acetate (10 mL×3). The organic phase was washed with 30 mL of water (10 mL×3) and dried over anhydrous sodium sulfate. After the desiccant was filtered off, the solvent was removed under reduced pressure to give the crude product, which was separated with preparative HPLC (neutral condition) to give Compound WX03.

MS-ESI m/z: 389.1 [M+H]+.

$^1$H NMR (400 MHz, DMSO-d6) δ ppm 1.29 (d, J=6.53 Hz, 3H) 2.18-2.26 (m, 1H) 2.21 (s, 1H) 2.26-2.27 (m, 1H) 3.23-3.30 (m, 1H) 3.24-3.31 (m, 1H) 3.48-3.59 (m, 1H) 3.69 (dd, J=11.42, 2.64 Hz, 1H) 3.77-3.88 (m, 1H) 3.77-3.84 (m, 1H) 4.02 (br dd, J=11.29, 3.01 Hz, 1H) 4.20 (s, 2H) 4.17-4.22 (m, 1H) 4.26 (br d, J=13.55 Hz, 1H) 4.54-4.80 (m, 1H) 4.65 (br s, 1H) 6.64-6.85 (m, 1H) 6.69-6.83 (m, 1H) 6.71-6.82 (m, 1H) 6.78 (s, 1H) 6.96 (s, 1H) 6.92-7.03 (m, 1H) 7.21 (t, J=7.78 Hz, 1H) 7.27-7.33 (m, 1H) 7.29 (br s, 1H) 7.46 (t, J=2.64 Hz, 1H) 7.55 (d, J=8.03 Hz, 1H) 8.11 (d, J=7.28 Hz, 1H) 11.27 (br s, 1H).

Example 4: Compound WX04

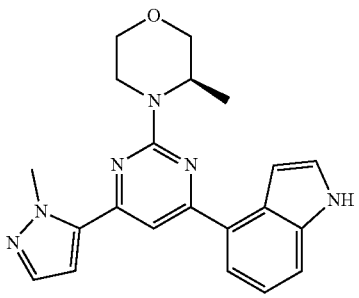

Synthesis Scheme

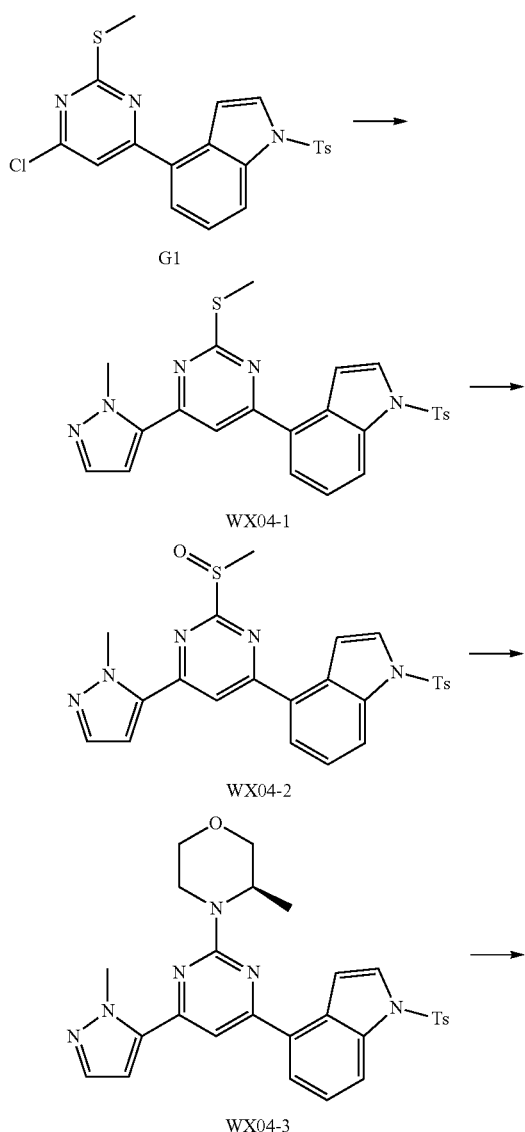

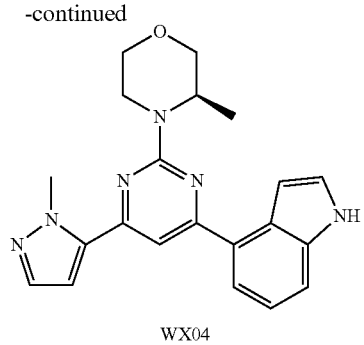

WX04

Step 1: Synthesis of Compound WX04-1

To a solution of Compound G1 (0.3 g, 697.77 μmol) in 1,4-dioxane (5 mL) were added 1-methylpyrazole-5-pinacol borate (188.74 mg, 907.10 μmol), bistriphenylphosphine palladium dichloride (48.98 mg, 69.78 μmol) and sodium carbonate (2 M, 1.05 mL). The reaction solution was stirred at 90° C. under the protection of nitrogen for 15 h. The reaction solution was filtered through celite and the filtrate was extracted with 60 mL of ethyl acetate (20 mL×3). The organic phase was washed with 45 mL of water (15 mL×3) and dried over anhydrous sodium sulfate. After the desiccant was filtered off, the solvent was removed under reduced pressure to give the crude product, which was purified with silica gel column (petroleum ether/ethyl acetate=1:0,3:1) to give Compound WX04-1.

MS-ESI m/z: 476.1 [M+H]+.

Step 2: Synthesis of Compound WX04-2

To a solution of Compound WX04-1 (0.205 g, 431.05 μmol) in dichloromethane (5 mL) was added m-chloroperoxybenzoic acid (87.51 mg, 431.05 μmol). The reaction solution was stirred at 20° C. for 15 h. The reaction solution was quenched at 20° C. with 20 mL of saturated sodium sulfite solution and then extracted with 40 mL of dichloromethane (20 mL×2). The organic phase was washed with 45 mL of water (15 mL×3) and dried over anhydrous sodium sulfate. After the desiccant was filtered off, the solvent was removed under reduced pressure to give crude WX04-2.

MS-ESI m/z: 492.0 [M+H]+.

Step 3: Synthesis of Compound WX04-3

To a solution of Compound WX04-2 (213.90 mg, 435.12 μmol) and (R)-3-methylmorpholine (220.06 mg, 2.18 mmol) in 1,4-dioxane (5 mL) was added diisopropylethylamine (562.36 mg, 4.35 mmol). The reaction solution was stirred at 100° C. for 65 h. The reaction solution was extracted with 60 mL of ethyl acetate (20 mL×3) and the organic phase was washed with 60 mL of water (20 mL×3) and dried over anhydrous sodium sulfate. After the desiccant was filtered off, the solvent was removed under reduced pressure to give crude WX04-3.

MS-ESI m/z: 529.1 [M+H]+.

Step 4: Synthesis of Compound WX04

To a solution of Compound WX04-3 (0.35 g, 662.10 μmol) in methanol (5 mL) was added sodium hydroxide (2 M, 993.14 μL). The reaction mixture was stirred at 60° C. for 17 h. The reaction solution was extracted with 40 mL of ethyl acetate (20 mL×2) and the organic phase was washed with 60 mL of water (20 mL×3) and dried over anhydrous sodium sulfate. After the desiccant was filtered off, the solvent was removed under reduced pressure to give the crude product, which was purified with preparative HPLC (neutral condition) to give Compound WX04.

MS-ESI m/z: 375.0 [M+H]+

$^1$H NMR (400 MHz, CHLOROFORM-d) δ ppm 1.43 (d, J=6.78 Hz, 3H) 3.44 (td, J=12.99, 3.89 Hz, 1H) 3.65 (td, J=11.86, 2.89 Hz, 1H) 3.77-3.83 (m, 1H) 3.84-3.89 (m, 1H) 4.07 (dd, J=11.29, 3.51 Hz, 1H) 4.35 (s, 3H) 4.54 (br d, J=13.80 Hz, 1H) 4.90 (br d, J=4.02 Hz, 1H) 6.78 (d, J=2.01 Hz, 1H) 7.16 (br s, 1H) 7.30-7.35 (m, 1H) 7.35-7.38 (m, 2H) 7.52-7.57 (m, 2H) 7.69 (d, J=7.53 Hz, 1H) 8.35 (br s, 1H)

Example 5: Compound WX05

Synthesis Scheme

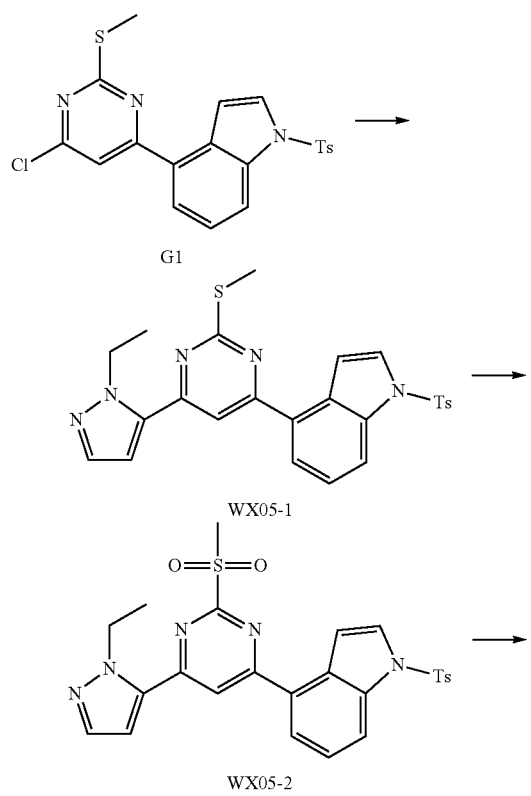

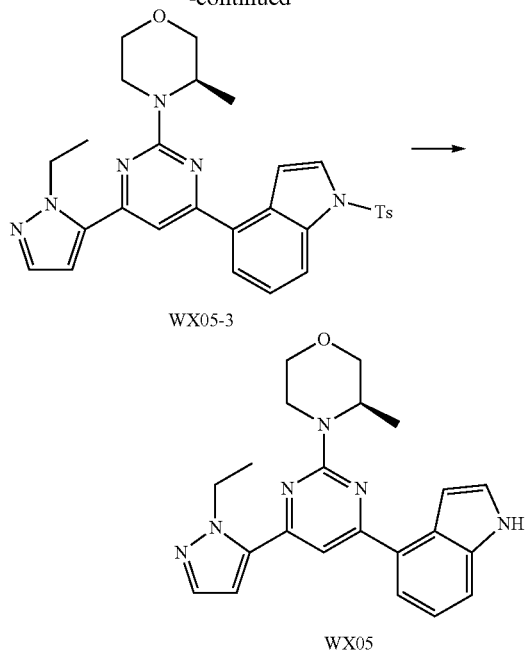

Step 1: Synthesis of Compound WX05-1

Except using corresponding raw materials, the procedures identical to those used for Compound WX04-1 in synthesis Example 4 were used to give WX05-1.

MS-ESI m/z: 490.1 [M+H]+.

Step 2: Synthesis of Compound WX05-2

To a solution of Compound WX05-1 (0.193 g, 394.19 μmol) in dichloromethane (5 mL) was added m-chloroperoxybenzoic acid (80.03 mg, 394.19 μmol). The reaction solution was stirred at 20° C. for 15 h. The reaction solution was quenched with saturated sodium sulfite solution at 20° C. and extracted with 40 mL of dichloromethane (20 mL×2). The organic phase was washed with 45 mL of water (15 mL×3) and dried over anhydrous sodium sulfate. After the desiccant was filtered off, the solvent was removed under reduced pressure to give crude WX05-2.

MS-ESI m/z: 522.1 [M+H]+.

Step 3: Synthesis of Compound WX05-3

Except using corresponding raw materials, the procedures identical to those used for Compound WX04-3 in synthesis Example 4 were used to give crude WX05-3.

MS-ESI m/z: 543.1 [M+H]+.

Step 4: Synthesis of Compound WX05

Except using corresponding raw materials, the procedures identical to those used for Compound WX04 in synthesis Example 4 were used to give Compound WX05.

MS-ESI m/z: 389.0 [M+H]+.

$^1$H NMR (400 MHz, CHLOROFORM-d) δ ppm 1.42 (d, J=6.78 Hz, 3H) 2.29 (s, 3H) 3.43 (td, J=12.86, 3.39 Hz, 1H) 3.59-3.69 (m, 1H) 3.75-3.81 (m, 1H) 3.83-3.88 (m, 1H) 4.06 (br dd, J=11.04, 3.26 Hz, 1H) 4.17 (br s, 1H) 4.15 (s, 2H) 4.56 (br d, J=12.05 Hz, 1H) 4.92 (br d, J=5.02 Hz, 1H) 7.17

(br s, 1H) 7.20 (s, 1H) 7.29-7.35 (m, 1H) 7.37 (br s, 1H) 7.40 (s, 1H) 7.55 (d, J=8.03 Hz, 1H) 7.68 (d, J=7.28 Hz, 1H) 8.42 (br s, 1H).

Example 6: Compound WX06

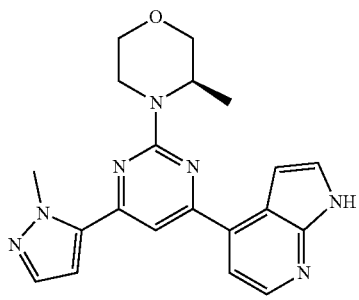

Synthesis Scheme

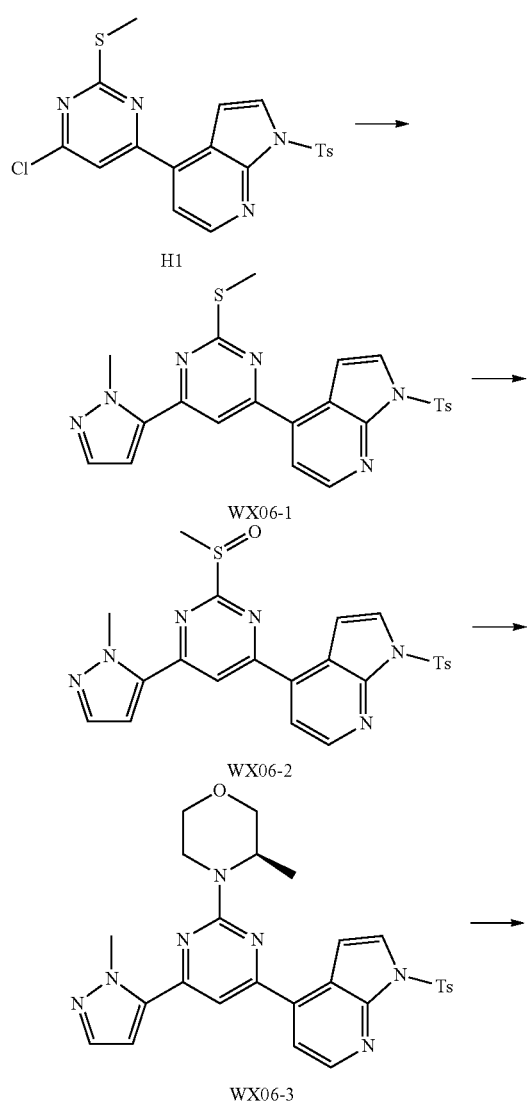

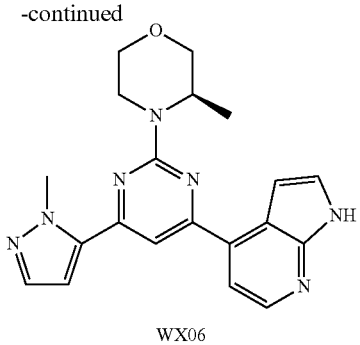

WX06

Step 1: Synthesis of Compound WX06-1

To a solution of Compound H1 (200.46 mg, 465.18 μmol) in 1,4-dioxane (5 mL) were added 1-methylpyrazole-5-pinacol borate (125.82 mg, 604.73 μmol), bistriphenylphosphine palladium dichloride (16.33 mg, 23.26 μmol) and sodium carbonate (2 M, 697.77 uL). The reaction solution was stirred under the protection of nitrogen at 90° C. for 15 h. After the reaction solution was filtered through celite, the filtrate was extracted with 60 mL of ethyl acetate (20 mL×3), and the organic phase was washed with 45 mL of water (15 mL×3) and dried over anhydrous sodium sulfate. After the desiccant was filtered off, the solvent was removed under reduced pressure to give the crude product, which was purified with silica gel column (petroleum ether/ethyl acetate=1:0,3:1) to give Compound WX06-1.

MS-ESI m/z: 477.0 [M+H]+.

Step 2: Synthesis of Compound WX06-2

To a solution of Compound WX06-1 (0.21 g, 440.65 μmol) in dichloromethane (5 mL) was added m-chloroperoxybenzoic acid (89.46 mg, 440.65 μmol). The reaction solution was stirred at 20° C. for 15 h. The reaction solution was quenched at 20° C. with 20 mL of saturated sodium sulfite solution and then extracted with 40 mL of dichloromethane (20 mL×2). The organic phase was washed with 45 mL of water (15 mL×3) and dried over anhydrous sodium sulfate. After the desiccant was filtered off, the solvent was removed under reduced pressure to give crude WX06-2.

MS-ESI m/z: 493.0 [M+H]+.

Step 3: Synthesis of Compound WX06-3

To a solution of Compound WX06-2 (226.45 mg, 459.74 μmol) and (R)-3-methylmorpholine (232.50 mg, 2.30 mmol) in 1,4-dioxane (5 mL) was added diisopropylethylamine (594.17 mg, 4.60 mmol). The reaction solution was stirred at 100° C. for 65 h. The reaction solution was extracted with 60 mL of ethyl acetate (20 mL×3) and the organic phase was washed with 30 mL of water (10 mL×3) and dried over anhydrous sodium sulfate. After the desiccant was filtered off, the solvent was removed under reduced pressure to give crude WX06-3.

MS-ESI m/z: 530.1 [M+H]+.

Step 4: Synthesis of Compound WX06

To a solution of Compound WX06-3 (0.330 g, 623.10 μmol) in methanol (5 mL) was added sodium hydroxide (2 M, 934.65 uL). The reaction solution was stirred at 60° C.

for 17 h. The reaction solution was extracted with 60 mL of ethyl acetate (20 mL×3) and the organic phase was washed with 45 mL of water (15 mL×3) and dried over anhydrous sodium sulfate. After the desiccant was filtered off, the solvent was removed under reduced pressure to give the crude product, which was purified with preparative HPLC (neutral condition) to give Compound WX06.

MS-ESI m/z: 376.1[M+H]+.

¹H NMR (400 MHz, CHLOROFORM-d) δ ppm 1.43 (br d, J=6.78 Hz, 3H) 3.37-3.53 (m, 1H) 3.60-3.71 (m, 1H) 3.78-3.84 (m, 1H) 3.84-3.91 (m, 1H) 4.09 (br d, J=9.04 Hz, 1H) 4.35 (s, 3H) 4.54 (br d, J=13.30 Hz, 1H) 5.04 (s, 1H) 4.88 (br d, J=4.52 Hz, 1H) 6.75-6.88 (m, 1H) 6.81 (s, 1H) 6.98-7.13 (m, 1H) 7.06 (br s, 1H) 7.40 (s, 1H) 7.50 (br s, 1H) 7.56 (s, 1H) 7.62 (br d, J=5.02 Hz, 1H) 8.47 (br d, J=4.77 Hz, 1H) 9.84 (br s, 1H).

Example 7: Compound WX07

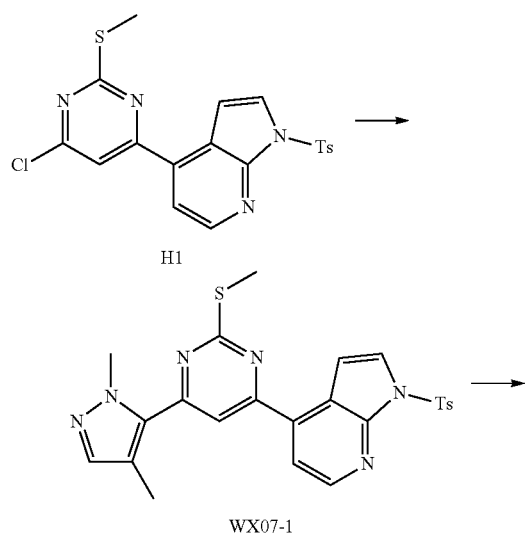

Synthesis Scheme

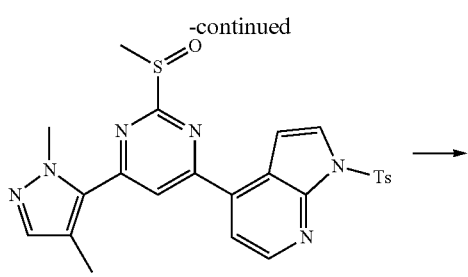

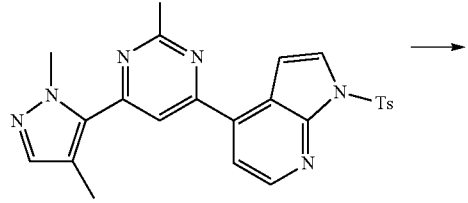

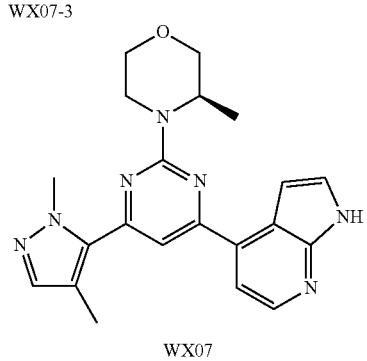

Step 1: Synthesis of Compound WX07-1

Except using corresponding raw materials, the procedures identical to those used for Compound WX06-1 in synthesis Example 6 were used to give WX07-1.

MS-ESI m/z: 491.1 [M+H]+.

Step 2: Synthesis of Compound WX07-2

Except using corresponding raw materials, the procedures identical to those used for Compound WX06-2 in synthesis Example 6 were used to give crude WX07-2.

MS-ESI m/z: 507.1 [M+H]+.

Step 3: Synthesis of Compound WX07-3

Except using corresponding raw materials, the procedures identical to those used for Compound WX06-3 in synthesis Example 6 were used to give crude WX07-3.

MS-ESI m/z: 544.2 [M+H]+.

Step 4: Synthesis of Compound WX07

Except using corresponding raw materials, the procedures identical to those used for Compound WX06 in synthesis Example 6 were used to give Compound WX07.

MS-ESI m/z: 390.0 [M+H]+.

¹H NMR (400 MHz, CHLOROFORM-d) δ ppm 1.43 (d, J=6.78 Hz, 3H) 2.31 (s, 3H) 3.44 (td, J=12.86, 3.64 Hz, 1H) 3.64 (td, J=11.92, 3.01 Hz, 1H) 3.77-3.82 (m, 1H) 3.84-3.89 (m, 1H) 4.07 (dd, J=11.54, 3.51 Hz, 1H) 4.16 (s, 3H) 4.55 (br d, J=13.30 Hz, 1H) 4.90 (br d, J=4.77 Hz, 1H) 7.06 (br s, 1H) 7.24 (s, 1H) 7.41 (s, 1H) 7.48 (br s, 1H) 7.59-7.66 (m, 1H) 8.46 (br s, 1H) 9.09 (br s, 1H).

Example 8: Compound WX08

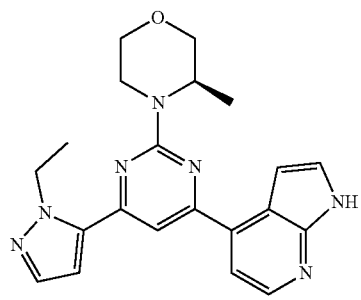

WX08

Synthesis Scheme

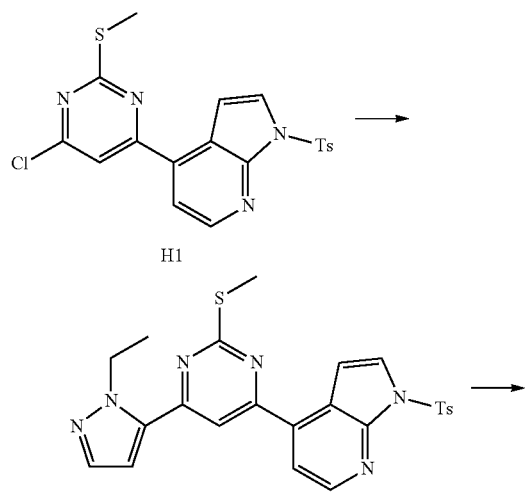

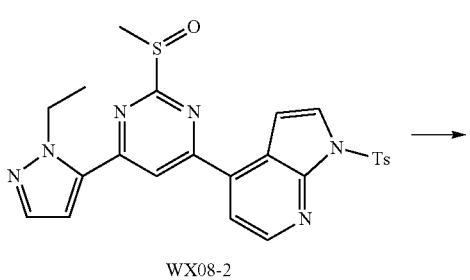

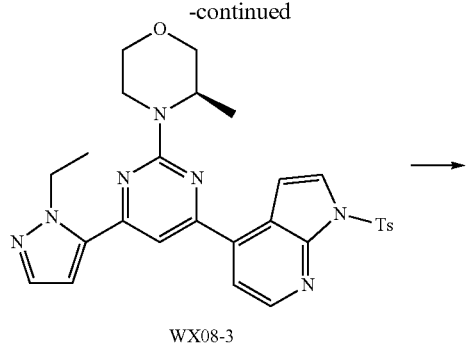

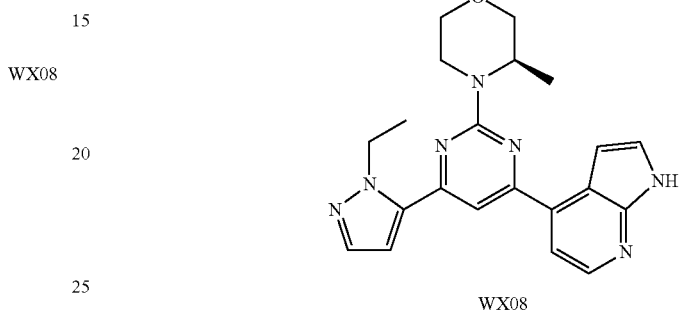

Step 1: Synthesis of Compound WX08-1

Except using corresponding raw materials, the procedures identical to those used for Compound WX06-1 in synthesis Example 6 were used to give WX08-1.

MS-ESI m/z: 491.3 [M+H]+.

Step 2: Synthesis of Compound WX08-2

Except using corresponding raw materials, the procedures identical to those used for Compound WX06-2 in synthesis Example 6 were used to give crude WX08-2.

MS-ESI m/z: 507.1 [M+H]+.

Step 3: Synthesis of Compound WX08-3

Except using corresponding raw materials, the procedures identical to those used for Compound WX06-3 in synthesis Example 6 were used to give crude WX08-3.

MS-ESI m/z: 544.2 [M+H]+.

Step 4: Synthesis of Compound WX08

Except using corresponding raw materials, the procedures identical to those used for Compound WX06 in synthesis Example 6 were used to give Compound WX08.

MS-ESI m/z: 390.0 [M+H]+. ¹H NMR (400 MHz, CHLOROFORM-d) δ ppm 1.29 (br s, 3H) 1.39 (br s, 3H) 3.32 (br s, 1H) 3.51 (br d, J=11.04 Hz, 1H) 3.59-3.81 (m, 1H) 3.71 (br d, J=16.56 Hz, 1H) 3.95 (br d, J=9.79 Hz, 1H) 4.39 (br d, J=11.80 Hz, 1H) 4.72 (br s, 3H) 6.66 (br s, 1H) 6.93 (br s, 1H) 7.13 (br s, 1H) 7.32-7.74 (m, 3H) 8.35 (br s, 1H) 9.83 (br s, 1H).

Example 9: Compound WX09

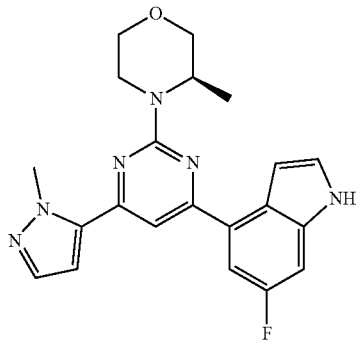

Synthesis Scheme

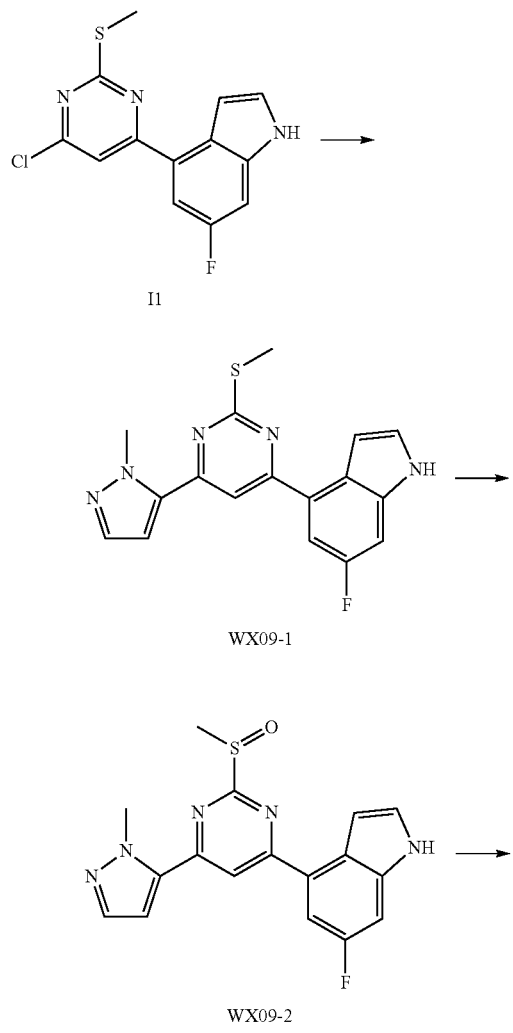

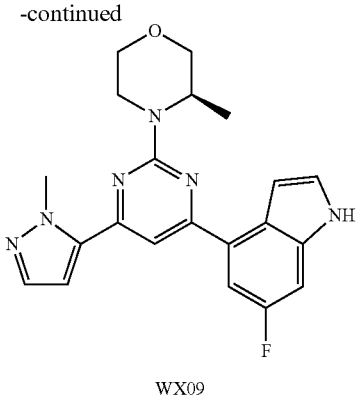

WX09

Step 1: Synthesis of Compound WX09-1

To a solution of Compound I1 (0.1 g, 340.43 μmol) in 1,4-dioxane (5 mL) were added 1-methylpyrazole-5-pinacol borate (92.08 mg, 442.56 μmol), bistriphenylphosphine palladium dichloride (11.95 mg, 17.02 μmol) and sodium carbonate (2 M, 510.64 μL). The reaction mixture was stirred under the protection of nitrogen at 90° C. for 15 h. After the reaction solution was filtered through celite, the filtrate was extracted with 60 mL of ethyl acetate (20 mL×3). The organic phase was washed with 45 mL of water (15 mL×3) and dried over anhydrous sodium sulfate. After the desiccant was filtered off, the solvent was removed under reduced pressure to give the crude product, which was purified with silica gel column (petroleum ether/ethyl acetate=1:0,3:1) to give Compound WX09-1.

MS-ESI m/z: 340.0[M+H]+.

Step 2: Synthesis of Compound WX09-2

To a solution of Compound WX09-1 (102 mg, 300.54 μmol) in dichloromethane (5 mL) was added m-chloroperoxybenzoic acid (61.02 mg, 300.54 μmol). The reaction solution was stirred at 20° C. for 15 h. The reaction solution was quenched at 20° C. with 20 mL of saturated sodium sulfite solution and then extracted with 40 mL of dichloromethane (20 mL×2). The organic phase was washed with 45 mL of water (15 mL×3) and dried over anhydrous sodium sulfate. After the desiccant was filtered off, the solvent was removed under reduced pressure to give crude WX09-2.

MS-ESI m/z: 356.0[M+H]+.

Step 3: Synthesis of Compound WX09

To a solution of Compound WX09-2 (206 mg, 579.65 μmol) and (R)-3-methylmorpholine (293.15 mg, 2.90 mmol)的 1,4-dioxane (5 mL) was added diisopropylethylamine (749.14 mg, 5.80 mmol). The reaction solution was stirred at 100° C. for 65 h. The reaction solution was extracted with 60 mL of dichloromethane (20 mL×3). The organic phase was washed with 30 mL of water (10 mL×3) and dried over anhydrous sodium sulfate. After the desiccant was filtered off, the solvent was removed under reduced pressure to give the crude product, which was purified with preparative HPLC (neutral condition) to give Compound WX09.

MS-ESI m/z: 393.0 [M+H]+.

1H NMR (400 MHz, CHLOROFORM-d) δ ppm 1.42 (d, J=6.78 Hz, 3H) 3.44 (td, J=12.86, 3.64 Hz, 1H) 3.65 (td, J=11.80, 2.76 Hz, 1H) 3.77-3.83 (m, 1H) 3.84-3.89 (m, 1H) 4.07 (dd, J=11.29, 3.51 Hz, 1H) 4.35 (s, 3H) 4.53 (br d, J=11.80 Hz, 1H) 4.88 (br d, J=6.53 Hz, 1H) 6.79 (d, J=1.76 Hz, 1H) 7.08 (br s, 1H) 7.23 (br d, J=8.78 Hz, 1H) 7.32-7.36 (m, 2H) 7.45-7.50 (m, 1H) 7.48 (dd, J=10.67, 2.13 Hz, 1H) 7.55 (d, J=2.01 Hz, 1H) 8.36 (br s, 1H).

Example 10: Compound WX10

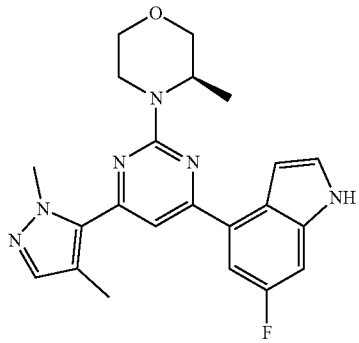

WX10

Synthesis Scheme

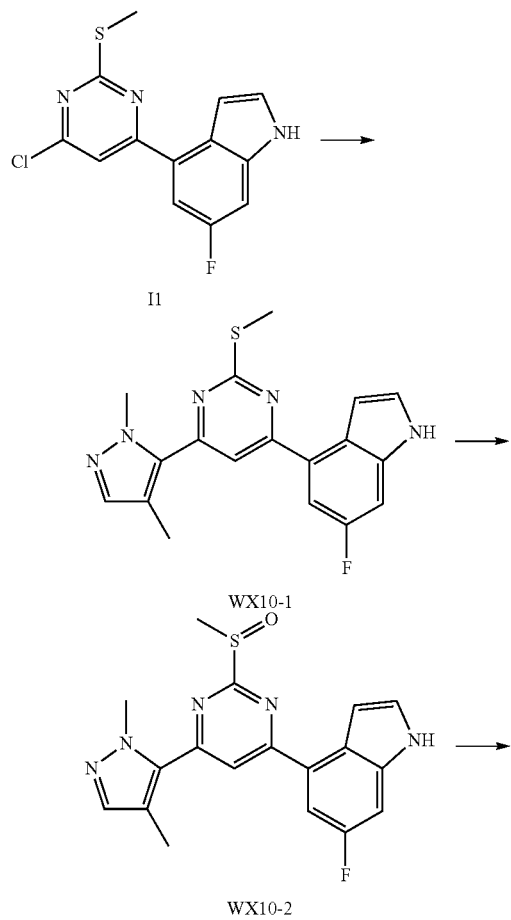

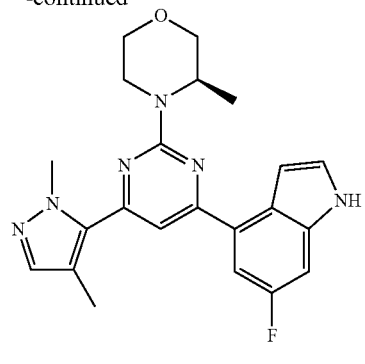

WX10

Step 1: Synthesis of Compound WX10-1

Except using corresponding raw materials, the procedures identical to those used for Compound WX09-1 in synthesis Example 9 were used to give WX10-1.

MS-ESI m/z: 353.9 [M+H]+

Step 2: Synthesis of Compound WX10-2

Except using corresponding raw materials, the procedures identical to those used for Compound WX09-2 in synthesis Example 9 were used to give crude WX10-2.

MS-ESI m/z: 370.0 [M+H]+.

Step 3: Synthesis of Compound WX10

Except using corresponding raw materials, the procedures identical to those used for Compound WX09 in synthesis Example 9 were used to give Compound WX10.

MS-ESI m/z: 407.0 [M+H]+.

$^1$H NMR (400 MHz, CHLOROFORM-d) δ ppm 1.42 (d, J=6.78 Hz, 3H) 2.30 (s, 3H) 3.43 (td, J=12.86, 3.64 Hz, 1H) 3.61-3.69 (m, 1H) 3.76-3.81 (m, 1H) 3.83-3.88 (m, 1H) 4.06 (dd, J=11.17, 3.39 Hz, 1H) 4.15 (s, 3H) 4.55 (br d, J=12.30 Hz, 1H) 4.91 (br d, J=4.52 Hz, 1H) 7.08 (br s, 1H) 7.16 (s, 1H) 7.23 (dd, J=8.78, 1.51 Hz, 1H) 7.34 (t, J=2.76 Hz, 1H) 7.40 (s, 1H) 7.48 (dd, J=10.54, 2.26 Hz, 1H) 8.50 (br s, 1H).

Example 11: Compound WX11

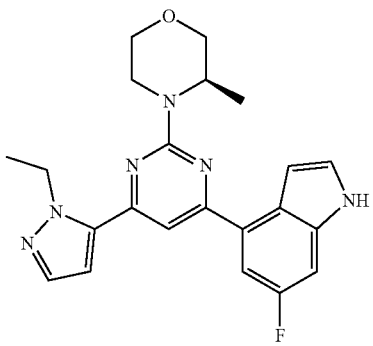

WX11

Synthesis Scheme

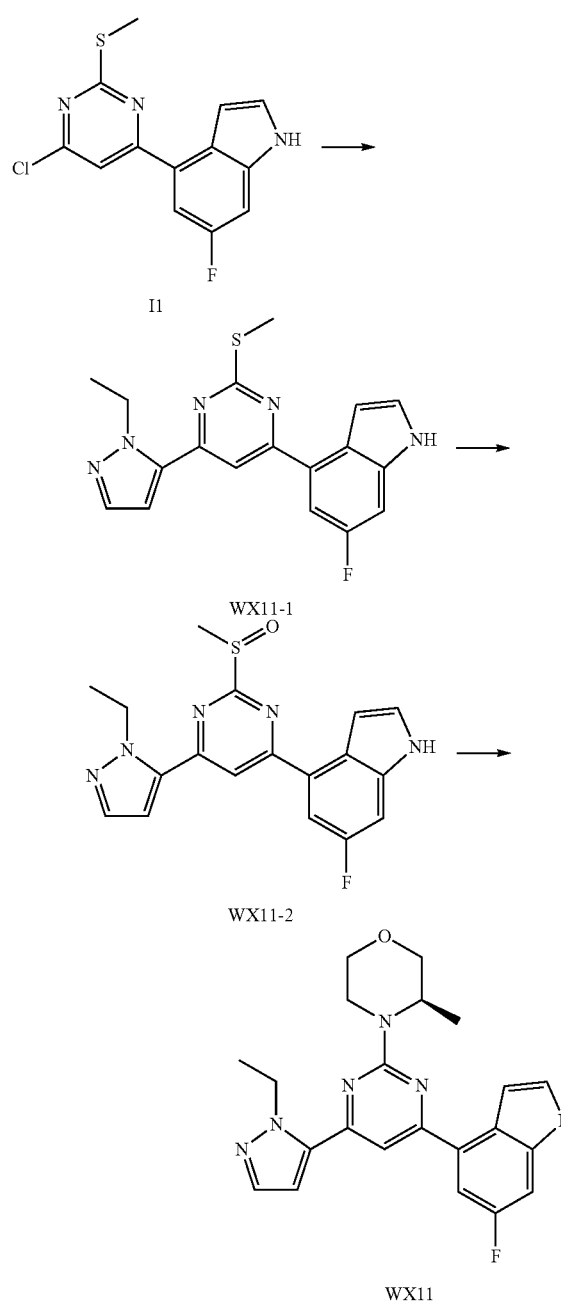

Step 1: Synthesis of Compound WX11-1

Except using corresponding raw materials, the procedures identical to those used for Compound WX09-1 in synthesis Example 9 were used to give WX11-1.
MS-ESI m/z: 354.0 [M+H]+.

Step 2: Synthesis of Compound WX11-2

Except using corresponding raw materials, the procedures identical to those used for Compound WX09-2 in synthesis Example 9 were used to give crude WX11-2.
MS-ESI m/z: 370.0[M+H]+.

Step 3: Synthesis of Compound WX11

Except using corresponding raw materials, the procedures identical to those used for Compound WX09 in synthesis Example 9 were used to give Compound WX11.
MS-ESI m/z: 407.0 [M+H]+.

$^1$H NMR (400 MHz, CHLOROFORM-d) δ ppm 1.42 (d, J=6.78 Hz, 3H) 1.52 (t, J=7.15 Hz, 3H) 3.40-3.48 (m, 1H) 3.64-3.69 (m, 1H) 3.77-3.82 (m, 1H) 3.83-3.89 (m, 1H) 4.04-4.10 (m, 1H) 4.53 (br d, J=13.05 Hz, 1H) 4.73-4.90 (m, 3H) 6.77 (d, J=1.76 Hz, 1H) 7.08 (br s, 1H) 7.23 (br d, J=8.78 Hz, 1H) 7.33 (s, 2H) 7.48 (dd, J=10.67, 1.88 Hz, 1H) 7.57 (d, J=1.51 Hz, 1H) 8.42 (br s, 1H).

Example 12: Compound WX12

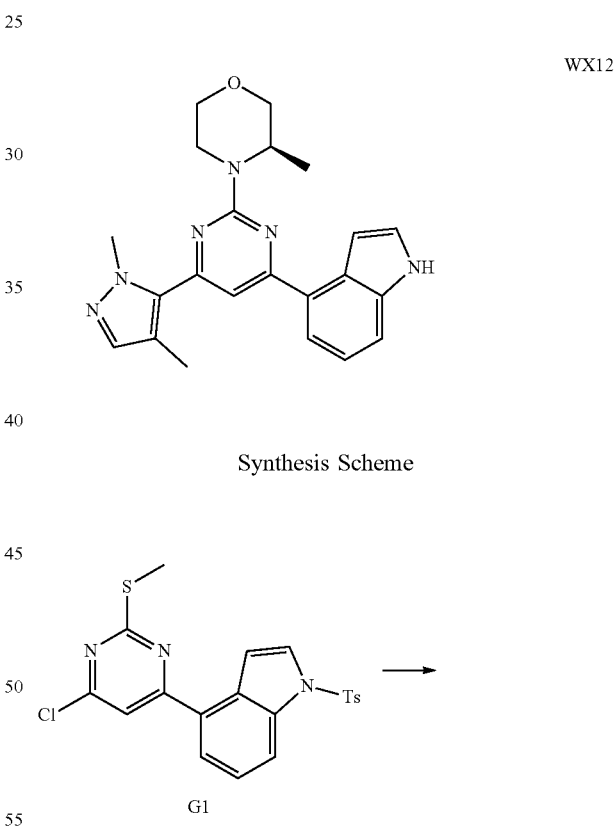

Synthesis Scheme

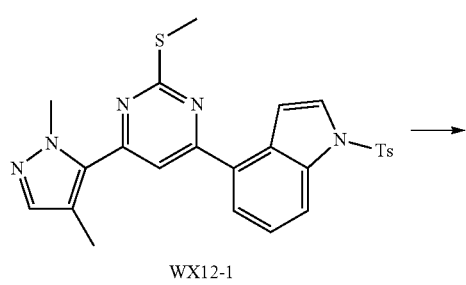

85

[Structure: WX12-2]

[Structure: WX12-3]

[Structure: WX12]

Step 1: Synthesis of Compound WX12-1

Except using corresponding raw materials, the procedures identical to those used for Compound WX04-1 in synthesis Example 4 were used to give WX12-1.

MS-ESI m/z: 490.1 [M+H]+.

Step 2: Synthesis of Compound WX12-2

Except using corresponding raw materials, the procedures identical to those used for Compound WX04-2 in synthesis Example 4 were used to give yellow crude WX12-2.

MS-ESI m/z: 522.1 [M+H]+.

Step 3: Synthesis of Compound WX12-3

Except using corresponding raw materials, the procedures identical to those used for Compound WX04-3 in synthesis Example 4 were used to give crude WX12-3.

MS-ESI m/z: 543.1 [M+H]+.

Step 4: Synthesis of Compound WX12

Except using corresponding raw materials, the procedures identical to those used for Compound WX04 in synthesis Example 4 were used to give Compound WX12.

MS-ESI m/z: 389.0 [M+H]+.

86

$^1$H NMR (400 MHz, CHLOROFORM-d) δ ppm 1.41-1.45 (m, 1H) 1.43 (d, J=6.78 Hz, 2H) 1.53 (t, J=7.15 Hz, 3H) 3.45 (td, J=12.92, 3.51 Hz, 1H) 3.66 (td, J=11.73, 2.64 Hz, 1H) 3.77-3.83 (m, 1H) 3.84-3.89 (m, 1H) 4.07 (br dd, J=11.29, 3.01 Hz, 1H) 4.55 (br d, J=13.55 Hz, 1H) 4.74-4.86 (m, 2H) 4.88 (br d, J=7.03 Hz, 1H) 6.76 (d, J=1.51 Hz, 1H) 7.16 (br s, 1H) 7.30-7.35 ((m, 1H) 7.37 (s, 2H) 7.52-7.58 (m, 2H) 7.69 (d, J=7.28 Hz, 1H) 8.41 (br s, 1H).

Example 13: Compound WX13

[Structure: WX13]

Synthesis Scheme

[Structure: D1]

[Structure: WX13]

Step 1: Synthesis of Compound WX13

To a solution of Compound D1 (0.075 g, 228.11 μmol) in 1,4-dioxane (5 mL) were added 1,4-dimethylpyrazole-5-pinacol borate (75.99 mg, 342.17 μmol), bistriphenylphosphine palladium dichloride (8.01 mg, 11.41 μmol) and sodium carbonate (2 M, 342.17 μL). The reaction solution was stirred under the protection of nitrogen at 90° C. for 15 h. After the reaction solution was filtered through celite, the filtrate was extracted with 30 mL of ethyl acetate (10 mL×3), and the organic phase was washed with 30 mL of water (10 mL×3) and dried over anhydrous sodium sulfate. After the desiccant was filtered off, the solvent was removed under reduced pressure to give the crude product, which was purified with preparative HPLC (neutral condition) to give Compound WX13.

MS-ESI m/z: 389.0 [M+H]+.

$^1$H NMR (400 MHz, CHLOROFORM-d) δ ppm 1.43 (d, J=6.78 Hz, 3H) 2.25 (s, 3H) 3.43 (td, J=12.74, 3.89 Hz, 1H) 3.69 (td, J=11.92, 3.01 Hz, 1H) 3.80-3.85 (m, 1H) 3.87-3.92 (m, 1H) 4.12 (dd, J=11.29, 3.51 Hz, 1H) 4.15-4.20 ((m, 1H) 4.16 (s, 2H) 4.34 (s, 1H) 4.27 (br d, J=13.30 Hz, 1H) 4.51 (br d, J=4.02 Hz, 1H) 6.41-6.56 (m, 1H) 6.47 (s, 1H) 7.29-7.36 (m, 1H) 7.33-7.35 (m, 1H) 7.41 (s, 1H) 7.50-7.58 (m, 1H) 7.52-7.56 (m, 1H) 8.25-8.37 (m, 2H).

Example 14: Compound WX14

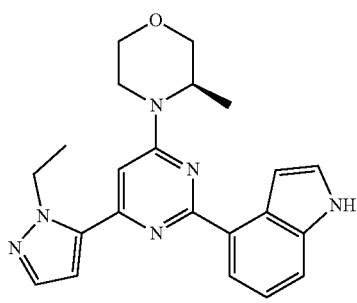

WX14

Synthesis Scheme

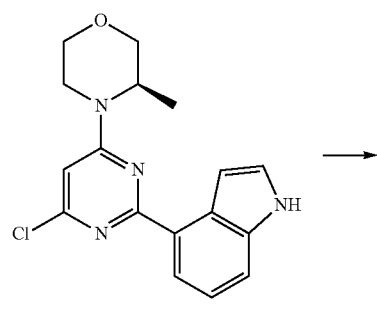

D1

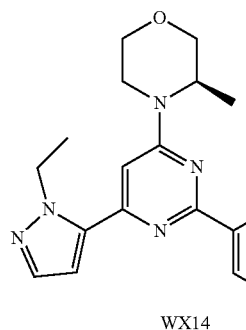

WX14

Step 1: Synthesis of Compound WX14

To a solution of Compound D1 (0.075 g, 228.11 μmol) in 1,4-dioxane (5 mL) were added 1-ethylpyrazole-5-pinacol borate (75.99 mg, 342.17 μmol), bistriphenylphosphine palladium dichloride (8.01 mg, 11.41 μmol) and sodium carbonate (2 M, 342.17 μL). The reaction mixture was stirred under the protection of nitrogen at 90° C. for 15 h. After the reaction solution was filtered through celite, the filtrate was extracted with 30 mL of ethyl acetate (10 mL×3), and the organic phase was washed with 30 mL of water (10 mL×3) and dried over anhydrous sodium sulfate. After the desiccant was filtered off, the solvent was removed under reduced pressure to give the crude product, which was purified with preparative HPLC (neutral condition) to give Compound WX14.

MS-ESI m/z: 389.0 [M+H]+.

$^1$H NMR (400 MHz, CHLOROFORM-d) δ ppm 1.43 (d, J=6.78 Hz, 3H) 1.51 (t, J=7.15 Hz, 3H) 3.44 (td, J=12.74, 3.89 Hz, 1H) 3.68 (td, J=11.92, 3.01 Hz, 1H) 3.79-3.86 (m, 1H) 3.87-3.92 (m, 1H) 4.11 (dd, J=11.42, 3.64 Hz, 1H) 4.23 (br d, J=13.05 Hz, 1H) 4.58 (br d, J=4.77 Hz, 1H) 4.86 (q, J=7.03 Hz, 2H) 6.63 (s, 1H) 6.65 (d, J=2.01 Hz, 1H) 7.30-7.36 (m, 2H) 7.50 (br s, 1H) 7.54 (d, J=8.03 Hz, 1H) 7.57 (d, J=1.76 Hz, 1H) 8.26 (d, J=7.53 Hz, 1H) 8.35 (br s, 1H).

Example 15: Compound WX15

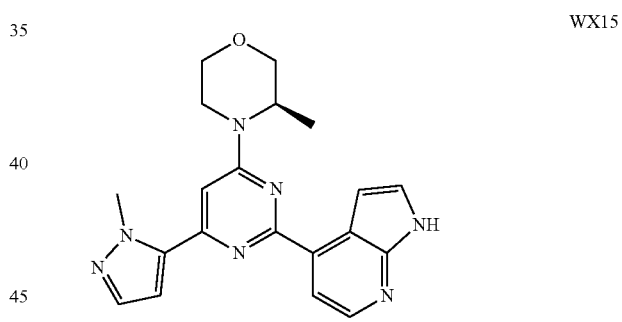

WX15

Synthesis Scheme

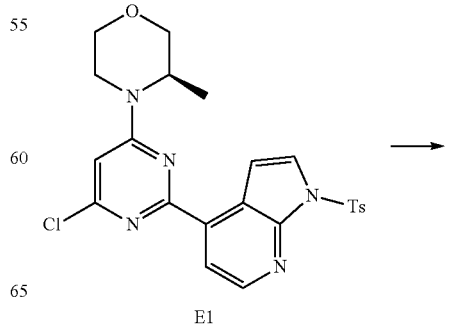

E1

89

-continued

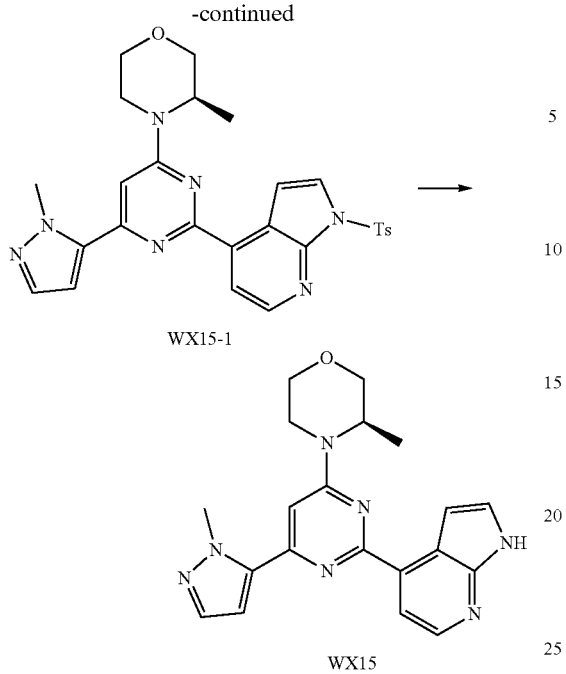

Step 1: Synthesis of Compound WX15-1

To a solution of Compound E1 (0.05 g, 103.31 μmol) in 1,4-dioxane (5 mL) were added 1-methylpyrazole-5-pinacol borate (25.79 mg, 123.97 μmol), bistriphenylphosphine palladium dichloride (7.25 mg, 10.33 μmol) and sodium carbonate (2 M, 154.97 μL). The reaction mixture was stirred under the protection of nitrogen at 90° C. for 15 h. After the reaction solution was filtered through celite, the filtrate was extracted with 30 mL of ethyl acetate (10 mL×3), and the organic phase was washed with 45 mL of water (15 mL×3) and dried over anhydrous sodium sulfate. After the desiccant was filtered off, the solvent was removed under reduced pressure to give crude WX15-1.

MS-ESI m/z: 530.2 [M+H]+.

Step 2: Synthesis of Compound WX15

To a solution of Compound WX15-1 (103 mg, 194.48 μmol) in methanol (2 mL) was added sodium hydroxide (2 M, 291.72 μL). The reaction mixture was stirred at 60° C. for 15 h. The reaction solution was extracted with 60 mL of ethyl acetate (20 mL×3), and the organic phase was washed with 60 mL of water (20 mL×3) and dried over anhydrous sodium sulfate. After the desiccant was filtered off, the solvent was removed under reduced pressure to give the crude product, which was purified with preparative HPLC (neutral condition) to give Compound WX15.

MS-ESI m/z: 376.0[M+H]+.

$^1$H NMR (400 MHz, CHLOROFORM-d) δ ppm 1.44 (d, J=6.78 Hz, 3H) 3.45 (td, J=12.74, 3.89 Hz, 1H) 3.68 (td, J=11.92, 3.01 Hz, 1H) 3.80-3.85 (m, 1H) 3.88-3.94 (m, 1H) 4.13 (dd, J=11.29, 3.51 Hz, 1H) 4.22 (br d, J=13.05 Hz, 1H) 4.38 (s, 3H) 4.58 (br d, J=4.77 Hz, 1H) 6.66-6.71 (m, 2H) 7.37 (d, J=1.51 Hz, 1H) 7.45-7.50 (m, 1H) 7.56 (d, J=2.01 Hz, 1H) 8.13 (d, J=5.02 Hz, 1H) 8.47 (d, J=5.02 Hz, 1H) 9.74 (br s, 1H).

90

Example 16: Compound WX16

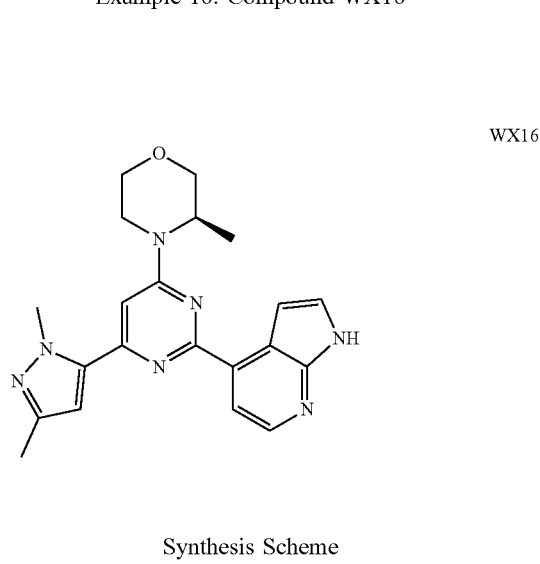

Synthesis Scheme

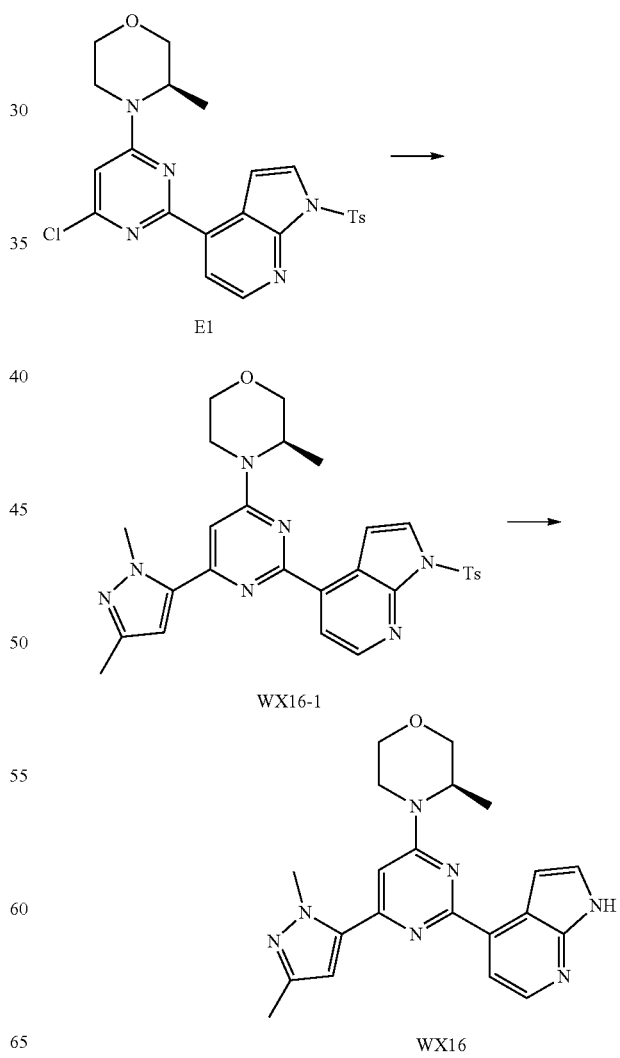

Step 1: Synthesis of Compound WX16-1

Except using corresponding raw materials, the procedures identical to those used for Compound WX15-1 in synthesis Example 15 were used to give crude WX16-1.

MS-ESI m/z: 544.1[M+H]+.

Step 2: Synthesis of Compound WX16

Except using corresponding raw materials, the procedures identical to those used for Compound WX15 in synthesis Example 15 were used to give Compound WX16.

MS-ESI m/z: 390.0 [M+H]+

$^1$H NMR (400 MHz, CHLOROFORM-d) δ ppm 1.43 (d, J=6.78 Hz, 3H) 2.34 (s, 3H) 3.44 (td, J=12.61, 3.89 Hz, 1H) 3.67 (td, J=11.80, 3.01 Hz, 1H) 3.78-3.85 (m, 1H) 3.87-3.93 (m, 1H) 4.12 (dd, J=11.29, 3.76 Hz, 1H) 4.21 (br d, J=12.80 Hz, 1H) 4.30 (s, 3H) 4.56 (br d, J=4.52 Hz, 1H) 6.47 (s, 1H) 6.66 (s, 1H) 7.3

Example 17: Compound WX17

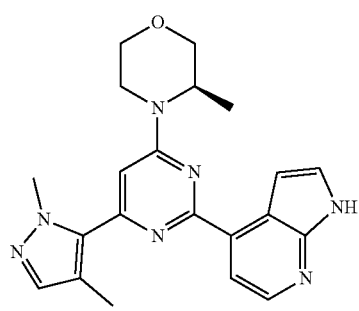
WX17

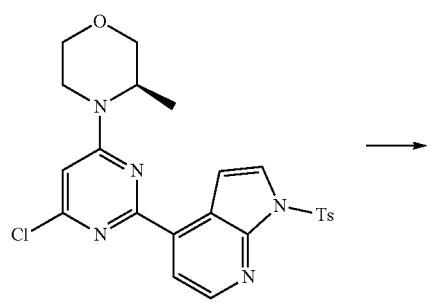
E1

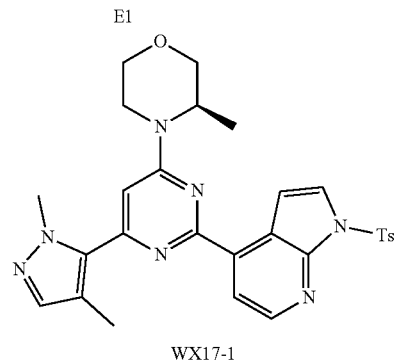
WX17-1

WX17

Step 1: Synthesis of Compound WX17-1

Except using corresponding raw materials, the procedures identical to those used for Compound WX15-1 in synthesis Example 15 were used to give crude WX17-1.

MS-ESI m/z: 544.1[M+H]+.

Step 2: Synthesis of Compound WX17

Except using corresponding raw materials, the procedures identical to those used for Compound WX15 in synthesis Example 15 were used to give Compound WX17.

MS-ESI m/z: 390.0 [M+H]+.

$^1$H NMR (400 MHz, CHLOROFORM-d) δ ppm 1.45 (d, J=6.78 Hz, 3H) 2.25 (s, 3H) 3.45 (td, J=12.80, 3.76 Hz, 1H) 3.69 (td, J=11.92, 2.76 Hz, 1H) 3.80-3.86 (m, 1H) 3.88-3.93 (m, 1H) 4.11-4.17 (m, 4H) 4.26 (br d, J=12.80 Hz, 1H) 4.50 (br s, 1H) 6.54 (s, 1H) 7.38-7.44 (m, 2H) 7.46 (br s, 1H) 8.15 (br d, J=3.51 Hz, 1H) 8.46 (br s, 1H) 9.67 (br s, 1H).

Example 18: Compound WX18

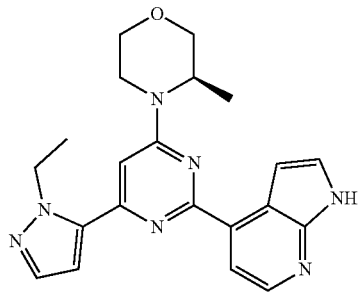
WX18

Synthesis Scheme

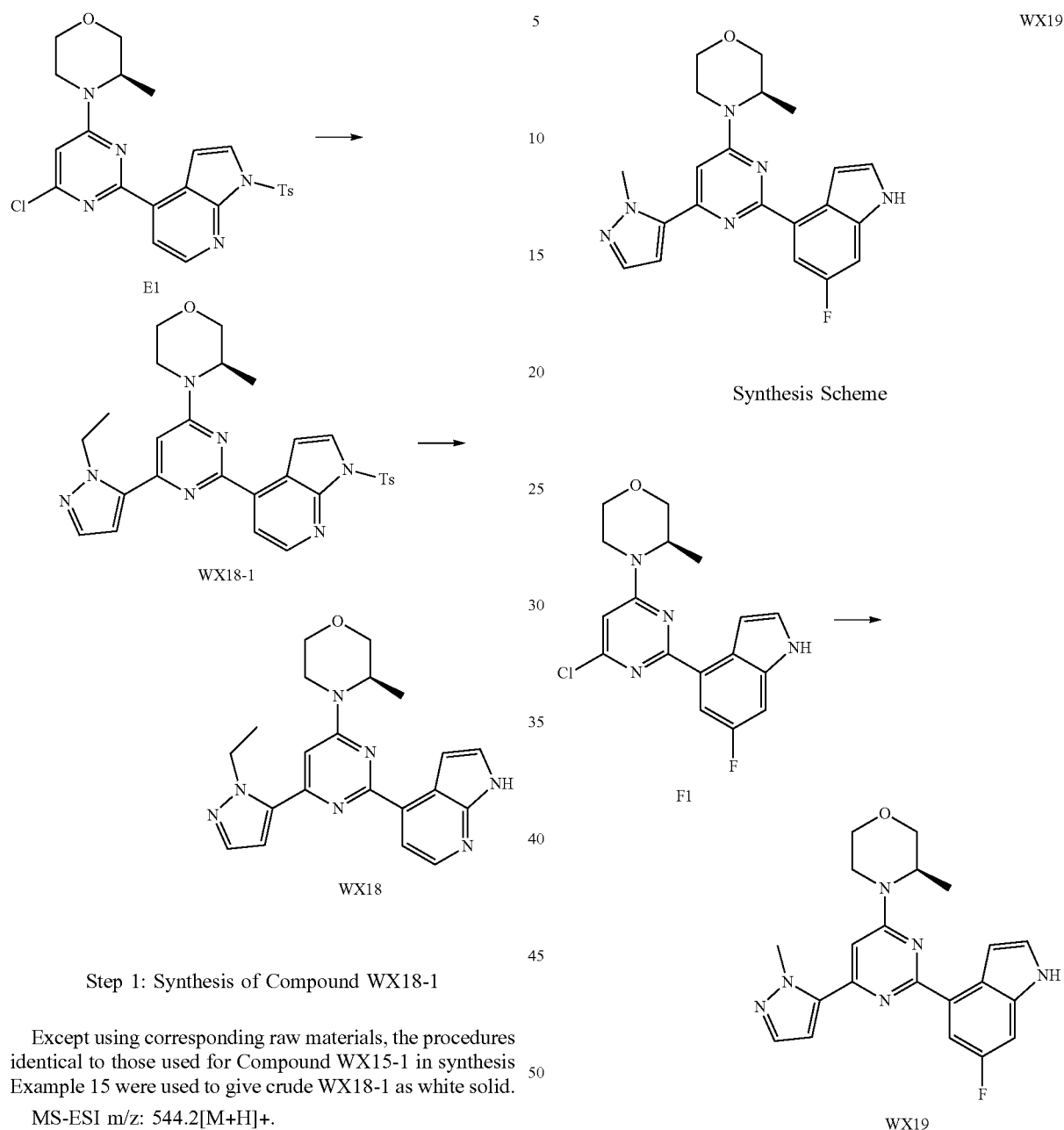

Step 1: Synthesis of Compound WX18-1

Except using corresponding raw materials, the procedures identical to those used for Compound WX15-1 in synthesis Example 15 were used to give crude WX18-1 as white solid.

MS-ESI m/z: 544.2[M+H]+.

Step 2: Synthesis of Compound WX18

Except using corresponding raw materials, the procedures identical to those used for Compound WX15 in synthesis Example 15 were used to give Compound WX18.

MS-ESI m/z: 390.0 [M+H]+.

$^1$H NMR (400 MHz, CHLOROFORM-d) δ ppm 1.46 (br d, J=6.53 Hz, 3H) 1.51 (br t, J=6.90 Hz, 3H) 3.42-3.55 (m, 1H) 3.68 (br t, J=11.67 Hz, 1H) 3.75-3.86 (m, 1H) 3.89-3.97 (m, 1H) 4.11-4.22 (m, 2H) 4.54 (br s, 1H) 4.69-4.82 (m, 2H) 6.70 (s, 1H) 6.78 (br s, 1H) 7.51-7.60 (m, 1H) 7.60-7.70 (m, 2H) 8.38 (br d, J=18.32 Hz, 2H) 12.42 (br s, 1H).

Example 19: Compound WX19

Step 1: Synthesis of Compound WX19

To a solution of Compound F1 (50 mg, 144.18 μmol) in 1,4-dioxane (5 mL) were added 1-methylpyrazole-5-pinacol borate (36.00 mg, 173.02 μmol), bistriphenylphosphine palladium dichloride (10.12 mg, 14.42 μmol) and sodium carbonate (2 M, 216.27 μL). The reaction solution was stirred under the protection of nitrogen at 9° C. for 15 h. After the reaction solution was filtered through celite, the filtrate was extracted with 30 mL of ethyl acetate (10 mL×3), and the organic phase was washed with 45 mL of water (15 mL×3) and dried over anhydrous sodium sulfate. After the desiccant was filtered off, the solvent was removed under reduced pressure to give the crude product, which was purified with preparative HPLC (neutral condition) to give Compound WX19.

MS-ESI m/z: 393.0 [M+H]+.

$^1$H NMR (400 MHz, CHLOROFORM-d) δ ppm 1.43 (d, J=6.78 Hz, 3H) 3.43 (td, J=12.61, 3.89 Hz, 1H) 3.67 (td, J=11.80, 2.76 Hz, 1H) 3.79-3.84 (m, 1H) 3.87-3.92 (m, 1H) 4.11 (dd, J=11.54, 3.51 Hz, 1H) 4.22 (br d, J=13.05 Hz, 1H) 4.36 (s, 3H) 4.56 (br s, 1H) 6.64 (s, 1H) 6.62-6.65 (m, 1H) 6.67 (d, J=1.76 Hz, 1H) 7.23 (br d, J=7.78 Hz, 1H) 7.32 (br s, 1H) 7.48 (br s, 1H) 7.55 (d, J=1.76 Hz, 1H) 8.03 (dd, J=11.17, 1.88 Hz, 1H) 8.34 (br s, 1H).

Example 20: Compound WX20

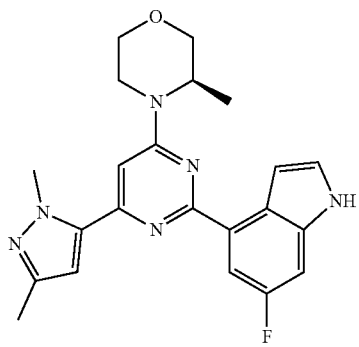

Synthesis Scheme

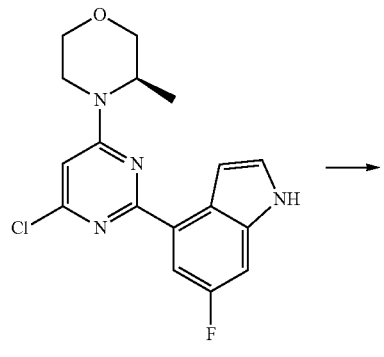

Step 1: Synthesis of Compound WX20

Except using corresponding raw materials, the procedures identical to those used for Compound WX19 in synthesis Example 19 were used to give Compound WX20.

MS-ESI m/z: 407.0 [M+H]+.

$^1$H NMR (400 MHz, CHLOROFORM-d) δ ppm 1.42 (d, J=6.78 Hz, 3H) 2.34 (s, 3H) 3.42 (td, J=12.74, 3.64 Hz, 1H) 3.66 (td, J=11.80, 2.76 Hz, 1H) 3.78-3.83 (m, 1H) 3.86-3.92 (m, 1H) 4.11 (br dd, J=11.42, 3.39 Hz, 1H) 4.21 (br d, J=13.30 Hz, 1H) 4.28 (s, 3H) 4.55 (br d, J=5.02 Hz, 1H) 6.46 (s, 1H) 6.61 (s, 1H) 7.21 (br d, J=7.53 Hz, 1H) 7.31 (br s, 1H) 7.48 (br s, 1H) 8.02 (dd, J=11.17, 1.63 Hz, 1H) 8.41 (br s, 1H).

Example 21: Compound WX21

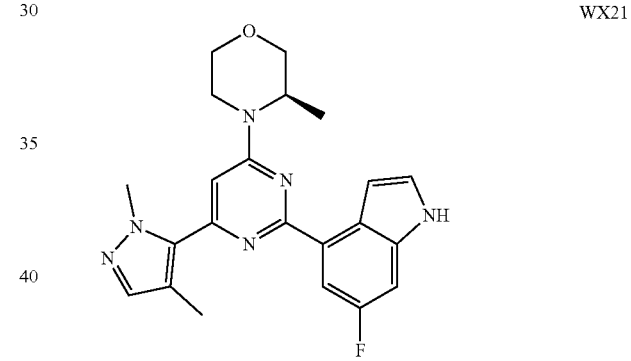

Synthesis Scheme

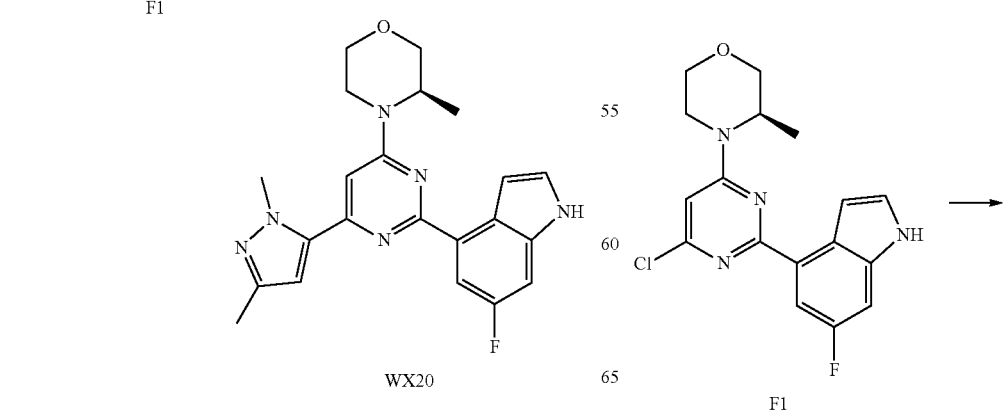

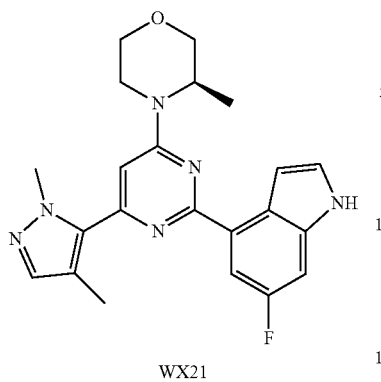

WX21

Step 1: Synthesis of Compound WX21

Except using corresponding raw materials, the procedures identical to those used for Compound WX19 in synthesis Example 19 were used to give Compound WX21.

MS-ESI m/z: 407.0 [M+H]+.

$^1$H NMR (400 MHz, CHLOROFORM-d) δ ppm 1.29 (d, J=6.78 Hz, 3H) 2.10 (s, 3H) 3.28 (td, J=12.74, 3.64 Hz, 1H) 3.54 (td, J=11.86, 2.64 Hz, 1H) 3.66-3.71 (m, 1H) 3.73-3.77 (m, 1H) 3.95-4.01 (m, 4H) 4.11 (br d, J=12.30 Hz, 1H) 4.34 (br s, 1H) 6.34 (s, 1H) 7.05-7.16 (m, 2H) 7.36 (br s, 1H) 7.90 (br d, J=10.54 Hz, 1H) 8.35 (br s, 1H).

Example 22: Compound WX22

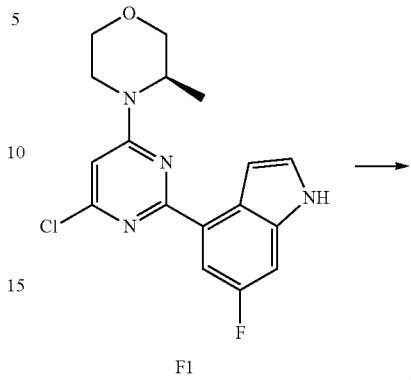

Synthesis Scheme

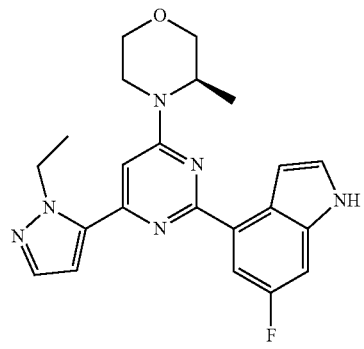

Step 1: Synthesis of Compound WX22

Except using corresponding raw materials, the procedures identical to those used for Compound WX19 in synthesis Example 19 were used to give Compound WX22.

MS-ESI m/z: 407.0 [M+H]+.

$^1$H NMR (400 MHz, CHLOROFORM-d) δ ppm 1.43 (d, J=6.78 Hz, 3H) 1.52 (t, J=7.15 Hz, 3H) 3.43 (td, J=12.80, 3.76 Hz, 1H) 3.67 (td, J=11.92, 2.76 Hz, 1H) 3.78-3.84 (m, 1H) 3.87-3.92 (m, 1H) 4.11 (dd, J=11.54, 3.51 Hz, 1H) 4.21 (br d, J=13.05 Hz, 1H) 4.56 (br d, J=5.02 Hz, 1H) 4.83 (q, J=7.03 Hz, 2H) 6.62-6.66 (m, 2H) 7.22 (dd, J=8.66, 1.88 Hz, 1H) 7.31 (t, J=2.64 Hz, 1H) 7.46 (br s, 1H) 7.57 (d, J=1.76 Hz, 1H) 8.01 (dd, J=11.42, 2.13 Hz, 1H) 8.49 (br s, 1H).

Example 23: Compound WX23

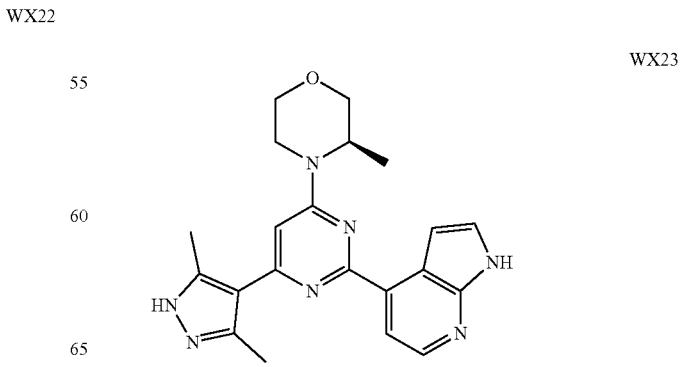

Synthesis Scheme

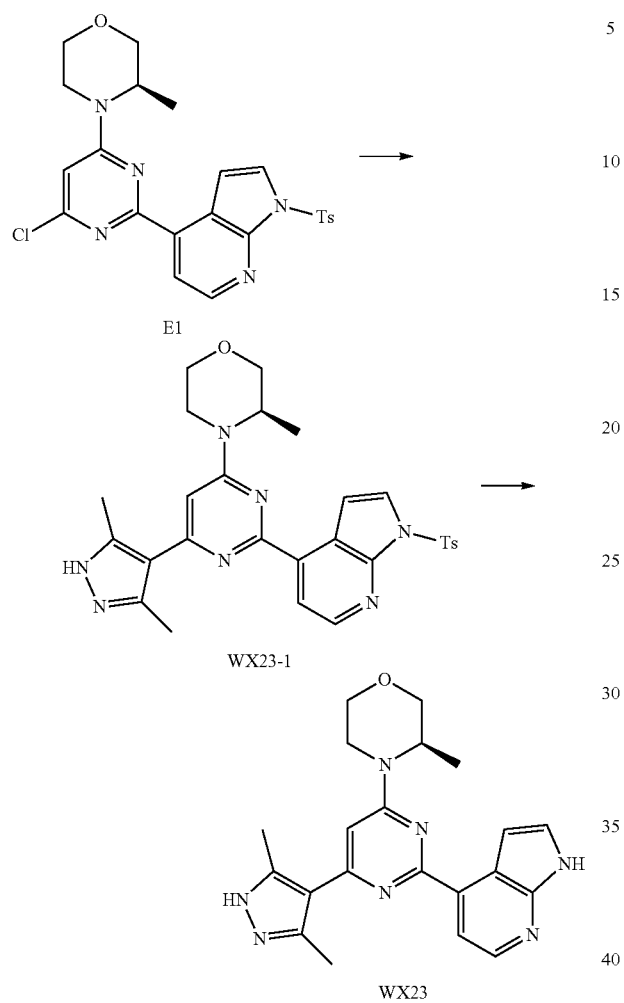

Step 1: Synthesis of Compound WX23-1

At room temperature, to a solution of Compound E1 (0.16 g, 330.60 μmol) in 1,4-dioxane (2.00 mL) were added 3,5-dimethylpyrazole-4-boric acid pinacol ester (110.13 mg, 495.90 μmol), tris(dibenzylacetone) dipalladium (30.27 mg, 33.06 μmol), 4,5-bis(diphenylphosphino)-9,9-dimethylxanthene (38.26 mg, 66.12 μmol), potassium phosphate (210.53 mg, 991.80 μmol), and water (0.2 mL), which was stirred at 120° C. in a microwave instrument for 20 min. The reaction system was cooled and then diluted with ethyl acetate (50 mL). The organic phase was washed with water (30 mL) and saturated brine (30 mL) and dried over anhydrous sodium sulfate. After the desiccant was filtered off, the solvent was removed under reduced pressure to give the crude product, which was purified with column chromatography (petroleum ether/ethyl acetate=4/1, 2/1) to give Compound WX23-1.

MS m/z: 544.1[M+H]$^+$.

Step 2: Synthesis of Compound WX23

At room temperature, to a solution of Compound WX23-1 (0.045 g, 82.78 μmol) in methanol (10.00 mL) was added sodium hydroxide solution (2 M, 206.94 μL), which was stirred at 30° C. for 16 h. The reaction system was concentrated under reduced pressure at 45° C. to give a mixture, which was dissolved with ethyl acetate (30 mL), washed with water (20 mL) and dried over anhydrous sodium sulfate. After the desiccant was filtered off, the solvent was removed under reduced pressure to give the crude product, which was purified with column chromatography (dichloromethane/methanol=100/1, 10/1) to give Compound WX23.

$^1$H NMR (400 MHz, DMSO-d$_6$) δ ppm 1.30 (br d, J=7.03 Hz, 3H) 2.43-2.45 (m, 6H) 3.37-3.42 (m, 1H) 3.51-3.62 (m, 1H) 3.71 (br d, J=11.54 Hz, 1H) 3.82 (br d, J=11.54 Hz, 1H) 4.03 (br d, J=10.04 Hz, 1H) 4.21 (br d, J=12.55 Hz, 1H) 4.60 (br s, 1H) 6.67 (s, 1H) 7.24 (br s, 1H) 7.58 (br s, 1H) 8.02 (d, J=4.77 Hz, 1H) 8.34 (d, J=5.02 Hz, 1H) 11.77 (br s, 1H) 12.54 (br s, 1H).

MS m/z: 390.0[M+H]$^+$.

Example 24: Compound WX24

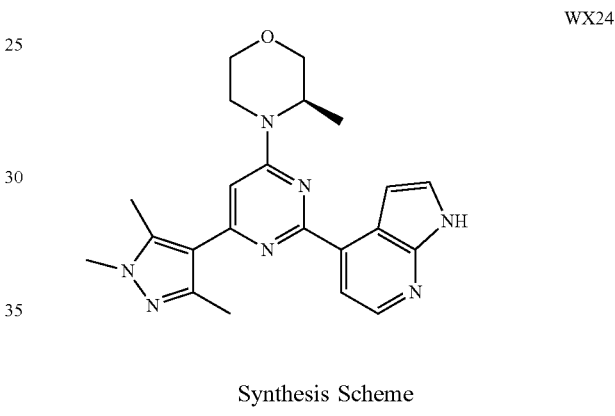

Synthesis Scheme

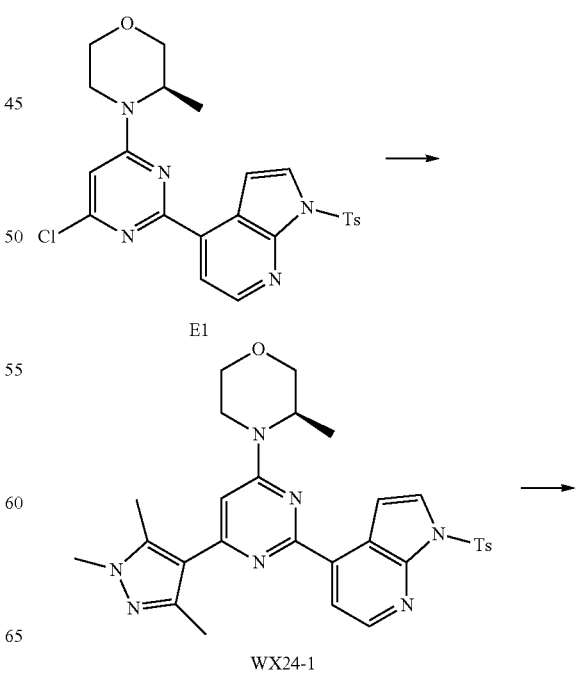

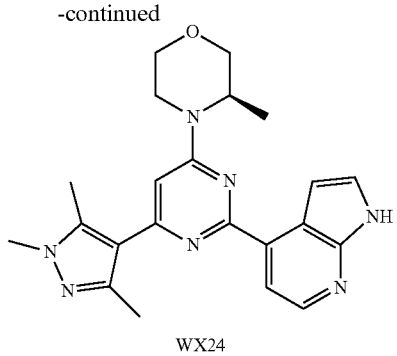

WX24

Step 1: Synthesis of Compound WX24-1

Except using corresponding raw materials, the procedures identical to those used for Compound WX23-1 in Example 23 were used to give the crude product, which was purified with column chromatography (petroleum ether: ethyl acetate=2/1, 1/2) to give WX24-1.

MS m/z: 558.1[M+H]$^+$.

Step 2: Synthesis of Compound WX24

At room temperature, to a solution of Compound WX24-1 (0.105 g, 188.28 μmol) in methanol (10.00 mL) was added sodium hydroxide solution (2 M, 941.42 μL), which was stirred at 30° C. for 15 h. The reaction system was concentrated under reduced pressure at 45° C. to give a mixture, which was dissolved with dichloromethane (30 mL), washed with water (20 mL) and saturated brine (20 mL), and dried over anhydrous sodium sulfate. After the desiccant was filtered off, the solvent was removed under reduced pressure to give the crude product, which was purified with column chromatography (dichloromethane/methanol=100/1, 12/1) to give Compound WX24.

$^1$H NMR (400 MHz, DMSO-d$_6$) δ ppm 1.27 (d, J=6.53 Hz, 3H) 2.36 (s, 3H) 2.51 (br s, 3H) 3.30 (br s, 1H) 3.50-3.57 (m, 1H) 3.68 (br d, J=8.53 Hz, 1H) 3.73 (s, 3H) 3.77-3.84 (m, 1H) 4.01 (br d, J=8.53 Hz, 1H) 4.20 (br d, J=11.29 Hz, 1H) 4.55 (br s, 1H) 6.63 (s, 1H) 7.22 (dd, J=3.26, 2.01 Hz, 1H) 7.56 (t, J=2.89 Hz, 1H) 7.99 (d, J=5.02 Hz, 1H) 8.32 (d, J=5.02 Hz, 1H) 11.75 (br s, 1H).

MS m/z: 404.0[M+H]$^+$.

Example 25: Compound WX25

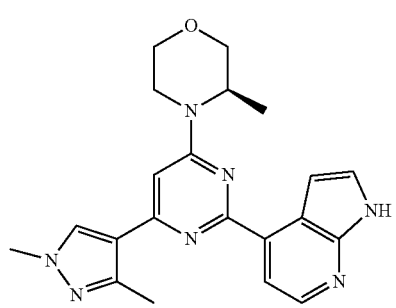

WX25

Synthesis Scheme

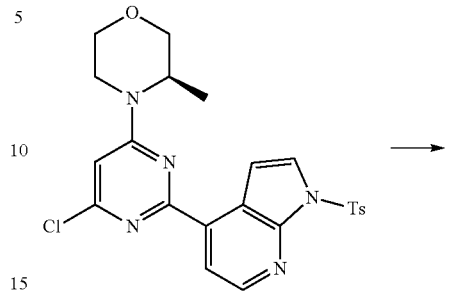

E1

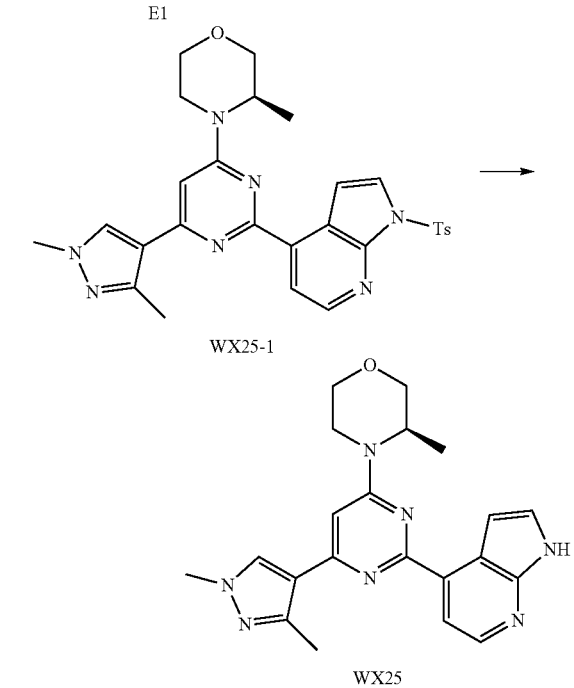

Step 1: Synthesis of Compound WX25-1

Except using corresponding raw materials, the procedures identical to those used for Compound WX23-1 in Example 23 were used to give the crude product, which was purified with column chromatography (petroleum ether: ethyl acetate=2/1, 1/2) to give Compound WX25-1.

MS m/z: 544.1[M+H]$^+$

Step 2: Synthesis of Compound WX25

Except using corresponding raw materials, the procedures identical to those used for Compound WX23 in Example 23 were used to give the crude product, which was purified with column chromatography (dichloromethane: methanol=100/1, 10/1) to give Compound WX25.

$^1$H NMR (400 MHz, DMSO-d$_6$) δ ppm 1.27 (d, J=6.78 Hz, 3H) 2.55 (s, 3H) 3.20-3.27 (m, 1H) 3.49-3.58 (m, 1H) 3.68 (dd, J=11.29, 2.76 Hz, 1H) 3.78-3.85 (m, 4H) 4.01 (br d, J=8.28 Hz, 1H) 4.18 (br d, J=13.80 Hz, 1H) 4.60 (br s, 1H) 6.85 (s, 1H) 7.23 (dd, J=3.26, 2.01 Hz, 1H) 7.57 (t, J=2.89 Hz, 1H) 8.02 (d, J=5.02 Hz, 1H) 8.32 (d, J=5.02 Hz, 1H) 8.40 (s, 1H) 11.75 (br s, 1H).

MS m/z: 390.0[M+H]+.

Example 26: Compound WX26

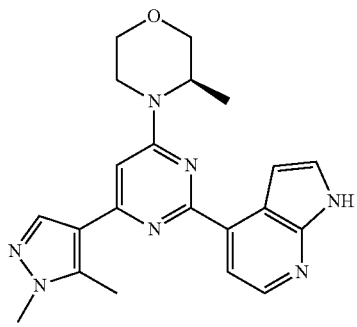

Synthesis Scheme

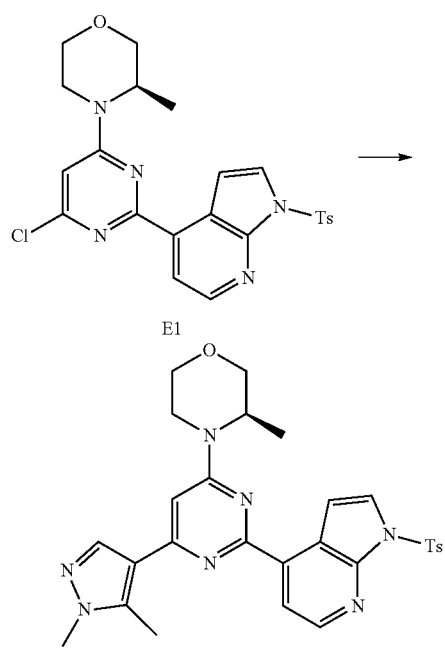

Step 1: Synthesis of Compound WX26-1

Except using corresponding raw materials, the procedures identical to those used for Compound WX23-1 in Example 23 were used to give the crude product, which was purified with column chromatography (petroleum ether: ethyl acetate=2/1, 1/2) to give Compound WX26-1.

MS m/z: 544.2[M+H]+.

Step 2: Synthesis of Compound WX26

Except using corresponding raw materials, the procedures identical to those used for Compound WX23 in Example 23 were used to give the crude product, which was purified with column chromatography (dichloromethane: methanol=100/1, 12/1) to give Compound WX26.

$^1$H NMR (400 MHz, DMSO-$d_6$) δ ppm 1.27 (d, J=6.78 Hz, 3H) 2.74 (s, 3H) 3.22-3.28 (m, 1H) 3.48-3.57 (m, 1H) 3.68 (dd, J=11.54, 2.76 Hz, 1H) 3.78-3.84 (m, 4H) 3.96-4.04 (m, 1H) 4.21 (br d, J=12.55 Hz, 1H) 4.65 (br s, 1H) 6.92 (s, 1H) 7.21 (dd, J=3.26, 2.01 Hz, 1H) 7.55-7.59 (m, 1H) 7.98 (d, J=5.02 Hz, 1H) 8.11 (s, 1H) 8.33 (d, J=5.02 Hz, 1H) 11.76 (br s, 1H).

MS m/z: 390.1[M+H]+.

Example 27: Compound WX27

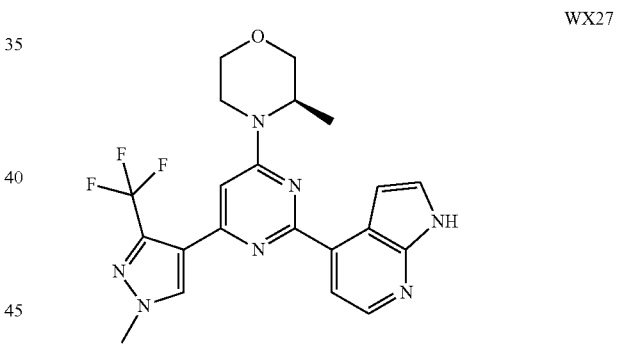

Synthesis Scheme

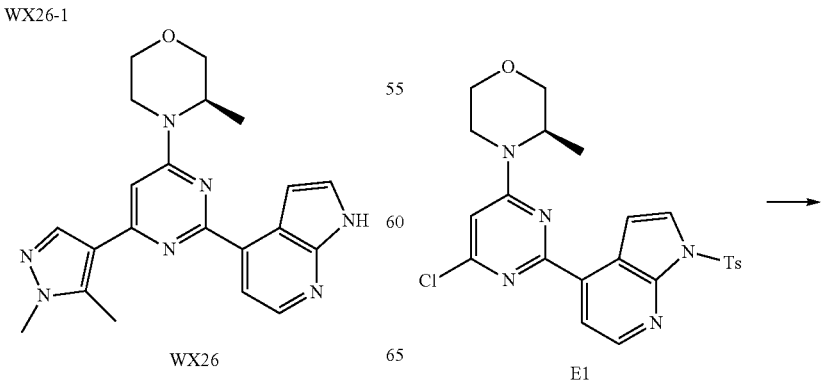

105

-continued

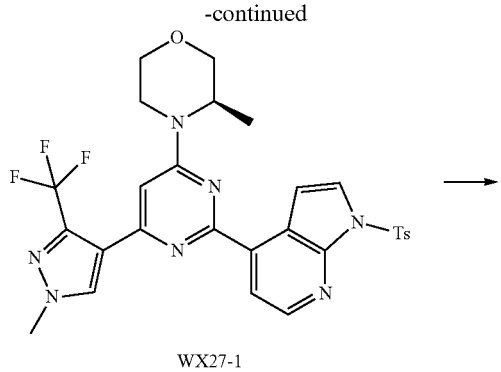

WX27-1

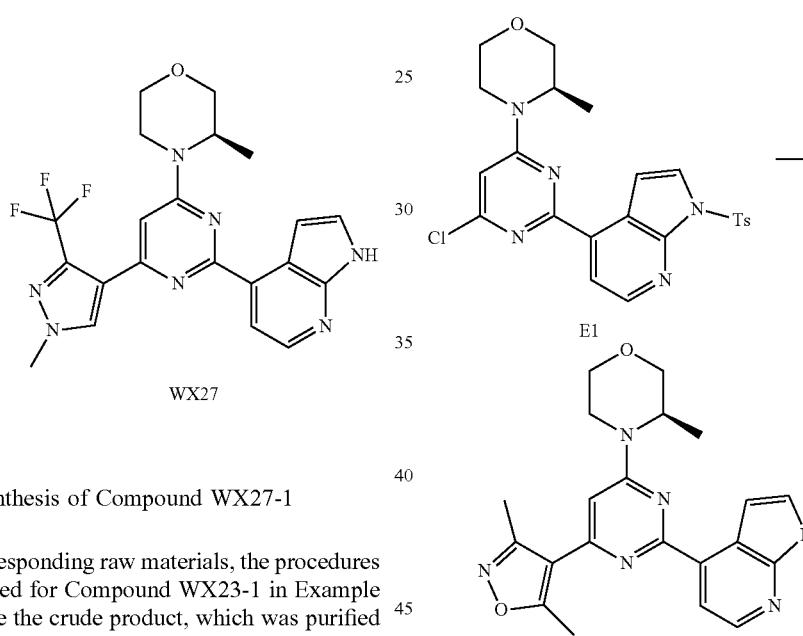

WX27

Step 1: Synthesis of Compound WX27-1

Except using corresponding raw materials, the procedures identical to those used for Compound WX23-1 in Example 23 were used to give the crude product, which was purified with column chromatography (petroleum ether: ethyl acetate=4/1, 2/1) to give Compound WX27-1.

MS m/z: 598.1[M+H]$^+$.

Step 2: Synthesis of Compound WX27

Except using corresponding raw materials, the procedures identical to those used for Compound WX23 in Example 23 were used to give the crude product, which was purified with column chromatography (dichloromethane: methanol=100/1, 20/1) to give Compound WX27.

$^1$H NMR (400 MHz, DMSO-d$_6$) δ ppm 1.29 (d, J=6.76 Hz, 3H) 3.25-3.30 (m, 1H) 3.54 (td, J=11.84, 3.14 Hz, 1H) 3.69 (dd, J=11.52, 2.76 Hz, 1H) 3.82 (d, J=11.28 Hz, 1H) 3.98-4.06 (m, 4H) 4.19 (br d, J=11.52 Hz, 1H) 4.56 (br s, 1H) 6.95 (s, 1H) 7.22 (dd, J=3.40, 1.88 Hz, 1H) 7.55-7.59 (m, 1H) 8.07 (d, J=5.28 Hz, 1H) 8.32 (d, J=5.04 Hz, 1H) 8.67 (s, 1H) 11.77 (br s, 1H).

MS m/z: 444.0[M+H]$^+$.

106

Example 28: Compound WX28

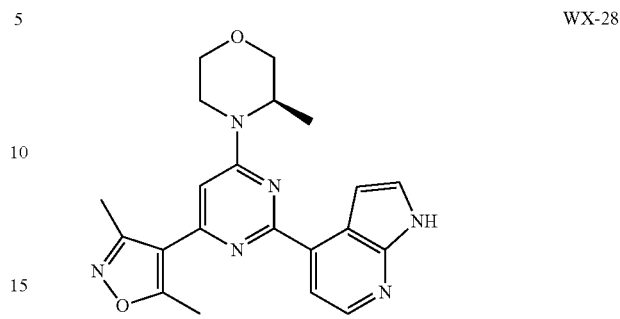

WX-28

Synthesis Scheme

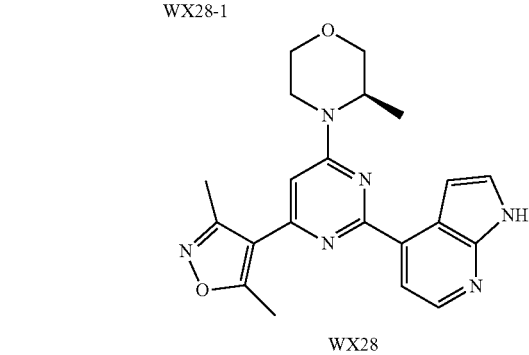

Step 1: Synthesis of Compound WX28-1

Except using corresponding raw materials, the procedures identical to those used for Compound WX23-1 in Example 23 were used to give the crude product, which was purified with column chromatography (petroleum ether: ethyl acetate=2/1, 2/1) to give Compound WX28-1.

MS m/z: 545.1[M+H]⁺

Step 2: Synthesis of Compound WX28

Except using corresponding raw materials, the procedures identical to those used for Compound WX23 in Example 23 were used to give the crude product, which was purified with column chromatography (dichloromethane: methanol=100/1, 9/1) to give Compound WX28.

¹H NMR (400 MHz, DMSO-d₆) δ ppm 1.32 (br d, J=6.28 Hz, 3H) 2.31-2.47 (m, 3H) 2.70 (br s, 3H) 3.56 (br t, J=11.16 Hz, 1H) 3.71 (br d, J=11.28 Hz, 1H) 3.79-3.89 (m, 1H) 4.04 (br d, J=8.76 Hz, 1H) 4.27 (br d, J=10.56 Hz, 1H) 4.64 (br s, 1H) 6.84 (br s, 1H) 7.22 (br s, 1H) 7.60 (br s, 1H) 8.02 (br s, 1H) 8.36 (br s, 1H) 11.82 (br s, 1H).

MS m/z: 391.0[M+H]⁺.

Example 29: Compound WX29

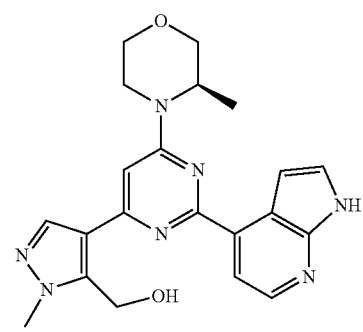

WX29

Synthesis Scheme

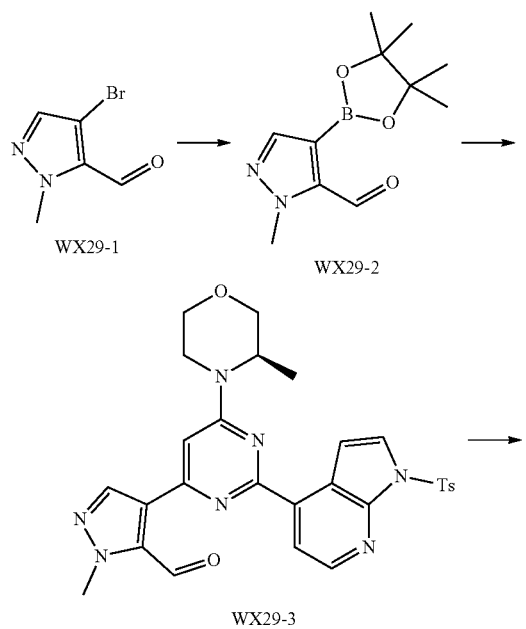

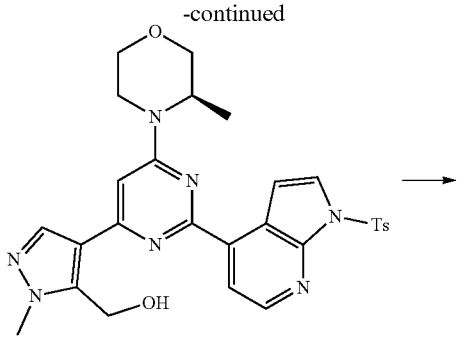

WX29-4

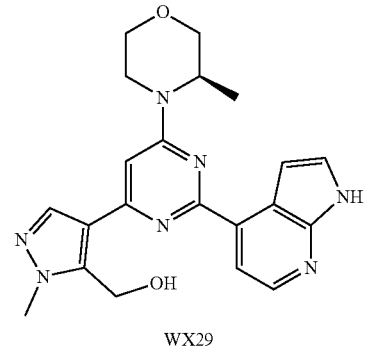

WX29

Step 1: Synthesis of Compound WX29-2

At room temperature, to a solution of Compound WX29-1 (0.3 g, 1.59 mmol) in 1,4-dioxane (8 mL) were added bispinacol borate (90.16 mg, 464.91 μmol), [1,1'-bis(diphenylphosphino)ferrocene]palladium dichloride dichloromethane complex (64.81 mg, 79.36 μmol), and potassium acetate (467.32 mg, 4.76 mmol), which was stirred at 100° C. in a microwave instrument for 1 h. The reaction system was cooled and then diluted with ethyl acetate (30 mL). After filtration, the solvent was removed under reduced pressure to give the crude product, which was purified with column chromatography (petroleum ether/ethyl acetate=10/1,5/1) to give Compound WX29-2.

MS m/z: 237.0[M+H]⁺.

Step 2: Synthesis of Compound WX29-3

At room temperature, to a solution of Compound E1 (0.15, 309.94 μmol) in 1,4-dioxane (2.00 mL) were added WX29-2 (87.80 mg, 371.93 μmol), tris(dibenzylacetone)dipalladium (28.38 mg, 30.99 μmol), 4,5-bis(diphenylphosphino)-9,9-dimethylxanthene (35.87 mg, 61.99 μmol), potassium phosphate (197.37 mg, 929.82 μmol), and water (0.2 mL), which was stirred at 120° C. in a microwave instrument for 20 min. The reaction system was cooled and then diluted with ethyl acetate (30 mL). The organic phase was washed with water (30 mL) and dried over anhydrous sodium sulfate. After the desiccant was filtered off, the solvent was removed under reduced pressure to give the crude product, which was purified with column chromatography (petroleum ether/ethyl acetate=2/1,1/2) to give Compound WX29-3. MS m/z: 558.1[M+H]⁺.

Step 3: Synthesis of Compound WX29-4

At room temperature, to a solution of Compound WX29-3 (0.12 g, 215.20 μmol) in methanol (8.00 mL) was added sodium borohydride (16.28 mg, 430.40 µmol), which was stirred at 30° C. for 4 h. The reaction system was concentrated under reduced pressure at 45° C. to give a mixture, which was dissolved with ethyl acetate (30 mL), washed with water (20 mL) and dried over anhydrous sodium sulfate. After the desiccant was filtered off, the solvent was removed under reduced pressure to give crude Compound WX29-4.

MS m/z: 560.1[M+H]$^+$.

Step 4: Synthesis of Compound WX29

At room temperature, to a solution of Compound WX29-4 (0.09 g, 150.60 µmol) in methanol (10.00 mL) was added sodium hydroxide solution (2 M, 753.00 µL), which was stirred at 30° C. for 15 h. The reaction system was concentrated under reduced pressure at 45° C. to give a mixture, which was dissolved with dichloromethane (30 mL), washed with saturated brine (20 mL) and dried over anhydrous sodium sulfate. After the desiccant was filtered off, the solvent was removed under reduced pressure to give the crude product, which was purified with column chromatography (dichloromethane/methanol=100/1, 15/1) to give Compound WX29.

$^1$H NMR (400 MHz, DMSO-d$_6$) δ ppm 1.30 (d, J=6.52 Hz, 3H) 3.26-3.30 (m, 1H) 3.51-3.60 (m, 1H) 3.71 (br d, J=9.04 Hz, 1H) 3.79-3.87 (m, 1H) 3.93 (s, 3H) 4.04 (br d, J=8.04 Hz, 1H) 4.24 (br d, J=12.56 Hz, 1H) 4.65 (br s, 1H) 5.05 (br d, J=4.52 Hz, 2H) 5.61 (br s, 1H) 7.04 (s, 1H) 7.23 (br s, 1H) 7.60 (t, J=2.76 Hz, 1H) 7.98 (d, J=4.76 Hz, 1H) 8.15 (s, 1H) 8.36 (d, J=5.04 Hz, 1H) 11.79 (br s, 1H).

MS m/z: 406.0[M+H]$^+$.

Example 30: Compound WX30

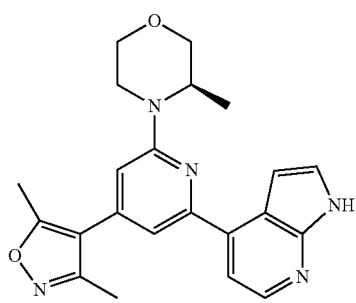

WX30

Synthesis Scheme

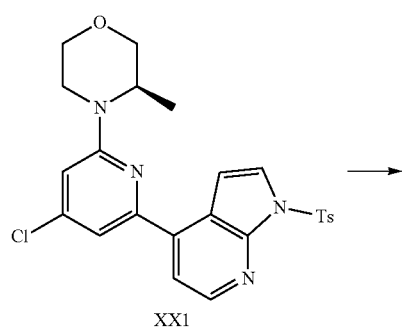

XX1

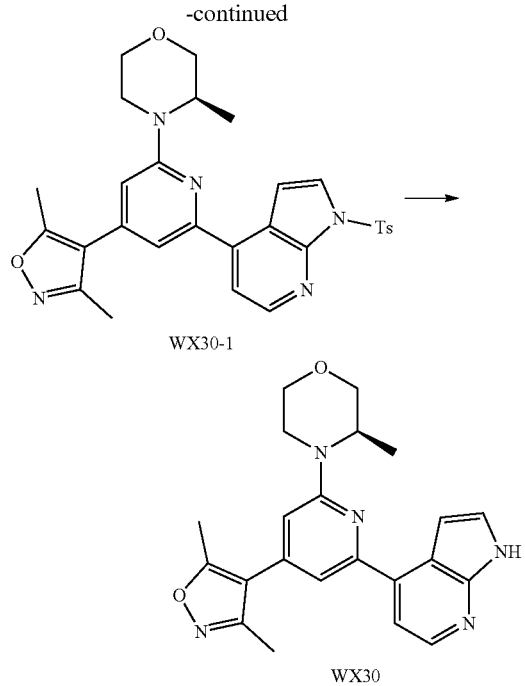

WX30-1

WX30

Step 1: Synthesis of Compound WX30-1

At room temperature, to a solution of Compound XX1 (0.1 g, 207.05 µmol) in 1,4-dioxane (10.00 mL) were added 3,5-dimethylisoxazole-4-boric acid pinacol ester (55.42 mg, 248.46 µmol), tris(dibenzylacetone) dipalladium (18.96 mg, 20.70 µmol), 4,5-bis(diphenylphosphino)-9,9-dimethylxanthene (23.96 mg, 41.41 µmol), potassium phosphate (131.85 mg, 621.14 µmol) and water (0.2 mL), which was stirred at 120° C. in a microwave instrument for 20 min. The reaction system was cooled and then diluted with ethyl acetate (30 mL). The organic phase was washed with water (30 mL) and dried over anhydrous sodium sulfate. After the desiccant was filtered off, the solvent was removed under reduced pressure to give the crude product, which was purified with column chromatography (petroleum ether/ethyl acetate=2/1,1/1) to give Compound WX30-1.

MS m/z: 566.1[M+Na]$^+$.

Step 2: Synthesis of Compound WX30

At room temperature, to a solution of Compound WX30-1 (0.06 g, 110.37 µmol) in methanol (10.00 mL) was added sodium hydroxide solution (2 M, 551.84 uL), which was stirred at 40° C. for 15 h. The reaction system was concentrated under reduced pressure at 45° C. to give a mixture, which was dissolved with ethyl acetate (30 mL), washed with water (20 mL) and dried over anhydrous sodium sulfate. After the desiccant was filtered off, the solvent was removed under reduced pressure to give the crude product, which was purified with column chromatography (dichloromethane/methanol=40/1, 20/1) to give Compound WX30.

$^1$H NMR (400 MHz, DMSO-d$_6$) δ ppm 1.23 (d, J=6.53 Hz, 3H) 2.34 (s, 3H) 2.52 (br s, 3H) 3.20 (td, J=12.67, 3.76 Hz, 1H) 3.50-3.60 (m, 1H) 3.66-3.73 (m, 1H) 3.76-3.82 (m, 1H) 4.00 (dd, J=11.04, 3.01 Hz, 1H) 4.10 (br d, J=11.29 Hz, 1H) 4.50 (br d, J=6.78 Hz, 1H) 6.80 (s, 1H) 6.93 (dd, J=3.39, 1.88 Hz, 1H) 7.27 (s, 1H) 7.55-7.60 (m, 2H) 8.30 (d, J=5.02 Hz, 1H) 11.79 (br s, 1H).

MS m/z: 390.2[M+H]⁺.

Example 31: Compound WX31

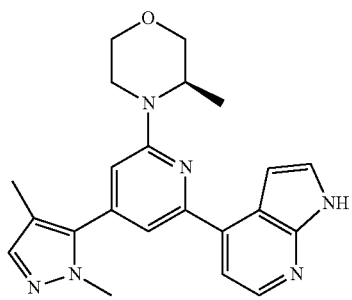

WX31

Synthesis Scheme

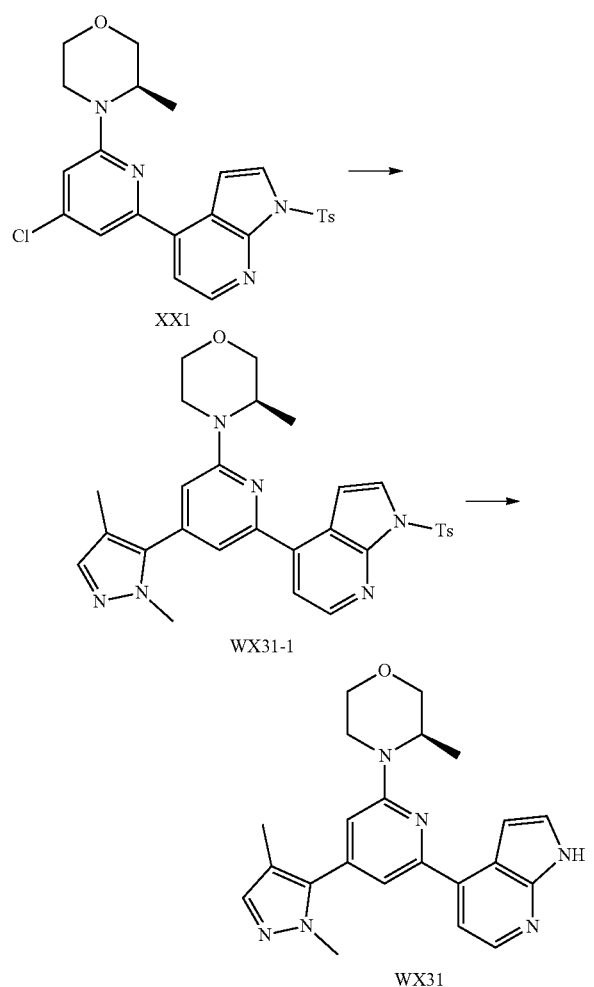

Step 1: Synthesis of Compound WX31-1

Except using corresponding raw materials, the procedures identical to those used for Compound WX30-1 in Example 30 were used to give the crude product, which was purified with column chromatography (dichloromethane: methanol=30/1, 10/1) to give Compound WX31-1.
MS m/z: 543.1[M+H]⁺.

Step 2: Synthesis of Compound WX31

Except using corresponding raw materials, the procedures identical to those used for Compound WX30 in Example 30 were used to give the crude product, which was purified with column chromatography (dichloromethane: methanol=30/1, 10/1) to give Compound WX31.
¹H NMR (400 MHz, DMSO-d₆) δ ppm 1.24 (d, J=6.53 Hz, 3H) 2.08 (s, 3H) 3.21 (td, J=12.61, 3.64 Hz, 1H) 3.55 (td, J=11.73, 2.89 Hz, 1H) 3.67-3.73 (m, 1H) 3.76-3.81 (m, 1H) 3.84 (s, 3H) 3.97-4.02 (m, 1H) 4.14 (br d, J=12.05 Hz, 1H) 4.50 (br d, J=6.27 Hz, 1H) 6.84 (s, 1H) 6.93 (dd, J=3.39, 1.88 Hz, 1H) 7.28 (s, 1H) 7.39 (s, 1H) 7.56-7.60 (m, 2H) 8.30 (d, J=5.02 Hz, 1H) 11.80 (br s, 1H).
MS m/z: 389.2[M+H]⁺.

Example 32: Compound WX32

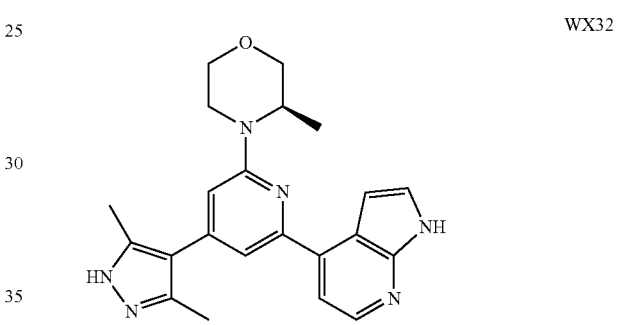

WX32

Synthesis Scheme

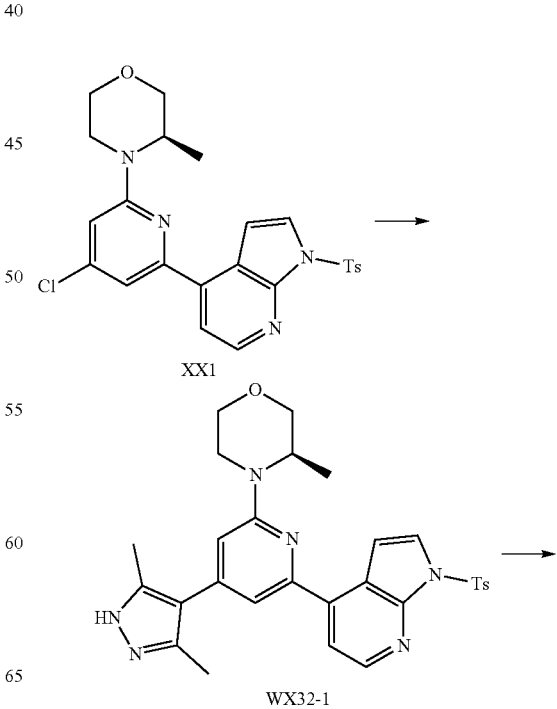

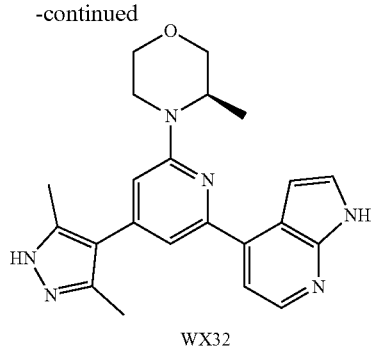

WX32

Except using corresponding raw materials, the procedures identical to those used for Compound WX0-1 in Example 30 were used to give the crude product, which was purified with column chromatography (dichloromethane: methanol=30/1, 10/1) to give Compound WX32-1.

MS m/z: 543.1[M+H]$^+$.

Step 2: Synthesis of Compound WX32

Except using corresponding raw materials, the procedures identical to those used for Compound WX30 in Example 30 were used to give the crude product, which was purified with column chromatography (dichloromethane: methanol=30/1, 10/1) to give Compound WX32.

$^1$H NMR (400 MHz, DMSO-d$_6$) δ ppm 1.22 (d, J=6.53 Hz, 3H) 2.27-2.39 (m, 6H) 3.18 (td, J=12.61, 3.64 Hz, 1H) 3.50-3.59 (m, 1H) 3.65-3.73 (m, 1H) 3.75-3.81 (m, 1H) 3.95-4.03 (m, 1H) 4.07 (br d, J=11.54 Hz, 1H) 4.47 (br d, J=5.27 Hz, 1H) 6.68 (s, 1H) 6.91 (dd, J=3.39, 1.88 Hz, 1H) 7.21 (s, 1H) 7.52-7.59 (m, 2H) 8.29 (d, J=5.02 Hz, 1H) 11.76 (br s, 1H) 12.48 (br s, 1H).

MS m/z: 389.2[M+H]$^+$.

Example 33: Compound WX33

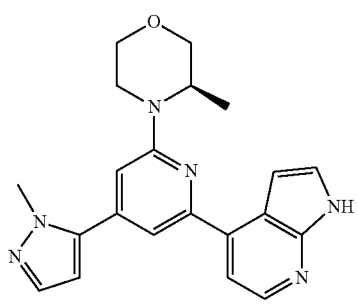

WX33

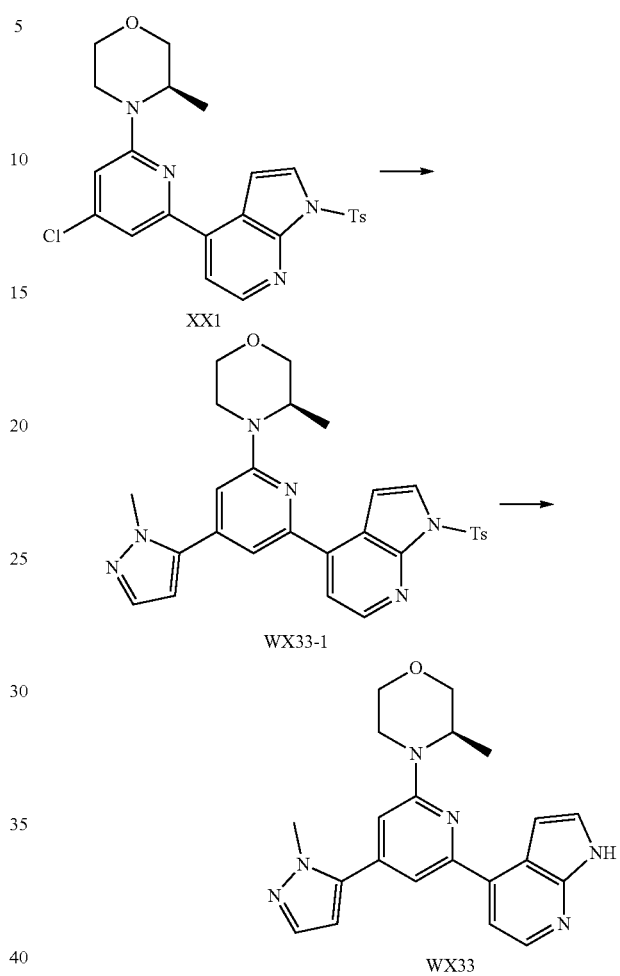

Step 1: Synthesis of Compound WX33-1

Except using corresponding raw materials, the procedures identical to those used for Compound WX30-1 in Example 30 were used to give the crude product, which was purified with column chromatography (dichloromethane: methanol=30/1, 10/1) to give Compound WX33-1.

MS m/z: 529.1[M+H]$^+$.

Step 2: Synthesis of Compound WX33

Except using corresponding raw materials, the procedures identical to those used for Compound WX30 in Example 30 were used to give the crude product, which was purified with column chromatography (dichloromethane: methanol=30/1, 10/1) to give Compound WX33.

$^1$H NMR (400 MHz, DMSO-d$_6$) δ ppm 1.24 (d, J=6.53 Hz, 3H) 3.22 (td, J=12.61, 3.64 Hz, 1H) 3.55 (td, J=11.73, 2.64 Hz, 1H) 3.67-3.74 (m, 1H) 3.76-3.81 (m, 1H) 3.99 (s, 4H) 4.11 (br d, J=11.54 Hz, 1H) 4.55 (br d, J=7.03 Hz, 1H) 6.67 (d, J=1.76 Hz, 1H) 6.89-7.01 (m, 2H) 7.40 (s, 1H) 7.54 (d, J=1.76 Hz, 1H) 7.56-7.58 (m, 1H) 7.60 (d, J=5.02 Hz, 1H) 8.31 (d, J=5.02 Hz, 1H) 11.79 (br s, 1H) MS m/z: 375.2[M+H]$^+$.

Example 34

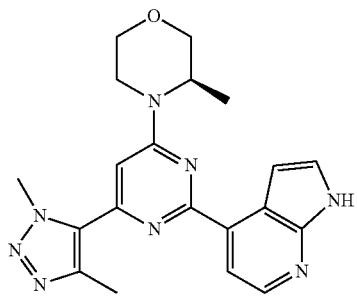
WX34

Synthesis Scheme

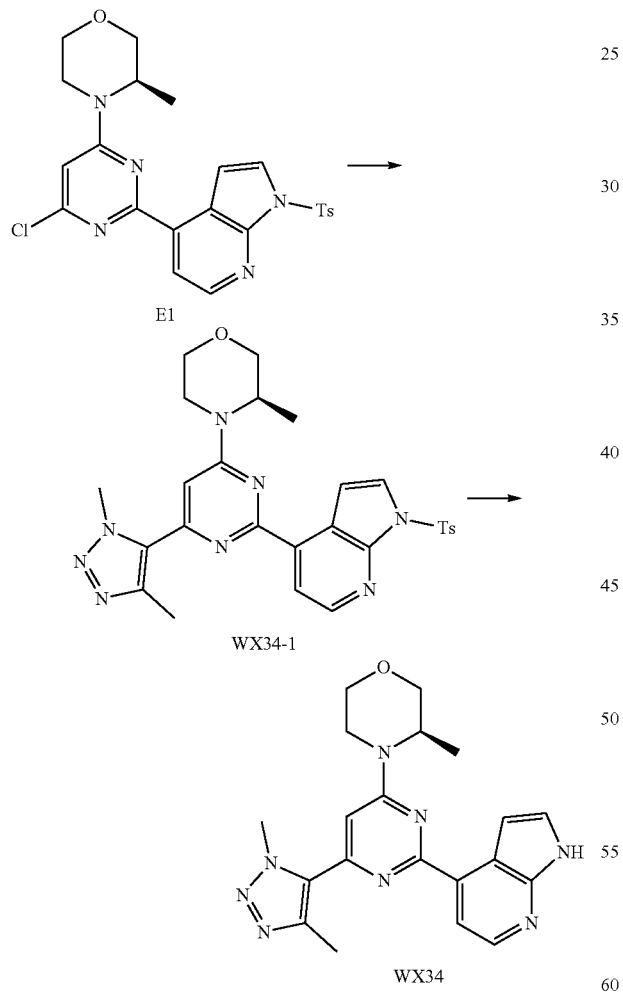

Step 1: Synthesis of Compound WX34-1

Except using corresponding raw materials, the procedures identical to those used for Compound WX15-1 in synthesis Example 15 were used to give the crude product, which was separated with column chromatography to give Compound WX34-1.

MS-ESI m/z: 545.4[M+H]+.

Step 2: Synthesis of Compound 34

Except using corresponding raw materials, the procedures identical to those used for Compound WX15 in synthesis Example 15 were used to give Compound WX34.

MS-ESI m/z: 391.1 [M+H]+.

$^1$H NMR (400 MHz, DMSO-$d_6$) δ ppm 1.32 (d, J=6.53 Hz, 3H) 2.47 (s, 3H) 3.37 (br d, J=3.51 Hz, 1H) 3.56 (td, J=11.80, 2.76 Hz, 1H) 3.71 (dd, J=11.42, 2.89 Hz, 1H) 3.79-3.89 (m, 1H) 4.04 (dd, J=11.17, 3.39 Hz, 1H) 4.22-4.37 (m, 4H) 4.65 (br s, 1H) 6.99 (s, 1H) 7.20 (dd, J=3.39, 1.88 Hz, 1H) 7.61 (t, J=3.01 Hz, 1H) 8.02 (d, J=5.02 Hz, 1H) 8.36 (d, J=5.02 Hz, 1H) 11.85 (br s, 1H).

Example 35

Synthesis Scheme

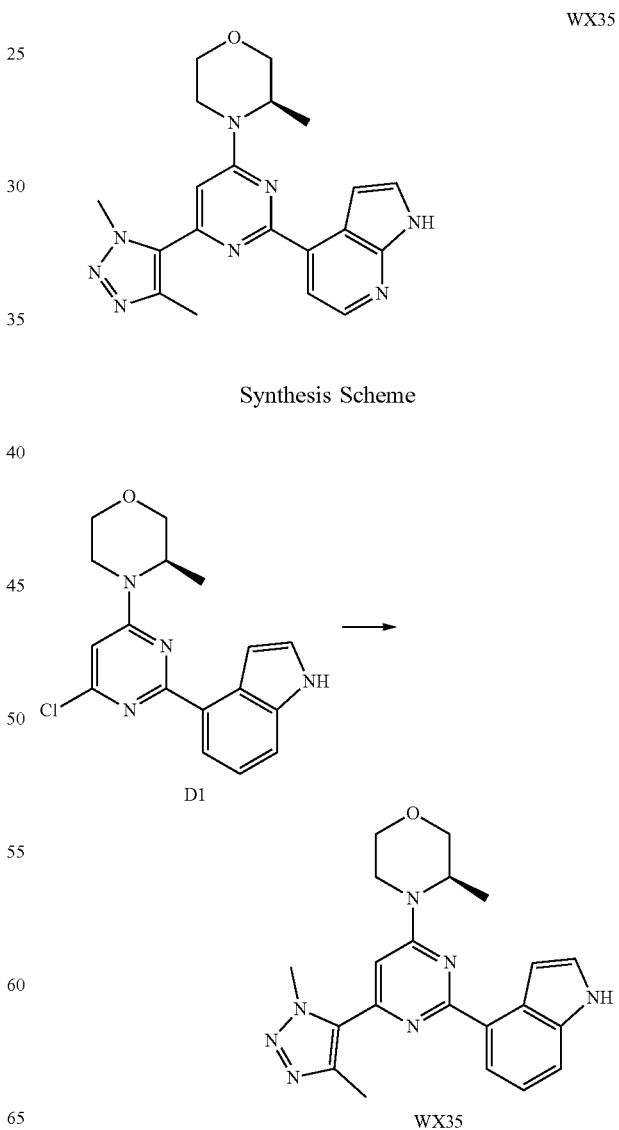

Step 1: Synthesis of Compound WX35

Except using corresponding raw materials, the procedures identical to those used for Compound WX13 in synthesis Example 13 were used to give Compound WX35.

MS-ESI m/z: 390.3 [M+H]+.

$^1$H NMR (400 MHz, CDCl$_3$) δ ppm 1.28 (s, 3H) 2.58 (br s, 3H) 3.49 (s, 1H) 3.73 (s, 1H) 3.91 (br s, 2H) 4.14 (br s, 1H) 4.29 (s, 1H) 4.39 (br s, 3H) 4.53 (s, 1H) 6.52 (s, 1H) 7.34 (br s, 1H) 7.38 (br s, 1H) 7.48 (br s, 1H) 7.57 (s, 1H) 8.27 (br d, J=7.53 Hz, 1H) 8.37 (s, 1H)

Example 36

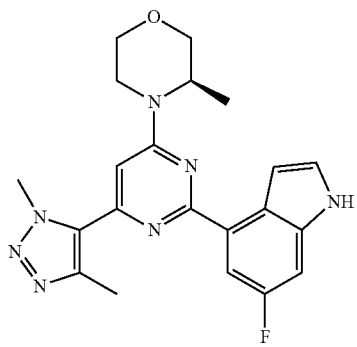

WX36

Synthesis Scheme

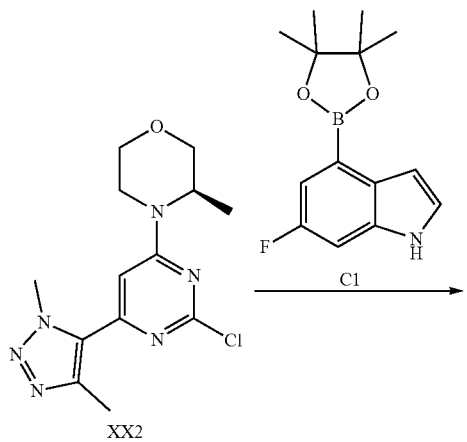

Step 1: Synthesis of Compound WX36

Except using corresponding raw materials, the procedures identical to those used for Compound WX13 in synthesis Example 13 were used to give Compound WX36.

MS-ESI m/z: 408.1 [M+H]+.

$^1$H NMR (400 MHz, DMSO-d$_6$) δ ppm 1.32 (d, J=6.78 Hz, 3H) 2.46 (s, 3H) 3.36 (br d, J=4.27 Hz, 1H) 3.50-3.62 (m, 1H) 3.67-3.74 (m, 1H) 3.79-3.86 (m, 1H) 4.04 (dd, J=10.92, 3.14 Hz, 1H) 4.25 (s, 3H) 4.29 (br d, J=11.29 Hz, 1H) 4.63 (br s, 1H) 6.93 (s, 1H) 7.29 (br s, 1H) 7.36 (dd, J=9.29, 2.01 Hz, 1H) 7.48 (t, J=2.64 Hz, 1H) 7.90 (dd, J=11.29, 2.51 Hz, 1H) 11.36 (br s, 1H)

Example 37

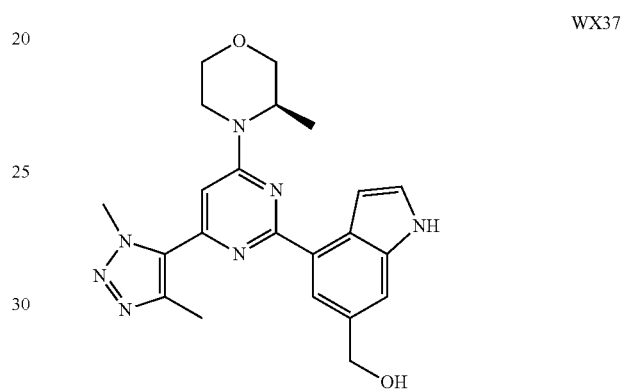

WX37

Synthesis Scheme

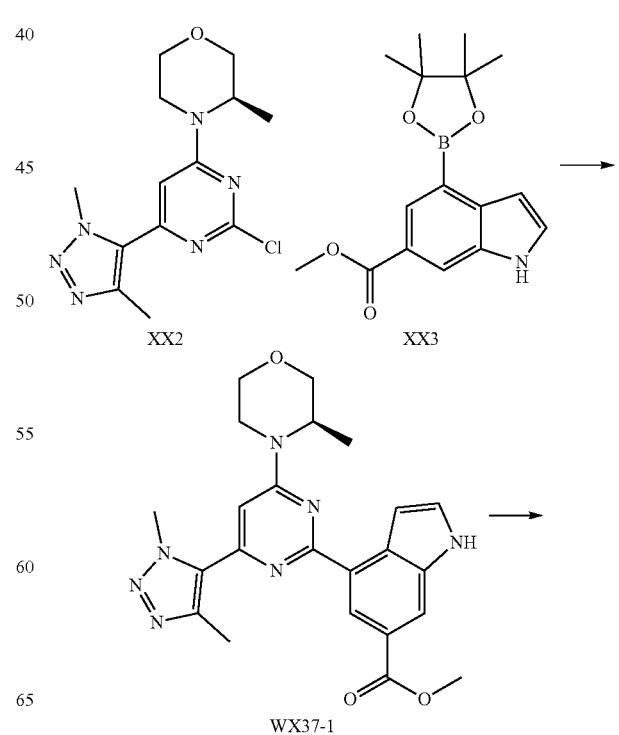

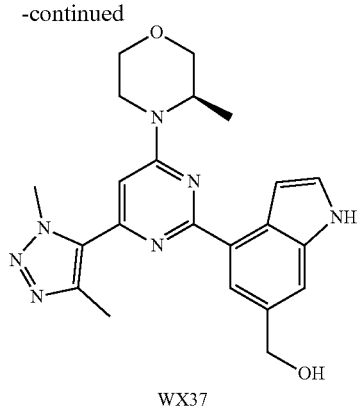

WX37

Step 1: Synthesis of Compound WX37-1

Except using corresponding raw materials, the procedures identical to those used for Compound WX13 in synthesis Example 13 were used to give Compound WX37-1.

MS-ESI m/z: 411.3 [M+H]+.

Step 2: Synthesis of Compound WX37

At 0° C., to a solution of Compound WX37-1 (0.15 g, 335.20 μmol) in tetrahydrofuran (10 mL) was added lithium aluminum hydride (25.44 mg, 670.41 μmol), and the reaction mixture was stirred at 0° C. for 0.5 h.

At 0° C., the reaction solution was added with anhydrous sodium sulfate, quenched with water (1 ml) and filtered. The filtrate was concentrated to give the crude product, which was separated with column chromatography to give Compound WX37.

MS-ESI m/z: 420.3 [M+H]+.

$^1$H NMR (400 MHz, DMSO-d$_6$) δ ppm 1.32 (d, J=6.78 Hz, 3H) 1.34-1.34 (m, 1H) 2.46 (s, 3H) 3.39 (br s, 1H) 3.56 (td, J=11.92, 3.01 Hz, 1H) 3.71 (dd, J=11.54, 2.76 Hz, 1H) 3.83 (d, J=11.54 Hz, 1H) 4.04 (br dd, J=11.42, 3.14 Hz, 1H) 4.25 (s, 3H) 4.30 (br d, J=12.80 Hz, 1H) 4.65 (s, 3H) 6.88 (s, 1H) 7.24 (br s, 1H) 7.43 (t, J=2.64 Hz, 1H) 7.52 (s, 1H) 8.10 (s, 1H) 11.23 (br s, 1H).

Example 38

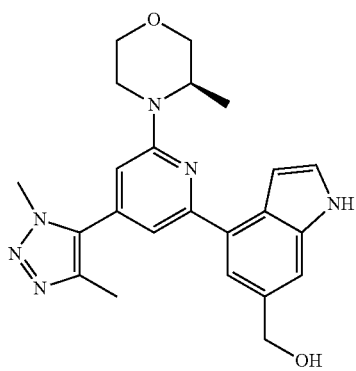

WX38

Synthesis Scheme

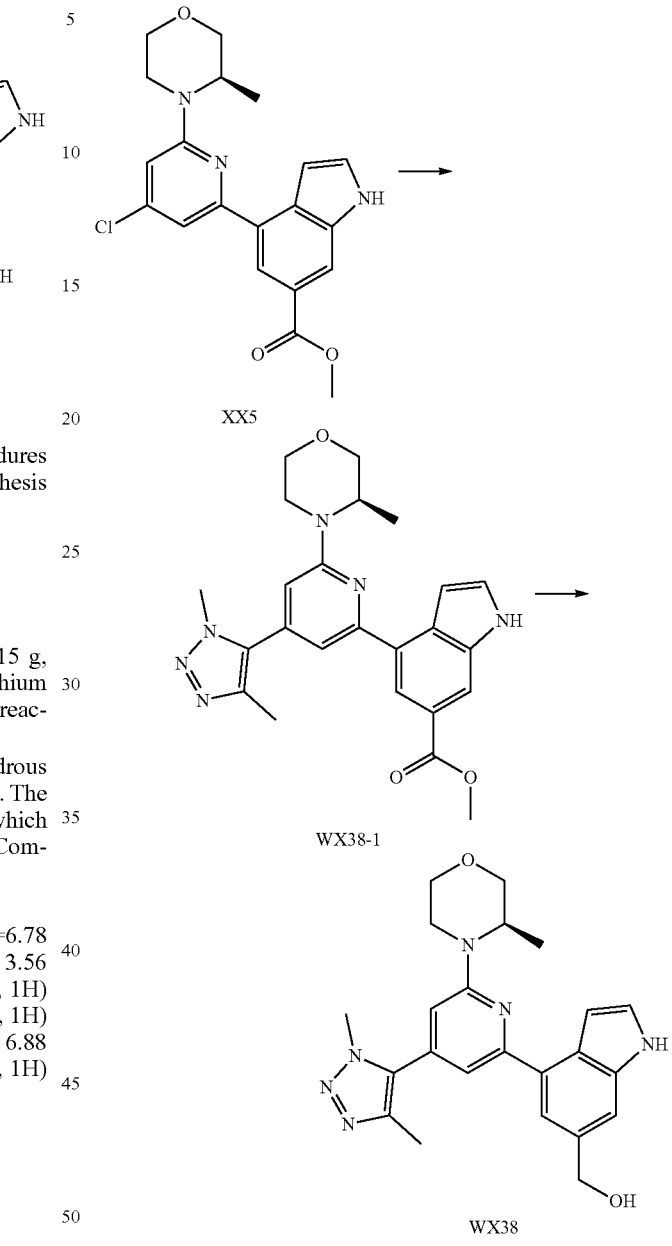

Step 1: Synthesis of Compound WX38-1

To a solution of Compound XX5 (0.28 g, 725.68 μmol) in N,N-dimethylformamide (5 mL) were added 1,4-dimethyl-1H-1,2,3-triazole (140.95 mg, 1.45 mmol), bis(triphenylphosphine) palladium dichloride (50.94 mg, 72.57 μmol), and tetramethylammonium acetate (115.98 mg, 870.82 μmol). The reaction mixture was stirred in a sealed tube at 140° C. with heating for 4 h, and then diluted with ethyl acetate (50 mL), washed with water (20 mL) and saturated brine (20 ml), dried over anhydrous sodium sulfate, and filtered. The solution was concentrated to give the crude product, which was separated with column chromatography to give Compound WX38-1.

MS-ESI m/z: 447.3 [M+H]+.

Step 2: Synthesis of Compound WX38

Except using corresponding raw materials, the procedures identical to those used for Compound WX37 in synthesis Example WX37 were used to give Compound WX38.

MS-ESI m/z: 419.3 [M+H]+.

$^1$H NMR (400 MHz, DMSO-d$_6$) δ ppm 1.23 (br d, J=6.53 Hz, 3H) 2.32 (s, 3H) 3.16-3.23 (m, 1H) 3.50-3.60 (m, 1H) 3.67-3.73 (m, 1H) 3.75-3.81 (m, 1H) 4.00 (br d, J=8.28 Hz, 1H) 4.05 (s, 3H) 4.13 (br d, J=11.80 Hz, 1H) 4.50 (br d, J=4.77 Hz, 1H) 4.63 (d, J=5.52 Hz, 2H) 5.13 (t, J=5.65 Hz, 1H) 6.79 (s, 1H) 6.88 (br s, 1H) 7.16 (s, 1H) 7.40 (br s, 1H) 7.46 (d, J=11.80 Hz, 2H) 11.21 (br s, 1H)

Example 39

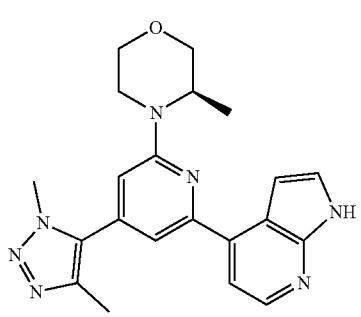

WX39

Synthesis Scheme

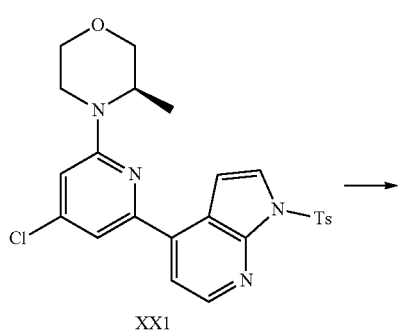

XX1

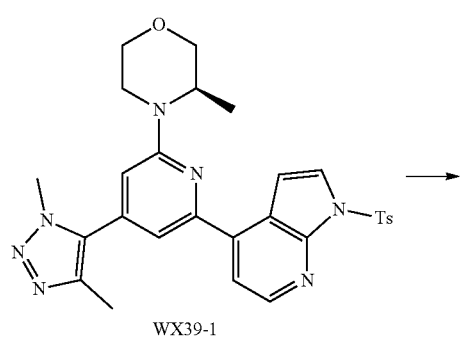

WX39-1

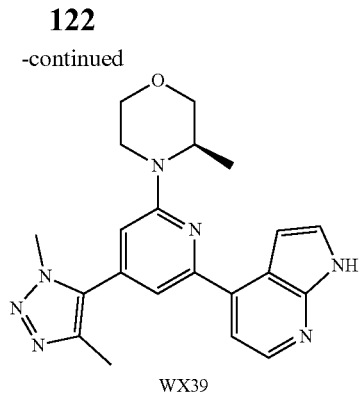

WX39

Step 1: Synthesis of Compound WX39-1

Except using corresponding raw materials, the procedures identical to those used for Compound WX38-1 in synthesis Example Intermediate WX38-1 were used to give Compound WX39-1.

MS-ESI m/z: 544.4 [M+H]+.

Step 2: Synthesis of Compound WX39

Except using corresponding raw materials, the procedures identical to those used for Compound WX15 in synthesis Example 15 were used to give Compound WX39.

MS-ESI m/z: 390.1 [M+H]+.

$^1$H NMR (400 MHz, DMSO-d$_6$) δ ppm 1.24 (d, J=6.78 Hz, 3H) 2.33 (s, 3H) 3.18-3.26 (m, 1H) 3.55 (td, J=11.86, 2.64 Hz, 1H) 3.66-3.74 (m, 1H) 3.76-3.82 (m, 1H) 4.01 (dd, J=11.42, 3.14 Hz, 1H) 4.06 (s, 3H) 4.14 (br d, J=10.79 Hz, 1H) 4.51 (br d, J=7.03 Hz, 1H) 6.92 (s, 1H) 6.95 (dd, J=3.51, 2.01 Hz, 1H) 7.36 (s, 1H) 7.57-7.61 (m, 2H) 8.31 (d, J=5.02 Hz, 1H) 11.80 (br s, 1H)

Example 40

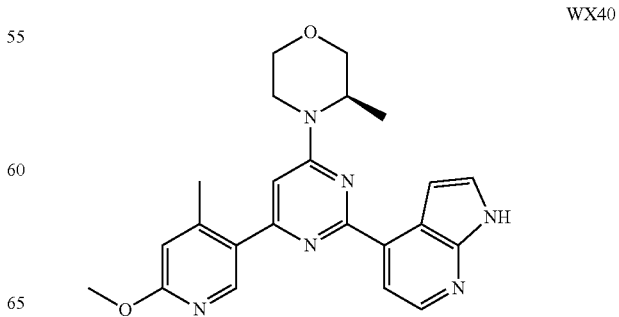

WX40

Synthesis Scheme

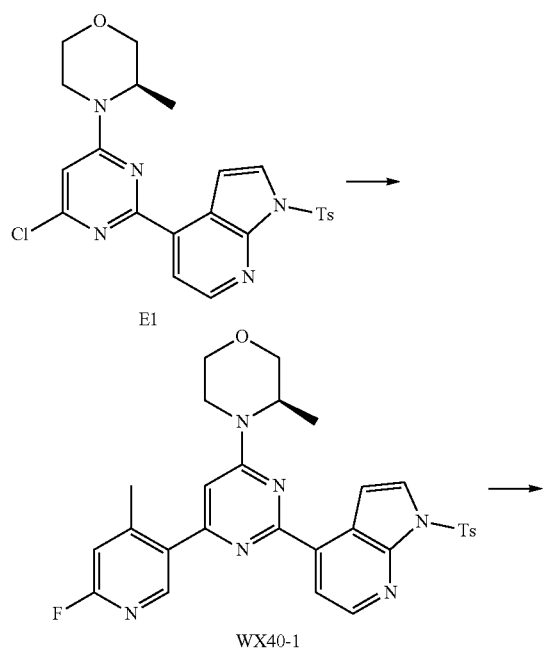

Step 1: Synthesis of Compound WX40-1

Except using corresponding raw materials, the procedures identical to those used for Compound WX15-1 in synthesis Example Intermediate WX15-1 were used to give Compound WX40-1.

MS-ESI m/z: 559.1[M+H]+.

Step 2: Synthesis of Compound WX40

To a solution of Compound WX40-1 (0.095 g, 170.06 μmol) in methanol (15 mL) was added 2M sodium hydroxide (2M, 1 mL). The reaction mixture was stirred at 15-20° C. for 72 h, and then diluted with water (30 mL). The aqueous phase was extracted with dichloromethane (50 mL×3). The organic phases were combined, dried over anhydrous sodium sulfate and filtered. The filtrate was rotated to dryness to give the crude product, which was separated with column chromatography to give Compound WX40.

MS-ESI m/z: 417.0 [M+H]+.

$^1$H NMR (CDCl$_3$, 400 MHz): δ=9.53 (br s, 1H), 8.44 (d, J=5.0 Hz, 1H), 8.27-8.34 (m, 1H), 8.14 (d, J=5.1 Hz, 1H), 7.37-7.47 (m, 2H), 6.72 (s, 1H), 6.55 (s, 1H), 4.62 (s, 1H), 4.53 (br s, 1H), 4.26 (br d, J=13.3 Hz, 1H), 3.97-4.02 (m, 3H), 3.87-3.94 (m, 1H), 3.79-3.86 (m, 1H), 3.69 (td, J=11.9, 3.1 Hz, 1H), 3.44 (td, J=12.8, 3.9 Hz, 1H), 2.54 (s, 3H), 1.44 ppm (d, J=6.9 Hz, 3H)

Example 41

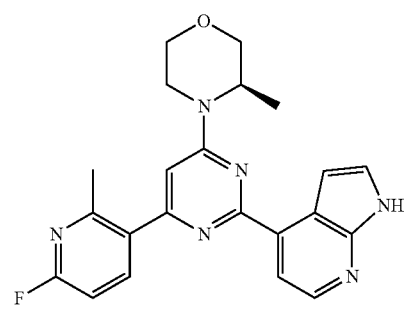

Synthesis Scheme

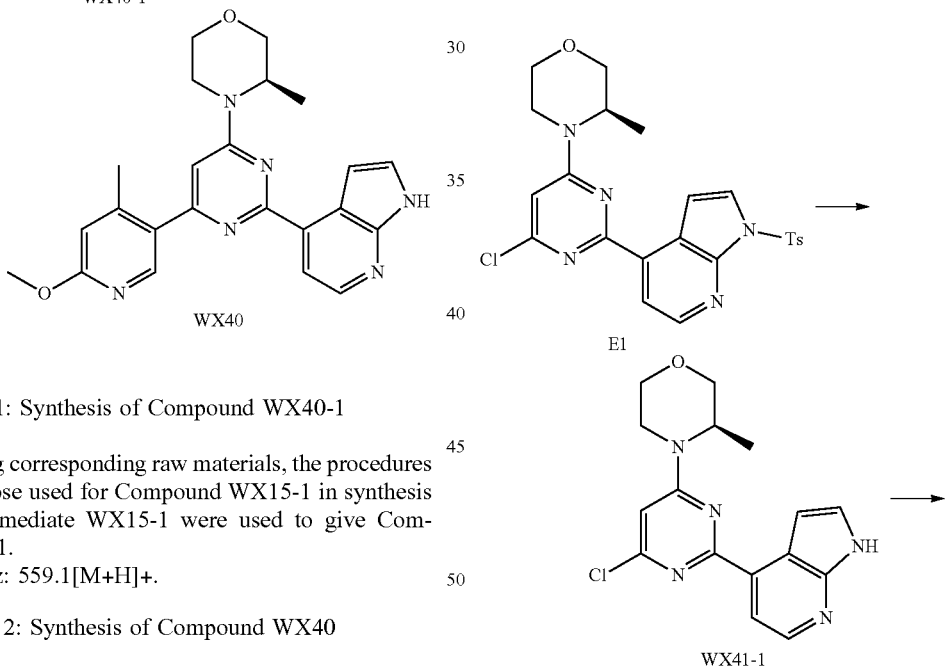

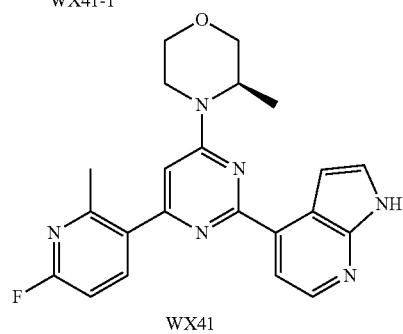

Step 1: Synthesis of Compound WX41-1

To a solution of Compound E1 (2 g, 4.13 mmol) in ethanol (25 mL) was added 2M sodium hydroxide (10.33 mL) and the reaction mixture was stirred at 15-20° C. for 14 h and then heated to 60° C. with stirring for 5 h. The reaction solution was adjusted to pH 6-7 with 2M hydrochloric acid, diluted with water (40 mL) and extracted with ethyl acetate (60 mL×3). The organic phases were combined, washed with saturated brine (80 mL), dried over anhydrous sodium sulfate and filtered. The filtrate was rotated to dryness to give crude Compound WX41-1.

MS-ESI m/z: 330.0 [M+H]+.

Step 2: Synthesis of Compound WX41

To a solution of Compound WX41-1 (0.06 g, 181.94 µmol), 2-fluoro-6-methylpyridine-5-boric acid (42.28 mg, 272.91 µmol) and tetrakis (triphenylphosphine) palladium (14.72 mg, 12.74 µmol) in 1,4-dioxane (8 mL) was added 2M sodium carbonate (2M, 272.91 µL) aqueous solution, which was purged with nitrogen three times. The reaction mixture was stirred with heating at 95° C. for 5 h and then filtered. The solution was concentrated to give the crude product, which was separated with column chromatography to give WX41.

MS-ESI m/z: 405.2 [M+H]+.

$^1$H NMR (CHLOROFORM-d, 400 MHz): δ=10.24 (br s, 1H), 8.47 (d, J=5.0 Hz, 1H), 8.15 (d, J=5.3 Hz, 1H), 7.98 (t, J=8.0 Hz, 1H), 7.45-7.57 (m, 1H), 7.36-7.41 (m, 1H), 6.91 (dd, J=8.3, 3.0 Hz, 1H), 6.55 (s, 1H), 4.54 (br s, 1H), 4.27 (br d, J=12.3 Hz, 1H), 4.13 (dd, J=11.5, 3.5 Hz, 1H), 3.88-3.96 (m, 1H), 3.78-3.86 (m, 1H), 3.69 (td, J=11.9, 3.0 Hz, 1H), 3.45 (td, J=12.8, 3.8 Hz, 1H), 2.71 (s, 3H), 1.45 ppm (d, J=6.8 Hz, 3H)

Example WX42

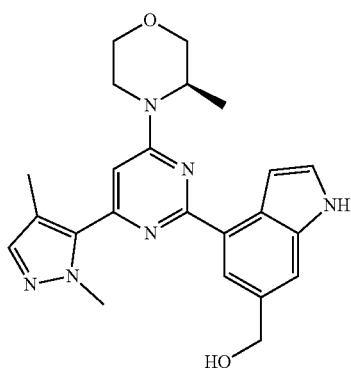

WX42

Synthesis Scheme

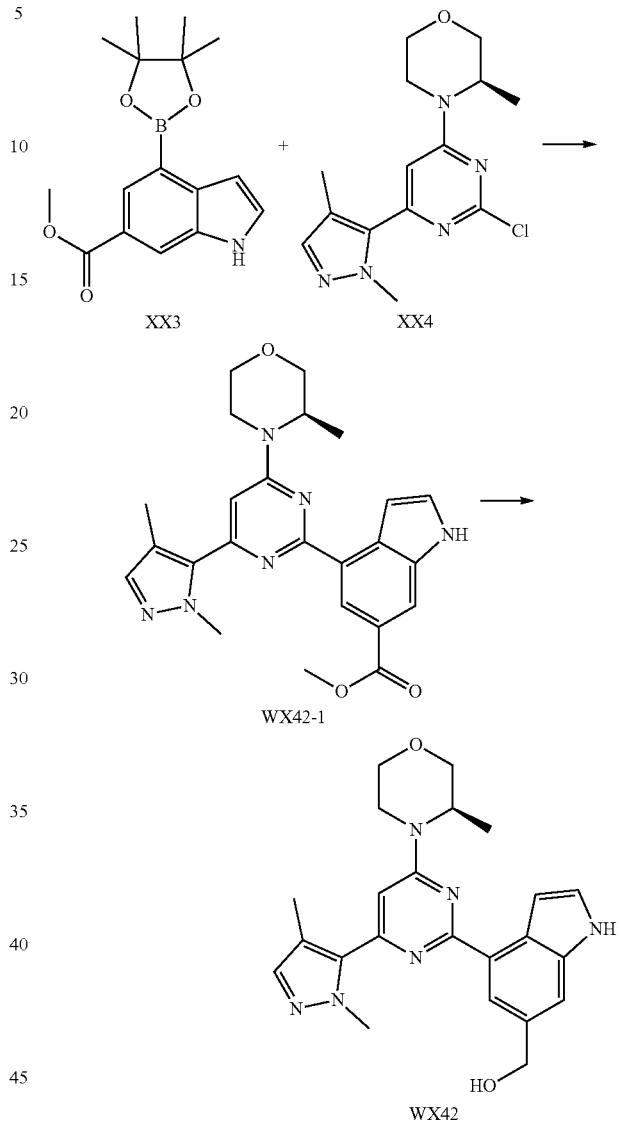

Step 1: Synthesis of Compound WX42-1

Except using corresponding raw materials, the procedures identical to those used for Compound WX37-1 in synthesis Example WX37 were used to give Compound WX42-1:

To a solution of Compound XX4 (0.11 g, 357.40 µmol), XX3 (161.44 mg, 536.10 µmol) and tetrakis (triphenylphosphine) palladium (0.03 g, 25.96 µmol) in 1,4-dioxane (8 mL) was added 2M sodium carbonate (534.1 µL) aqueous solution, which was purged with nitrogen three times. The reaction mixture was stirred with heating at 100° C. for 5 h and then filtered. The solution was concentrated to give the crude product, which was separated with column chromatography (ethyl acetate/petroleum ether: 20-55%) to give Compound WX42-1.

MS-ESI m/z: 447.1[M+H]+.

Step 2: Synthesis of Compound WX42

Except using corresponding raw materials, the procedures identical to those used for Compound WX37 in synthesis Example WX37 were used to give Compound WX42:

At the condition of 0-5° C., to a solution of Compound WX42-1 (0.13 g, 291.15 μmol) in tetrahydrofuran (10 mL) was added lithium aluminum hydride (0.05 g, 1.32 mmol). The reaction mixture was stirred at 0-5° C. for 1 h and then heated to 25° C. with stirring for 2 h. At 0-5° C., to the reaction were successively added slowly one drop of water, two drops of 10% sodium hydroxide and three drops of water, which was then filtered. The filtrate was concentrated to give the crude product, which was separated with column chromatography (ethyl acetate/petroleum ether: 50-100%) to give Compound WX42.

MS-ESI m/z: 419.2 [M+H]+.

$^1$H NMR (CDCl$_3$, 400 MHz): δ=8.44 (br s, 1H), 8.25 (s, 1H), 7.54 (s, 1H), 7.49 (br s, 1H), 7.41 (s, 1H), 7.32 (t, J=2.8 Hz, 1H), 6.47 (s, 1H), 4.87 (s, 2H), 4.48 (br d, J=4.5 Hz, 1H), 4.29 (br d, J=13.8 Hz, 1H), 4.14 (s, 3H), 4.11 ((m, 1H), 3.86-3.94 (m, 1H), 3.79-3.86 (m, 1H), 3.69 (td, J=11.9, 3.1 Hz, 1H), 3.43 (td, J=12.7, 3.9 Hz, 1H), 2.24 (s, 3H), 1.70 (t, J=6.0 Hz, 1H), 1.43 ppm (d, J=6.8 Hz, 3H)

Example 43

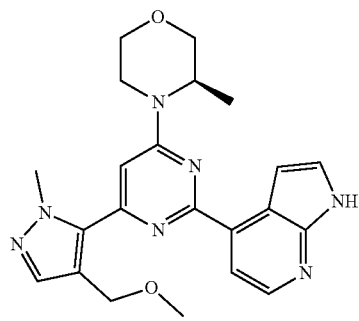

WX43

Synthesis Scheme

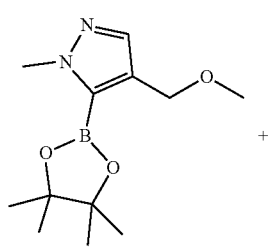

+

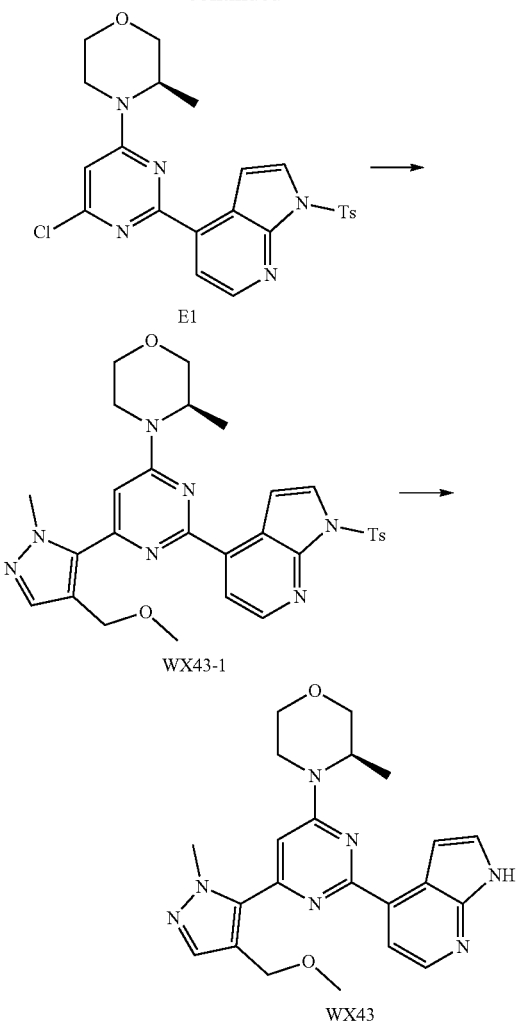

Step 1: Synthesis of Compound WX43-1

Except using corresponding raw materials, the procedures identical to those used for Compound WX15-1 in synthesis Example 15 were used to give crude WX43-1.

MS-ESI m/z: 574.4 [M+H]+.

Step 2: Synthesis of Compound WX43

Except using corresponding raw materials, the procedures identical to those used for Compound WX15 in synthesis Example 15 were used to give Compound WX43.

MS-ESI m/z: 420.1 [M+H]+.

$^1$H NMR (CHLOROFORM-d, 400 MHz): δ=9.74 (br s, 1H), 8.46 (br s, 1H), 8.16 (br s, 1H), 7.60 (s, 1H), 7.48 (d, J=3.3 Hz, 1H), 7.40 (d, J=3.0 Hz, 1H), 7.09 (s, 1H), 4.53 (br s, 1H), 4.38 (s, 2H), 4.26 (s, 4H), 4.13 (dd, J=11.4, 3.6 Hz, 1H), 3.88-3.95 (m, 1H), 3.79-3.85 (m, 1H), 3.65-3.74 (m, 1H), 3.39-3.49 (m, 4H), 1.45 ppm (d, J=6.8 Hz, 3H).

Example 44

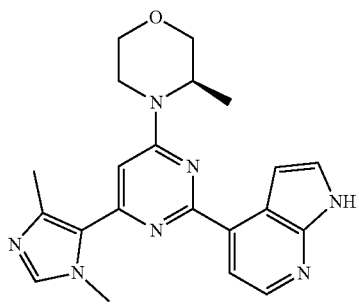

WX44

Synthesis Scheme

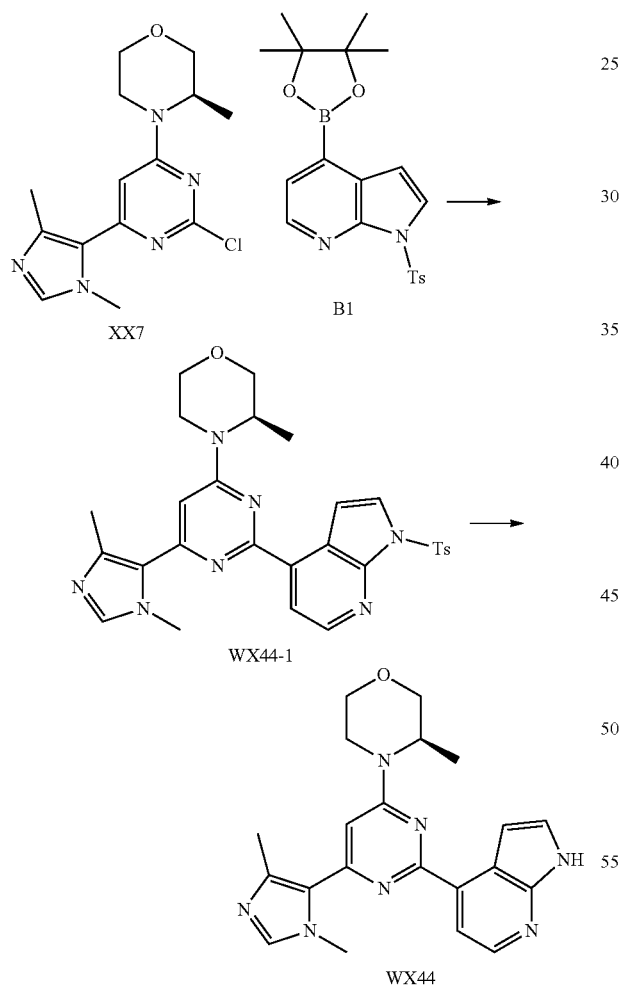

Step 1: Synthesis of Compound WX44-1

To a solution of Compound XX7 (0.05 g, 162.45 μmol), B1 (77.64 mg, 194.95 μmol) and tetrakis (triphenylphosphine) palladium(18.77 mg, 16.25 μmol) in 1,4-dioxane (5 mL) was added 2M sodium carbonate (2 M, 243.68 uL) aqueous solution, which was purged with nitrogen three times. The reaction mixture was stirred with heating at 100° C. for 14 h and then filtered. The solution was concentrated to give the crude product, which was separated with column chromatography to give Compound WX44-1.

MS-ESI m/z: 544.4 [M+H]+.

Step 2: Synthesis of Compound WX44

Except using corresponding raw materials, the procedures identical to those used for Compound WX15 in synthesis Example 15 were used to give Compound WX44.

MS-ESI m/z: 390.3 [M+H]+.

$^1$H NMR (CHLOROFORM-d, 400 MHz): δ=9.09 (br s, 1H), 8.43 (d, J=5.0 Hz, 1H), 8.09 (d, J=5.0 Hz, 1H), 7.53 (br s, 1H), 7.44 (br s, 1H), 7.35 (d, J=2.3 Hz, 1H), 6.53 (s, 1H), 4.51 (br d, J=5.4 Hz, 1H), 4.23 (br d, J=12.6 Hz, 1H), 4.13 (dd, J=11.5, 3.5 Hz, 1H), 3.97 (s, 3H), 3.89-3.93 (m, 1H), 3.80-3.86 (m, 1H), 3.64-3.70 (m, 1H), 3.44 (td, J=12.7, 3.9 Hz, 1H), 2.48 (s, 3H), 1.44 ppm (d, J=6.8 Hz, 3H).

Example 45

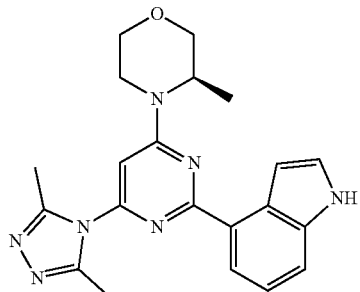

WX45

Synthesis Scheme

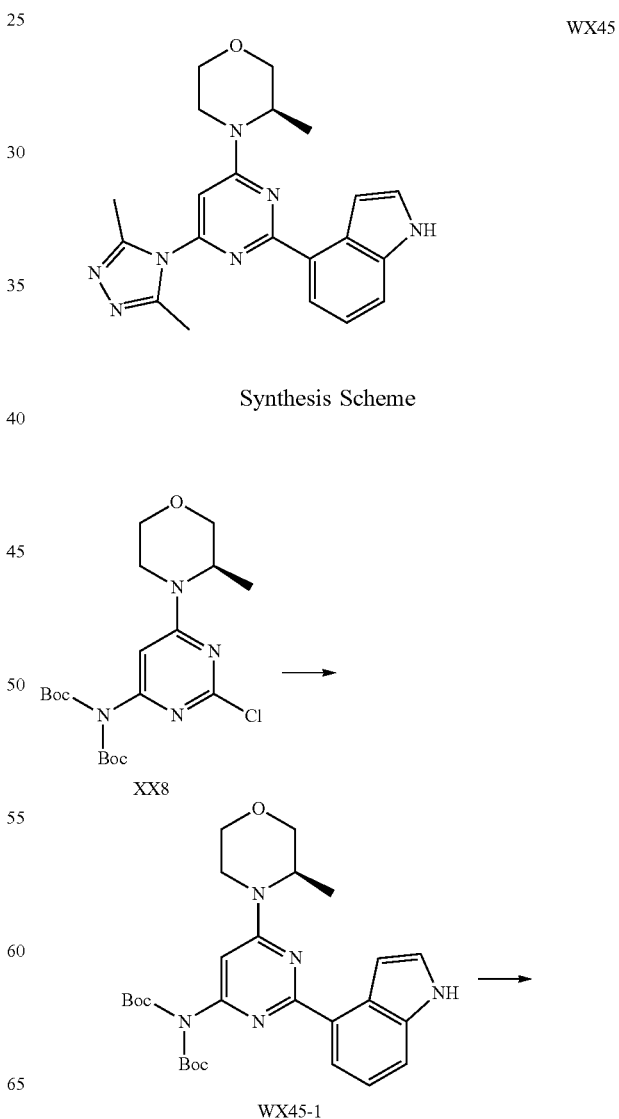

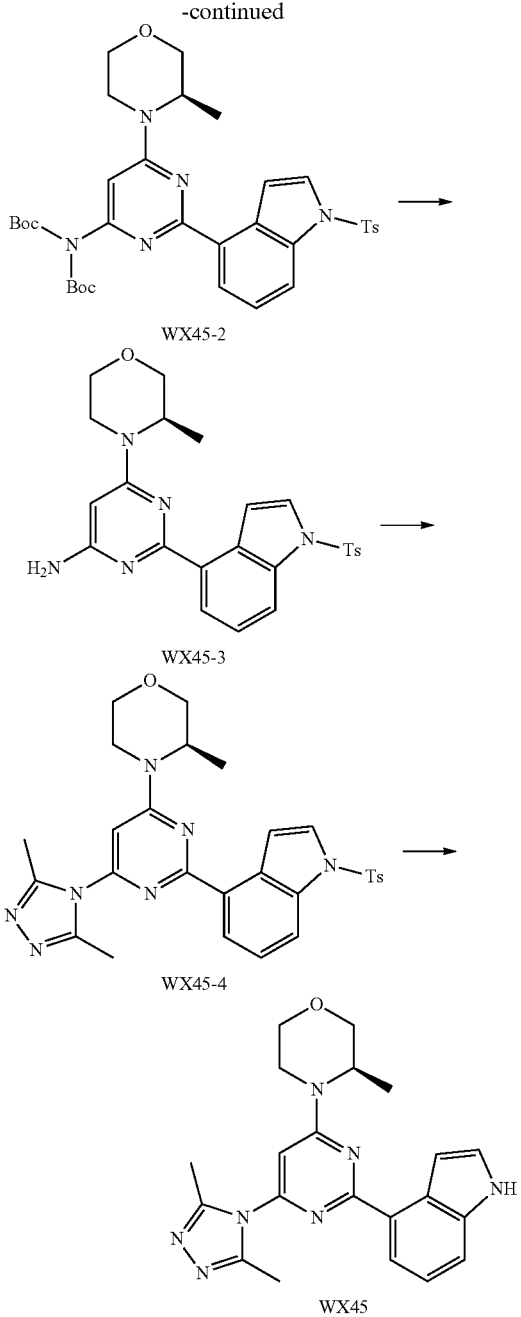

Step 1: Synthesis of Compound WX45-1

To a solution of Compound XX8 (1.6 g, 3.73 mmol), indole-4-boric acid pinacol ester (1.18 g, 4.85 mmol) and bis(triphenylphosphine) palladium dichloride (183.28 mg, 261.13 μmol) in 1,4-dioxane (20 mL) was added 2M sodium carbonate (2 M, 5.6 mL) aqueous solution, which was purged with nitrogen three times.

The reaction mixture was stirred with heating at 95° C. for 16 h and then filtered. The solution was concentrated to give the crude product, which was separated with column chromatography to give Compound WX45-1.

MS-ESI m/z: 510.8 [M+H]+.

Step 2: Synthesis of Compound WX45-2

At 0-5° C., to a solution of Compound WX45-1 (1.25 g, 2.45 mmol) in N'N-dimethylformamide (10 mL) was added sodium hydride (127.54 mg, 3.19 mmol, purity: 60%). The reaction mixture was stirred at 0-5° C. for 10 min, to which was added p-toluenesulfonyl chloride (561.17 mg, 2.94 mmol). The reaction mixture was stirred at 0-5° C. for 50 min, quenched with water (30 mL) and extracted with ethyl acetate (40 mL×3). The organic phases were combined and washed successively with water (30 mL×2) and saturated brine (50 mL×2). The organic phase was dried over anhydrous sodium sulfate, filtered and concentrated to give crude Compound WX45-2.

MS-ESI m/z: 664.5 [M+H]+.

Step 3: Synthesis of Compound WX45-3

To a solution of Compound WX45-2 (1.7 g, 2.56 mmol) in 1,4-dioxane (10 mL) was added 4M hydrochloric acid/1,4-dioxane (4 M, 5 mL). The reaction mixture was stirred at 30° C. for 2 h, adjusted to pH=7-8 with saturated sodium bicarbonate, diluted with water (30 mL) and extracted with ethyl acetate (40 mL×3). The organic phases were combined, washed with saturated brine (50 mL), dried over anhydrous sodium sulfate, filtered and concentrated to give the crude product, which was separated with column chromatography (ethyl acetate/petroleum ether: 25-75%) to give Compound WX45-3.

MS-ESI m/z: 464.7 [M+H]+.

Step 4: Synthesis of Compound WX45-4

To a solution of Compound WX45-3 (0.3 g, 647.18 μmol), 2,5-dimethyl-1,3,4-oxadiazole (190.47 mg, 1.94 mmol) in 1-methyl-2-pyrrolidone (3 mL) was added anhydrous p-toluenesulfonic acid (111.45 mg, 647.18 μmol) and the reaction mixture was stirred at 200° C. with microwave for 1.5 h. The reaction solution was diluted with water (20 mL) and extracted with dichloromethane (30 mL×4). The organic phases were combined, washed with saturated brine (50 mL), and dried over anhydrous sodium sulfate. The filtered organic phase was concentrated to give the crude product, which was separated with column chromatography (methanol/dichloromethane: 0-10) to give Compound WX45-4.

MS-ESI m/z: 544.4 [M+H]+.

Step 5: Synthesis of Compound WX45

Except using corresponding raw materials, the procedures identical to those used for Compound WX15 in synthesis Example 15 were used to give Compound WX45.

MS-ESI m/z: 390.3 [M+H]+.

$^1$H NMR (CDCl$_3$, 400 MHz): δ=8.60 (br s, 1H), 8.26 (dd, J=7.5, 0.8 Hz, 1H), 7.58 (d, J=8.0 Hz, 1H), 7.45 (t, J=2.3 Hz, 1H), 7.36 (t, J=2.8 Hz, 1H), 7.31 (t, J=7.8 Hz, 1H), 6.20-6.25 (m, 1H), 4.49 (br s, 1H), 4.25 (br d, J=12.3 Hz, 1H), 4.13 (dd, J=11.5, 3.8 Hz, 1H), 3.88-3.96 (m, 1H), 3.80-3.87 (m, 1H), 3.68 (td, J=11.9, 3.1 Hz, 1H), 3.47 (td, J=12.8, 3.9 Hz, 1H), 2.54 (s, 6H), 1.45 ppm (d, J=6.8 Hz, 3H).

Example 46

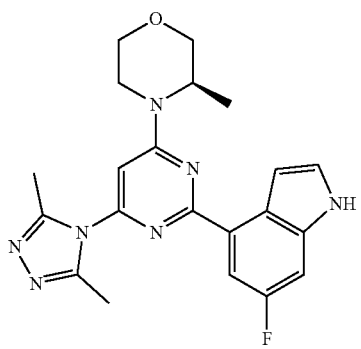

Synthesis Scheme

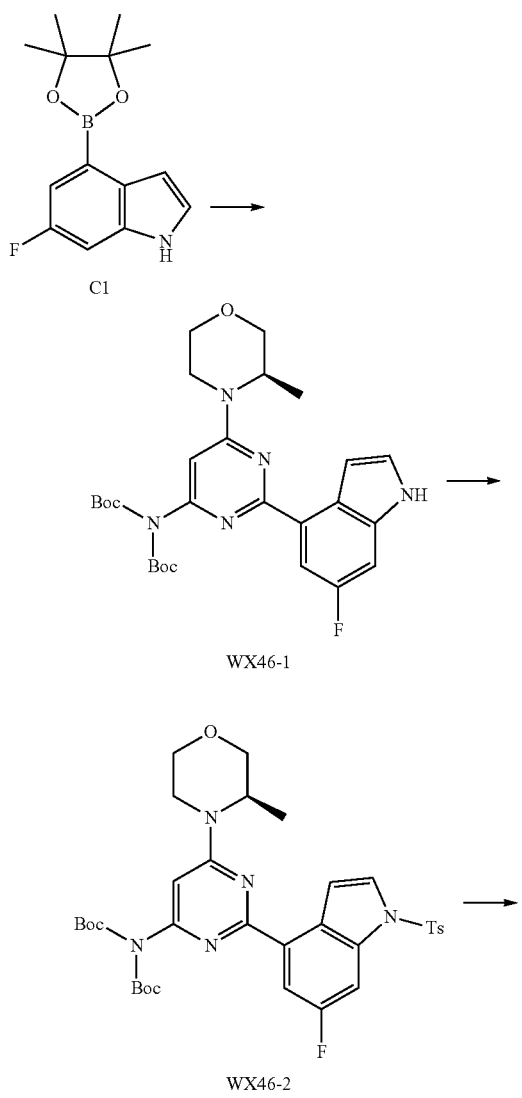

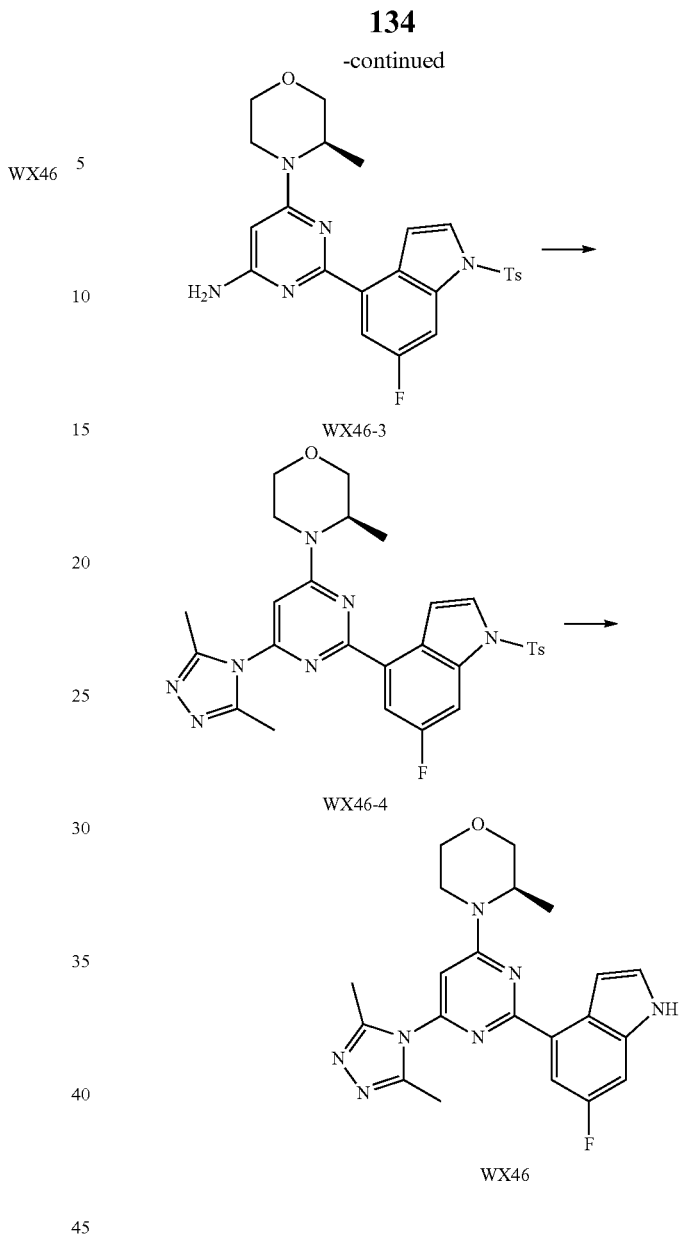

Step 1: Synthesis of Compound WX46-1

To a solution of Compound C1 (1.3 g, 3.03 mmol), XX8 (830.95 mg, 3.18 mmol) and bis(triphenylphosphine) palladium dichloride (148.92 mg, 212.17 μmol) in 1,4-dioxane (20 mL) was added 2M sodium carbonate (2 M, 4.55 mL) aqueous solution, which was purged with nitrogen three times. The reaction mixture was stirred with heating at 85° C. for 16 h and then filtered. The solution was concentrated to give the crude product, which was separated with column chromatography to give Compound WX46-1.

MS-ESI m/z: 528.4 [M+H]+.

Step 2: Synthesis of Compound WX46-2

At 0-5° C., to a solution of Compound WX46-1 (1.35 g, 2.56 mmol) in N'N-dimethylformamide (10 mL) was added sodium hydride (133.06 mg, 3.33 mmol, 60% purity). The reaction mixture was stirred at 0-5° C. for 10 min, to which was added p-toluenesulfonyl chloride (585.40 mg, 3.07 mmol). The reaction mixture was stirred at 0-5° C. for 30 min, quenched with water (30 mL) and extracted with ethyl acetate (40 mL×3). The organic phases were combined and washed successively with water (30 mL×2) and saturated brine (50 mL×2). The organic phase was dried over anhydrous sodium sulfate, filtered and concentrated to give crude Compound WX46-2.

MS-ESI m/z: 682.5 [M+H]+.

Step 3: Synthesis of Compound WX46-3

To a solution of Compound WX46-2 (1.75 g, 2.56 mmol) in 1,4-dioxane (10 mL) was added 4M hydrochloric acid/1,4-dioxane (4 M, 10 mL). The reaction mixture was stirred at 30° C. for 12 h, adjusted to pH=7-8 with saturated sodium bicarbonate, diluted with water (40 mL) and extracted with ethyl acetate (50 mL×3). The organic phases were combined, washed with saturated brine (50 mL), dried over anhydrous sodium sulfate, filtered and concentrated to give the crude product, which was separated with column chromatography to give Compound WX46-3.

MS-ESI m/z: 482.3 [M+H]+.

Step 4: Synthesis of Compound WX46-4

Except using corresponding raw materials, the procedures identical to those used for Compound WX15-1 in synthesis Example 15 were used to give Compound WX46-4.

MS-ESI m/z: 562.4 [M+H]+.

Step 5: Synthesis of Compound WX46

Except using corresponding raw materials, the procedures identical to those used for Compound WX15 in synthesis Example 15 were used to give Compound WX46.

MS-ESI m/z: 408.2 [M+H]+.

$^1$H NMR (CHLOROFORM-d, 400 MHz): δ=8.27-8.59 (m, 1H), 7.93-7.96 (m, 1H), 7.34 (t, J=2.3 Hz, 1H), 7.26 (t, J=2.8 Hz, 1H), 7.20 (br d, J=2.4 Hz, 1H), 6.16-6.22 (m, 1H), 4.40 (br s, 1H), 4.17 (br d, J=10.6 Hz, 1H), 4.06 (dd, J=11.6, 3.7 Hz, 1H), 3.79-3.87 (m, 1H), 3.72-3.78 (m, 1H), 3.61 (td, J=11.9, 3.0 Hz, 1H), 3.39 (td, J=12.8, 3.9 Hz, 1H), 2.46 (s, 6H), 1.37 ppm (d, J=6.8 Hz, 3H).

Example 47

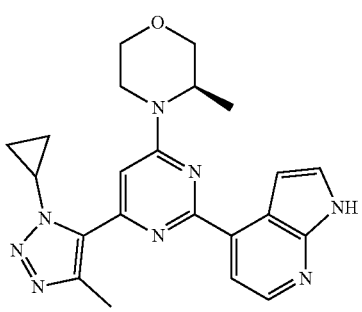

WX47

Synthesis Scheme

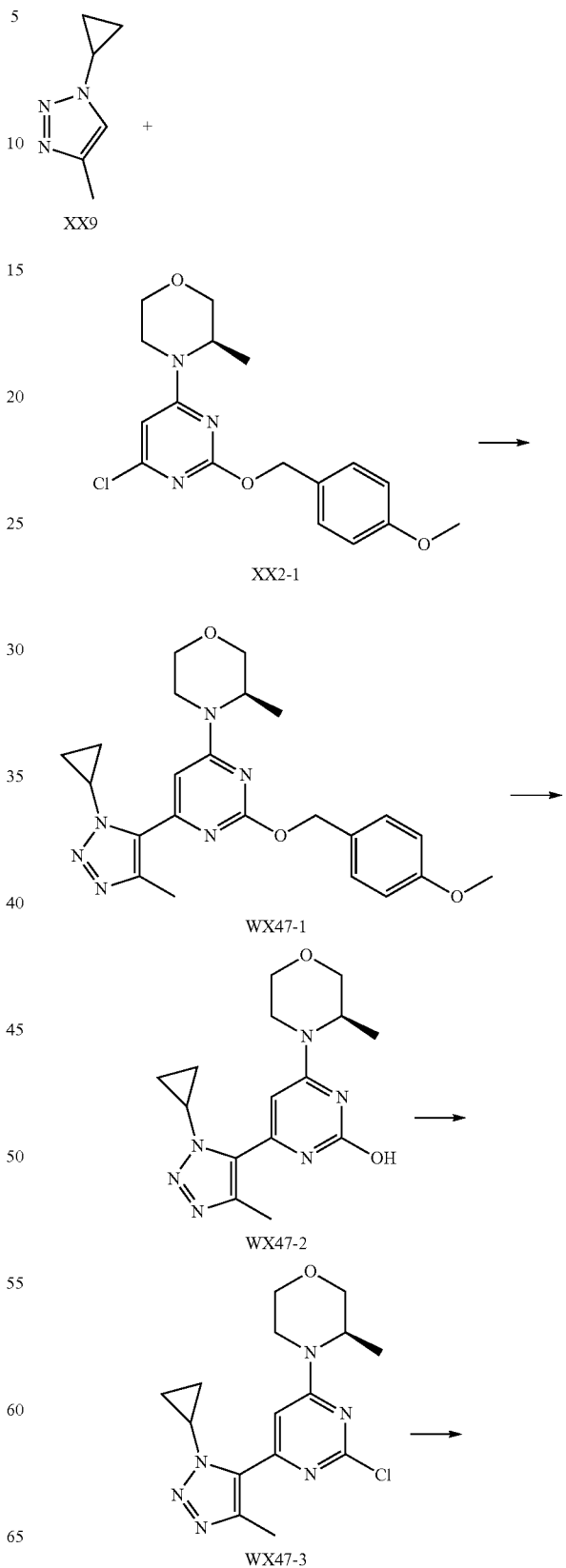

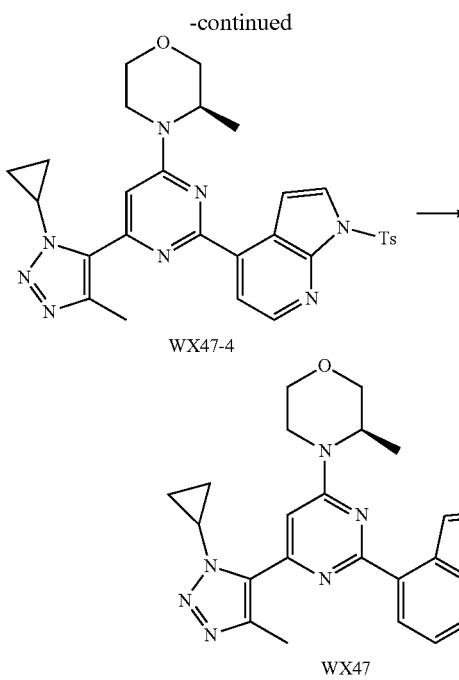

WX47-4

WX47

Step 1: Synthesis of Compound WX47-1

To a solution of Compound XX9 (0.3 g, 857.61 μmol), XX2-1 (126.74 mg, 1.03 mmol), potassium carbonate (237.05 mg, 1.72 mmol), tricyclohexylphosphine (126.74 mg, 1.03 mmol) and trimethylacetic acid (17.52 mg, 171.52 μmol) in N,N-dimethylacetamide (2 mL) was added palladium acetate (19.25 mg, 85.76 μmol). The reaction was purged with nitrogen three times and stirred at 130-150° C. for 18 h. The reaction solution was concentrated to give the crude product, which was separated with column chromatography to give Compound WX47-1.

MS-ESI m/z: 437.4 [M+H]+.

Step 2: Synthesis of Compound WX47-2

To a solution of Compound WX47-1 (0.45 g, 1.03 mmol) in ethanol (25 mL) was added Pd/C (0.1 g, 1.03 mmol, purity: 10%). The reaction was purged with hydrogen several times and stirred 16 h under hydrogen (15 psi) at 30° C. The reaction solution was filtered through celite and the filtrate was concentrated to give crude Compound WX47-2.

MS-ESI m/z: 317.2 M+H]+.

Step 3: Synthesis of Compound WX47-3

To the solvent of phosphorus oxychloride (11.75 g, 76.63 mmol) was added WX47-2 (0.33 g, 1.04 mmol) and the reaction was heated to 30° C. and stirred under nitrogen atmosphere for 5 h. The reaction solution was concentrated and then diluted with dichloromethane (50 mL). The organic phase was adjusted to pH 8 with saturated sodium bicarbonate, extracted with dichloromethane (30 mL×8). The organic phases were combined, dried over anhydrous sodium sulfate, filtered and concentrated to give Compound WX47-3.

MS-ESI m/z: 335.2 M+H]+.

Step 4: Synthesis of Compound WX47-4

Except using corresponding raw materials, the procedures identical to those used for Compound WX15-1 in synthesis Example 15 were used to give Compound WX47-4.

MS-ESI m/z: 571.4 M+H]+.

Step 5: Synthesis of Compound WX47

Except using corresponding raw materials, the procedures identical to those used for Compound WX15 in synthesis Example 15 were used to give Compound WX47.

MS-ESI m/z: 417.3 M+H]+.

$^1$H NMR (CDCl$_3$, 400 MHz): δ=9.41 (br s, 1H), 8.45 (d, J=5.0 Hz, 1H), 8.13 (d, J=5.0 Hz, 1H), 7.45-7.51 (m, 1H), 7.39 (dd, J=3.5, 2.0 Hz, 1H), 6.62 (s, 1H), 4.52 (br s, 1H), 4.28-4.31 (m, 1H), 4.25 (tt, J=7.5, 3.8 Hz, 1H), 4.12-4.17 (m, 1H), 3.89-3.95 (m, 1H), 3.79-3.88 (m, 1H), 3.70 (td, J=11.9, 3.0 Hz, 1H), 3.47 (td, J=12.7, 3.8 Hz, 1H), 2.54 (s, 3H), 1.46 (d, J=6.8 Hz, 3H), 1.35-1.42 (m, 2H), 1.04-1.14 ppm (m, 2H).

Example 48

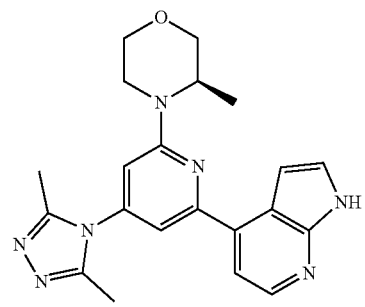

WX48

Synthesis Scheme

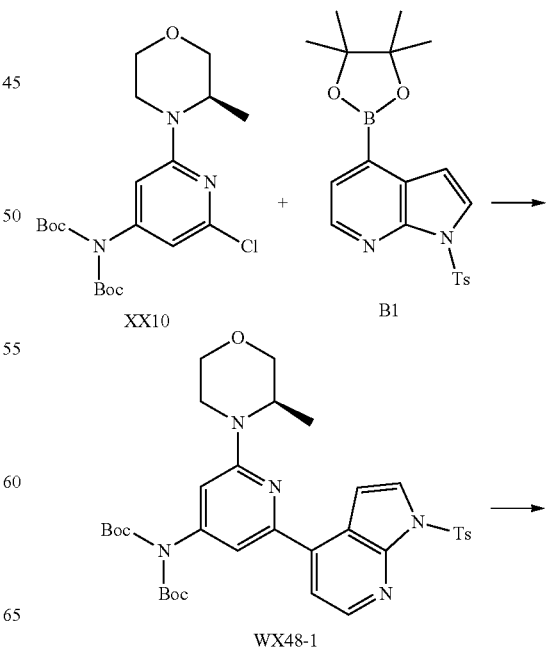

WX48-1

-continued

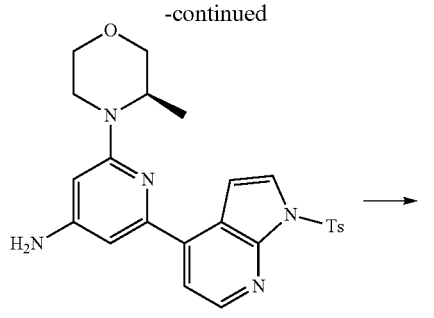

WX48-2

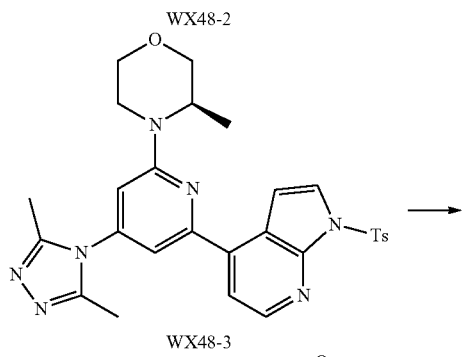

WX48-3

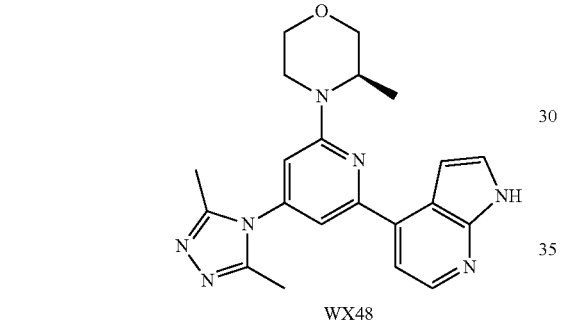

WX48

Step 1: Synthesis of Compound WX48-1

To a solution of Compound XX10 (1.6 g, 3.74 mmol), B1 (2.23 g, 5.61 mmol) and tetrakis (triphenylphosphine) palladium (18.77 mg, 16.25 μmol) in 1,4-dioxane (5 mL) was added 2M sodium carbonate (2 M, 4.67 mL) aqueous solution, which was purged with nitrogen three times. The reaction mixture was stirred with heating at 100° C. for 20 h and then filtered. The solution was concentrated to give the crude product, which was separated with column chromatography to give Compound WX48-1.

MS-ESI m/z: 664.5 M+H]+.

Step 2: Synthesis of Compound WX48-2

To a solution of Compound WX48-1 (2 g, 3.01 mmol) in 1,4-dioxane (10 mL) was added 4M hydrochloric acid/1,4-dioxane (4 M, 5 mL) solution. The reaction mixture was stirred at 30° C. for 35 min, adjusted to pH=7-8 with saturated sodium bicarbonate, diluted with water (30 mL) and extracted with dichloromethane (40 mL×3). The organic phases were combined, washed with saturated brine (50 mL), dried over anhydrous sodium sulfate, filtered and concentrated to give the crude product, which was separated with column chromatography to give Compound WX48-2.

MS-ESI m/z: 464.7 M+H]+.

Step 3: Synthesis of Compound WX48-3

To a solution of Compound WX48-2 (0.3 g, 647.18 μmol), 2,5-dimethyl-1,3,4-oxadiazole (1240.00 mg, 2.45 mmol) in 1-methyl-2-pyrrolidone (2 mL) was added anhydrous p-toluenesulfonic acid (111.44 mg, 647.18 μmol) and the reaction mixture was stirred at 200° C. with microwave for 1.5 h. The reaction was concentrated under reduced pressure to give the crude product, which was separated with column chromatography to give Compound WX48-3.

MS-ESI m/z: 544.1 M+H]+.

Step 4: Synthesis of Compound WX48

Except using corresponding raw materials, the procedures identical to those used for Compound WX15 in synthesis Example 15 were used to give Compound WX48.

MS-ESI m/z: 390.3 M+H]+.

$^1$H NMR (CHLOROFORM-d, 400 MHz): δ=9.75 (br s, 1H), 8.44 (d, J=5.0 Hz, 1H), 7.56 (d, J=5.0 Hz, 1H), 7.42-7.51 (m, 1H), 7.06 (d, J=1.3 Hz, 1H), 6.94 (dd, J=3.4, 1.9 Hz, 1H), 6.38 (d, J=1.3 Hz, 1H), 4.39 (br d, J=6.5 Hz, 1H), 4.04-4.21 (m, 2H), 3.87-3.95 (m, 1H), 3.78-3.86 (m, 1H), 3.69 (td, J=12.0, 3.1 Hz, 1H), 3.39 (td, J=12.6, 3.9 Hz, 1H), 2.41 (s, 6H), 1.39 ppm (d, J=6.8 Hz, 3H)

Example 49

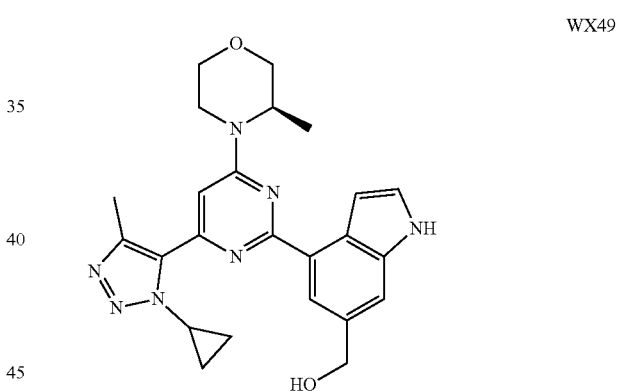

WX49

Synthesis Scheme

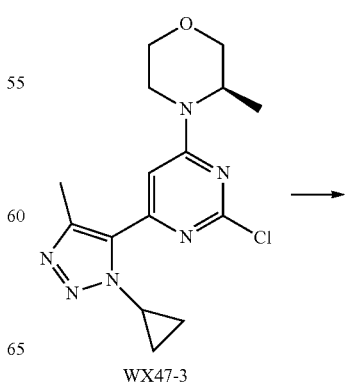

WX47-3

3.73 (m, 2H), 3.45 (td, J=12.8, 4.0 Hz, 1H), 2.52 (s, 3H), 1.44 (d, J=6.8 Hz, 3H), 1.33-1.40 (m, 2H), 1.02-1.11 ppm (m, 2H).

Example 50

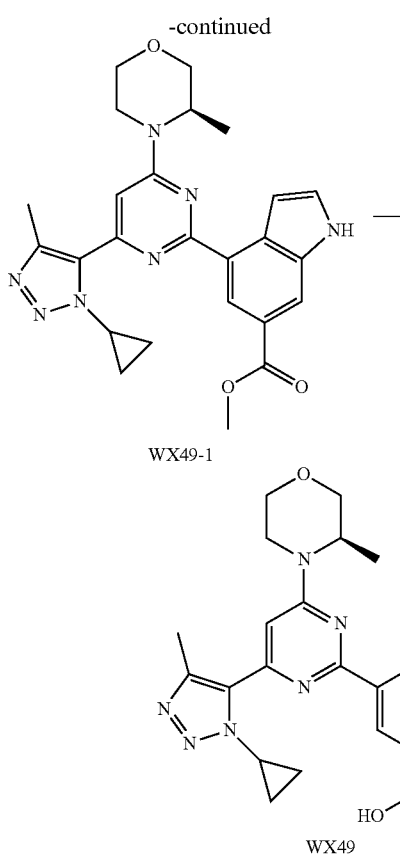

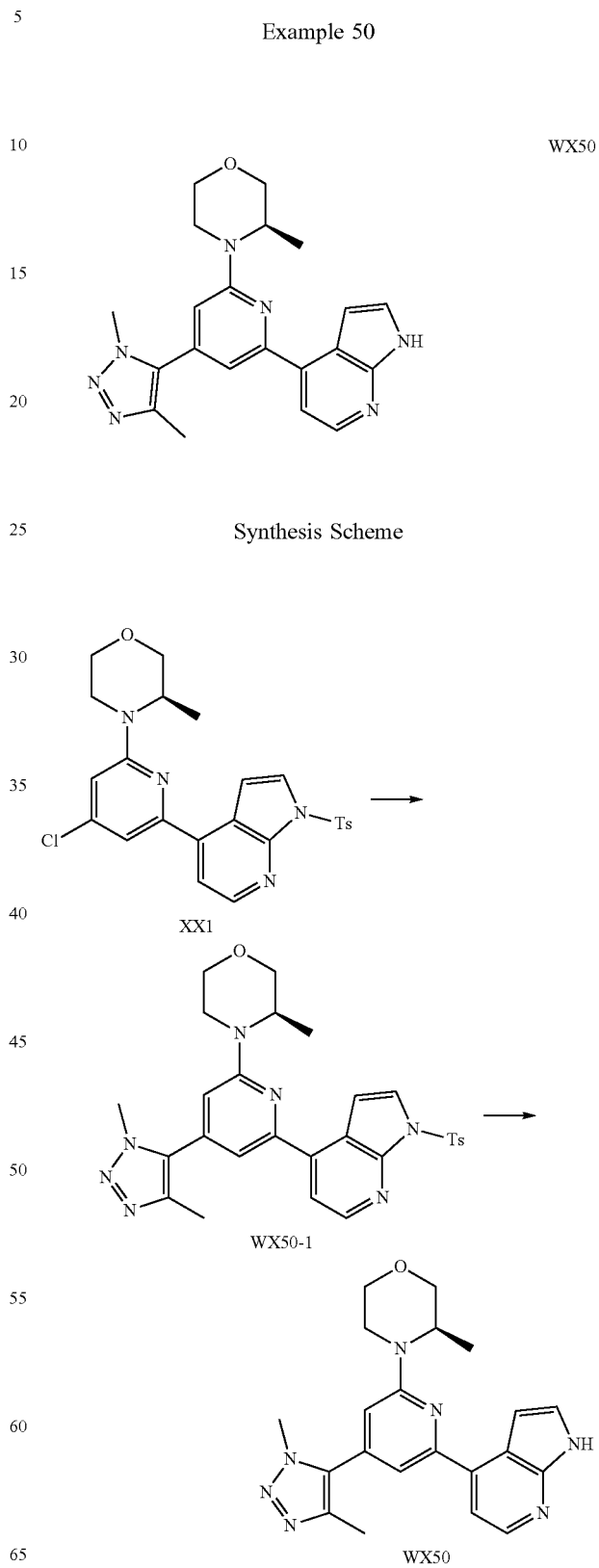

Step 1: Synthesis of Compound WX49-1

To a solution of Compound WX47-3 (0.1 g, 298.68 μmol), XX3 (125.93 mg, 418.16 μmol) and tetrakis (triphenylphosphine) palladium (24.16 mg, 20.91 μmol) in 1,4-dioxane (8 mL) was added 2M sodium carbonate (2 M, 448.02 μL) aqueous solution, which was purged with nitrogen three times. The reaction mixture was stirred with heating at 90° C. for 16 h and then filtered. The solution was concentrated to give the crude product, which was separated with column chromatography to give Compound WX49-1.

MS-ESI m/z: 474.4 M+H]+.

Step 2: Synthesis of Compound WX49

At the condition of 0-5° C., to a solution of Compound WX49-1 (0.06 g, 126.71 μmol) in tetrahydrofuran (10 mL) was added lithium aluminum hydride (0.05 g, 1.32 mmol). The reaction was warmed to 30° C. with stirring for 3 h. At 0-5° C., to the reaction were successively added slowly one drop of water, two drops of 10% sodium hydroxide and three drops of water, which was then filtered. The filtrate was concentrated to give the crude product, which was separated with column chromatography to give Compound WX49.

MS-ESI m/z: 446.1 M+H]+.

$^1$H NMR (CHLOROFORM-d, 400 MHz): δ=8.43 (br s, 1H), 8.27 (d, J=1.0 Hz, 1H), 7.57 (s, 1H), 7.50 (t, J=2.3 Hz, 1H), 7.34 (t, J=2.8 Hz, 1H), 6.54 (s, 1H), 4.88 (s, 2H), 4.50 (br d, J=4.5 Hz, 1H), 4.21-4.35 (m, 2H), 4.13 (dd, J=11.4, 3.6 Hz, 1H), 3.88-3.93 (m, 1H), 3.79-3.88 (m, 1H), 3.64-

Step 1: Synthesis of Compound WX50-1

Except using corresponding raw materials, the procedures identical to those used for Compound WX30-1 in Example 30 were used to give the crude product, which was separated with column chromatography (ethyl acetate/petroleum ether: 0-60%) to give WX50-1.

MS-ESI: 544.4 [M+H]+

Step 2: Synthesis of Compound WX50

Except using corresponding raw materials, the procedures identical to those used for Compound WX30 in Example 30 were used to give the crude product, which was purified with column chromatography (dichloromethane: methanol=30/1, 10/1) to give Compound WX50.

MS-ESI: 390.1 [M+H]+

$^1$H NMR (400 MHz, DMSO-d$_6$) δ ppm 1.24 (d, J=6.78 Hz, 3H) 2.33 (s, 3H) 3.22 (td, J=12.67, 4.02 Hz, 1H) 3.37-3.42 (m, 1H) 3.55 (td, J=11.86, 2.64 Hz, 1H) 3.66-3.73 (m, 1H) 3.76-3.83 (m, 1H) 4.01 (dd, J=11.42, 3.14 Hz, 1H) 4.06 (s, 3H) 4.14 (br d, J=10.79 Hz, 1H) 4.51 (br d, J=7.03 Hz, 1H) 6.92 (s, 1H) 6.95 (dd, J=3.51, 2.01 Hz, 1H) 7.36 (s, 1H) 7.57-7.61 (m, 2H) 8.31 (d, J=5.02 Hz, 1H) 11.80 (br s, 1H)

Example 51

WX51

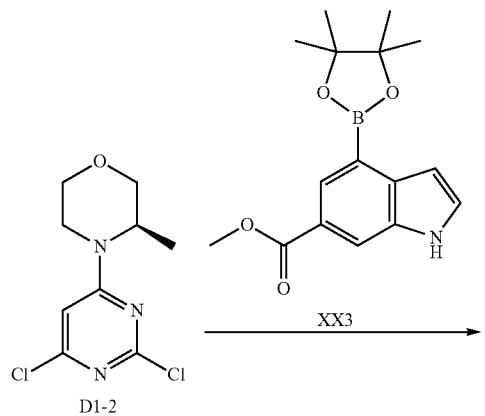

Synthesis Scheme

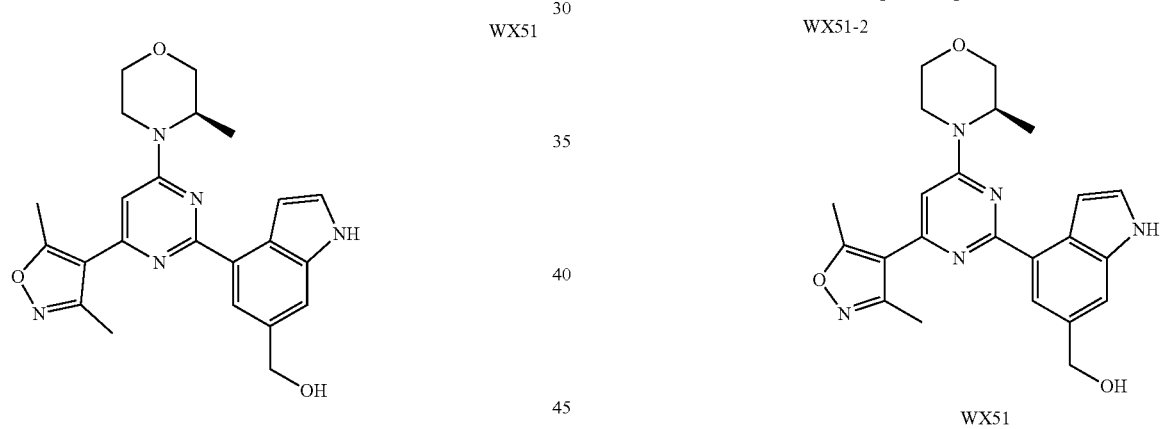

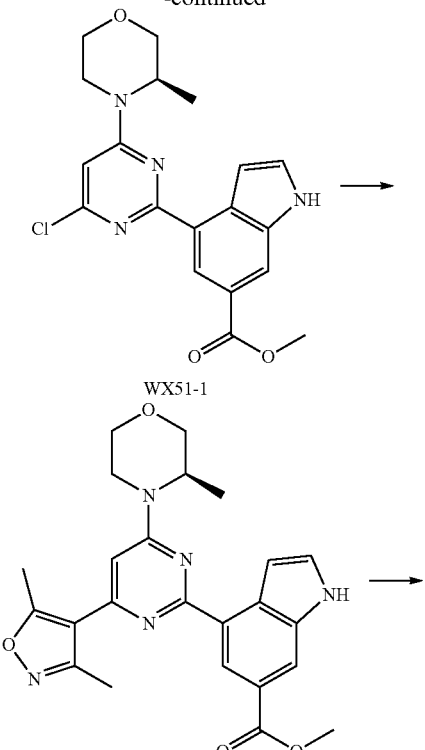

Step 1: Synthesis of Compound WX51-1

To a solution of Compound D1-2 (4.51 g, 18.18 mmol), XX3 (4.96 g, 16.47 mmol) and bis(triphenylphosphine) palladium dichloride (893.11 mg, 1.27 mmol) in 1,4-dioxane (60 mL) was added 2M sodium carbonate (27.27 mL) aqueous solution, which was purged with nitrogen three times. The reaction mixture was stirred at 110° C. with heating for 15 h and then filtered. The solution was concentrated to give the crude product, which was separated with column chromatography (ethyl acetate/petroleum ether: 15-35%) to give WX51-1.

MS-ESI: 386.9[M+H]+

Step 2: Synthesis of Compound WX51-2

At room temperature, to a solution of Compound WX51-1 (0.21 g, 542.87 μmol) in 1,4-dioxane (10 mL) were added 3,5-dimethylisoxazole-4-boric acid pinacol ester (181.65 mg, 814.31 μmol), tetrakis (triphenylphosphine) palladium (62.73 mg, 54.29 μmol), sodium carbonate (2 M, 814.31 μL), which was stirred at 100° C. under nitrogen atmosphere for 12 h. The reaction system was cooled to room temperature, diluted with ethyl acetate (50 mL), washed with water (20 ml) and saturated brine (20 ml), respectively, dried over anhydrous sodium sulfate and filtered. The solvent was removed under reduce pressure to give the crude product, which was purified with column chromatography (petroleum ether/ethyl acetate: 33%~50%) to give Compound WX51-2.

MS-ESI: 448.3[M+H]+

Step 3: Synthesis of Compound WX51

Except using corresponding raw materials, the procedures identical to those used for Compound WX37 in synthesis Example WX37 were used to give Compound WX50.

MS-ESI m/z: 420.1 [M+H]+.

$^1$H NMR (400 MHz, DMSO-d$_6$) δ ppm 1.30 (d, J=6.78 Hz, 3H) 2.48 (s, 3H) 2.68 (s, 3H) 3.24-3.30 (m, 1H) 3.51-3.61 (m, 1H) 3.67-3.74 (m, 1H) 3.79-3.86 (m, 1H) 4.03 (br d, J=7.78 Hz, 1H) 4.26 (br d, J=13.05 Hz, 1H) 4.58-4.63 (m, 1H) 4.65 (d, J=5.77 Hz, 2H) 5.16 (t, J=5.77 Hz, 1H) 5.76 (s, 1H) 6.73 (s, 1H) 7.25 (br s, 1H) 7.41 (t, J=2.64 Hz, 1H) 7.50 (s, 1H) 8.09 (d, J=1.25 Hz, 1H) 11.20 (br s, 1H)

Example 52

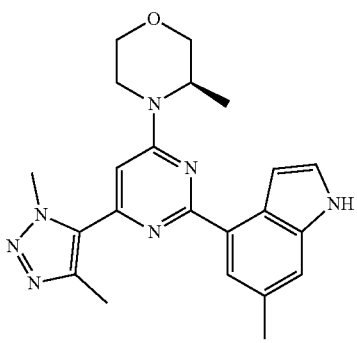

WX52

Synthesis Scheme

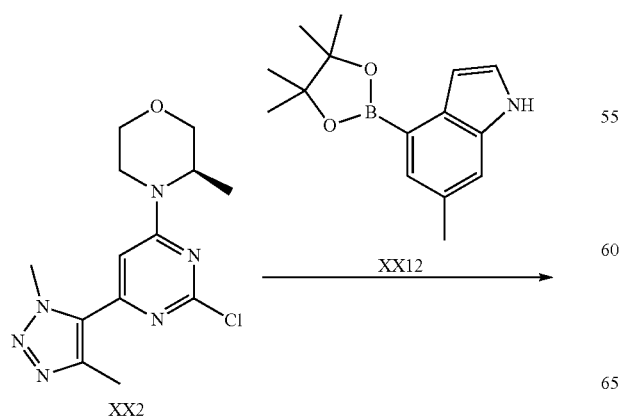

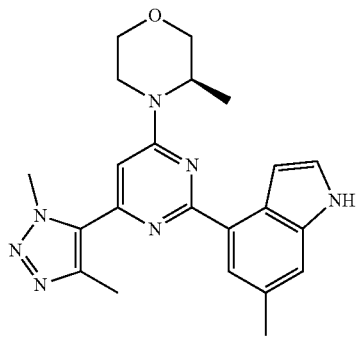

WX52

Step 1: Synthesis of Compound WX52

Except using corresponding raw materials, the procedures identical to those used for Compound WX13 in synthesis Example 13 were used to give Compound WX52.

MS-ESI m/z: 404.21 [M+H]+.

$^1$H NMR (400 MHz, CHLOROFORM-d) δ=8.15 (br s, 1H), 7.99 (s, 1H), 7.30 (t, J=2.3 Hz, 1H), 7.28 (s, 1H), 7.20 (br s, 1H), 6.41 (s, 1H), 4.44 (br s, 1H), 4.28 (s, 3H), 4.19 (br d, J=12.5 Hz, 1H), 4.05 (dd, J=3.6, 11.4 Hz, 1H), 3.85-3.80 (m, 1H), 3.77-3.72 (m, 1H), 3.61 (dt, J=3.0, 11.9 Hz, 1H), 3.36 (dt, J=4.0, 12.7 Hz, 1H), 2.48 (s, 3H), 2.47 (s, 3H), 1.36 (d, J=6.8 Hz, 3H)

Example 53

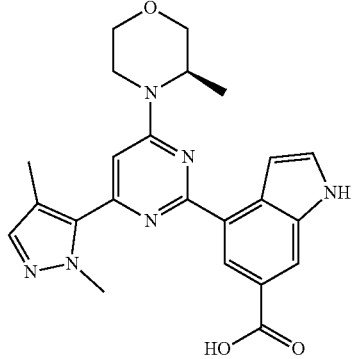

WX53

147
Synthesis Scheme

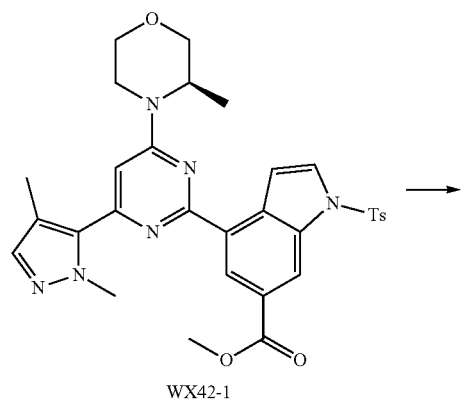

Step 1: Synthesis of Compound WX53

To a solution of Compound WX42-1 (100 mg, 166.48 µmol) in 1,4-dioxane (2 mL) was added 2M sodium hydroxide aqueous solution (0.25 mL). The reaction mixture was stirred with heating at 80° C. for 1.5 h, then adjusted to pH 5 with hydrochloric acid, and then extracted with dichloromethane and water. The organic phase was washed once with saturated brine, dried over anhydrous sodium sulfate, and concentrated to give the crude product, which was separated with pre-HPLC (neutral condition) to give Compound 2.

MS-ESI m/z: 433.31 [M+H]+.

$^1$H NMR (400 MHz, DMSO-$d_6$) δ=11.65 (br s, 1H), 8.78 (d, J=1.5 Hz, 1H), 8.17 (s, 1H), 7.69 (t, J=2.8 Hz, 1H), 7.41 (s, 1H), 7.38 (br s, 1H), 6.82 (s, 1H), 4.60 (br s, 1H), 4.29 (br d, J=11.3 Hz, 1H), 4.05 (br s, 1H), 4.03 (s, 3H), 3.86-3.80 (m, 1H), 3.71 (br d, J=9.4 Hz, 1H), 3.61-3.53 (m, 1H), 3.28 (s, 1H), 2.20 (s, 3H), 1.32 (d, J=6.6 Hz, 3H).

148
Example 54

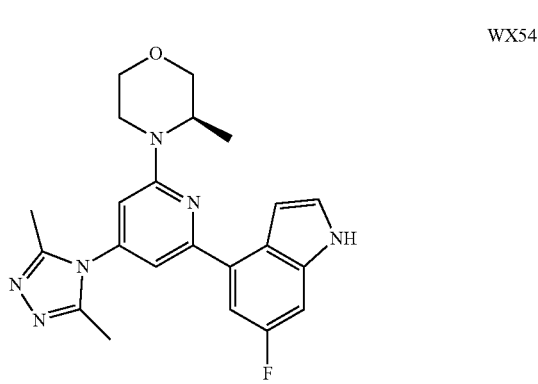 [SMILES: Cc1nnc(C)n1-c1cc(-c2cc(F)cc3[nH]ccc23)nc(N2CCOC[C@H]2C)c1]

Synthesis Scheme

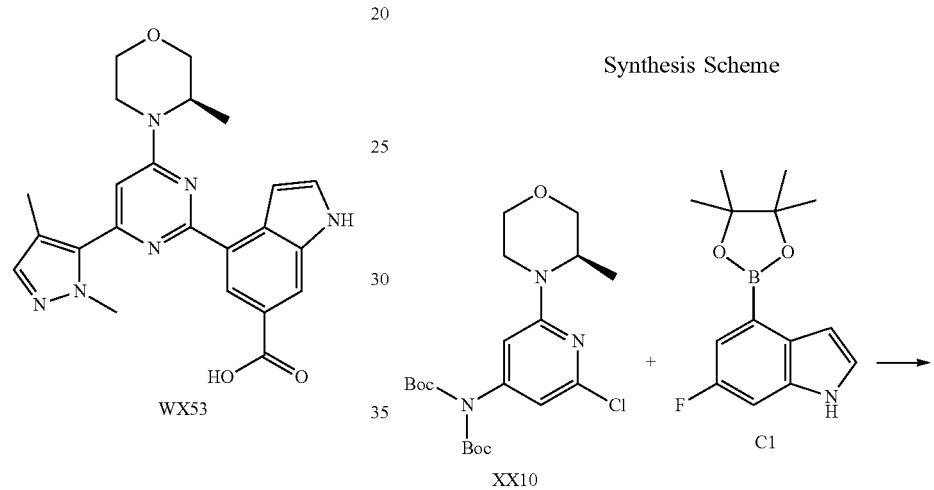

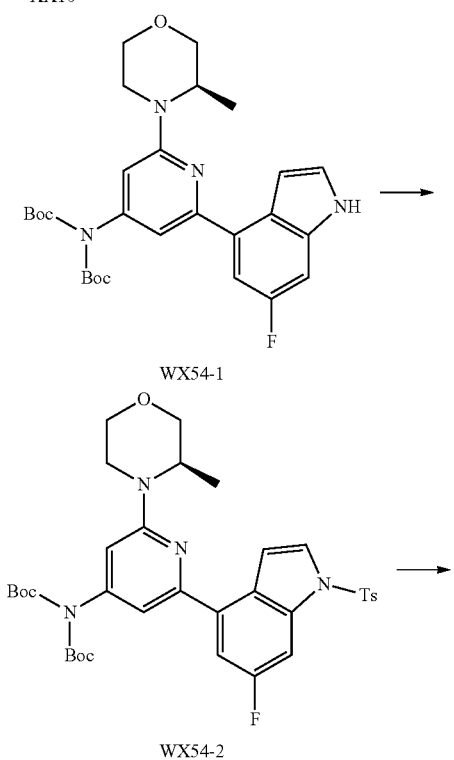

-continued

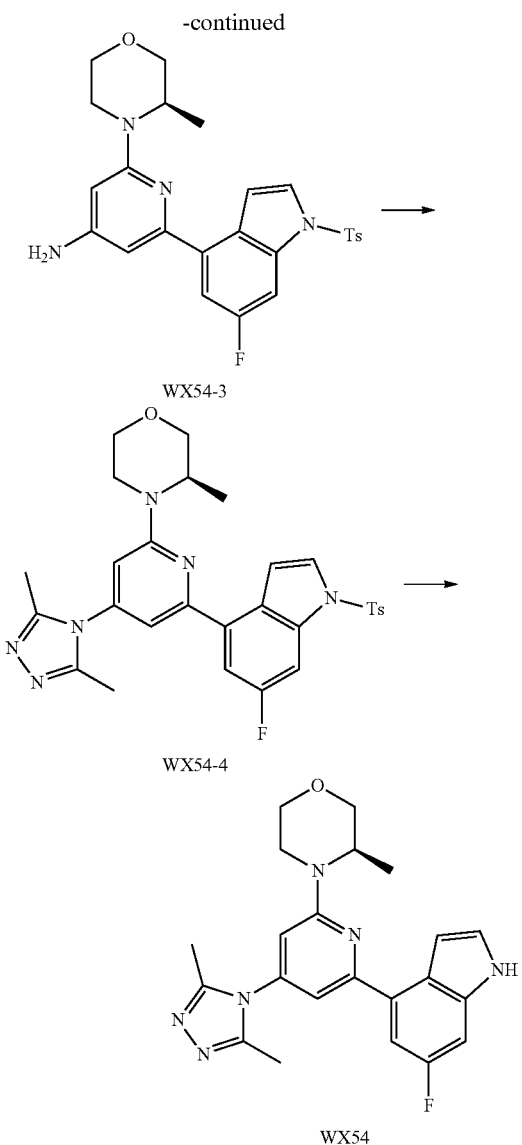

Step 1: Synthesis of Compound WX54-1

To a solution of Compound XX10 (0.35 g, 817.91 μmol), C1 (256.27 mg, 981.49 μmol) and tetrakis (triphenylphosphine) palladium ((66.16 mg, 57.25 μmol) of 1,4-dioxane (8 mL)) was added 2M sodium carbonate (2 M, 1.02 mL) aqueous solution, which was purged with nitrogen three times. The reaction mixture was stirred with heating at 90° C. for 36 h and then filtered. The solution was concentrated to give the crude product, which was separated with column chromatography (ethyl acetate/petroleum ether: 15-45%) to give Compound WX54-1.

MS-ESI m/z: 527.4 [M+H]+.

Step 2: Synthesis of Compound WX54-2

At 0-5° C., to a solution of Compound WX54-1 (0.43 g, 816.56 mmol) in N'N-dimethylformamide (10 mL) was added sodium hydride (37.56 mg, 939.05 mmol, purity: 60%). The reaction mixture was stirred at 0-5° C. for 15 min, to which was added p-toluenesulfonyl chloride (186.81 mg, 979.87 μmol). The reaction mixture was stirred at 0-5° C. for 2 h, quenched with water (40 mL) at 0-5° C. and extracted with ethyl acetate (50 mL*3). The organic phases were combined, washed with saturated brine (80 mL), dried over anhydrous sodium sulfate, filtered and concentrated to give WX54-2.

MS-ESI m/z: 681.5 [M+H]+.

Step 3: Synthesis of Compound WX54-3

To solution of Compound WX54-2 (0.56 g, 822.58 mmol) in 1,4-dioxane (10 mL) was added 4M hydrochloric acid/ 1,4-dioxane (4 M, 4.67 mL). The reaction mixture was stirred at 30° C. for 36 h, adjusted to pH=7-8 with saturated sodium bicarbonate, diluted with water (30 mL) and extracted with dichloromethane (40 mL*3). The organic phases were combined, washed with saturated brine (50 mL), dried over anhydrous sodium sulfate, filtered and concentrated to give the crude product, which was separated with column chromatography (ethyl acetate/petroleum ether: 25-50%) to give Compound WX54-3.

MS-ESI m/z: 481.3 [M+H]$^+$

Step 4: Synthesis of Compound WX54-4

To a solution of Compound WX54-3 (0.12 g, 249.71 μmol), 2,5-dimethyl-1,3,4-oxadiazole (97.99 mg, 998.85 μmol) in 1-methyl-2-pyrrolidone (2 mL) was added anhydrous p-toluenesulfonic acid (43.00 mg, 249.71 μmol), which was stirred at 220° C. with microwave for 1.5 h. The reaction solution was concentrated to give the crude product, which was separated with column chromatography (methanol/dichloromethane: 2-8%) to give Compound WX54-4.

MS-ESI m/z: 561.4[M+H]$^+$

Step 5: Synthesis of Compound WX54

To a solution of Compound WX54-4 (0.05 g, 89.18 μmol) in 1,4-dioxane (10 mL) was added 2M sodium hydroxide (2 M, 3 mL). The reaction mixture was stirred at 80° C. for 12 h, adjusted to pH=7 with 1M hydrochloric acid, diluted with water (15 mL) and extracted with dichloromethane (25 mL*3). The organic phases were combined, washed with saturated brine (30 mL), and dried over anhydrous sodium sulfate. The filtered organic phase was concentrated to give the crude product, which was separated with column chromatography (methanol/dichloromethane: 10:1) to give Compound WX54.

MS-ESI m/z: 407.2 [M+H]$^+$ $^1$H NMR (CHLOROFORM-d, 400 MHz): δ=8.50 (br s, 1H), 7.32 (dd, J=10.5, 2.3 Hz, 1H), 7.25 (t, J=2.8 Hz, 1H), 7.12 (dd, J=8.9, 1.6 Hz, 1H), 6.88 (s, 1H), 6.85 (br s, 1H), 6.26 (s, 1H), 4.30 (br d, J=6.0 Hz, 1H), 3.97-4.08 (m, 2H), 3.72-3.83 (m, 2H), 3.60 (td, J=11.9, 3.1 Hz, 1H), 3.29 (td, J=12.7, 3.9 Hz, 1H), 2.34 (s, 6H), 1.30 ppm (d, J=6.8 Hz, 3H).

Example 55

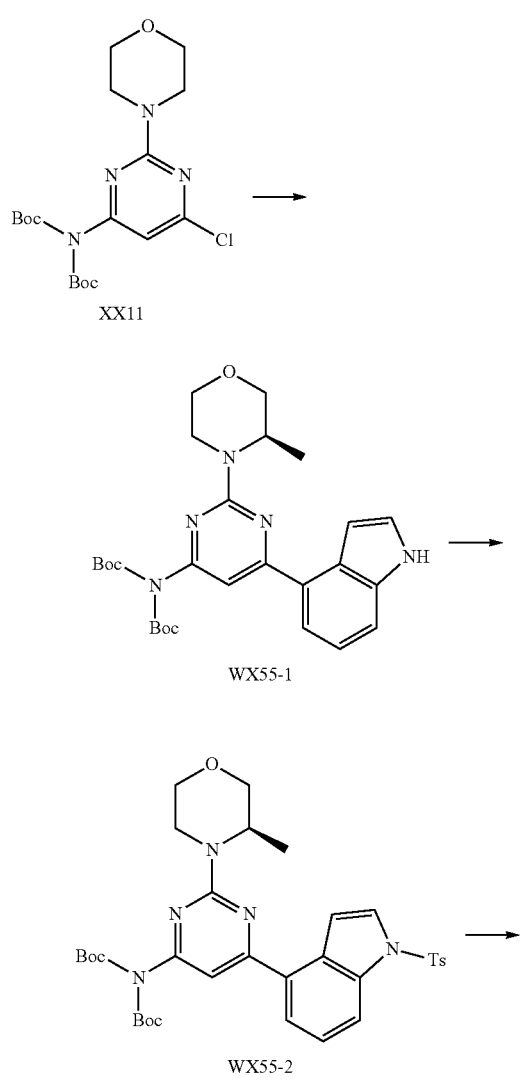

Synthesis Scheme

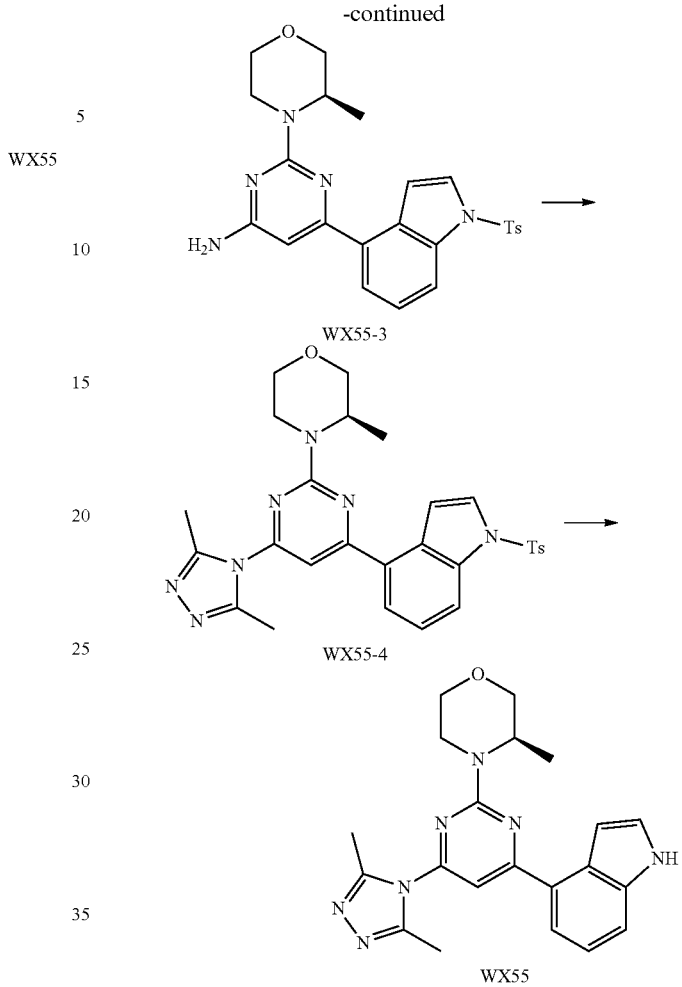

Step 1: Synthesis of Compound WX55-1

Except using corresponding raw materials, the procedures identical to those used for Compound WX54-1 in synthesis Example 54 were used to give Compound WX55-1.
MS-ESI m/z: 510.4 [M+H]$^+$

Step 2: Synthesis of Compound WX55-2

Except using corresponding raw materials, the procedures identical to those used for Compound WX54-2 in synthesis Example 54 were used to give Compound WX55-2.
MS-ESI m/z: 664.5 [M+H]$^+$

Step 3: Synthesis of Compound WX55-3

Except using corresponding raw materials, the procedures identical to those used for Compound WX54-3 in synthesis Example 54 were used to give Compound WX55-3.
MS-ESI m/z: 464.3 [M+H]$^+$

Step 4: Synthesis of Compound WX55-4

Except using corresponding raw materials, the procedures identical to those used for Compound WX54-3 in synthesis Example 54 were used to give Compound WX55-4.
MS-ESI m/z: 544.4 [M+H]$^+$ Step 5: Synthesis of Compound WX55

Except using corresponding raw materials, the procedures identical to those used for Compound WX54 in synthesis Example 54 were used to give Compound WX55.

MS-ESI m/z: 390.2 [M+H]$^+$ $^1$H NMR (CHLOROFORM-d, 400 MHz): δ=8.80 (br s, 1H), 7.68 (d, J=7.5 Hz, 1H), 7.62 (d, J=8.1 Hz, 1H), 7.41-7.45 (m, 1H), 7.34 (t, J=7.8 Hz, 1H), 7.13 (br s, 1H), 6.95 (s, 1H), 4.85 (br s, 1H), 4.54 (br d, J=12.8 Hz, 1H), 4.08 (dd, J=11.4, 3.1 Hz, 1H), 3.83-3.92 (m, 1H), 3.74-3.83 (m, 1H), 3.64 (td, J=11.9, 2.6 Hz, 1H), 3.45 (td, J=12.9, 3.4 Hz, 1H), 2.58 (s, 6H), 1.44 ppm (d, J=6.8 Hz, 3H)

Example 56

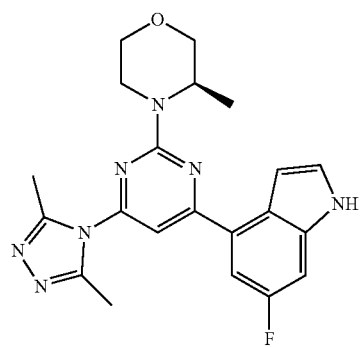

WX56

Synthesis Scheme

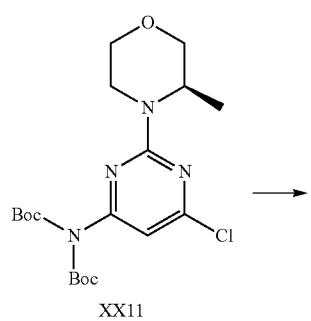

XX11

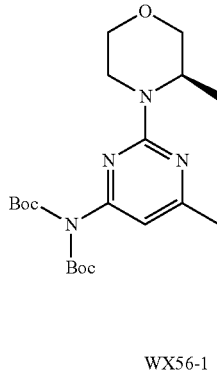

WX56-1

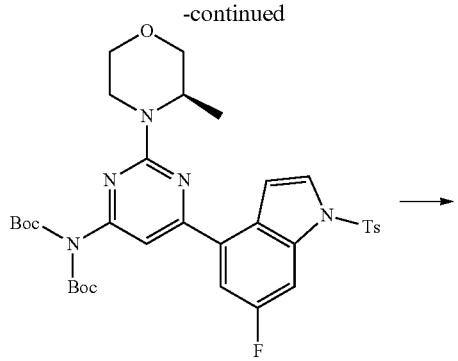

WX56-2

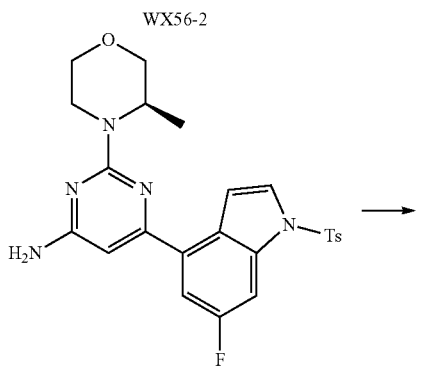

WX56-3

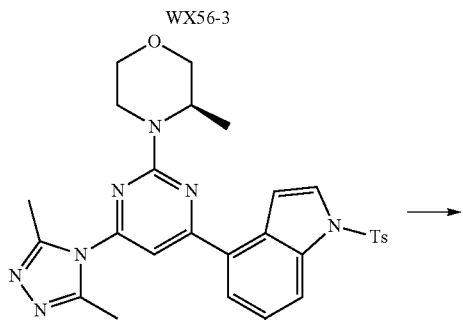

WX56-4

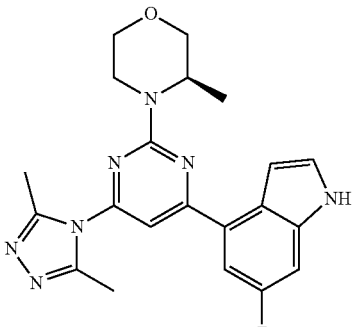

WX56

Step 1: Synthesis of Compound WX56-1

Except using corresponding raw materials, the procedures identical to those used for Compound WX54-1 in synthesis Example 54 were used to give Compound WX56-1.

MS-ESI m/z: 528.4 [M+H]$^+$

Step 2: Synthesis of Compound WX56-2

Except using corresponding raw materials, the procedures identical to those used for Compound WX54-2 in synthesis Example 54 were used to give Compound WX56-2.
MS-ESI m/z: 682.5 [M+H]$^+$

Step 3: Synthesis of Compound WX56-3

Except using corresponding raw materials, the procedures identical to those used for Compound WX54-3 in synthesis Example 54 were used to give Compound WX56-3.
MS-ESI m/z: 482.6 [M+H]$^+$

Step 4: Synthesis of Compound WX56-4

Except using corresponding raw materials, the procedures identical to those used for Compound WX54-3 in synthesis Example 54 were used to give Compound WX564.
MS-ESI m/z: 562.3 [M+H]$^+$

Step 5: Synthesis of Compound WX56

Except using corresponding raw materials, the procedures identical to those used for Compound WX54 in synthesis Example 54 were used to give Compound WX56.
MS-ESI m/z: 407.9 [M+H]$^+$
$^1$H NMR (400 MHz, CHLOROFORM-d) δ=8.47 (br s, 1H), 7.48 (br d, J=10.6 Hz, 1H), 7.39 (br s, 1H), 7.31 (s, 1H), 7.03 (br s, 1H), 6.92 (s, 1H), 4.84 (br s, 1H), 4.51 (br s, 1H), 4.08 (br d, J=10.4 Hz, 1H), 3.90-3.83 (m, 1H), 3.81-3.75 (m, 1H), 3.64 (br t, J=11.6 Hz, 1H), 3.50-3.39 (m, 1H), 2.58 (s, 6H), 1.44 (br d, J=6.5 Hz, 3H).

Example 57

WX57

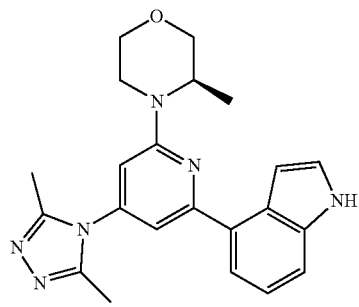

Synthesis Scheme

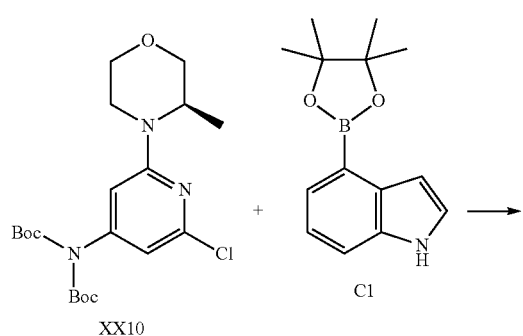

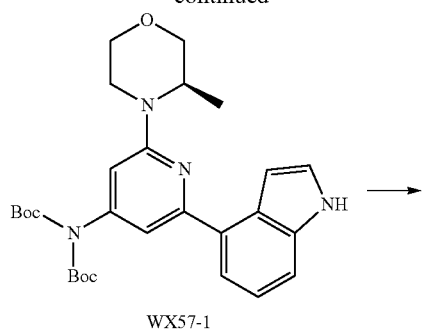

WX57-1

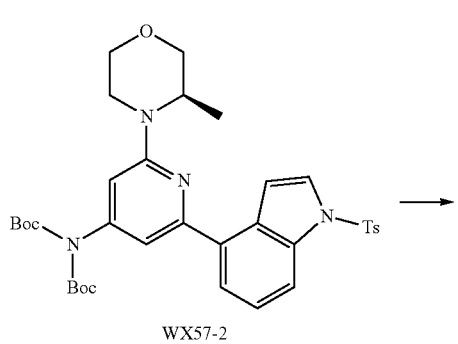

WX57-2

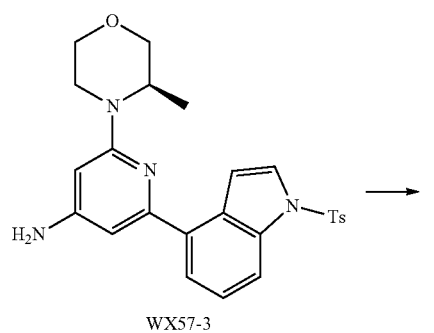

WX57-3

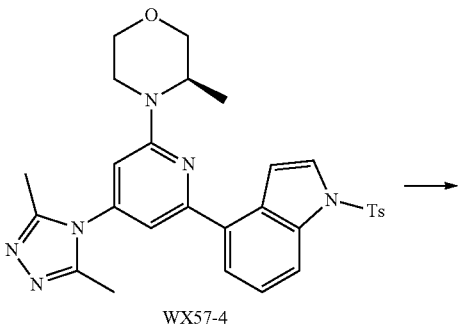

WX57-4

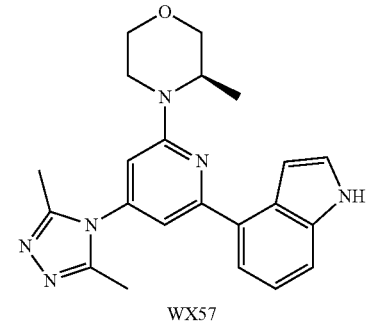

WX57

Step 1: Synthesis of Compound WX57-1

Except using corresponding raw materials, the procedures identical to those used for Compound WX54-1 in synthesis Example 54 were used to give Compound WX57-1.
MS-ESI m/z: 509.4 [M+H]+.

Step 2: Synthesis of Compound WX57-2

Except using corresponding raw materials, the procedures identical to those used for Compound WX54-2 in synthesis Example 54 were used to give Compound WX57-2.
MS-ESI m/z: 663.5 [M+H]+.

Step 3: Synthesis of Compound WX57-3

Except using corresponding raw materials, the procedures identical to those used for Compound WX54-3 in synthesis Example 54 were used to give Compound WX57-3.
MS-ESI m/z: 463.3 [M+H]$^+$

Step 4: Synthesis of Compound WX57-4

Except using corresponding raw materials, the procedures identical to those used for Compound WX54-4 in synthesis Example 54 were used to give Compound WX57-4.
MS-ESI m/z: 542.9 [M+H]$^+$

Step 5: Synthesis of Compound WX57

Except using corresponding raw materials, the procedures identical to those used for Compound WX54 in synthesis Example 54 were used to give Compound WX57.
MS-ESI m/z: 389.0 [M+H]$^+$
$^1$H NMR (400 MHz, CHLOROFORM-d) δ ppm 1.38 (d, J=6.78 Hz, 3H) 2.41 (s, 6H) 3.37 (td, J=12.67, 4.02 Hz, 1H) 3.68 (td, J=11.86, 3.14 Hz, 1H) 3.80-3.89 (m, 2H) 4.05-4.15 (m, 2H) 4.39 (br d, J=6.78 Hz, 1H) 6.28 (d, J=1.25 Hz, 1H) 6.98 (d, J=1.00 Hz, 1H) 7.01 (br s, 1H) 7.28-7.33 (m, 1H) 7.36 (t, J=2.89 Hz, 1H) 7.52 (d, J=8.28 Hz, 1H) 7.58 (d, J=7.28 Hz, 1H) 8.69 (br s, 1H)

Experimental Example 1: In Vitro Evaluation

IC$_{50}$ values were determined to evaluate the inhibitory activity of the tested compounds on human ATR kinase.

ATR/ATRIP(h) was incubated in assay buffer containing 50 nM GST-cMyc-p53 and Mg/ATP (according to concentration required). The reaction was initiated by adding Mg/ATP mixture. After incubating for 30 min at room temperature, a stop solution containing EDTA to was added to terminate the reaction. Finally, detecting buffer containing d$^2$-labeled anti-GST monoclonal antibody and europium-labeled anti-phospho Ser15 antibody against phosphorylated p$^{53}$ were added. Then the plate was read in time-resolved fluorescence mode and homogeneous time resolution was performed.

The fluorescence (HTRF) signal was determined according to the formula HTRF=10000×(Em665 nm/Em620 nm).

IC$_{50}$ data was analyzed using XLFit version 5.3 (ID Business Solutions). Non-linear regression analysis was used to fit the sigmoidal dose response (variable slope) curve. The experimental results were shown in Table 1.

TABLE 1

In vitro screening test results of the present compounds

| Compound | ATR average IC$_{50}$(nM) |
|---|---|
| WX01 | 119 |
| WX02 | 72 |
| WX03 | 72 |
| WX04 | 91 |
| WX05 | 53 |
| WX06 | 245 |
| WX07 | 75 |
| WX08 | 126 |
| WX09 | 369 |
| WX10 | 80 |
| WX11 | 191 |
| WX12 | 41 |
| WX13 | 24 |
| WX14 | 50 |
| WX15 | 159 |
| WX16 | 97 |
| WX17 | 12 |
| WX18 | 83 |
| WX19 | 81 |
| WX20 | 69 |
| WX21 | 27 |
| WX22 | 65 |
| WX23 | 115 |
| WX24 | 18 |
| WX25 | 92 |
| WX26 | 123 |
| WX27 | 123 |
| WX28 | 47 |
| WX29 | 96 |
| WX30 | 35 |
| WX31 | 39 |
| WX32 | 35 |
| WX33 | 198 |
| WX34 | 69 |
| WX35 | 19 |
| WX36 | 14 |
| WX37 | 16 |
| WX38 | 78 |
| WX39 | 42 |
| WX40 | 15 |
| WX41 | 78 |
| WX42 | 29 |
| WX43 | 65 |
| WX44 | 65 |
| WX45 | 69 |
| WX46 | 31 |
| WX47 | 64 |
| WX48 | 105 |
| WX49 | 26 |
| WX50 | 42 |
| WX51 | 32 |
| WX52 | 20 |
| WX53 | 83 |
| WX54 | 27 |
| WX55 | 20 |
| WX56 | 46 |
| WX57 | 28 |

Conclusion: The present compounds have good inhibitory activity against ATR.

Experimental Example 2: In Vitro Cell Viability Test

In this experiment, inhibitory effect of the compounds on cell proliferation was investigated by testing influence on cell viability in vitro in tumor cell line LoVo.

CellTiter-Glo Luminescence Cell Viability Test

The following protocols were performed according to instruction of PromegaCellTiter-Glo Luminescence cell viability test Kit (Promega-G7573).

(1) Thawing CellTiter-Glo buffer and allowing it to acclimate to room temperature.
(2) Allowing CellTiter-Glo substrate to acclimate to room temperature.
(3) Adding CellTiter-Glo buffer to a bottle of CellTiter-Glo substrate to dissolve the substrate to prepare CellTiter-Glo working solution.
(4) Vortexing slowly to full dissolution.
(5) Removing the cell culture plate and balancing it to room temperature for 30 min.
(6) Adding 50 μL (equivalent to half volume of cell culture medium in each well) of CellTiter-Glo working solution to each well, wrapping the cell plate with aluminum foil to protect from light.
(7) Shaking the culture plate on an orbital shaker for 2 min to induce cell lysis.
(8) Placing the culture plate at room temperature for 10 min to stabilize the luminescence signal.
(9) Detecting the luminescence signal on SpectraMax i3x of Molecular Devices plate reader.

Data Analysis

The following formula was used to calculate the inhibition rate of the test compound (Inhibition rate, IR):

IR(%)=(1−(RLU Compound−RLU Blank control)/(RLU Vehicle control−RLU Blank control))*100%.

The inhibition rates of different concentrations of compounds were calculated in Excel, and GraphPad Prism software was used to make the inhibition curve and calculate relevant parameters, including the minimum inhibition rate, the maximum inhibition rate and $IC_{50}$.

The experimental results were shown in Table 2.

TABLE 2

Results of LoVo cell proliferation inhibition in vitro

| | AZD6738 | WX15 | WX42 | WX45 | WX46 | WX47 |
|---|---|---|---|---|---|---|
| IC50 (uM) | 0.82 | 0.41 | 0.51 | 0.75 | 0.35 | 0.76 |

Conclusion: The present compounds have a good inhibitory effect on LoVo tumor cells with mutations in ATM signaling pathway.

Experimental Example 3: Study on Pharmacokinetic Properties In Vivo

Testing samples: On the basis of the above experiments, some of the highly active compounds with representative structures were selected for further experiments.

Experimental method: The purpose of this study was to determine the pharmacokinetic parameters of the compounds and calculate the oral bioavailability in female Balb/c Nude mice.

The project involved 6 female Balb/c Nude mice. 3 mice were administered intravenously at a dose of 1 mg/kg, and plasma samples were collected at 0 h (before administration) and 0.0833, 0.25, 0.5, 1, 2, 4, 6, 8 and 24 h after administration, other 3 mice were given by oral gavage at a dose of 10 mg/kg or 25 mg/kg, and plasma samples were collected at 0 h (before dosing) and 0.5, 1, 2, 3, 4, 6, 8, 24 h after administration. Then LC/MS/MS analysis was performed for the collected samples and data was collected. The collected analysis data was calculated for relevant pharmacokinetic parameters with Phoenix WinNonlin 6.2.1 software.

The experimental results were shown in Table 3.1 and Table 3.2.

| 3.1 Intravenous administration results | | | | |
|---|---|---|---|---|
| | WX15 (1 mg/kg) | WX34 (1 mg/kg IV) | WX42 (1 mg/kg IV) | WX45 (1 mg/kg IV) |
| $C_0$ (nM) | 1962 | 1260 | 1955 | 1579 |
| Cl (mL/min/kg) | 47.0 | 53.9 | 34.3 | 48.3 |
| $V_{dss}$ (L/kg) | 2.21 | 3.72 | 2.21 | 2.59 |
| $T_{1/2}$ (h) | 0.78 | 1.22 | 2.57 | 0.99 |
| $AUC_{0-t}$ (nM·h) | 905 | 787 | 1087 | 880 |

| 3.2 Oral administration results | | | | | |
|---|---|---|---|---|---|
| | WX15 (10 mg/kg) | WX34 (10 mg/kg) | WX42 (10 mg/kg) | WX45 (10 mg/kg) | WX46 (25 mg/kg) |
| Cmax (nM) | 4560 | 2863 | 6500 | 7717 | 10600 |
| $T_{1/2}$ (h) | 1.23 | 1.16 | 2.02 | 1.69 | 0.892 |
| $AUC_{0-t}$ (nM·h) | 8747 | 5681 | 14983 | 10911 | 26206 |
| F (%) | 96.0 | 71.7 | 129.0 | 123.0 | — |

Note:
"—" indicates that no relevant test was done; $C_0$ (nM) is drug concentration at 0 min in vivo; Cl (mL/min/kg) is drug clearance rate in vivo; $V_{dss}$ (L/kg) is distribution volume of drug in vivo; $T_{1/2}$ (h) is half-life; $AUC_{0-t}$ (nM·h) is drug exposure in vivo; Cmax (nM) is highest concentration of drug in vivo.

Conclusion: The present compounds have good absorption and exposure at oral administration, and is suitable for oral administration.

Experimental Example 4: Study on In Vivo Efficacy in Colorectal Cancer LoVo CDX Model Purpose:

LoVo is a colorectal adenocarcinoma tumor cell line with MRE11A mutation (MRE11A is a key component of DNA double-strand break repairing ATM signaling pathway), which is sensitive to ATR inhibitor. In this experiment, the colorectal cancer LoVo CDX model was used to verify the inhibitory effect of ATR inhibitor as monotherapy on tumors with defect in ATM signaling pathway.

Procedures:

1. LABORATORY ANIMAL

Species: mouse
Strain: BALB/c nude mice
Supplier: Beijing Vital River Laboratory Animal Technology Co., Ltd.
Weeks and weight: 6-8 weeks, weight 18-22 g
Gender: female

2. CELL CULTURE

Human colorectal cancer LoVo cells (ECACC, CatLog: 87060101), in vitro monolayer culture, culture conditions: Ham's F-12 medium with 10% fetal bovine serum, 100 U/mL penicillin, 100 μg/mL streptomycin and 2 mM glutamine, 37° C., 5% $CO_2$ culture. General passage with trypsin-EDTA digestion was performed twice a week. When the cell saturation was 80%-90%, the cells were collected, counted, and inoculated. 0.1 mL ($10 \times 10^6$) of LoVo cells were subcutaneously inoculated into the right back of each nude mouse. When the mean tumor volume reached 173 mm³, grouping and administration were initiated.

3. PREPARATION AND DOSE OF TESTING SUBSTANCES

1) Compound WX15

25.51 mg of WX15 was weighed and dissolved in 0.500 mL of DMSO, which were added with 2.000 mL of propylene glycol and 2.500 mL of deionized water, vortexed for homogeneous mixing, adjusted to PH=6.0, to obtain a clear solution. The preparing processes of Compound WX42, Compound WX45, Compound WX46 were referred to Compound WX15.

Dosage: All test compounds were administered orally at 25 mg/kg twice a day, with an interval of 8 h in a day.

4. TUMOR MEASUREMENT AND EXPERIMENTAL INDICATORS

A vernier caliper was used to measure the tumor diameter twice a week. The formula for calculating the tumor volume: V=0.5a×b², a and b represent the long and short diameters of the tumor, respectively. Antitumor efficacy of the compound was evaluated by TGI (%) or relative tumor proliferation rate T/C (%). Relative tumor proliferation rate T/C (%)=TRTV/CRTV×100% (TRTV: mean RTV value of treatment group; CRTV: mean RTV value of negative control group). The relative tumor volume (relative tumor volume, RTV) was calculated based on the tumor measurement results and the calculation formula was RTV=Vt/V0, where V0 is the tumor volume measured at grouping administration (i.e. D0), Vt is the tumor volume at a measurement, and data on the same day was used for TRTV and CRTV.

TGI (%) reflects the tumor growth inhibition rate. TGI (%)=[1−(mean tumor volume at the end of administration in a treatment group−mean tumor volume at the beginning of administration in this treatment group)/(mean tumor volume at the end of treatment in the solvent control group−mean tumor volume at the beginning of treatment in the solvent control group)]×100%.

At the end of the experiment, the tumor weights were weighed, and the T/C weight percentage was calculated. Tweight and Cweight represent the tumor weights of the administration group and the vehicle control group, respectively.

5. EXPERIMENTAL RESULTS

This experiment evaluated the efficacy of the compounds in human colorectal cancer xenograft model, with the solvent control group as reference. The tumor volumes of each group at different time points were shown in FIG. 1. At day 17 of administration, T/C and TGI of WX42 (25 mg/kg) group were 27.8% and 90.7%, respectively, as compared with the vehicle control group; T/C and TGI of WX45 (25 mg/kg) group were 32.3% and 79.9% respectively, as compared with the vehicle control group; T/C and TGI of WX46 (25 mg/kg) group were 43.8% and 79.9% respectively, as compared with vehicle control group; T/C and TGI of WX15 (25 mg/kg) group were 46.7% and 66.8%, respectively, as compared with the vehicle control group.

6. CONCLUSION

In this experiment, the present compounds had inhibitory effect on growth of tumor-bearing mice of human colorectal cancer LoVo cell subcutaneous xenograft tumor model.

The invention claimed is:

1. A compound of formula (I), or a tautomer or a pharmaceutically acceptable salt thereof,

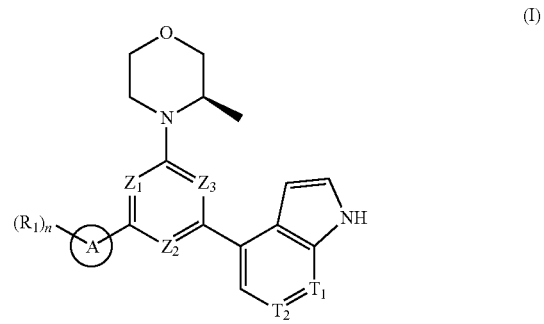

(I)

wherein, n is 1, 2, 3 or 4;

$Z_1$, $Z_2$, and $Z_3$ are each independently selected from the group consisting of CH and N, and at least one of $Z_1$, $Z_2$ and $Z_3$ is N;

$T_1$ and $T_2$ are each independently selected from the group consisting of $C(R_2)$ and N;

ring A is selected from the group consisting of 5-6 membered heteroaryl;

$R_1$ is each independently selected from the group consisting of H, F, Cl, Br, I, OH, $NH_2$, $C_{1-6}$ alkyl, $C_{1-6}$ alkoxy and $C_{3-6}$ cycloalkyl, wherein the $C_{1-6}$ alkyl, $C_{1-6}$ alkoxy and $C_{3-6}$ cycloalkyl are optionally substituted by 1, 2 or 3 R;

$R_2$ is each independently selected from the group consisting of H, F, Cl, Br, I, OH, $NH_2$, COOH and $C_{1-3}$ alkyl, wherein the $C_{1-3}$ alkyl is optionally substituted by 1, 2 or 3 R;

R is each independently selected from the group consisting of F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted by 1, 2 or 3 R';

R' is each independently selected from the group consisting of F, Cl, Br, I, OH and $NH_2$;

the 5-6 membered heteroaryl comprises 1, 2, 3 or 4 heteroatoms or heteroradicals independently selected from the group consisting of —NH—, —O—, —S— and N;

provided that the compound of formula (I) is not:
  (3R)-3-methyl-4-[6-(pyridin-3-yl)-2-[1H-pyrrolo[2,3-b]pyridin-4-yl]pyrimidin-4-yl]morpholine,
  (R)-4-(2-(1H-pyrrolo[2,3-b]pyridin-4-yl)-6-(6-(trifluoromethyl)pyridin-3-yl)pyrimidin-4-yl)-3-methylmorpholine, or
  (R)-5-(6-(3-methylmorpholino)-2-(1H-pyrrolo[2,3-b]pyridin-4-yl)pyrimidin-4-yl)pyridin-2-amine.

2. The compound according to claim 1, or the tautomer or the pharmaceutically acceptable salt thereof, wherein, R is each independently selected from the group consisting of H, F, Cl, Br, I, OH, $NH_2$, $CH_3$, Et and —O—$CH_3$.

3. The compound according to claim 1, or the tautomer or the pharmaceutically acceptable salt thereof, wherein, $R_1$ is each independently selected from the group consisting of H, F, Cl, Br, I, OH, $NH_2$, $C_{1-3}$ alkyl, $C_{1-3}$ alkoxy and cyclopropyl, wherein the $C_{1-3}$ alkyl, $C_{1-3}$ alkoxy and cyclopropyl are optionally substituted by 1, 2 or 3 R.

4. The compound according to claim 3, or the tautomer or the pharmaceutically acceptable salt thereof, wherein, $R_1$ is each independently selected from the group consisting of H, F, Cl, Br, I, OH, $NH_2$, $CH_3$, $CH_2F$, $CHF_2$, $CF_3$, Et, —$CH_2OH$, —O—$CH_3$,

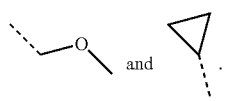 and

5. The compound according to claim 1, or the tautomer or the pharmaceutically acceptable salt thereof, wherein, $R_2$ is each independently selected from the group consisting of H, F, Cl, Br, I, OH, $NH_2$, COOH, $CH_3$, Et and —$CH_2$—OH.

6. The compound according to claim 1, or the tautomer or the pharmaceutically acceptable salt thereof, wherein, ring A is selected from the group consisting of pyrazolyl, isoxazolyl, oxazolyl, imidazolyl, 1,2,3-triazolyl, 1,2,4-triazolyl and pyridyl.

7. The compound according to claim 6, or the tautomer or the pharmaceutically acceptable salt thereof, wherein, ring A is selected from the group consisting of

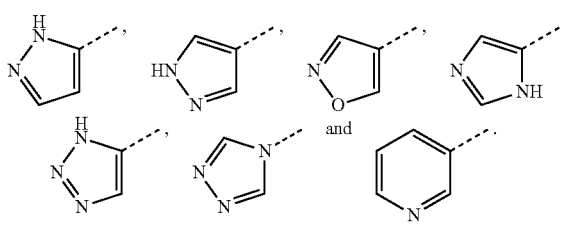

8. The compound according to claim 1, or the tautomer or the pharmaceutically acceptable salt thereof, wherein, the structural unit

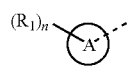

is selected from the group consisting of

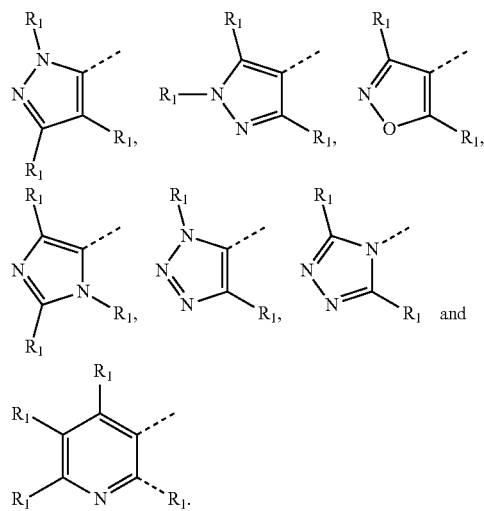

9. The compound according to claim 8, or the tautomer or the pharmaceutically acceptable salt thereof, wherein, the structural unit

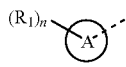

is selected from the group consisting of

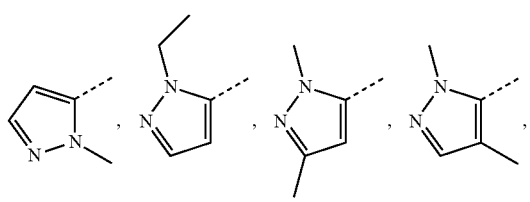

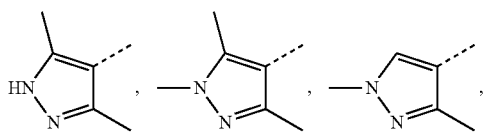

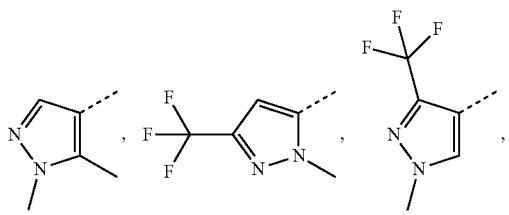

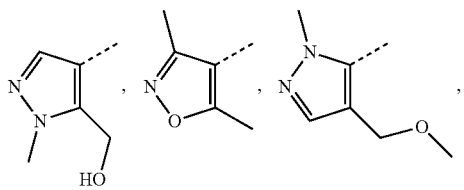

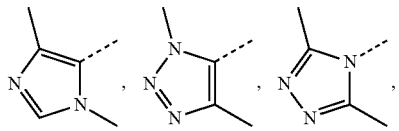

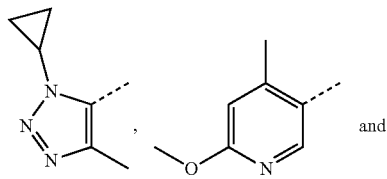 and

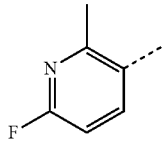

10. The compound according to claim 1, or the tautomer or the pharmaceutically acceptable salt thereof, wherein, the structural unit

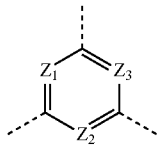

is selected from the group consisting of

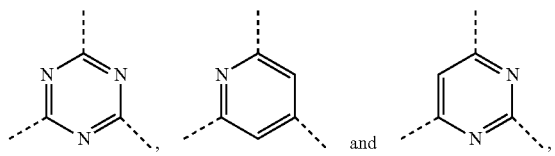

11. The compound according to claim 1, or the tautomer or the pharmaceutically acceptable salt thereof, wherein, the structural unit

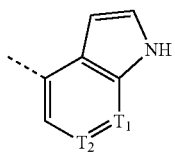

is selected from the group consisting of

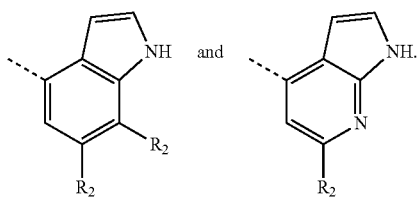

12. The compound according to claim 1, or the tautomer or the pharmaceutically acceptable salt thereof, wherein the compound is selected from

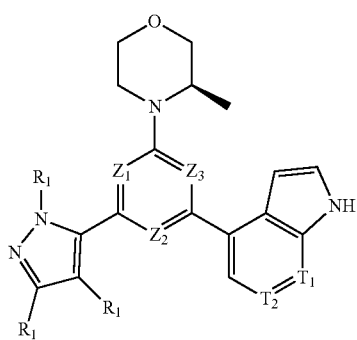
(II-1)

-continued

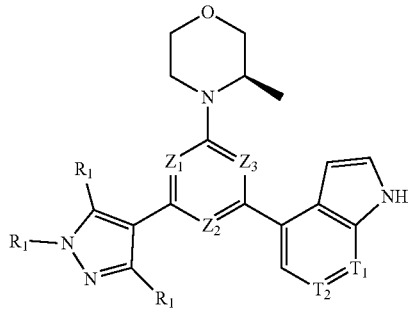
(II-2)

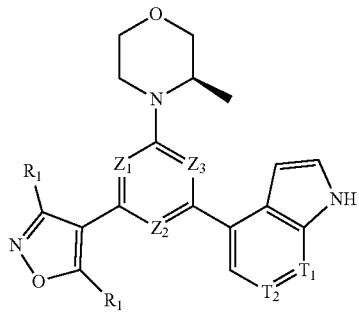
(II-3)

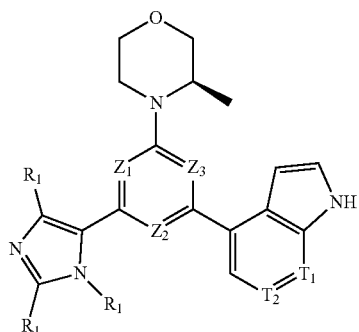
(II-4)

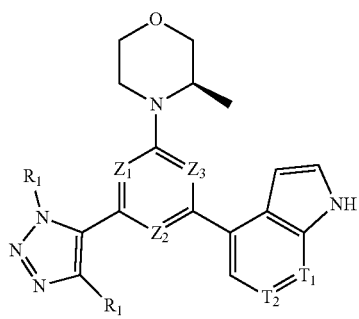
(II-5)

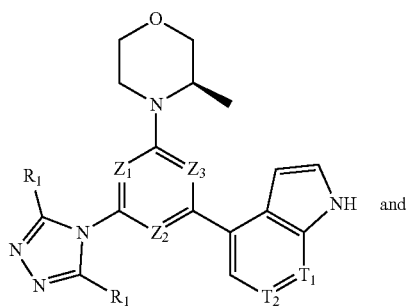
(II-6)

and

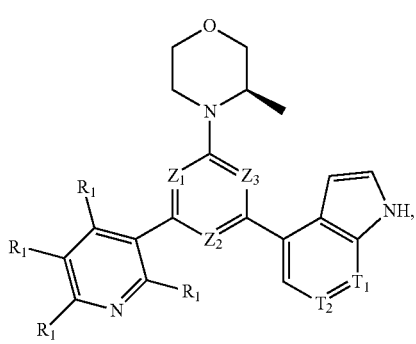
(II-7)
wherein,
$T_1$, and $T_2$ are each independently selected from the group consisting of $C(R_2)$ and N;
and $R_1$, $R_2$, $Z_1$, $Z_2$ and $Z_3$ are defined as in claim 1.
13. The compound according to claim 12, or the tautomer or the pharmaceutically acceptable salt thereof, wherein the compound is selected from
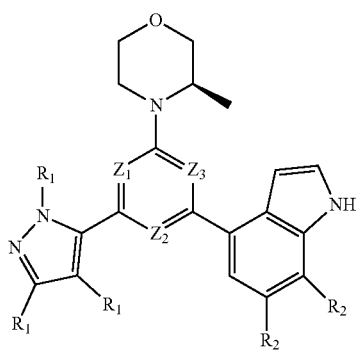
(I-1)
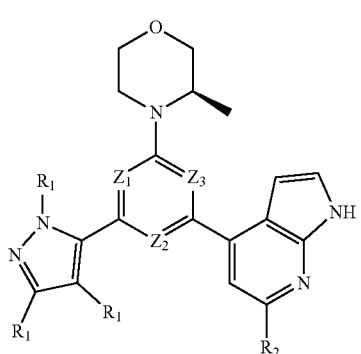
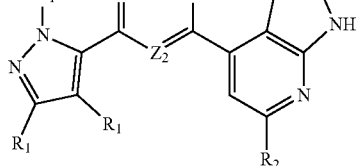
(I-2)
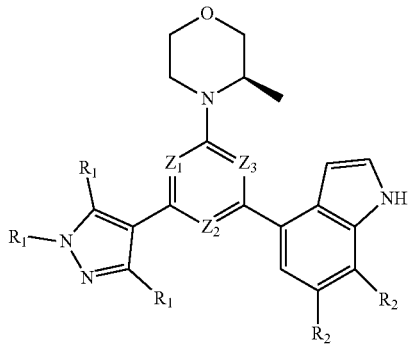
(I-3)
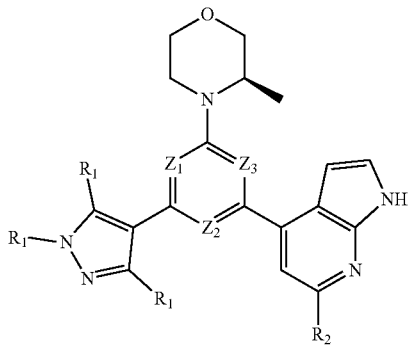
(I-4)
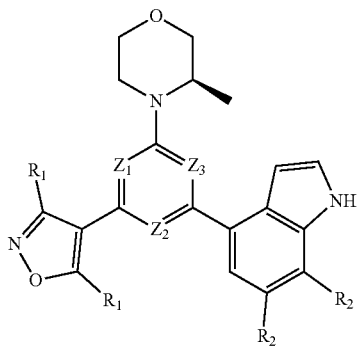
(I-5)
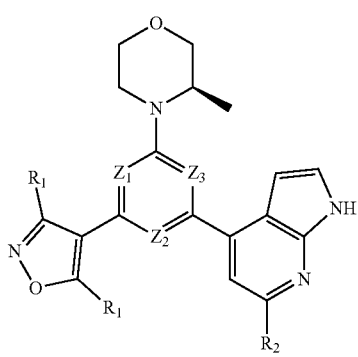
(I-6)
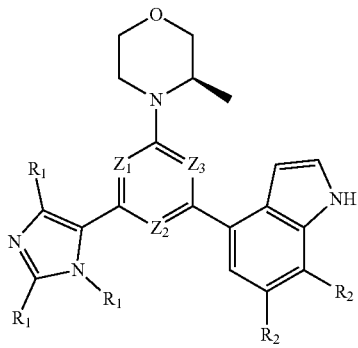
(II-4A)

(II-4B)
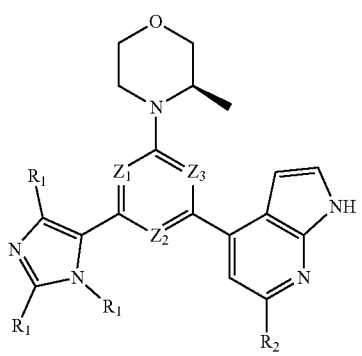
(II-5A)
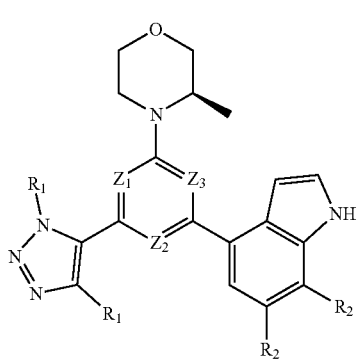
(II-5B)
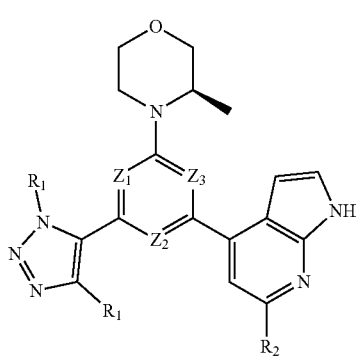
(II-6A)
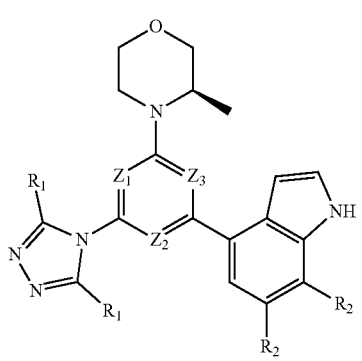
(II-6B)
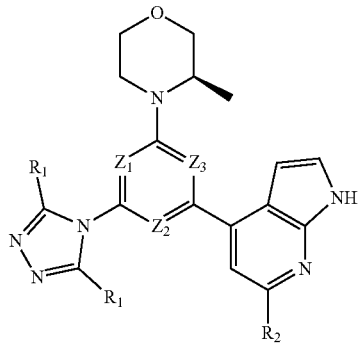
(II-7A)
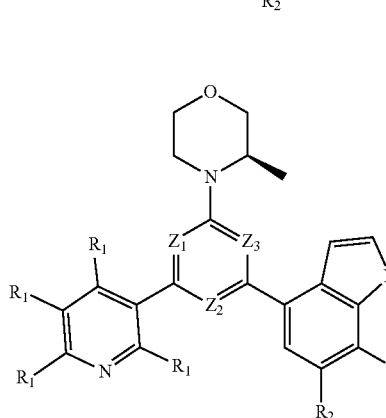
and
(II-7B)
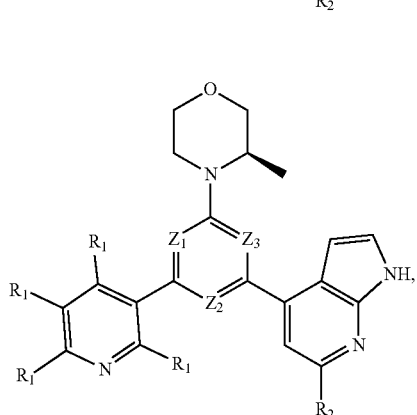
wherein,
$R_1$, $R_2$, $Z_1$, $Z_2$, and $Z_3$ are defined as in claim 12.
14. A compound or a tautomer or a pharmaceutically acceptable salt thereof, selected from
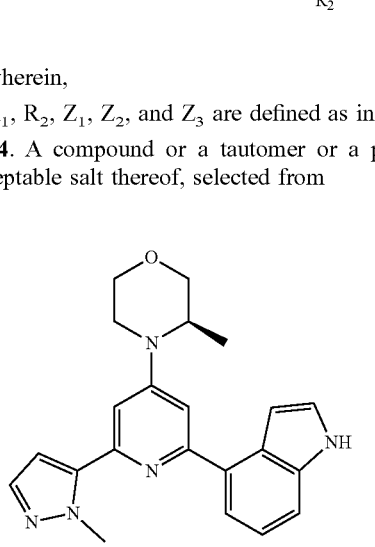

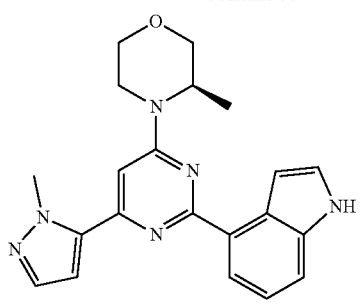
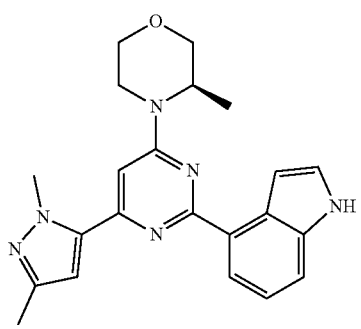
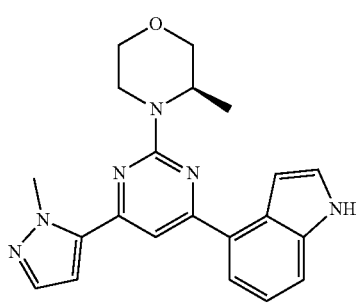
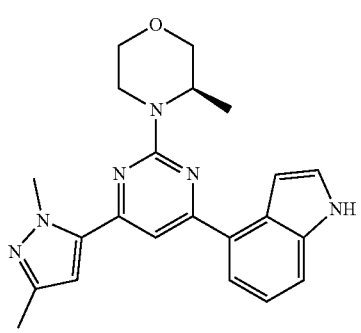
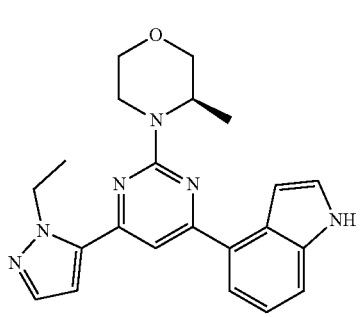
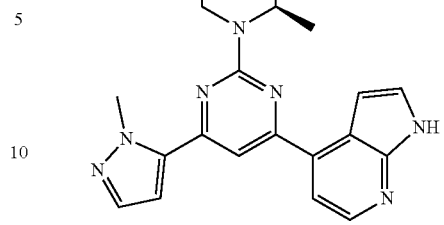
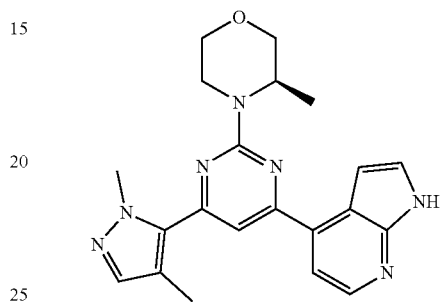
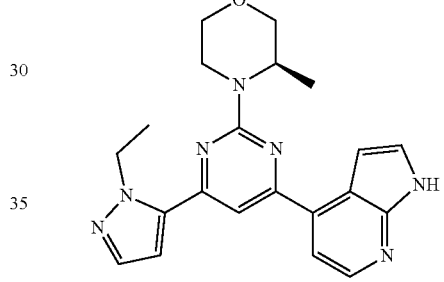
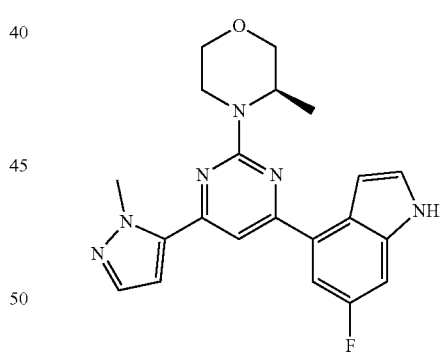
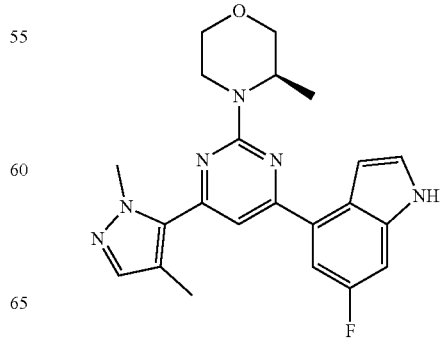

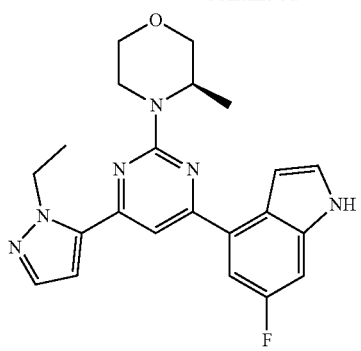
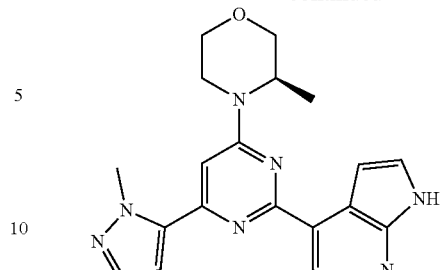
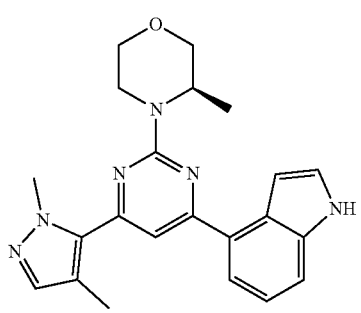
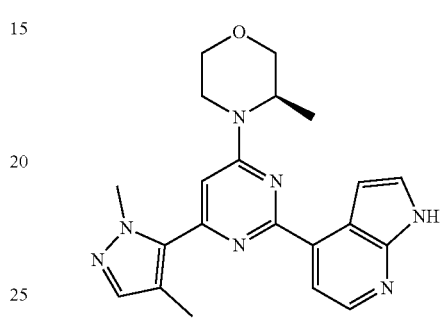
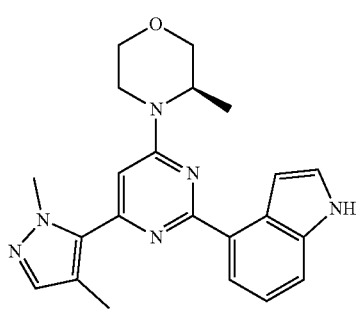
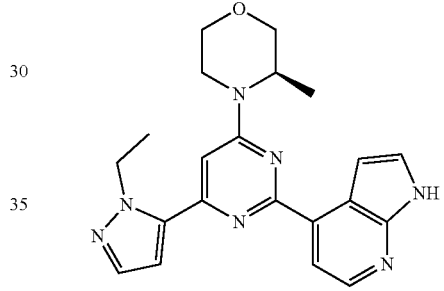
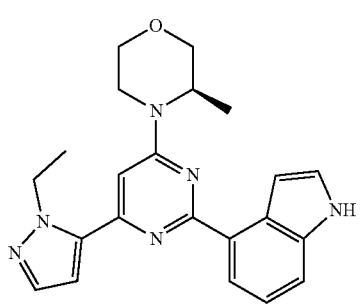
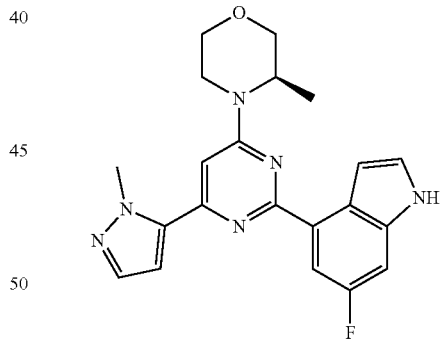
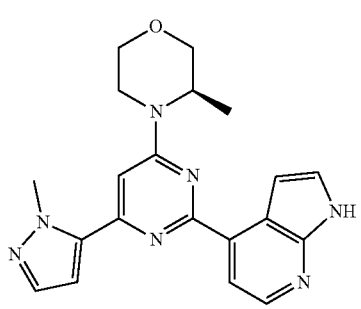
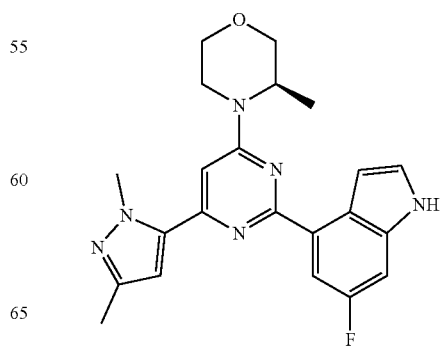

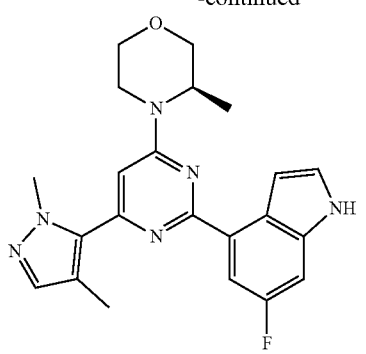
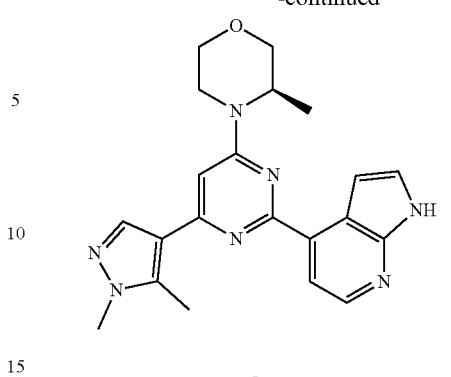
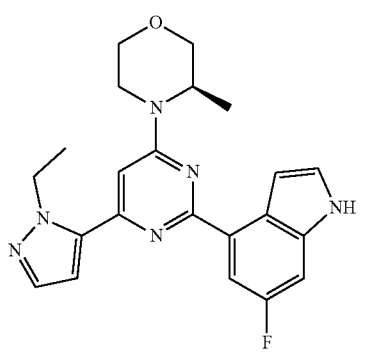
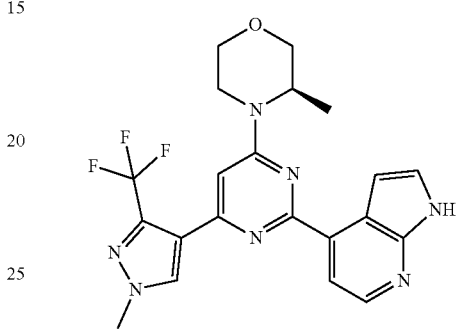
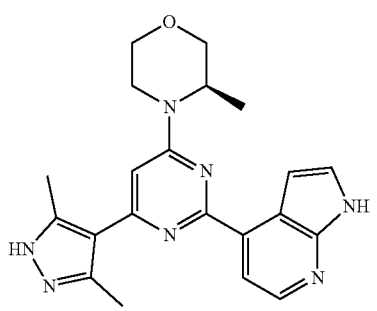
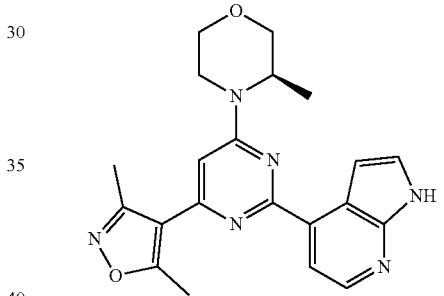
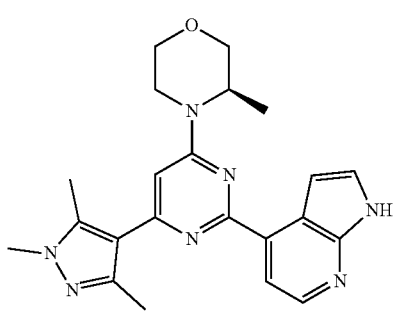
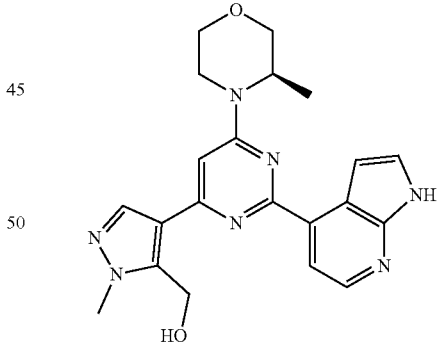
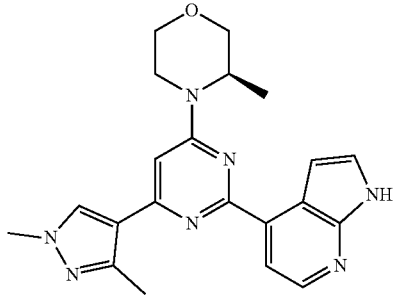
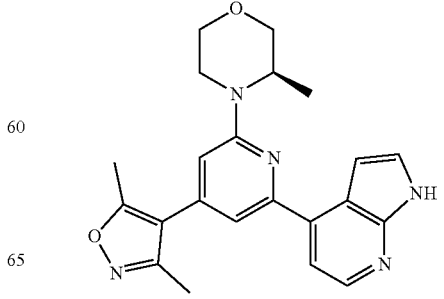

177
-continued
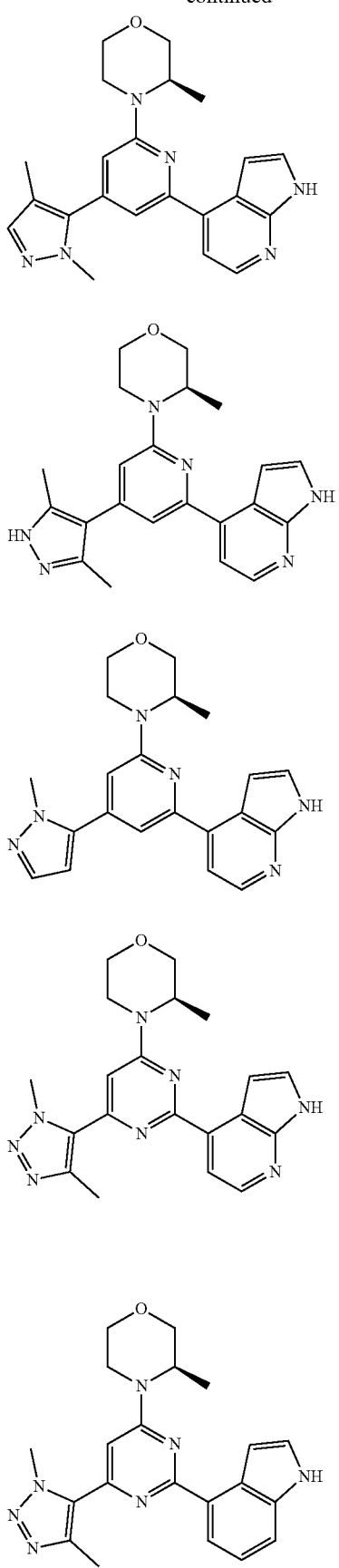
178
-continued
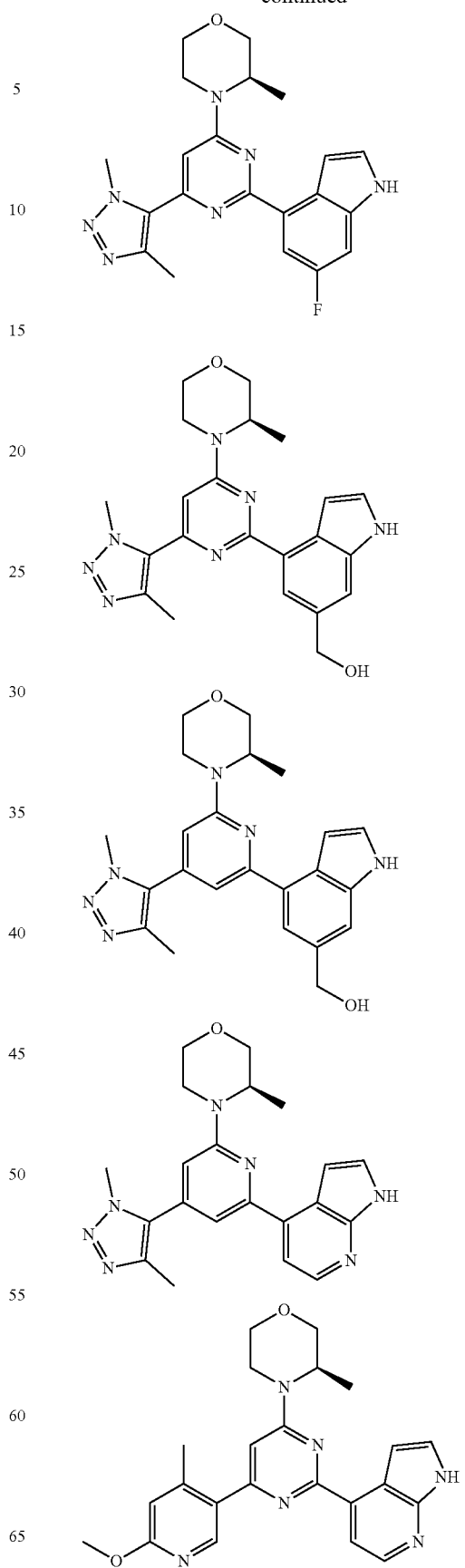

179
-continued
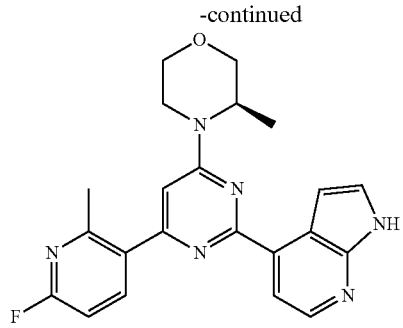
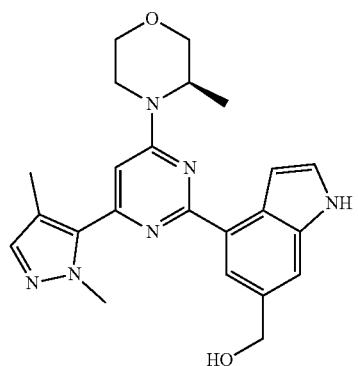
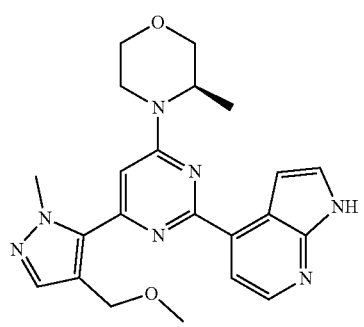
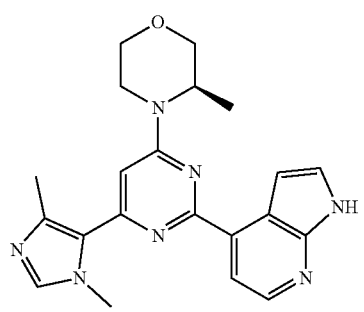
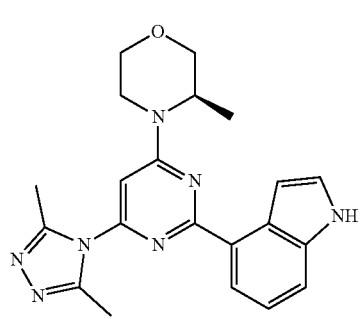
180
-continued
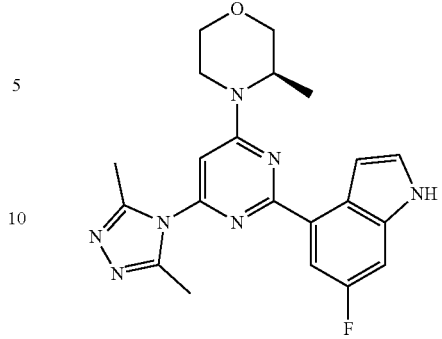
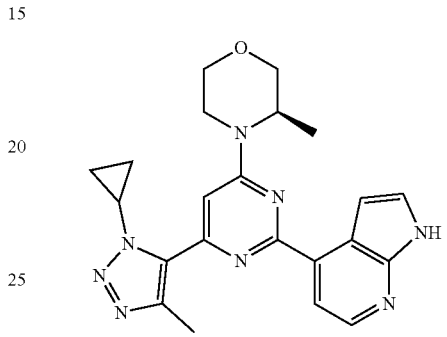
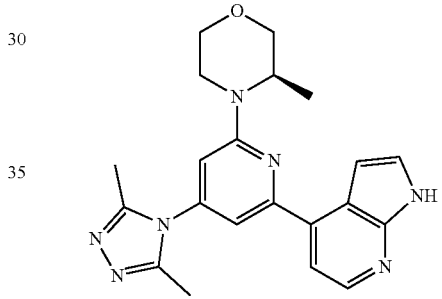
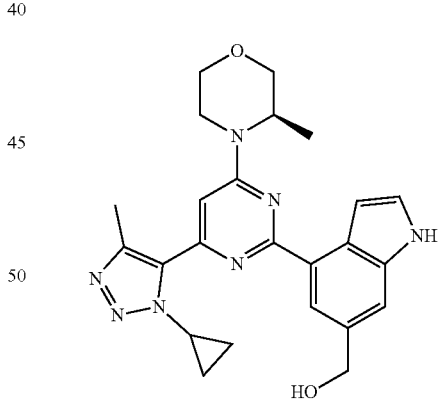
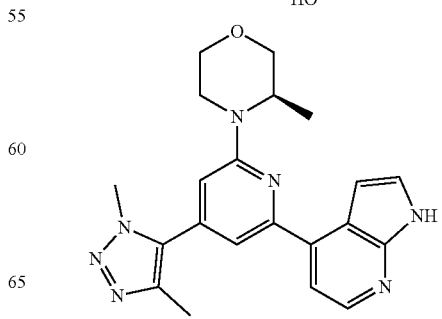

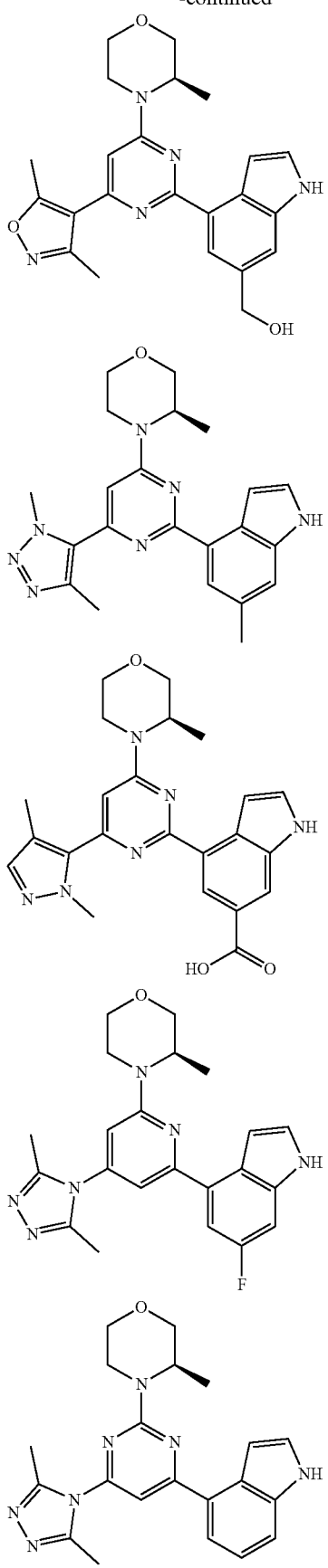

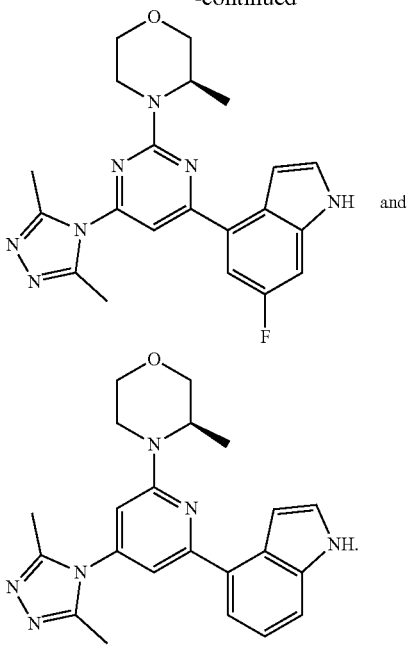

15. A method for treating an ATR associated disease, comprising administering the compound of formula (I) according to claim 1, or the tautomer or the pharmaceutically acceptable salt thereof to a subject in need thereof; wherein the ATR associated disease is a solid tumor or a hematologic tumor, wherein, in the compound of formula (I), $Z_1$, $Z_2$ and $Z_3$ are not N at the same time.

16. A method for treating an ATR associated disease, comprising administering the compound according to claim 14, or the tautomer or the pharmaceutically acceptable salt thereof to a subject in need thereof, wherein the ATR associated disease is a solid tumor or a hematologic tumor.

17. A pharmaceutical composition comprising the compound according to claim 1, or the tautomer or the pharmaceutically acceptable salt thereof.

18. The compound of formula (I) according to claim 1, or the tautomer or the pharmaceutically acceptable salt thereof,

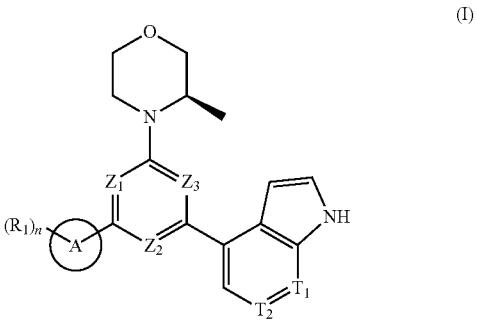

wherein, n is 1, 2, 3 or 4;

$Z_1$, $Z_2$, and $Z_3$ are each independently selected from the group consisting of CH and N, and at least one of $Z_1$, $Z_2$ and $Z_3$ is N;

$T_1$ and $T_2$ are each independently selected from the group consisting of $C(R_2)$ and N;

$R_2$ is each independently selected from the group consisting of H, F, Cl, Br, I, OH, $NH_2$, COOH and $C_{1-3}$ alkyl, wherein the $C_{1-3}$ alkyl is optionally substituted by 1, 2 or 3 R;

R is each independently selected from the group consisting of F, Cl, Br, I, OH, $NH_2$, $C_{1-3}$ alkyl and $C_{1-3}$ alkoxy, wherein the $C_{1-3}$ alkyl and $C_{1-3}$ alkoxy are optionally substituted by 1, 2 or 3 R';

R' is each independently selected from the group consisting of F, Cl, Br, I, OH and $NH_2$; and ring A is selected from the group consisting of pyrazolyl, isoxazolyl, oxazolyl, imidazolyl, 1,2,3-triazolyl and 1,2,4-triazolyl; and $R_1$ is each independently selected from the group consisting of H, F, Cl, Br, I, OH, $NH_2$, $C_{1-6}$ alkyl, $C_{1-6}$ alkoxy and $C_{3-6}$ cycloalkyl, wherein the $C_{1-6}$ alkyl, $C_{1-6}$ alkoxy and $C_{3-6}$ cycloalkyl are optionally substituted by 1, 2 or 3 R;

or the structural unit

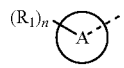

is selected from the group consisting of

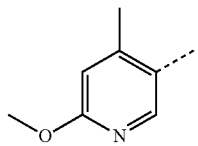 and 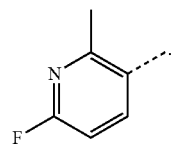

19. A method for treating an ATR associated disease, comprising administering the compound of formula (I) according to claim 18, or the tautomer or the pharmaceutically acceptable salt thereof to a subject in need thereof; wherein the ATR associated disease is a solid tumor or a hematologic tumor;

wherein, in the compound of formula (I), $Z_1$, $Z_2$ and $Z_3$ are not N at the same time.

* * * * *